US011926827B2

(12) United States Patent
Calamini et al.

(10) Patent No.: US 11,926,827 B2
(45) Date of Patent: Mar. 12, 2024

(54) MAPT RNA INTERFERENCE AGENTS

(71) Applicant: Eli Lilly and Company, Indianapolis, IN (US)

(72) Inventors: Barbara Calamini, Acton, MA (US); Sarah Katharina Fritschi, Frankfurt am Main (DE); Rebecca Ruth Miles, Pendleton, IN (US); Andrew Peter McCarthy, Arlington, MA (US); Douglas Raymond Perkins, New Palestine, IN (US); Keith Geoffrey Phillips, Newburyport, MA (US); Kaushambi Roy, North Chelmsford, MA (US); Isabel Cristina Gonzalez Valcarcel, Indianapolis, IN (US); Jibo Wang, Carmel, IN (US); Shih-Ying Wu, Needham, MA (US); Jeremy S. York, Noblesville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/311,354

(22) Filed: May 3, 2023

(65) Prior Publication Data
US 2023/0340482 A1    Oct. 26, 2023

Related U.S. Application Data

(63) Continuation of application No. 18/064,391, filed on Dec. 12, 2022.

(60) Provisional application No. 63/288,846, filed on Dec. 13, 2021.

(51) Int. Cl.
C12N 15/113        (2010.01)

(52) U.S. Cl.
CPC ........ *C12N 15/113* (2013.01); *C12N 2310/14* (2013.01); *C12N 2310/315* (2013.01); *C12N 2310/351* (2013.01); *C12N 2320/32* (2013.01)

(58) Field of Classification Search
CPC .............. C12N 15/133; C12N 2310/14; C12N 2310/315; C12N 2310/351
See application file for complete search history.

(56) References Cited

FOREIGN PATENT DOCUMENTS

| WO | WO2004/058940 A2 | 7/2004 |
|----|------------------|--------|
| WO | WO2016/151523 A1 | 9/2016 |
| WO | WO202/188626 A1  | 9/2021 |
| WO | WO2021/202511 A2 | 10/2021 |
| WO | WO2023/064707 A1 | 4/2023 |

OTHER PUBLICATIONS

Xu et al. Current Gene Therapy 14, 343-351 (Year: 2014).*
Stoyka et al. 8(3) ENEURO.0458-20.2021,1-15 (Year: 2021).*
Leveille Etinne et al: "Tau and MAPT Genetics in Tauopathies and Synucleinopathies", Parkinsonism and Related Disorders, vol. 90, Sep. 1, 2021 pp. 142-154.
Hu Bo, et al: "Therapeutic siRNA: State of the Art". Signal Transduction and Targeted Therapy, vol. 5, No. 1, 101, Dec. 1, 2020, pp. 1-25.

* cited by examiner

*Primary Examiner* — Brian Whiteman
(74) *Attorney, Agent, or Firm* — Xiaoguang Gao

(57) ABSTRACT

Provided herein are MAPT RNAi agents and compositions comprising a MAPT RNAi agent. Also provided herein are methods of using the MAPT RNAi agents or compositions comprising a MAPT RNAi agent for reducing MAPT expression and/or treating tauopathy in a subject.

30 Claims, No Drawings
Specification includes a Sequence Listing.

MAPT RNA INTERFERENCE AGENTS

SEQUENCE LISTING

The present application is being filed along with a Sequence Listing in ST.26 XML format. The Sequence Listing is provided as a file titled "30170A_v2" created May 15, 2023 and is 958 kilobytes in size. The Sequence Listing information in the ST.26 XML format is incorporated herein by reference in its entirety.

BACKGROUND

Microtubule associated protein Tau is encoded by the MAPT gene located on chromosome 17. Tau protein interacts with tubulin to stabilize the microtubules and promote tubulin assembly into microtubules. MAPT transcripts are differentially expressed throughout the body, predominantly in the central and peripheral nervous system.

The MAPT gene consists of 16 exons. Alternative mRNA splicing gives rise to multiple MAPT isoforms. At least six Tau isoforms exist in human brain, ranging from 352 to 441 amino acids long. Alternative splicing of exons 2 and/or 3 leads to inclusion of zero, one, or two copies of the N-terminal acidic domain, which are referred to as 0N, 1N, or 2N Tau, respectively. The Tau isoforms that include exon 10, which encodes an additional microtubule-binding domain, are referred to as "4R Tau", as it has four microtubule-binding domains. The Tau isoforms without exon 10 are referred to as "3R Tau", as it has three microtubule-binding domains.

Mutations in MAPT and hyperphosphorylation of Tau protein can cause aggregation and deposition of Tau in pathogenic neurofibrillary tangles, causing progressive neurodegenerative disorders such as Alzheimer's disease, frontotemporal dementia (FTD), progressive supranuclear palsy (PSP), and other tauopathies.

RNA interference (RNAi) is a highly conserved regulatory mechanism in which RNA molecules are involved in sequence-specific suppression of gene expression by double-stranded RNA molecules (dsRNA) (Fire et al., Nature 391:806-811, 1998).

There are currently no FDA-approved disease-modifying therapeutic agents specifically for reducing MAPT and treating tauopathies. Aducanumab, which targets amyloid beta protein (AB), is the only disease-modifying medication currently approved to treat Alzheimer's disease. Accordingly, there remains a need for therapeutic agents that can inhibit or adjust the expression of the MAPT gene for treating tauopathies, e.g., by utilizing RNAi.

SUMMARY OF INVENTION

Provided herein are MAPT RNAi agents and compositions comprising a MAPT RNAi agent. Also provided herein are methods of using the MAPT RNAi agents or compositions comprising a MAPT RNAi agent for reducing MAPT expression and/or treating tauopathy in a subject.

In one aspect, provided herein are MAPT RNAi agents having a sense strand and an antisense strand, wherein the sense strand and the antisense strand form a duplex, wherein the sense strand and the antisense strand comprise a pair of nucleic acid sequences selected from the group consisting of:

(a) the sense strand comprises a first nucleic acid sequence having at least 95% sequence identity to SEQ ID NO: 1, and the antisense strand comprises a second nucleic acid sequence having at least 95% sequence identity to SEQ ID NO: 2;

(b) the sense strand comprises a first nucleic acid sequence having at least 95% sequence identity to SEQ ID NO: 3, and the antisense strand comprises a second nucleic acid sequence having at least 95% sequence identity to SEQ ID NO: 4;

(c) the sense strand comprises a first nucleic acid sequence having at least 95% sequence identity to SEQ ID NO: 5, and the antisense strand comprises a second nucleic acid sequence having at least 95% sequence identity to SEQ ID NO: 6;

(d) the sense strand comprises a first nucleic acid sequence having at least 95% sequence identity to SEQ ID NO: 7, and the antisense strand comprises a second nucleic acid sequence having at least 95% sequence identity to SEQ ID NO: 8;

(e) the sense strand comprises a first nucleic acid sequence having at least 95% sequence identity to SEQ ID NO: 9, and the antisense strand comprises a second nucleic acid sequence having at least 95% sequence identity to SEQ ID NO: 10;

(f) the sense strand comprises a first nucleic acid sequence having at least 95% sequence identity to SEQ ID NO: 11, and the antisense strand comprises a second nucleic acid sequence having at least 95% sequence identity to SEQ ID NO: 12;

(g) the sense strand comprises a first nucleic acid sequence having at least 95% sequence identity to SEQ ID NO:13, and the antisense strand comprises a second nucleic acid sequence having at least 95% sequence identity to SEQ ID NO: 14;

(h) the sense strand comprises a first nucleic acid sequence having at least 95% sequence identity to SEQ ID NO:15, and the antisense strand comprises a second nucleic acid sequence having at least 95% sequence identity to SEQ ID NO: 16;

(i) the sense strand comprises a first nucleic acid sequence having at least 95% sequence identity to SEQ ID NO:17, and the antisense strand comprises a second nucleic acid sequence having at least 95% sequence identity to SEQ ID NO: 18;

(j) the sense strand comprises a first nucleic acid sequence having at least 95% sequence identity to SEQ ID NO:19, and the antisense strand comprises a second nucleic acid sequence having at least 95% sequence identity to SEQ ID NO: 20;

(k) the sense strand comprises a first nucleic acid sequence having at least 95% sequence identity to SEQ ID NO:21, and the antisense strand comprises a second nucleic acid sequence having at least 95% sequence identity to SEQ ID NO: 22; and (l) the sense strand comprises a first nucleic acid sequence having at least 95% sequence identity to SEQ ID NO:23, and the antisense strand comprises a second nucleic acid sequence having at least 95% sequence identity to SEQ ID NO: 24;

(m) the sense strand comprises a first nucleic acid sequence having at least 95% sequence identity to SEQ ID NO: 55, and the antisense strand comprises a second nucleic acid sequence having at least 95% sequence identity to SEQ ID NO: 16;

(n) the sense strand comprises a first nucleic acid sequence having at least 95% sequence identity to SEQ ID NO: 56, and the antisense strand comprises a second nucleic acid sequence having at least 95% sequence identity to SEQ ID NO: 16;
(o) the sense strand comprises a first nucleic acid sequence having at least 95% sequence identity to SEQ ID NO: 57, and the antisense strand comprises a second nucleic acid sequence having at least 95% sequence identity to SEQ ID NO: 58;
(p) the sense strand comprises a first nucleic acid sequence having at least 95% sequence identity to SEQ ID NO: 59, and the antisense strand comprises a second nucleic acid sequence having at least 95% sequence identity to SEQ ID NO: 58;
(q) the sense strand comprises a first nucleic acid sequence having at least 95% sequence identity to SEQ ID NO: 60, and the antisense strand comprises a second nucleic acid sequence having at least 95% sequence identity to SEQ ID NO: 61;
(r) the sense strand comprises a first nucleic acid sequence having at least 95% sequence identity to SEQ ID NO: 62, and the antisense strand comprises a second nucleic acid sequence having at least 95% sequence identity to SEQ ID NO: 61;
(s) the sense strand comprises a first nucleic acid sequence having at least 95% sequence identity to SEQ ID NO: 117, and the antisense strand comprises a second nucleic acid sequence having at least 95% sequence identity to SEQ ID NO: 118; and
(t) the sense strand comprises a first nucleic acid sequence having at least 95% sequence identity to SEQ ID NO: 119, and the antisense strand comprises a second nucleic acid sequence having at least 95% sequence identity to SEQ ID NO: 16,
wherein optionally one or more nucleotides of the sense strand and the antisense strand are independently modified nucleotides, and wherein optionally one or more internucleotide linkages of the sense strand and the antisense strand are modified internucleotide linkages.

In some embodiments, the sense strand and the antisense strand of the MAPT RNAi agent described herein comprise a pair of nucleic acid sequences selected from the group consisting of:
(a) the sense strand comprises a first nucleic acid sequence of SEQ ID NO: 1, and the antisense strand comprises a second nucleic acid sequence of SEQ ID NO: 2;
(b) the sense strand comprises a first nucleic acid sequence of SEQ ID NO: 3, and the antisense strand comprises a second nucleic acid sequence of SEQ ID NO: 4;
(c) the sense strand comprises a first nucleic acid sequence of SEQ ID NO: 5, and the antisense strand comprises a second nucleic acid sequence of SEQ ID NO: 6;
(d) the sense strand comprises a first nucleic acid sequence of SEQ ID NO: 7, and the antisense strand comprises a second nucleic acid sequence of SEQ ID NO: 8;
(e) the sense strand comprises a first nucleic acid sequence of SEQ ID NO: 9, and the antisense strand comprises a second nucleic acid sequence of SEQ ID NO: 10;
(f) the sense strand comprises a first nucleic acid sequence of SEQ ID NO: 11, and the antisense strand comprises a second nucleic acid sequence of SEQ ID NO: 12;
(g) the sense strand comprises a first nucleic acid sequence of SEQ ID NO:13, and the antisense strand comprises a second nucleic acid sequence of SEQ ID NO: 14;
(h) the sense strand comprises a first nucleic acid sequence of SEQ ID NO: 15, and the antisense strand comprises a second nucleic acid sequence of SEQ ID NO: 16;
(i) the sense strand comprises a first nucleic acid sequence of SEQ ID NO: 17, and the antisense strand comprises a second nucleic acid sequence of SEQ ID NO: 18;
(j) the sense strand comprises a first nucleic acid sequence of SEQ ID NO: 19, and the antisense strand comprises a second nucleic acid sequence of SEQ ID NO: 20;
(k) the sense strand comprises a first nucleic acid sequence of SEQ ID NO:21, and the antisense strand comprises a second nucleic acid sequence of SEQ ID NO: 22;
(l) the sense strand comprises a first nucleic acid sequence of SEQ ID NO:23, and the antisense strand comprises a second nucleic acid sequence of SEQ ID NO: 24;
(m) the sense strand comprises a first nucleic acid sequence of SEQ ID NO: 55, and the antisense strand comprises a second nucleic acid sequence of SEQ ID NO: 16;
(n) the sense strand comprises a first nucleic acid sequence of SEQ ID NO: 56, and the antisense strand comprises a second nucleic acid sequence of SEQ ID NO: 16;
(o) the sense strand comprises a first nucleic acid sequence of SEQ ID NO: 57, and the antisense strand comprises a second nucleic acid sequence of SEQ ID NO: 58;
(p) the sense strand comprises a first nucleic acid sequence of SEQ ID NO: 59, and the antisense strand comprises a second nucleic acid sequence of SEQ ID NO: 58;
(q) the sense strand comprises a first nucleic acid sequence of SEQ ID NO: 60, and the antisense strand comprises a second nucleic acid sequence of SEQ ID NO: 61;
(r) the sense strand comprises a first nucleic acid sequence of SEQ ID NO: 62, and the antisense strand comprises a second nucleic acid sequence of SEQ ID NO: 61;
(s) the sense strand comprises a first nucleic acid sequence of SEQ ID NO: 117, and the antisense strand comprises a second nucleic acid sequence of SEQ ID NO: 118; and
(t) the sense strand comprises a first nucleic acid sequence of SEQ ID NO: 119, and the antisense strand comprises a second nucleic acid sequence of SEQ ID NO: 16.

In some embodiments, the sense strand and the antisense strand of the MAPT RNAi agent described herein have a pair of nucleic acid sequences selected from the group consisting of:
(a) the sense strand has a first nucleic acid sequence of SEQ ID NO: 1, and the antisense strand has a second nucleic acid sequence of SEQ ID NO: 2;
(b) the sense strand has a first nucleic acid sequence of SEQ ID NO: 3, and the antisense strand has a second nucleic acid sequence of SEQ ID NO: 4;
(c) the sense strand has a first nucleic acid sequence of SEQ ID NO: 5, and the antisense strand has a second nucleic acid sequence of SEQ ID NO: 6;
(d) the sense strand has a first nucleic acid sequence of SEQ ID NO: 7, and the antisense strand has a second nucleic acid sequence of SEQ ID NO: 8;

(e) the sense strand has a first nucleic acid sequence of SEQ ID NO: 9, and the antisense strand has a second nucleic acid sequence of SEQ ID NO: 10;
(f) the sense strand has a first nucleic acid sequence of SEQ ID NO: 11, and the antisense strand has a second nucleic acid sequence of SEQ ID NO: 12;
(g) the sense strand has a first nucleic acid sequence of SEQ ID NO:13, and the antisense strand has a second nucleic acid sequence of SEQ ID NO: 14;
(h) the sense strand has a first nucleic acid sequence of SEQ ID NO:15, and the antisense strand has a second nucleic acid sequence of SEQ ID NO: 16;
(i) the sense strand has a first nucleic acid sequence of SEQ ID NO:17, and the antisense strand has a second nucleic acid sequence of SEQ ID NO: 18;
(j) the sense strand has a first nucleic acid sequence of SEQ ID NO:19, and the antisense strand has a second nucleic acid sequence of SEQ ID NO: 20;
(k) the sense strand has a first nucleic acid sequence of SEQ ID NO:21, and the antisense strand has a second nucleic acid sequence of SEQ ID NO: 22;
(l) the sense strand has a first nucleic acid sequence of SEQ ID NO:23, and the antisense strand has a second nucleic acid sequence of SEQ ID NO: 24;
(m) the sense strand has a first nucleic acid sequence of SEQ ID NO: 55, and the antisense strand has a second nucleic acid sequence of SEQ ID NO: 16;
(n) the sense strand has a first nucleic acid sequence of SEQ ID NO: 56, and the antisense strand has a second nucleic acid sequence of SEQ ID NO: 16;
(o) the sense strand has a first nucleic acid sequence of SEQ ID NO: 57, and the antisense strand has a second nucleic acid sequence of SEQ ID NO: 58;
(p) the sense strand has a first nucleic acid sequence of SEQ ID NO: 59, and the antisense strand has a second nucleic acid sequence of SEQ ID NO: 58;
(q) the sense strand has a first nucleic acid sequence of SEQ ID NO: 60, and the antisense strand has a second nucleic acid sequence of SEQ ID NO: 61;
(r) the sense strand has a first nucleic acid sequence of SEQ ID NO: 62, and the antisense strand has a second nucleic acid sequence of SEQ ID NO: 61;
(s) the sense strand has a first nucleic acid sequence of SEQ ID NO: 117, and the antisense strand has a second nucleic acid sequence of SEQ ID NO: 118; and
(t) the sense strand has a first nucleic acid sequence of SEQ ID NO: 119, and the antisense strand has a second nucleic acid sequence of SEQ ID NO: 16.

The MAPT RNAi agents described herein may include modifications. The modifications can be made to one or more nucleotides of the sense strand and/or antisense strand or to the internucleotide linkages. In some embodiments, one or more nucleotides of the sense strand are modified nucleotides. In some embodiments, each nucleotide of the sense strand is a modified nucleotide. In some embodiments, one or more nucleotides of the antisense strand are modified nucleotides. In some embodiments, each nucleotide of the antisense strand is a modified nucleotide. In some embodiments, the modified nucleotide is a 2'-fluoro modified nucleotide, 2'-O-methyl modified nucleotide, or 2'-O-alkyl modified nucleotide, e.g., e.g., 2'-O—C16 alkyl modified nucleotide. In some embodiments, the sense strand has four 2'-fluoro modified nucleotides at positions 7, 9, 10, 11 from the 5' end of the sense strand. In some embodiments, nucleotides at positions other than positions 7, 9, 10, and 11 of the sense strand are 2'-O-methyl modified nucleotides or 2'-O—C16 alkyl modified nucleotides. In some embodiments, the antisense strand has four 2'-fluoro modified nucleotides at positions 2, 6, 14, 16 from the 5' end of the antisense strand. In some embodiments, nucleotides at positions other than positions 2, 6, 14 and 16 of the antisense strand are 2'-O-methyl modified nucleotides or 2'-O—C16 alkyl modified nucleotides. In some embodiments, the sense strand has three 2'-fluoro modified nucleotides, e.g., at positions 9, 10, 11 from the 5' end of the sense strand. In some embodiments, the other nucleotides of the sense strand are 2'-O-methyl modified nucleotides. In some embodiments, the antisense strand has five 2'-fluoro modified nucleotides, e.g., at positions 2, 5, 7, 14, 16 from the 5' end of the antisense strand. In some embodiments, the antisense strand has five 2'-fluoro modified nucleotides, e.g., at positions 2, 5, 8, 14, 16 from the 5' end of the antisense strand. In some embodiments, the antisense strand has five 2'-fluoro modified nucleotides, e.g., at positions 2, 3, 7, 14, 16 from the 5' end of the antisense strand. In some embodiments, the other nucleotides of the antisense strand are 2'-O-methyl modified nucleotides. In some embodiments, the sense strand comprises an abasic moiety or inverted abasic moiety.

In some embodiments, the first nucleotide from the 5' end of the antisense strand is a modified nucleotide that has a phosphate analog, e.g., a 5'-vinylphosphonate. In some embodiments, the sense strand comprises an abasic moiety or inverted abasic moiety. In some embodiments, the sense strand and the antisense strand have one or more modified internucleotide linkages, e.g., phosphorothioate linkage. In some embodiments, the sense strand has four or five phosphorothioate linkages. In some embodiments, the antisense strand has four or five phosphorothioate linkages. In some embodiments, the sense strand has four phosphorothioate linkages and the antisense strand has four phosphorothioate linkages.

In some embodiments, provided herein are MAPT RNAi agents having a sense strand and an antisense strand, wherein the sense strand and the antisense strand form a duplex, wherein the sense strand and the antisense strand comprise a pair of nucleic acid sequences selected from the group consisting of:
(a) the sense strand comprises a first nucleic acid sequence of SEQ ID NO: 25, and the antisense strand comprises a second nucleic acid sequence of SEQ ID NO: 26;
(b) the sense strand comprises a first nucleic acid sequence of SEQ ID NO: 27, and the antisense strand comprises a second nucleic acid sequence of SEQ ID NO: 28;
(c) the sense strand comprises a first nucleic acid sequence of SEQ ID NO: 29, and the antisense strand comprises a second nucleic acid sequence of SEQ ID NO: 30;
(d) the sense strand comprises a first nucleic acid sequence of SEQ ID NO: 31, and the antisense strand comprises a second nucleic acid sequence of SEQ ID NO: 32;
(e) the sense strand comprises a first nucleic acid sequence of SEQ ID NO: 33, and the antisense strand comprises a second nucleic acid sequence of SEQ ID NO: 34;
(f) the sense strand comprises a first nucleic acid sequence of SEQ ID NO: 35, and the antisense strand comprises a second nucleic acid sequence of SEQ ID NO: 36;
(g) the sense strand comprises a first nucleic acid sequence of SEQ ID NO: 37, and the antisense strand comprises a second nucleic acid sequence of SEQ ID NO: 38;

(h) the sense strand comprises a first nucleic acid sequence of SEQ ID NO: 39, and the antisense strand comprises a second nucleic acid sequence of SEQ ID NO: 40;
(i) the sense strand comprises a first nucleic acid sequence of SEQ ID NO: 41, and the antisense strand comprises a second nucleic acid sequence of SEQ ID NO: 42;
(j) the sense strand comprises a first nucleic acid sequence of SEQ ID NO: 43, and the antisense strand comprises a second nucleic acid sequence of SEQ ID NO: 44;
(k) the sense strand comprises a first nucleic acid sequence of SEQ ID NO: 45, and the antisense strand comprises a second nucleic acid sequence of SEQ ID NO: 46;
(l) the sense strand comprises a first nucleic acid sequence of SEQ ID NO: 47, and the antisense strand comprises a second nucleic acid sequence of SEQ ID NO: 48;
(m) the sense strand comprises a first nucleic acid sequence of SEQ ID NO: 63, and the antisense strand comprises a second nucleic acid sequence of SEQ ID NO: 40;
(n) the sense strand comprises a first nucleic acid sequence selected from any one of SEQ ID NOs: 64, 66-69, 71, 75-86, 93-100, and the antisense strand comprises a second nucleic acid sequence of SEQ ID NO: 65;
(o) the sense strand comprises a first nucleic acid sequence of SEQ ID NO: 64, and the antisense strand comprises a second nucleic acid sequence selected from any one of SEQ ID NOs: 70, 72-74;
(p) the sense strand comprises a first nucleic acid sequence selected from SEQ ID NO: 87 or 89, and the antisense strand comprises a second nucleic acid sequence of SEQ ID NO: 88;
(q) the sense strand comprises a first nucleic acid sequence selected from SEQ ID NO: 90 or 92, and the antisense strand comprises a second nucleic acid sequence of SEQ ID NO: 91;
(r) the sense strand comprises a first nucleic acid sequence of SEQ ID NO: 101, and the antisense strand comprises a second nucleic acid sequence of SEQ ID NO: 102;
(s) the sense strand comprises a first nucleic acid sequence of SEQ ID NO: 103, and the antisense strand comprises a second nucleic acid sequence of SEQ ID NO: 104;
(t) the sense strand comprises a first nucleic acid sequence of SEQ ID NO: 105, and the antisense strand comprises a second nucleic acid sequence selected from any one of SEQ ID NOs: 65, 106-108;
(u) the sense strand comprises a first nucleic acid sequence of SEQ ID NO: 109, and the antisense strand comprises a second nucleic acid sequence of SEQ ID NO: 65;
(v) the sense strand comprises a first nucleic acid sequence of SEQ ID NO: 110, and the antisense strand comprises a second nucleic acid sequence of SEQ ID NO: 40;
(w) the sense strand comprises a first nucleic acid sequence of SEQ ID NO: 111, and the antisense strand comprises a second nucleic acid sequence of SEQ ID NO: 112;
(x) the sense strand comprises a first nucleic acid sequence of SEQ ID NO: 113, and the antisense strand comprises a second nucleic acid sequence of SEQ ID NO: 114; and
(y) the sense strand comprises a first nucleic acid sequence of SEQ ID NO: 115, and the antisense strand comprises a second nucleic acid sequence of SEQ ID NO: 116.

In some embodiments, provided herein are MAPT RNAi agents having a sense strand and an antisense strand, wherein the sense strand and the antisense strand form a duplex, wherein the sense strand and the antisense strand have a pair of nucleic acid sequences selected from the group consisting of:
(a) the sense strand has a first nucleic acid sequence of SEQ ID NO: 25, and the antisense strand has a second nucleic acid sequence of SEQ ID NO: 26;
(b) the sense strand has a first nucleic acid sequence of SEQ ID NO: 27, and the antisense strand has a second nucleic acid sequence of SEQ ID NO: 28;
(c) the sense strand has a first nucleic acid sequence of SEQ ID NO: 29, and the antisense strand has a second nucleic acid sequence of SEQ ID NO: 30;
(d) the sense strand has a first nucleic acid sequence of SEQ ID NO: 31, and the antisense strand has a second nucleic acid sequence of SEQ ID NO: 32;
(e) the sense strand has a first nucleic acid sequence of SEQ ID NO: 33, and the antisense strand has a second nucleic acid sequence of SEQ ID NO: 34;
(f) the sense strand has a first nucleic acid sequence of SEQ ID NO: 35, and the antisense strand has a second nucleic acid sequence of SEQ ID NO: 36;
(g) the sense strand has a first nucleic acid sequence of SEQ ID NO: 37, and the antisense strand has a second nucleic acid sequence of SEQ ID NO: 38;
(h) the sense strand has a first nucleic acid sequence of SEQ ID NO: 39, and the antisense strand has a second nucleic acid sequence of SEQ ID NO: 40;
(i) the sense strand has a first nucleic acid sequence of SEQ ID NO: 41, and the antisense strand has a second nucleic acid sequence of SEQ ID NO: 42;
(j) the sense strand has a first nucleic acid sequence of SEQ ID NO: 43, and the antisense strand has a second nucleic acid sequence of SEQ ID NO: 44;
(k) the sense strand has a first nucleic acid sequence of SEQ ID NO: 45, and the antisense strand has a second nucleic acid sequence of SEQ ID NO: 46;
(l) the sense strand has a first nucleic acid sequence of SEQ ID NO: 47, and the antisense strand has a second nucleic acid sequence of SEQ ID NO: 48;
(m) the sense strand has a first nucleic acid sequence of SEQ ID NO: 63, and the antisense strand has a second nucleic acid sequence of SEQ ID NO: 40;
(n) the sense strand has a first nucleic acid sequence selected from any one of SEQ ID NOs: 64, 66-69, 71, 75-86, 93-100, and the antisense strand has a second nucleic acid sequence of SEQ ID NO: 65;
(o) the sense strand has a first nucleic acid sequence of SEQ ID NO: 64, and the antisense strand has a second nucleic acid sequence selected from any one of SEQ ID NOs: 70, 72-74;
(p) the sense strand has a first nucleic acid sequence selected from SEQ ID NO: 87 or 89, and the antisense strand has a second nucleic acid sequence of SEQ ID NO: 88;
(q) the sense strand has a first nucleic acid sequence selected from SEQ ID NO: 90 or 92, and the antisense strand has a second nucleic acid sequence of SEQ ID NO: 91;

(r) the sense strand has a first nucleic acid sequence of SEQ ID NO: 101, and the antisense strand has a second nucleic acid sequence of SEQ ID NO: 102;

(s) the sense strand has a first nucleic acid sequence of SEQ ID NO: 103, and the antisense strand has a second nucleic acid sequence of SEQ ID NO: 104;

(t) the sense strand has a first nucleic acid sequence of SEQ ID NO: 105, and the antisense strand has a second nucleic acid sequence selected from any one of SEQ ID NOs: 65, 106-108;

(u) the sense strand has a first nucleic acid sequence of SEQ ID NO: 109, and the antisense strand has a second nucleic acid sequence of SEQ ID NO: 65;

(v) the sense strand has a first nucleic acid sequence of SEQ ID NO: 110, and the antisense strand has a second nucleic acid sequence of SEQ ID NO: 40;

(w) the sense strand has a first nucleic acid sequence of SEQ ID NO: 111, and the antisense strand has a second nucleic acid sequence of SEQ ID NO: 112;

(x) the sense strand has a first nucleic acid sequence of SEQ ID NO: 113, and the antisense strand has a second nucleic acid sequence of SEQ ID NO: 114; and (y) the sense strand has a first nucleic acid sequence of SEQ ID NO: 115, and the antisense strand has a second nucleic acid sequence of SEQ ID NO: 116.

In some embodiments, the sense strand of the MAPT RNAi agent has a delivery moiety. In some embodiments, the sense strand of the MAPT RNAi agent has a delivery moiety conjugated to the 5' or 3' end of the sense strand. In some embodiments, the sense strand of the MAPT RNAi agent has a delivery moiety conjugated to a nucleotide of the sense strand. In some embodiments, the delivery moiety is α-tocopherol or palmitic acid. In some embodiments, the delivery moiety is conjugated to the 5' or 3' end of the sense stand via a linker, e.g., a linker of Table 5.

In a further aspect, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprises a pair of nucleic acid sequences selected from the group consisting of:

(a) the sense strand comprises a first nucleic acid sequence of SEQ ID NO: 1, and the antisense strand comprises a second nucleic acid sequence of SEQ ID NO: 2;

(b) the sense strand comprises a first nucleic acid sequence of SEQ ID NO: 3, and the antisense strand comprises a second nucleic acid sequence of SEQ ID NO: 4;

(c) the sense strand comprises a first nucleic acid sequence of SEQ ID NO: 5, and the antisense strand comprises a second nucleic acid sequence of SEQ ID NO: 6;

(d) the sense strand comprises a first nucleic acid sequence of SEQ ID NO: 7, and the antisense strand comprises a second nucleic acid sequence of SEQ ID NO: 8;

(e) the sense strand comprises a first nucleic acid sequence of SEQ ID NO: 9, and the antisense strand comprises a second nucleic acid sequence of SEQ ID NO: 10;

(f) the sense strand comprises a first nucleic acid sequence of SEQ ID NO: 11, and the antisense strand comprises a second nucleic acid sequence of SEQ ID NO: 12;

(g) the sense strand comprises a first nucleic acid sequence of SEQ ID NO: 13, and the antisense strand comprises a second nucleic acid sequence of SEQ ID NO: 14;

(h) the sense strand comprises a first nucleic acid sequence of SEQ ID NO: 15, and the antisense strand comprises a second nucleic acid sequence of SEQ ID NO: 16;

(i) the sense strand comprises a first nucleic acid sequence of SEQ ID NO: 17, and the antisense strand comprises a second nucleic acid sequence of SEQ ID NO: 18;

(j) the sense strand comprises a first nucleic acid sequence of SEQ ID NO:19, and the antisense strand comprises a second nucleic acid sequence of SEQ ID NO: 20;

(k) the sense strand comprises a first nucleic acid sequence of SEQ ID NO:21, and the antisense strand comprises a second nucleic acid sequence of SEQ ID NO: 22;

(l) the sense strand comprises a first nucleic acid sequence of SEQ ID NO:23, and the antisense strand comprises a second nucleic acid sequence of SEQ ID NO: 24;

(m) the sense strand comprises a first nucleic acid sequence of SEQ ID NO: 55, and the antisense strand comprises a second nucleic acid sequence of SEQ ID NO: 16;

(n) the sense strand comprises a first nucleic acid sequence of SEQ ID NO: 56, and the antisense strand comprises a second nucleic acid sequence of SEQ ID NO: 16;

(o) the sense strand comprises a first nucleic acid sequence of SEQ ID NO: 57, and the antisense strand comprises a second nucleic acid sequence of SEQ ID NO: 58;

(p) the sense strand comprises a first nucleic acid sequence of SEQ ID NO: 59, and the antisense strand comprises a second nucleic acid sequence of SEQ ID NO: 58;

(q) the sense strand comprises a first nucleic acid sequence of SEQ ID NO: 60, and the antisense strand comprises a second nucleic acid sequence of SEQ ID NO: 61;

(r) the sense strand comprises a first nucleic acid sequence of SEQ ID NO: 62, and the antisense strand comprises a second nucleic acid sequence of SEQ ID NO: 61;

(s) the sense strand comprises a first nucleic acid sequence of SEQ ID NO: 117, and the antisense strand comprises a second nucleic acid sequence of SEQ ID NO: 118; and (t) the sense strand comprises a first nucleic acid sequence of SEQ ID NO: 119, and the antisense strand comprises a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a dsRNA having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:
(a) the sense strand has a first nucleic acid sequence of SEQ ID NO: 1, and the antisense strand has a second nucleic acid sequence of SEQ ID NO: 2;
(b) the sense strand has a first nucleic acid sequence of SEQ ID NO: 3, and the antisense strand has a second nucleic acid sequence of SEQ ID NO: 4;
(c) the sense strand has a first nucleic acid sequence of SEQ ID NO: 5, and the antisense strand has a second nucleic acid sequence of SEQ ID NO: 6;
(d) the sense strand has a first nucleic acid sequence of SEQ ID NO: 7, and the antisense strand has a second nucleic acid sequence of SEQ ID NO: 8;
(e) the sense strand has a first nucleic acid sequence of SEQ ID NO: 9, and the antisense strand has a second nucleic acid sequence of SEQ ID NO: 10;
(f) the sense strand has a first nucleic acid sequence of SEQ ID NO: 11, and the antisense strand has a second nucleic acid sequence of SEQ ID NO: 12;
(g) the sense strand has a first nucleic acid sequence of SEQ ID NO:13, and the antisense strand has a second nucleic acid sequence of SEQ ID NO: 14;
(h) the sense strand has a first nucleic acid sequence of SEQ ID NO:15, and the antisense strand has a second nucleic acid sequence of SEQ ID NO: 16;
(i) the sense strand has a first nucleic acid sequence of SEQ ID NO:17, and the antisense strand has a second nucleic acid sequence of SEQ ID NO: 18;
(j) the sense strand has a first nucleic acid sequence of SEQ ID NO:19, and the antisense strand has a second nucleic acid sequence of SEQ ID NO: 20;
(k) the sense strand has a first nucleic acid sequence of SEQ ID NO:21, and the antisense strand has a second nucleic acid sequence of SEQ ID NO: 22;
(l) the sense strand has a first nucleic acid sequence of SEQ ID NO:23, and the antisense strand has a second nucleic acid sequence of SEQ ID NO: 24;
(m) the sense strand has a first nucleic acid sequence of SEQ ID NO: 55, and the antisense strand has a second nucleic acid sequence of SEQ ID NO: 16;
(n) the sense strand has a first nucleic acid sequence of SEQ ID NO: 56, and the antisense strand has a second nucleic acid sequence of SEQ ID NO: 16;
(o) the sense strand has a first nucleic acid sequence of SEQ ID NO: 57, and the antisense strand has a second nucleic acid sequence of SEQ ID NO: 58;
(p) the sense strand has a first nucleic acid sequence of SEQ ID NO: 59, and the antisense strand has a second nucleic acid sequence of SEQ ID NO: 58;
(q) the sense strand has a first nucleic acid sequence of SEQ ID NO: 60, and the antisense strand has a second nucleic acid sequence of SEQ ID NO: 61;
(r) the sense strand has a first nucleic acid sequence of SEQ ID NO: 62, and the antisense strand has a second nucleic acid sequence of SEQ ID NO: 61;
(s) the sense strand has a first nucleic acid sequence of SEQ ID NO: 117, and the antisense strand has a second nucleic acid sequence of SEQ ID NO: 118; and
(t) the sense strand has a first nucleic acid sequence of SEQ ID NO: 119, and the antisense strand has a second nucleic acid sequence of SEQ ID NO: 16,
wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a dsRNA having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprise a pair of nucleic acid sequences selected from the group consisting of:
(a) the sense strand comprises a first nucleic acid sequence of SEQ ID NO: 25, and the antisense strand comprises a second nucleic acid sequence of SEQ ID NO: 26;
(b) the sense strand comprises a first nucleic acid sequence of SEQ ID NO: 27, and the antisense strand comprises a second nucleic acid sequence of SEQ ID NO: 28;
(c) the sense strand comprises a first nucleic acid sequence of SEQ ID NO: 29, and the antisense strand comprises a second nucleic acid sequence of SEQ ID NO: 30;
(d) the sense strand comprises a first nucleic acid sequence of SEQ ID NO: 31, and the antisense strand comprises a second nucleic acid sequence of SEQ ID NO: 32;
(e) the sense strand comprises a first nucleic acid sequence of SEQ ID NO: 33, and the antisense strand comprises a second nucleic acid sequence of SEQ ID NO: 34;
(f) the sense strand comprises a first nucleic acid sequence of SEQ ID NO: 35, and the antisense strand comprises a second nucleic acid sequence of SEQ ID NO: 36; (g) the sense strand comprises a first nucleic acid sequence of SEQ ID NO: 37, and the antisense strand comprises a second nucleic acid sequence of SEQ ID NO: 38;
(h) the sense strand comprises a first nucleic acid sequence of SEQ ID NO: 39, and the antisense strand comprises a second nucleic acid sequence of SEQ ID NO: 40;
(i) the sense strand comprises a first nucleic acid sequence of SEQ ID NO: 41, and the antisense strand comprises a second nucleic acid sequence of SEQ ID NO: 42;
(j) the sense strand comprises a first nucleic acid sequence of SEQ ID NO: 43, and the antisense strand comprises a second nucleic acid sequence of SEQ ID NO: 44;
(k) the sense strand comprises a first nucleic acid sequence of SEQ ID NO: 45, and the antisense strand comprises a second nucleic acid sequence of SEQ ID NO: 46;
(l) the sense strand comprises a first nucleic acid sequence of SEQ ID NO: 47, and the antisense strand comprises a second nucleic acid sequence of SEQ ID NO: 48;
(m) the sense strand comprises a first nucleic acid sequence of SEQ ID NO: 105, and the antisense strand comprises a second nucleic acid sequence selected from SEQ ID NO: 65, 106-108;
(n) the sense strand comprises a first nucleic acid sequence of SEQ ID NO: 109, and the antisense strand comprises a second nucleic acid sequence of SEQ ID NO: 65;
(o) the sense strand comprises a first nucleic acid sequence of SEQ ID NO: 110, and the antisense strand comprises a second nucleic acid sequence of SEQ ID NO: 40;

(p) the sense strand comprises a first nucleic acid sequence of SEQ ID NO: 111, and the antisense strand comprises a second nucleic acid sequence of SEQ ID NO: 112;

(q) the sense strand comprises a first nucleic acid sequence of SEQ ID NO: 113, and the antisense strand comprises a second nucleic acid sequence of SEQ ID NO: 114; and (r) the sense strand comprises a first nucleic acid sequence of SEQ ID NO: 115, and the antisense strand comprises a second nucleic acid sequence of SEQ ID NO: 116.

In some embodiments, provided herein are MAPT RNAi agents of Formula (I): R-L-D, wherein R is a dsRNA having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:

(a) the sense strand has a first nucleic acid sequence of SEQ ID NO: 25, and the antisense strand has a second nucleic acid sequence of SEQ ID NO: 26;

(b) the sense strand has a first nucleic acid sequence of SEQ ID NO: 27, and the antisense strand has a second nucleic acid sequence of SEQ ID NO: 28;

(c) the sense strand has a first nucleic acid sequence of SEQ ID NO: 29, and the antisense strand has a second nucleic acid sequence of SEQ ID NO: 30;

(d) the sense strand has a first nucleic acid sequence of SEQ ID NO: 31, and the antisense strand has a second nucleic acid sequence of SEQ ID NO: 32;

(e) the sense strand has a first nucleic acid sequence of SEQ ID NO: 33, and the antisense strand has a second nucleic acid sequence of SEQ ID NO: 34;

(f) the sense strand has a first nucleic acid sequence of SEQ ID NO: 35, and the antisense strand has a second nucleic acid sequence of SEQ ID NO: 36;

(g) the sense strand has a first nucleic acid sequence of SEQ ID NO: 37, and the antisense strand has a second nucleic acid sequence of SEQ ID NO: 38;

(h) the sense strand has a first nucleic acid sequence of SEQ ID NO: 39, and the antisense strand has a second nucleic acid sequence of SEQ ID NO: 40;

(i) the sense strand has a first nucleic acid sequence of SEQ ID NO: 41, and the antisense strand has a second nucleic acid sequence of SEQ ID NO: 42;

(j) the sense strand has a first nucleic acid sequence of SEQ ID NO: 43, and the antisense strand has a second nucleic acid sequence of SEQ ID NO: 44;

(k) the sense strand has a first nucleic acid sequence of SEQ ID NO: 45, and the antisense strand has a second nucleic acid sequence of SEQ ID NO: 46;

(l) the sense strand has a first nucleic acid sequence of SEQ ID NO: 47, and the antisense strand has a second nucleic acid sequence of SEQ ID NO: 48;

(m) the sense strand has a first nucleic acid sequence of SEQ ID NO: 105, and the antisense strand has a second nucleic acid sequence selected from SEQ ID NO: 65, 106-108;

(n) the sense strand has a first nucleic acid sequence of SEQ ID NO: 109, and the antisense strand has a second nucleic acid sequence of SEQ ID NO: 65;

(o) the sense strand has a first nucleic acid sequence of SEQ ID NO: 110, and the antisense strand has a second nucleic acid sequence of SEQ ID NO: 40;

(p) the sense strand has a first nucleic acid sequence of SEQ ID NO: 111, and the antisense strand has a second nucleic acid sequence of SEQ ID NO: 112;

(q) the sense strand has a first nucleic acid sequence of SEQ ID NO: 113, and the antisense strand has a second nucleic acid sequence of SEQ ID NO: 114; and (r) the sense strand has a first nucleic acid sequence of SEQ ID NO: 115, and the antisense strand has a second nucleic acid sequence of SEQ ID NO: 116.

In another aspect, provided herein are pharmaceutical compositions comprising a MAPT RNAi agent described herein and a pharmaceutically acceptable carrier. Also provided herein are pharmaceutical compositions comprising a means for reducing MAPT expression in a cell and a pharmaceutically acceptable carrier.

In another aspect, provided herein are methods of reducing MAPT expression in a patient in need thereof, and such method comprises administering to the patient an effective amount of a MAPT RNAi agent or a pharmaceutical composition described herein.

In another aspect, provided herein are methods of treating a tauopathy in a patient in need thereof, and such method comprises administering to the patient an effective amount of the MAPT RNAi agent or a pharmaceutical composition described herein.

Also provided herein are methods of reducing MAPT expression in a cell (e.g., a neuron), and such methods can include introducing a MAPT RNAi agent described herein into the cell; and incubating the cell for a time sufficient for degradation of MAPT mRNA, thereby reducing MAPT expression in the cell.

In another aspect, provided herein are MAPT RNAi agents or pharmaceutical compositions comprising a MAPT RNAi agent for use in reducing MAPT expression. Also provided herein are MAPT RNAi agents or the pharmaceutical composition comprising a MAPT RNAi agent for use in a therapy. Also provided herein are MAPT RNAi agents or pharmaceutical compositions comprising a MAPT RNAi agent for use in the treatment of a tauopathy. Also provided herein are uses of MAPT RNAi agents in the manufacture of a medicament for the treatment of a tauopathy.

DETAILED DESCRIPTION

Provided herein are MAPT RNAi agents and compositions comprising a MAPT RNAi agent. Also provided herein are methods of using the MAPT RNAi agents or compositions comprising a MAPT RNAi agent for reducing MAPT expression and/or treating tauopathy in a subject.

In some embodiments, provided herein are MAPT RNAi agents having a sense strand and an antisense strand, and the sense strand and the antisense strand form a duplex. The antisense strand is complimentary to a region of MAPT mRNA. In a further embodiment, the sense strand and the antisense strand are each 15-30 nucleotides in length, e.g., 20-25 nucleotides in length. In some embodiments, provided herein are MAPT RNAi agents having a sense strand of 21 nucleotides and an antisense strand of 23 nucleotides. In some embodiments, the sense strand and antisense strand of the MAPT RNAi agent may have overhangs at either the 5' end or the 3' end (i.e., 5' overhang or 3' overhang). For example, the sense strand and the antisense strand may have 5' or 3' overhangs of 1 to 5 nucleotides or 1 to 3 nucleotides. In some embodiments, the antisense strand comprises a 3' overhang of two nucleotides. In some embodiments, the sense strand and antisense strand sequences of the MAPT RNAi agents are provided in Table 1.

Provided herein are MAPT RNAi agents having a sense strand and an antisense strand, wherein the sense strand and the antisense strand form a duplex, wherein the sense strand and the antisense strand comprise a pair of nucleic acid sequences selected from the group consisting of:

(a) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 1, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 2;

(b) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 3, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 4;

(c) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 5, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 6;

(d) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 7, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 8;

(e) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 9, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 10;

(f) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 11, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 12;

(g) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:13, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 14;

(h) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:15, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16;

(i) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:17, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 18;

(j) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:19, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 20;

(k) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:21, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 22; and (l) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:23, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 24;

(m) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 55, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16;

(n) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 56, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16;

(o) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 57, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 58;

(p) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 59, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 58;

(q) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 60, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 61;

(r) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 62, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 61;

(s) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 117, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 118;

(t) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 119, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 1, and the antisense strand comprises a second nucleic acid sequence having at least 95% (e.g., about 95%, about 96%, about 97%, about 98%, about 99%, or about 100%) sequence identity to SEQ ID NO: 2, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 3, and the antisense strand comprises a second nucleic acid sequence having at least 95% (e.g., about 95%, about 96%, about 97%, about 98%, about 99%, or about 100%) sequence identity to SEQ ID NO: 4, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 5, and the antisense strand comprises a second nucleic acid sequence having at least 95% (e.g., about 95%, about 96%, about 97%, about 98%, about 99%, or about 100%) sequence identity to SEQ ID NO: 6, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 7, and the antisense strand comprises a second nucleic acid sequence having at least 95% (e.g., about 95%, about 96%, about 97%, about 98%, about 99%, or about 100%) sequence identity to SEQ ID NO: 8, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 9, and the antisense strand comprises a second nucleic acid sequence having at least 95% (e.g., about 95%, about 96%, about 97%, about 98%, about 99%, or about 100%) sequence identity to SEQ ID NO: 10, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 11, and the antisense strand comprises a second nucleic acid sequence having at least 95% (e.g., about 95%, about 96%, about 97%, about 98%, about 99%, or about 100%) sequence identity to SEQ ID NO: 12, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 13, and the antisense strand comprises a second nucleic acid sequence having at least 95% (e.g., about 95%, about 96%, about 97%, about 98%, about 99%, or about 100%) sequence identity to SEQ ID NO: 14, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 15, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 17, and the antisense strand comprises a second nucleic acid sequence having at least 95% (e.g., about 95%, about 96%, about 97%, about 98%, about 99%, or about 100%) sequence identity to SEQ ID NO: 18, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 19, and the antisense strand comprises a second nucleic acid sequence having at least 95% (e.g., about 95%, about 96%, about 97%, about 98%, about 99%, or about 100%) sequence identity to SEQ ID NO: 20, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 21, and the antisense strand comprises a second nucleic acid sequence having at least 95% (e.g., about 95%, about 96%, about 97%, about 98%, about 99%, or about 100%) sequence identity to SEQ ID NO: 22, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 23, and the antisense strand comprises a second nucleic acid sequence having at least 95% (e.g., about 95%, about 96%, about 97%, about 98%, about 99%, or about 100%) sequence identity to SEQ ID NO: 24, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 55, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 56, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 57, and the antisense strand comprises a second nucleic acid sequence having at least 95% (e.g., about 95%, about 96%, about 97%, about 98%, about 99%, or about 100%) sequence identity to SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 59, and the antisense strand comprises a second nucleic acid sequence having at least 95% (e.g., about 95%, about 96%, about 97%, about 98%, about 99%, or about 100%) sequence identity to SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 60, and the antisense strand comprises a second nucleic acid sequence having at least 95% (e.g., about 95%, about 96%, about 97%, about 98%, about 99%, or about 100%) sequence identity to SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 62, and the antisense strand comprises a second nucleic acid sequence having at least 95% (e.g., about 95%, about 96%, about 97%, about 98%, about 99%, or about 100%) sequence identity to SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 117, and the antisense strand comprises a second nucleic acid sequence having at least 95% (e.g., about 95%, about 96%, about 97%, about 98%, about 99%, or about 100%) sequence identity to SEQ ID NO: 118, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 119, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages.

TABLE 1

Nucleic Acid Sequences of MAPT RNAi Agents

| MAPT RNAi Agent No. | Sense Strand (5' to 3') | SEQ ID NO | Start position of sense strand target region of human MAPT transcript NM_001123067.4 | Antisense Strand (5' to 3') | SEQ ID NO | Start position of antisense strand target region of human MAPT transcript NM_001123067.4 |
|---|---|---|---|---|---|---|
| 1 | ACAAGCUGACCUUCCGCGAGA | 1 | 1184 | UCUCGCGGAAGGUCAGCUUGUGG | 2 | 1182 |
| 2 | AGAUUGAAACCCACAAGCUGA | 3 | 1172 | UCAGCUUGUGGGUUUCAAUCUUU | 4 | 1170 |
| 3 | AAUAAAAAGAUUGAAACCCAA | 5 | 1165 | UUGGGUUUCAAUCUUUUUAUUUC | 6 | 1163 |
| 4 | GGAAAUAAAAGAUUGAAACA | 7 | 1162 | UGUUUCAAUCUUUUUAUUUCCUC | 8 | 1160 |
| 5 | GGCGGAGGAAAUAAAAAGAUA | 9 | 1156 | UAUCUUUUUAUUUCCUCCGCCAG | 10 | 1154 |
| 6 | GAAGUAAAAUCUGAGAAGCUA | 11 | 1075 | UAGCUUCUCAGAUUUUACUUCCA | 12 | 1073 |
| 7 | GGAAGUAAAAUCUGAGAAGCA | 13 | 1074 | UGCUUCUCAGAUUUUACUUCCAC | 14 | 1072 |
| 8 | GUGGAAGUAAAAUCUGAGAAA | 15 | 1072 | UUUCUCAGAUUUUACUUCCACCU | 16 | 1070 |
| 9 | CCAGGUGGAAGUAAAAUCUGA | 17 | 1068 | UCAGAUUUUACUUCCACCUGGCC | 18 | 1066 |
| 10 | CAAGUCCAAGAUCGGCUCCAA | 19 | 831 | UUGGAGCCGAUCUUGGACUUGAC | 20 | 829 |
| 11 | UCUGGUGAACCUCCAAAAUCA | 21 | 616 | UGAUUUUGGAGGUUCACCAGAGC | 22 | 614 |
| 12 | CAGGUGGAAGUAAAAUCUGAA | 23 | 1069 | UUCAGAUUUUACUUCCACCUGGC | 24 | 1067 |
| 25 | GUGGAAGUA(n)AAUCUGAGAAA, wherein (n) indicates an abasic moiety. | 55 | 1072 | UUUCUCAGAUUUUACUUCCACCU | 16 | 1070 |
| 26 | GUGGAAGU(n)AAAUCUGAGAAA, wherein (n) indicates an abasic moiety. | 56 | 1072 | UUUCUCAGAUUUUACUUCCACCU | 16 | 1070 |
| 27 | CCAAGUGUGGCUCAUUAGGCA | 57 | 1022 | UGCCUAAUGAGCCACACUUGGAG | 58 | 1020 |
| 28 | CCAAGUGU(n)GCUCAUUAGGCA, wherein (n) indicates an abasic moiety. | 59 | 1022 | UGCCUAAUGAGCCACACUUGGAG | 58 | 1020 |
| 29 | UGCAAAUA(n)UCUACAAACCAA, wherein (n) indicates an abasic moiety. | 60 | 980 | UUGGUUUGUAGACUAUUUGCACC | 61 | 978* |
| 30 | UGCAAAUAGUCUACAAACCAA | 62 | 980 | UUGGUUUGUAGACUAUUUGCACC | 61 | 978* |
| 77 | GUGGAAGUAAAAUCUGAGAAATT | 117 | 1072 | UUUCUCAGAUUUUACUUCCACUU | 118 | 1070** |
| 78 | GUGGAAGUAAAAUCUGAGAAG | 119 | 1072 | UUUCUCAGAUUUUACUUCCACCU | 16 | 1070 |

*The last nucleotide does not match the transcript.
**The last two nucleotides do not match the transcript.

In some embodiments, the sense strand and the antisense strand of the MAPT RNAi agent described herein comprise a pair of nucleic acid sequences selected from the group consisting of:

(a) the sense strand comprises a first nucleic acid sequence of SEQ ID NO: 1, and the antisense strand comprises a second nucleic acid sequence of SEQ ID NO: 2;

(b) the sense strand comprises a first nucleic acid sequence of SEQ ID NO: 3, and the antisense strand comprises a second nucleic acid sequence of SEQ ID NO: 4;

(c) the sense strand comprises a first nucleic acid sequence of SEQ ID NO: 5, and the antisense strand comprises a second nucleic acid sequence of SEQ ID NO: 6;

(d) the sense strand comprises a first nucleic acid sequence of SEQ ID NO: 7, and the antisense strand comprises a second nucleic acid sequence of SEQ ID NO: 8;

(e) the sense strand comprises a first nucleic acid sequence of SEQ ID NO: 9, and the antisense strand comprises a second nucleic acid sequence of SEQ ID NO: 10;

(f) the sense strand comprises a first nucleic acid sequence of SEQ ID NO: 11, and the antisense strand comprises a second nucleic acid sequence of SEQ ID NO: 12; (g) the sense strand comprises a first nucleic acid sequence of SEQ ID NO: 13, and the antisense strand comprises a second nucleic acid sequence of SEQ ID NO: 14;

(h) the sense strand comprises a first nucleic acid sequence of SEQ ID NO: 15, and the antisense strand comprises a second nucleic acid sequence of SEQ ID NO: 16;

(i) the sense strand comprises a first nucleic acid sequence of SEQ ID NO: 17, and the antisense strand comprises a second nucleic acid sequence of SEQ ID NO: 18;

(j) the sense strand comprises a first nucleic acid sequence of SEQ ID NO: 19, and the antisense strand comprises a second nucleic acid sequence of SEQ ID NO: 20;

(k) the sense strand comprises a first nucleic acid sequence of SEQ ID NO:21, and the antisense strand comprises a second nucleic acid sequence of SEQ ID NO: 22;

(l) the sense strand comprises a first nucleic acid sequence of SEQ ID NO:23, and the antisense strand comprises a second nucleic acid sequence of SEQ ID NO: 24;

(m) the sense strand comprises a first nucleic acid sequence of SEQ ID NO: 55, and the antisense strand comprises a second nucleic acid sequence of SEQ ID NO: 16;

(n) the sense strand comprises a first nucleic acid sequence of SEQ ID NO: 56, and the antisense strand comprises a second nucleic acid sequence of SEQ ID NO: 16;

(o) the sense strand comprises a first nucleic acid sequence of SEQ ID NO: 57, and the antisense strand comprises a second nucleic acid sequence of SEQ ID NO: 58;

(p) the sense strand comprises a first nucleic acid sequence of SEQ ID NO: 59, and the antisense strand comprises a second nucleic acid sequence of SEQ ID NO: 58;

(q) the sense strand comprises a first nucleic acid sequence of SEQ ID NO: 60, and the antisense strand comprises a second nucleic acid sequence of SEQ ID NO: 61;

(r) the sense strand comprises a first nucleic acid sequence of SEQ ID NO: 62, and the antisense strand comprises a second nucleic acid sequence of SEQ ID NO: 61;

(s) the sense strand comprises a first nucleic acid sequence of SEQ ID NO: 117, and the antisense strand comprises a second nucleic acid sequence of SEQ ID NO: 118; and (t) the sense strand comprises a first nucleic acid sequence of SEQ ID NO: 119, and the antisense strand comprises a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 1, and the antisense strand comprises a second nucleic acid sequence of SEQ ID NO: 2, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 3, and the antisense strand comprises a second nucleic acid sequence of SEQ ID NO: 4, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 5, and the antisense strand comprises a second nucleic acid sequence of SEQ ID NO: 6, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 7, and the antisense strand comprises a second nucleic acid sequence of SEQ ID NO: 8, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 9, and the antisense strand comprises a second nucleic acid sequence of SEQ ID NO: 10, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 11, and the antisense strand comprises a second nucleic acid sequence of SEQ ID NO: 12, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 13, and the antisense strand comprises a second nucleic acid sequence of SEQ ID NO: 14, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 15, and the antisense strand comprises a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 17, and the antisense strand comprises a second nucleic acid sequence of SEQ ID NO: 18, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 19, and the antisense strand comprises a second nucleic acid sequence of SEQ ID NO: 20, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 21, and the antisense strand comprises a second nucleic acid sequence of SEQ ID NO: 22, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 23, and the antisense strand comprises a second nucleic acid sequence of SEQ ID NO: 24, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 55, and the antisense strand comprises a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 56, and the antisense strand comprises a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 57, and the antisense strand comprises a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 59, and the antisense strand comprises a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 57, and the antisense strand comprises a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 60, and the antisense strand comprises a second nucleic acid sequence of SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 62, and the antisense strand comprises a second nucleic acid sequence of SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 117, and the antisense strand comprises a second nucleic acid sequence of SEQ ID NO: 118, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 119, and the antisense strand comprises a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages.

In some embodiments, the sense strand and the antisense strand of the MAPT RNAi agent described herein have a pair of nucleic acid sequences selected from the group consisting of:

(a) the sense strand has a first nucleic acid sequence of SEQ ID NO: 1, and the antisense strand has a second nucleic acid sequence of SEQ ID NO: 2;
(b) the sense strand has a first nucleic acid sequence of SEQ ID NO: 3, and the antisense strand has a second nucleic acid sequence of SEQ ID NO: 4;
(c) the sense strand has a first nucleic acid sequence of SEQ ID NO: 5, and the antisense strand has a second nucleic acid sequence of SEQ ID NO: 6;
(d) the sense strand has a first nucleic acid sequence of SEQ ID NO: 7, and the antisense strand has a second nucleic acid sequence of SEQ ID NO: 8;
(e) the sense strand has a first nucleic acid sequence of SEQ ID NO: 9, and the antisense strand has a second nucleic acid sequence of SEQ ID NO: 10;
(f) the sense strand has a first nucleic acid sequence of SEQ ID NO: 11, and the antisense strand has a second nucleic acid sequence of SEQ ID NO: 12;
(g) the sense strand has a first nucleic acid sequence of SEQ ID NO:13, and the antisense strand has a second nucleic acid sequence of SEQ ID NO: 14;
(h) the sense strand has a first nucleic acid sequence of SEQ ID NO:15, and the antisense strand has a second nucleic acid sequence of SEQ ID NO: 16;
(i) the sense strand has a first nucleic acid sequence of SEQ ID NO:17, and the antisense strand has a second nucleic acid sequence of SEQ ID NO: 18;
(j) the sense strand has a first nucleic acid sequence of SEQ ID NO:19, and the antisense strand has a second nucleic acid sequence of SEQ ID NO: 20;
(k) the sense strand has a first nucleic acid sequence of SEQ ID NO:21, and the antisense strand has a second nucleic acid sequence of SEQ ID NO: 22;
(l) the sense strand has a first nucleic acid sequence of SEQ ID NO:23, and the antisense strand has a second nucleic acid sequence of SEQ ID NO: 24;
(m) the sense strand has a first nucleic acid sequence of SEQ ID NO: 55, and the antisense strand has a second nucleic acid sequence of SEQ ID NO: 16;
(n) the sense strand has a first nucleic acid sequence of SEQ ID NO: 56, and the antisense strand has a second nucleic acid sequence of SEQ ID NO: 16;
(o) the sense strand has a first nucleic acid sequence of SEQ ID NO: 57, and the antisense strand has a second nucleic acid sequence of SEQ ID NO: 58;
(p) the sense strand has a first nucleic acid sequence of SEQ ID NO: 59, and the antisense strand has a second nucleic acid sequence of SEQ ID NO: 58;
(q) the sense strand has a first nucleic acid sequence of SEQ ID NO: 60, and the antisense strand has a second nucleic acid sequence of SEQ ID NO: 61;
(r) the sense strand has a first nucleic acid sequence of SEQ ID NO: 62, and the antisense strand has a second nucleic acid sequence of SEQ ID NO: 61;
(s) the sense strand has a first nucleic acid sequence of SEQ ID NO: 117, and the antisense strand has a second nucleic acid sequence of SEQ ID NO: 118; and
(t) the sense strand has a first nucleic acid sequence of SEQ ID NO: 119, and the antisense strand has a second nucleic acid sequence of SEQ ID NO: 16,
wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 1, and the antisense strand has a second nucleic acid sequence of SEQ ID NO: 2, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 3, and the antisense strand has a second nucleic acid sequence of SEQ ID NO: 4, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 5, and the antisense strand has a second nucleic acid sequence of SEQ ID NO: 6, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 7, and the antisense strand has a second nucleic acid sequence of SEQ ID NO: 8, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 9, and the antisense strand has a second nucleic acid sequence of SEQ ID NO: 10, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 11, and the antisense strand has a second nucleic acid sequence of SEQ ID NO: 12, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 13, and the antisense strand has a second nucleic acid sequence of SEQ ID NO: 14, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 15, and the antisense strand has a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 17, and the antisense strand has a second nucleic acid sequence of SEQ ID NO: 18, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 19, and the antisense strand has a second nucleic acid sequence of SEQ ID NO: 20, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 21, and the antisense strand has a second nucleic acid sequence of SEQ ID NO: 22, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 23, and the antisense strand has a second nucleic acid sequence of SEQ ID NO: 24, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 55, and the antisense strand has a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 56, and the antisense strand has a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 57, and the antisense strand has a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 59, and the antisense strand has a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 60, and the antisense strand has a second nucleic acid sequence of SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 62, and the antisense strand has a second nucleic acid sequence of SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 117, and the antisense strand has a second nucleic acid sequence of SEQ ID NO: 118, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 119, and the antisense strand has a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages.

In some embodiments, the MAPT RNAi agent described herein can comprise a sense strand that comprises a sequence that has 1, 2, or 3 differences from SEQ ID NO: 1, 3, 5, 7, 9, 11, 13, 15, 17, 19, 21, 23, 55, 56, 57, 59, 60, 62, 117, 119. In some embodiments, the MAPT RNAi agent described herein can comprise an antisense strand that comprises a sequence that has 1, 2, or 3 differences from SEQ ID NO: 2, 4, 6, 8, 10, 12, 14, 16, 18, 20, 22, 24, 58, 61, 118.

The MAPT RNAi agents described herein may include modifications. The modifications can be made to one or more nucleotides of the sense strand and/or antisense strand or to the internucleotide linkages, which are the bonds between two nucleotides in the sense or antisense strand. For example, some 2'-modifications of ribose or deoxyribose can increase RNA or DNA stability and half-life. Such 2'-modifications can be 2'-fluoro, 2'-O-methyl (i.e., 2'-methoxy), 2'-O-alkyl, e.g., 2'-O—C16 alkyl modified nucleotide, or 2'-O-methoxyethyl (2'-O-MOE).

In some embodiments, one or more nucleotides of the sense strand and/or the antisense strand are independently modified nucleotides, which means the sense strand and the antisense strand can have different modified nucleotides. In some embodiments, one or more nucleotides of the sense strand are modified nucleotides. In some embodiments, each nucleotide of the sense strand is a modified nucleotide. In some embodiments, one or more nucleotides of the antisense strand are modified nucleotides. In some embodiments, each nucleotide of the antisense strand is a modified nucleotide.

In some embodiments, the modified nucleotide is a 2'-fluoro modified nucleotide, 2'-O-methyl modified nucleotide, or 2'-O-alkyl modified nucleotide, e.g., 2'-O—C16 alkyl modified nucleotide. In some embodiments, each nucleotide of the sense strand and the antisense strand is independently a modified nucleotide, e.g., a 2'-fluoro modified nucleotide, 2'-O-methyl modified nucleotide, or 2'-O-alkyl modified nucleotide, e.g., 2'-O—C16 alkyl modified nucleotide.

In some embodiments, the sense strand has four 2'-fluoro modified nucleotides, e.g., at positions 7, 9, 10, 11 from the 5' end of the sense strand. In some embodiments, nucleotides at positions other than positions 7, 9, 10, and 11 of the sense strand are 2'-O-methyl modified nucleotides or 2'-O—C16 alkyl modified nucleotides. In some embodiments, the antisense strand has four 2'-fluoro modified nucleotides, e.g., at positions 2, 6, 14, 16 from the 5' end of the antisense strand. In some embodiments, nucleotides at positions other than positions 2, 6, 14 and 16 of the antisense strand are 2'-O-methyl modified nucleotides or 2'-O—C16 alkyl modified nucleotides.

In some embodiments, the sense strand has three 2'-fluoro modified nucleotides, e.g., at positions 9, 10, 11 from the 5' end of the sense strand. In some embodiments, the other nucleotides of the sense strand are 2'-O-methyl modified nucleotides. In some embodiments, the antisense strand has five 2'-fluoro modified nucleotides, e.g., at positions 2, 5, 7, 14, 16 from the 5' end of the antisense strand. In some embodiments, the antisense strand has five 2'-fluoro modified nucleotides, e.g., at positions 2, 5, 8, 14, 16 from the 5' end of the antisense strand. In some embodiments, the antisense strand has five 2'-fluoro modified nucleotides, e.g., at positions 2, 3, 7, 14, 16 from the 5' end of the antisense strand. In some embodiments, the other nucleotides of the antisense strand are 2'-O-methyl modified nucleotides. In some embodiments, the sense strand comprises an abasic moiety or inverted abasic moiety.

In some embodiments, the modified nucleotide is a 2'-O-alkyl modified nucleotide, e.g., 2'-O—C16 alkyl modified nucleotide, which can serve as a delivery moiety. In some embodiments, the 2'-O-alkyl modified nucleotide is a 2'-O-hexadecyl uridine, 2'-O-hexadecyl cytidine, 2'-O-hexadecyl guanine, or 2'-O-hexadecyl adenosine. In some embodiments, 2'-O-hexadecyl uridine, 2'-O-hexadecyl cytidine, 2'-O-hexadecyl guanine, or 2'-O-hexadecyl adenosine is a modified nucleotide in the sense strand.

In some embodiments, the first nucleotide from the 5' end of the antisense strand is a modified nucleotide that has a phosphate analog, e.g., 5'-vinylphosphonate (5'-VP).

In some embodiments, the sense strand comprises an abasic moiety or inverted abasic moiety, e.g., a moiety shown in Table 3.

In some embodiments, the sense strand and the antisense strand have one or more modified internucleotide linkages. In some embodiments, the modified internucleotide linkage is phosphorothioate linkage. In some embodiments, the sense strand has four or five phosphorothioate linkages. In some embodiments, the antisense strand has four or five phosphorothioate linkages. In some embodiments, the sense strand and the antisense strand each has four or five phosphorothioate linkages. In some embodiments, the sense strand has four phosphorothioate linkages and the antisense strand has four phosphorothioate linkages.

In a further aspect, provided herein are MAPT RNAi agent having a sense strand and an antisense strand, wherein the sense strand and the antisense strand form a duplex, wherein the sense strand and the antisense strand comprise a pair of nucleic acid sequences selected from the group consisting of:
- (a) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 25, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 26;
- (b) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 27, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 28;
- (c) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 29, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 30;
- (d) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 31, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 32;
- (e) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 33, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 34;
- (f) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 35, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 36;
- (g) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 37, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 38;
- (h) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 39, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 40;
- (i) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 41, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 42;
- (j) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 43, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 44;
- (k) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 45, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 46;
- (l) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 47, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 48;
- (m) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 63, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 40;

(n) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to any one of SEQ ID NOs: 64, 66-69, 71, 75-86, 93-100, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 65;

(o) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 64, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to any one of SEQ ID NOs: 70, 72-74;

(p) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 87 or 89, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 88;

(q) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 90 or 92, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 91;

(r) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 101, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 102;

(s) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 103, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 104;

(t) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 105, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to any one of SEQ ID NOs: 65, 106-108;

(u) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 109, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 65;

(v) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 110, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 40;

(w) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 111, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 112;

(x) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 113, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 114; and (y) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 115, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 116.

In some embodiments, provided herein are MAPT RNAi agent having a sense strand and an antisense strand, wherein the sense strand and the antisense strand form a duplex, wherein the sense strand and the antisense strand comprise a pair of nucleic acid sequences selected from the group consisting of:

(a) the sense strand comprises a first nucleic acid sequence of SEQ ID NO: 25, and the antisense strand comprises a second nucleic acid sequence of SEQ ID NO: 26;

(b) the sense strand comprises a first nucleic acid sequence of SEQ ID NO: 27, and the antisense strand comprises a second nucleic acid sequence of SEQ ID NO: 28;
(c) the sense strand comprises a first nucleic acid sequence of SEQ ID NO: 29, and the antisense strand comprises a second nucleic acid sequence of SEQ ID NO: 30;
(d) the sense strand comprises a first nucleic acid sequence of SEQ ID NO: 31, and the antisense strand comprises a second nucleic acid sequence of SEQ ID NO: 32;
(e) the sense strand comprises a first nucleic acid sequence of SEQ ID NO: 33, and the antisense strand comprises a second nucleic acid sequence of SEQ ID NO: 34;
(f) the sense strand comprises a first nucleic acid sequence of SEQ ID NO: 35, and the antisense strand comprises a second nucleic acid sequence of SEQ ID NO: 36;
(g) the sense strand comprises a first nucleic acid sequence of SEQ ID NO: 37, and the antisense strand comprises a second nucleic acid sequence of SEQ ID NO: 38;
(h) the sense strand comprises a first nucleic acid sequence of SEQ ID NO: 39, and the antisense strand comprises a second nucleic acid sequence of SEQ ID NO: 40;
(i) the sense strand comprises a first nucleic acid sequence of SEQ ID NO: 41, and the antisense strand comprises a second nucleic acid sequence of SEQ ID NO: 42;
(j) the sense strand comprises a first nucleic acid sequence of SEQ ID NO: 43, and the antisense strand comprises a second nucleic acid sequence of SEQ ID NO: 44;
(k) the sense strand comprises a first nucleic acid sequence of SEQ ID NO: 45, and the antisense strand comprises a second nucleic acid sequence of SEQ ID NO: 46;
(l) the sense strand comprises a first nucleic acid sequence of SEQ ID NO: 47, and the antisense strand comprises a second nucleic acid sequence of SEQ ID NO: 48;
(m) the sense strand comprises a first nucleic acid sequence of SEQ ID NO: 63, and the antisense strand comprises a second nucleic acid sequence of SEQ ID NO: 40;
(n) the sense strand comprises a first nucleic acid sequence selected from any one of SEQ ID NOs: 64, 66-69, 71, 75-86, 93-100, and the antisense strand comprises a second nucleic acid sequence of SEQ ID NO: 65;
(o) the sense strand comprises a first nucleic acid sequence of SEQ ID NO: 64, and the antisense strand comprises a second nucleic acid sequence selected from any one of SEQ ID NOs: 70, 72-74;
(p) the sense strand comprises a first nucleic acid sequence selected from SEQ ID NO: 87 or 89, and the antisense strand comprises a second nucleic acid sequence of SEQ ID NO: 88;
(q) the sense strand comprises a first nucleic acid sequence selected from SEQ ID NO: 90 or 92, and the antisense strand comprises a second nucleic acid sequence of SEQ ID NO: 91;
(r) the sense strand comprises a first nucleic acid sequence of SEQ ID NO: 101, and the antisense strand comprises a second nucleic acid sequence of SEQ ID NO: 102;
(s) the sense strand comprises a first nucleic acid sequence of SEQ ID NO: 103, and the antisense strand comprises a second nucleic acid sequence of SEQ ID NO: 104;
(t) the sense strand comprises a first nucleic acid sequence of SEQ ID NO: 105, and the antisense strand comprises a second nucleic acid sequence selected from any one of SEQ ID NOs: 65, 106-108;
(u) the sense strand comprises a first nucleic acid sequence of SEQ ID NO: 109, and the antisense strand comprises a second nucleic acid sequence of SEQ ID NO: 65;
(v) the sense strand comprises a first nucleic acid sequence of SEQ ID NO: 110, and the antisense strand comprises a second nucleic acid sequence of SEQ ID NO: 40;
(w) the sense strand comprises a first nucleic acid sequence of SEQ ID NO: 111, and the antisense strand comprises a second nucleic acid sequence of SEQ ID NO: 112;
(x) the sense strand comprises a first nucleic acid sequence of SEQ ID NO: 113, and the antisense strand comprises a second nucleic acid sequence of SEQ ID NO: 114; and
(y) the sense strand comprises a first nucleic acid sequence of SEQ ID NO: 115, and the antisense strand comprises a second nucleic acid sequence of SEQ ID NO: 116.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 25, and the antisense strand comprises a second nucleic acid sequence of SEQ ID NO: 26. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 27, and the antisense strand comprises a second nucleic acid sequence of SEQ ID NO: 28. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 29, and the antisense strand comprises a second nucleic acid sequence of SEQ ID NO: 30. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 31, and the antisense strand comprises a second nucleic acid sequence of SEQ ID NO: 32. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 33, and the antisense strand comprises a second nucleic acid sequence of SEQ ID NO: 34. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 35, and the antisense strand comprises a second nucleic acid sequence of SEQ ID NO: 36. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 37, and the antisense strand comprises a second nucleic acid sequence of SEQ ID NO: 38. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 39, and the antisense strand comprises a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 41, and the antisense strand comprises a second nucleic acid sequence of SEQ ID NO: 42. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 43, and the antisense strand comprises a second nucleic acid sequence of SEQ ID NO: 44. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 45, and the antisense strand comprises a second nucleic acid sequence of SEQ ID NO: 46. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 47, and the antisense strand comprises a second nucleic acid sequence of SEQ ID NO: 48.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 63, and the antisense strand comprises a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand comprises a first nucleic acid sequence selected from any one of SEQ ID NOs: 64, 66-69, 71, 75-86, 93-100, and the antisense strand comprises a second nucleic acid sequence of SEQ ID NO: 65. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 64, and the antisense strand comprises a second nucleic acid sequence selected from any one of SEQ ID NOs: 70, 72-74. In some embodiments, provided herein are MAPT RNAi agent having a sense strand and an antisense strand, wherein the sense strand and the antisense strand form a duplex, and wherein the sense strand comprises a first nucleic acid sequence selected from SEQ ID NO: 87 or 89, and the antisense strand comprises a second nucleic acid sequence of SEQ ID NO: 88. In some embodiments, provided herein are MAPT RNAi agent having a sense strand and an antisense strand, wherein the sense strand and the antisense strand form a duplex, and wherein the sense strand comprises a first nucleic acid sequence selected from SEQ ID NO: 90 or 92, and the antisense strand comprises a second nucleic acid sequence of SEQ ID NO: 91. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 101, and the antisense strand comprises a second nucleic acid sequence of SEQ ID NO: 102. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 103, and the antisense strand comprises a second nucleic acid sequence of SEQ ID NO: 104.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 105, and the antisense strand comprises a second nucleic acid sequence selected from any one of SEQ ID NOs: 65, 106-108. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 109, and the antisense strand comprises a second nucleic acid sequence of SEQ ID NO: 65. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 110, and the antisense strand comprises a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 111, and the antisense strand comprises a second nucleic acid sequence of SEQ ID NO: 112. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 113, and the antisense strand comprises a second nucleic acid sequence of SEQ ID NO: 114. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 115, and the antisense strand comprises a second nucleic acid sequence of SEQ ID NO: 116.

In some embodiments, the MAPT RNAi agent described herein can comprise a sense strand that comprises a sequence that has 1, 2, or 3 differences from SEQ ID NO: 25, 27, 29, 31, 33, 35, 37, 39, 41, 43, 45, 47, 63, 64, 66-69, 71, 75-87, 89, 90, 92-101, 103, 105, 109-111, 113, 115. In some embodiments, the MAPT RNAi agent described herein can comprise an antisense strand that comprises a sequence that has 1, 2, or 3 differences from SEQ ID NO: 26, 28, 30, 32, 34, 36, 38, 40, 42, 44, 46, 48, 65, 70, 72-74, 88, 91, 102, 104, 106-108, 112, 114, 116.

In some embodiments, provided herein are MAPT RNAi agent having a sense strand and an antisense strand, wherein the sense strand and the antisense strand form a duplex, wherein the sense strand and the antisense strand have a pair of nucleic acid sequences selected from the group consisting of:
  (a) the sense strand has a first nucleic acid sequence of SEQ ID NO: 25, and the antisense strand has a second nucleic acid sequence of SEQ ID NO: 26;
  (b) the sense strand has a first nucleic acid sequence of SEQ ID NO: 27, and the antisense strand has a second nucleic acid sequence of SEQ ID NO: 28;

(c) the sense strand has a first nucleic acid sequence of SEQ ID NO: 29, and the antisense strand has a second nucleic acid sequence of SEQ ID NO: 30;
(d) the sense strand has a first nucleic acid sequence of SEQ ID NO: 31, and the antisense strand has a second nucleic acid sequence of SEQ ID NO: 32;
(e) the sense strand has a first nucleic acid sequence of SEQ ID NO: 33, and the antisense strand has a second nucleic acid sequence of SEQ ID NO: 34;
(f) the sense strand has a first nucleic acid sequence of SEQ ID NO: 35, and the antisense strand has a second nucleic acid sequence of SEQ ID NO: 36;
(g) the sense strand has a first nucleic acid sequence of SEQ ID NO: 37, and the antisense strand has a second nucleic acid sequence of SEQ ID NO: 38;
(h) the sense strand has a first nucleic acid sequence of SEQ ID NO: 39, and the antisense strand has a second nucleic acid sequence of SEQ ID NO: 40;
(i) the sense strand has a first nucleic acid sequence of SEQ ID NO: 41, and the antisense strand has a second nucleic acid sequence of SEQ ID NO: 42;
(j) the sense strand has a first nucleic acid sequence of SEQ ID NO: 43, and the antisense strand has a second nucleic acid sequence of SEQ ID NO: 44;
(k) the sense strand has a first nucleic acid sequence of SEQ ID NO: 45, and the antisense strand has a second nucleic acid sequence of SEQ ID NO: 46;
(l) the sense strand has a first nucleic acid sequence of SEQ ID NO: 47, and the antisense strand has a second nucleic acid sequence of SEQ ID NO: 48;
(m) the sense strand has a first nucleic acid sequence of SEQ ID NO: 63, and the antisense strand has a second nucleic acid sequence of SEQ ID NO: 40;
(n) the sense strand has a first nucleic acid sequence selected from any one of SEQ ID NOs: 64, 66-69, 71, 75-86, 93-100, and the antisense strand has a second nucleic acid sequence of SEQ ID NO: 65;
(o) the sense strand has a first nucleic acid sequence of SEQ ID NO: 64, and the antisense strand has a second nucleic acid sequence selected from any one of SEQ ID NOs: 70, 72-74;
(p) the sense strand has a first nucleic acid sequence selected from SEQ ID NO: 87 or 89, and the antisense strand has a second nucleic acid sequence of SEQ ID NO: 88;
(q) the sense strand has a first nucleic acid sequence selected from SEQ ID NO: 90 or 92, and the antisense strand has a second nucleic acid sequence of SEQ ID NO: 91;
(r) the sense strand has a first nucleic acid sequence of SEQ ID NO: 101, and the antisense strand has a second nucleic acid sequence of SEQ ID NO: 102;
(s) the sense strand has a first nucleic acid sequence of SEQ ID NO: 103, and the antisense strand has a second nucleic acid sequence of SEQ ID NO: 104;
(t) the sense strand has a first nucleic acid sequence of SEQ ID NO: 105, and the antisense strand has a second nucleic acid sequence selected from any one of SEQ ID NOs: 65, 106-108;
(u) the sense strand has a first nucleic acid sequence of SEQ ID NO: 109, and the antisense strand has a second nucleic acid sequence of SEQ ID NO: 65;
(v) the sense strand has a first nucleic acid sequence of SEQ ID NO: 110, and the antisense strand has a second nucleic acid sequence of SEQ ID NO: 40;
(w) the sense strand has a first nucleic acid sequence of SEQ ID NO: 111, and the antisense strand has a second nucleic acid sequence of SEQ ID NO: 112;
(x) the sense strand has a first nucleic acid sequence of SEQ ID NO: 113, and the antisense strand has a second nucleic acid sequence of SEQ ID NO: 114; and
(y) the sense strand has a first nucleic acid sequence of SEQ ID NO: 115, and the antisense strand has a second nucleic acid sequence of SEQ ID NO: 116.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 25, and the antisense strand has a second nucleic acid sequence of SEQ ID NO: 26. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 27, and the antisense strand has a second nucleic acid sequence of SEQ ID NO: 28. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 29, and the antisense strand has a second nucleic acid sequence of SEQ ID NO: 30. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 31, and the antisense strand has a second nucleic acid sequence of SEQ ID NO: 32. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 33, and the antisense strand has a second nucleic acid sequence of SEQ ID NO: 34. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 35, and the antisense strand has a second nucleic acid sequence of SEQ ID NO: 36. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 37, and the antisense strand has a second nucleic acid sequence of SEQ ID NO: 38. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 39, and the antisense strand has a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 41, and the antisense strand has a second nucleic acid sequence of SEQ ID NO: 42. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 43, and the antisense strand has a second nucleic acid sequence of SEQ ID NO: 44. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 45, and the antisense strand has a second nucleic acid sequence of SEQ ID NO: 46. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 47, and the antisense strand has a second nucleic acid sequence of SEQ ID NO: 48.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 63, and the antisense strand has a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand has a first nucleic acid sequence selected from any one of SEQ ID NOs: 64, 66-69, 71, 75-86, 93-100, and the antisense strand has a second nucleic acid sequence of SEQ ID NO: 65. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 64, and the antisense strand has a second nucleic acid sequence selected from any one of SEQ ID NOs: 70, 72-74. In some embodiments, provided herein are MAPT RNAi agent having a sense strand and an antisense strand, wherein the sense strand and the antisense strand form a duplex, and wherein the sense strand has a first nucleic acid sequence selected from SEQ ID NO: 87 or 89, and the antisense strand has a second nucleic acid sequence of SEQ ID NO: 88. In some embodiments, provided herein are MAPT RNAi agent having a sense strand and an antisense strand, wherein the sense strand and the antisense strand form a duplex, and wherein the sense strand has a first nucleic acid sequence selected from SEQ ID NO: 90 or 92, and the antisense strand has a second nucleic acid sequence of SEQ ID NO: 91. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 101, and the antisense strand has a second nucleic acid sequence of SEQ ID NO: 102. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 103, and the antisense strand has a second nucleic acid sequence of SEQ ID NO: 104.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 105, and the antisense strand has a second nucleic acid sequence selected from any one of SEQ ID NOs: 65, 106-108. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 109, and the antisense strand has a second nucleic acid sequence of SEQ ID NO: 65. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 110, and the antisense strand has a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 111, and the antisense strand has a second nucleic acid sequence of SEQ ID NO: 112. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 113, and the antisense strand has a second nucleic acid sequence of SEQ ID NO: 114. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 115, and the antisense strand has a second nucleic acid sequence of SEQ ID NO: 116.

TABLE 2

MAPT RNAi Agents with Modifications

| MAPT RNAi Agent No. | Strand | Sequence from 5' to 3' end | SEQ ID NO |
|---|---|---|---|
| 13 | S | mA*mC*mAmAmGmCfUmGfAfCfCmUmUmCmCmGmCmGmA*mG*mA | 25 |
|  | AS | VPmU*fC*mUmCmGfCmGmGmAmAmGmGmUfCmAfGmCmUmUmGmU*mG*mG | 26 |
| 14 | S | mA*mG*mAmUmUmGfAmAfAfCfCmCmAmCmAmAmGmCmU*mG*mA | 27 |
|  | AS | VPmU*fC*mAmGmCfUmUmGmUmGmGmGmUfUmUfCmAmAmUmCmU*mU*mU | 28 |
| 15 | S | mA*mA*mUmAmAmAfAmAfGfAfUmUmGmAmAmAmCmC*mA*mA | 29 |
|  | AS | VPmU*fU*mGmGmGfUmUmUmCmAmAmUmCfUmUfUmUmUmAmUmU*mU*mC | 30 |
| 16 | S | mG*mG*mAmAmAmUfAmAfAfAfAmGmAmUmUmGmAmAmA*mC*mA | 31 |
|  | AS | VPmU*fG*mUmUmUfCmAmAmUmCmUmUmUfUmUfAmUmUmUmCmC*mU*mC | 32 |
| 17 | S | mG*mG*mCmGmGmAfGmGfAfAfAmUmAmAmAmAmAmGmA*mU*mA | 33 |
|  | AS | VPmU*fA*mUmCmUfUmUmUmUmAmUmUmUfCmCfUmCmCmGmC*mA*mG | 34 |

TABLE 2-continued

MAPT RNAi Agents with Modifications

| MAPT RNAi Agent No. | Strand | Sequence from 5' to 3' end | SEQ ID NO |
|---|---|---|---|
| 18 | S | mG*mA*mAmGmUmAfAmAfAfUfCmUmGmAmGmAmAmGmC*mU*mA | 35 |
|  | AS | VPmU*fA*mGmCmUfUmCmCmAmGmAmUfUmUfUmAmCmUmUmC*mC*mA | 36 |
| 19 | S | mG*mG*mAmAmGmUfAmAfAfUmCmUmGmAmGmAmAmG*mC*mA | 37 |
|  | AS | VPmU*fG*mCmUmUfCmUmCmCmAmGmAmUfUmUfUmAmCmUmUmC*mA*mC | 38 |
| 20 | S | mG*mU*mGmGmAmAfGmUfAfAfAmAmCmUmGmAmGmA*mA*mA | 39 |
|  | AS | VPmU*fU*mUmCmUfCmAmGmGmAmUmUmUfAmCfUmUmCmCmAmC*mC*mU | 40 |
| 21 | S | mC*mC*mAmGmUfGmGfAfAfGmUmAmAmAmUmCmU*mG*mA | 41 |
|  | AS | VPmU*fC*mAmGmAfUmUmUmAmCmUmUfCmCfAmCmCmUmGmG*mC*mC | 42 |
| 22 | S | mC*mA*mAmGmUmCfCmAfAfGfAmUmCmGmGmCmUmC*mA*mA | 43 |
|  | AS | VPmU*fU*mGmGmAfGmCmCmGmAmUmCmUfUmGfGmAmCmUmUmG*mA*mC | 44 |
| 23 | S | mU*mC*mUmGmUfGmAfAfCfCmUmCmCmAmAmAmAmU*mC*mA | 45 |
|  | AS | VPmU*fG*mAmUmUfUmUmGmGmAmGmGmUfUmCfAmCmCmAmGmA*mG*mC | 46 |
| 24 | S | mC*mA*mGmUmGfGmAfAfGfUmAmAmAmAmUmCmUmG*mA*mA | 47 |
|  | AS | VPmU*fU*mCmAmGfAmUmUmUmAmCmUfUmCfCmAmCmCmUmG*mG*mC | 48 |
| 31 | S | mG*mU*mGmGmAmAfGmUfAfAfA(Uhd)mCmUmGmAmGmA*mA*mA | 63 |
|  | AS | VPmU*fU*mUmCmUfCmAmGmAmUmUmUfAmCfUmUmCmCmAmC*mC*mU | 40 |
| 32 | S | mG*mU*mGmGmAmAmGmUfAfAfAmA(Uhd)mCmUmGmAmGmA*mA*mA | 64 |
|  | AS | VPmU*fU*mUmCfUmCmAfGmAmUmUmUmUfAmCfUmUmCmCmAmC*mC*mU | 65 |
| 33 | S | mG*mU*mGmGmAmAmAmGmUfAfAfA(Ahd)mUmCmUmGmAmGmA*mA*mA | 66 |
|  | AS | VPmU*fU*mUmCfUmCmAfGmAmUmUmUmUfAmCfUmUmCmCmAmC*mC*mU | 65 |
| 34 | S | mG*mU*mGmGmAmAmAmGmUfA(n)fAmA(Uhd)mCmUmGmAmGmA*mA*mA | 67 |
|  | AS | VPmU*fU*mUmCfUmCmAfGmAmUmUmUmUfAmCfUmUmCmCmAmC*mC*mU | 65 |
| 35 | S | mG*mU*mGmGmAmAmAGmUfA(n)fAmA(Uhd)mCmUmGmAmGmA*mA*mA | 68 |
|  | AS | VPmU*fU*mUmCfUmCmAfGmAmUmUmUmUfAmCfUmUmCmCmAmC*mC*mU | 65 |
| 36 | S | mG*mU*mGmGmAmAmAmGmU(n)fAfAmA(Uhd)mCmUmGmAmGmA*mA*mA | 69 |
|  | AS | VPmU*fU*mUmCfUmCmAfGmAmUmUmUmUfAmCfUmUmCmCmAmC*mC*mU | 65 |
| 37 | S | mG*mU*mGmGmAmAmAmGmUfAfAfAmA(Uhd)mCmUmGmAmGmA*mA*mA | 64 |
|  | AS | VPmU*fU*mUmCmUfCmAmGmAfUmUmUmUfAmCfUmUfCmCfAmC*mC*mU | 70 |
| 38 | S | mG*mU*mGmGmAmAmAmGmUfAfAfAmA(Uhd)mCfUmGmAmGmA*mA*mA | 71 |
|  | AS | VPmU*fU*mUmCfUmCmAfGmAmUmUmUmUfAmCfUmUmCmCmAmC*mC*mU | 65 |
| 39 | S | mG*mU*mGmGmAmAmAmGmUfAfAfAmA(Uhd)mCmUmGmAmGmA*mA*mA | 64 |
|  | AS | VPmU*fU*mUmCfUmCfAmGmAmUmUmUmUfAmCfUmUmCmCmAmC*mC*mU | 72 |
| 40 | S | mG*mU*mGmGmAmAmAmGmUfAfAfAmA(Uhd)mCmUmGmAmGmA*mA*mA | 64 |
|  | AS | VPmU*fU*fUmCmUfCmAfGmAmUmUmUmUfAmCfUmUmCmCmAmC*mC*mU | 73 |
| 41 | S | mG*mU*mGmGmAmAmAmGmUfAfAfAmA(Uhd)mCmUmGmAmGmA*mA*mA | 64 |
|  | AS | VPmU*fU*mUmCfUmCmAmGmAmUmUmUmUfAmCmUmUmCmCmAmC*mC*mU | 74 |
| 42 | S | mG*mU*mGmGmAmAmAmGmUfAfAfA(Uhd)fUmCfUmGmAmGmA*mA*mA | 75 |
|  | AS | VPmU*fU*mUmCfUmCmAfGmAmUmUmUmUfAmCfUmUmCmCmAmC*mC*mU | 65 |
| 43 | S | (Ghd)*mU*mGmGmAmAmAmGmUfAfAfAmAmUmCmUmGmAmGmA*mA*mA | 76 |
|  | AS | VPmU*fU*mUmCfUmCmAfGmAmUmUmUmUfAmCfUmUmCmCmAmC*mC*mU | 65 |
| 44 | S | mG*(Uhd)*mGmGmAmAmAmGmUfAfAfAmAmUmCmUmGmAmGmA*mA*mA | 77 |
|  | AS | VPmU*fU*mUmCfUmCmAfGmAmUmUmUmUfAmCfUmUmCmCmAmC*mC*mU | 65 |
| 45 | S | mG*mU*(Ghd)mGmAmAmAmGmUfAfAfAmAmUmCmUmGmAmGmA*mA*mA | 78 |
|  | AS | VPmU*fU*mUmCfUmCmAfGmAmUmUmUmUfAmCfUmUmCmCmAmC*mC*mU | 65 |
| 46 | S | mG*mU*mGmGmA(Ahd)mGmUfAfAfAmAmUmCmUmGmAmGmA*mA*mA | 79 |
|  | AS | VPmU*fU*mUmCfUmCmAfGmAmUmUmUmUfAmCfUmUmCmCmAmC*mC*mU | 65 |
| 47 | S | mG*mU*mGmGmAmAmAmG(Uhd)fAfAfAmAmUmCmUmGmAmGmA*mA*mA | 80 |
|  | AS | VPmU*fU*mUmCfUmCmAfGmAmUmUmUmUfAmCfUmUmCmCmAmC*mC*mU | 65 |

TABLE 2-continued

MAPT RNAi Agents with Modifications

| MAPT RNAi Agent No. | Strand | Sequence from 5' to 3' end | SEQ ID NO |
|---|---|---|---|
| 48 | S | mG*mU*mGmGmAmAmGmU(Ahd)fAfAmAmUmCmUmGmAmGmA*mA*mA | 81 |
|  | AS | VPmU*fU*mUmCfUmCmAfGmAmUmUmUmUfAmCfUmUmCmCmAmC*mC*mU | 65 |
| 49 | S | mG*mU*mGmGmAmAmGmUfA(Ahd)fAmAmUmCmUmGmAmGmA*mA*mA | 82 |
|  | AS | VPmU*fU*mUmCfUmCmAfGmAmUmUmUmUfAmCfUmUmCmCmAmC*mC*mU | 65 |
| 50 | S | mG*mU*mGmGmAmAmGmUfAfAfAmAmUmC(Uhd)mGmAmGmA*mA*mA | 83 |
|  | AS | VPmU*fU*mUmCfUmCmAfGmAmUmUmUmUfAmCfUmUmCmCmAmC*mC*mU | 65 |
| 51 | S | mG*mU*mGmGmAmAmGmUfAfAfAmAmUmCmUmGmAmG(Ahd)*mA*mA | 84 |
|  | AS | VPmU*fU*mUmCfUmCmAfGmAmUmUmUmUfAmCfUmUmCmCmAmC*mC*mU | 65 |
| 52 | S | mG*mU*mGmGmAmAmGmUfAfAfAmAmUmCmUmGmAmGmA*(Ahd)*mA | 85 |
|  | AS | VPmU*fU*mUmCfUmCmAfGmAmUmUmUmUfAmCfUmUmCmCmAmC*mC*mU | 65 |
| 53 | S | mG*mU*mGmGmAmAmGmUfAfAfAmAmUmCmUmGmAmGmA*mA*(Ahd) | 86 |
|  | AS | VPmU*fU*mUmCfUmCmAfGmAmUmUmUmUfAmCfUmUmCmCmAmC*mC*mU | 65 |
| 54 | S | mC*mC*mAmAmGmGmUfGfGfCmU(Chd)mAmUmUmAmGmG*mC*mA | 87 |
|  | AS | VPmU*fG*mCmCfUmAmAfUmGmAmGmCmCfAmCfAmCmUmUmGmG*mA*mG | 88 |
| 55 | S | mC*mC*mAmAmGmUmGmU(n)fGfCmU(Chd)mAmUmUmAmGmG*mC*mA | 89 |
|  | AS | VPmU*fG*mCmCfUmAmAfUmGmAmGmCmCfAmCfAmCmUmUmGmG*mA*mG | 88 |
| 56 | S | mU*mG*mCmAmAmAmUmA(n)fUfCmU(Ahd)mCmAmAmAmCmC*mA*mA | 90 |
|  | AS | VPmU*fU*mGmGfUmUmUfGmUmAmGmAmCfUmAfUmUmGmCmA*mC*mC | 91 |
| 57 | S | mU*mG*mCmAmAmAmUmAfGfUfCmU(Ahd)mCmAmAmAmCmC*mA*mA | 92 |
|  | AS | VPmU*fU*mGmGfUmUmUfGmUmAmGmAmCfUmAfUmUmGmCmA*mC*mC | 91 |
| 58 | S | mG*mU*mG(Ghd)mAmAmGmUfAfAfAmAmUmCmUmGmAmGmA*mA*mA | 93 |
|  | AS | VPmU*fU*mUmCfUmCmAfGmAmUmUmUmUfAmCfUmUmCmCmAmC*mC*mU | 65 |
| 59 | S | mG*mU*mGmG(Ahd)mAmGmUfAfAfAmAmUmCmUmGmAmGmA*mA*mA | 94 |
|  | AS | VPmU*fU*mUmCfUmCmAfGmAmUmUmUmUfAmCfUmUmCmCmAmC*mC*mU | 65 |
| 60 | S | mG*mU*mGmGmAmA(Ghd)mUfAfAfAmAmUmCmUmGmAmGmA*mA*mA | 95 |
|  | AS | VPmU*fU*mUmCfUmCmAfGmAmUmUmUmUfAmCfUmUmCmCmAmC*mC*mU | 65 |
| 61 | S | mG*mU*mGmGmAmAmGmUfAfA(Ahd)mAmUmCmUmGmAmGmA*mA*mA | 96 |
|  | AS | VPmU*fU*mUmCfUmCmAfGmAmUmUmUmUfAmCfUmUmCmCmAmC*mC*mU | 65 |
| 62 | S | mG*mU*mGmGmAmAmGmUfAfAfAmAmU(Chd)mUmGmAmGmA*mA*mA | 97 |
|  | AS | VPmU*fU*mUmCfUmCmAfGmAmUmUmUmUfAmCfUmUmCmCmAmC*mC*mU | 65 |
| 63 | S | mG*mU*mGmGmAmAmGmUfAfAfAmAmUmCmU(Ghd)mAmGmA*mA*mA | 98 |
|  | AS | VPmU*fU*mUmCfUmCmAfGmAmUmUmUmUfAmCfUmUmCmCmAmC*mC*mU | 65 |
| 64 | S | mG*mU*mGmGmAmAmGmUfAfAfAmAmUmCmUmG(Ahd)mGmA*mA*mA | 99 |
|  | AS | VPmU*fU*mUmCfUmCmAfGmAmUmUmUmUfAmCfUmUmCmCmAmC*mC*mU | 65 |
| 65 | S | mG*mU*mGmGmAmAmGmUfAfAfAmAmUmCmUmGmA(Ghd)mA*mA*mA | 100 |
|  | AS | VPmU*fU*mUmCfUmCmAfGmAmUmUmUmUfAmCfUmUmCmCmAmC*mC*mU | 65 |
| 66 | S | mC*mC*mAmGmGmUmGmGfAfAfGmU(Ahd)mAmAmAmUmCmU*mG*mA | 101 |
|  | AS | VPmU*fC*mAmGfAmUmUfUmUmAmCmUfCmCfAmCmCmUmGmG*mC*mC | 102 |
| 67 | S | mG*mG*mAmAmGmUmAmAfAfUmC(Uhd)mGmAmGmAmAmG*mC*mA | 103 |
|  | AS | VPmU*fG*mCmUfUmCmUfCmAmGmAmUmUfUmUfAmCmUmUmCmC*mA*mC | 104 |
| 68 | S | mG*mU*mGmGmAmAfGmUfAfAfAmAmUmCmUmGmAmGmAmA*mA* | 105 |
|  | AS | VPmU*fU*mUmCmUmCmAmAmGmAmUmUmUmUfAmCfUmUmCmCmAmC*mC*mU | 106 |
| 69 | S | mG*mU*mGmGmAmAfGmUfAfAfAmAmUmCmUmGmAmGmAmA*mA* | 105 |
|  | AS | VPmU*fU*mUfCmUfCfAmGfAmUmUmUmUfAmCfUmUmCmCmAmC*mC*mU | 107 |
| 70 | S | mG*mU*mGmGmAmAfGmUfAfAfAmAmUmCmUmGmAmGmAmA*mA* | 105 |
|  | AS | VPmU*fU*mUmCfUmCmAfGmAmUmUmUmUfAmCfUmUmCmCmAmC*mC*mU | 65 |
| 71 | S | mG*mU*mGmGmAmAfGmUfAfAfAmAmUmCmUmGmAmGmAmA*mA* | 105 |
|  | AS | VPmU*fU*mUmCfUfCfAfAfGmAmUmUmUmUfAmCfUmUmCmCmAmC*mC*mU | 108 |

TABLE 2-continued

MAPT RNAi Agents with Modifications

| MAPT RNAi Agent No. | Strand | Sequence from 5' to 3' end | SEQ ID NO |
|---|---|---|---|
| 72 | S | mG*mU*mGmGmAmAfGmUfA(n)fAmAmUmCmUmGmAmGmAmA*mA* | 109 |
|  | AS | VPmU*fU*mUmCfUmCmAfGmAmUmUmUmUfAmCfUmUmCmCmAmC*mC*mU | 65 |
| 73 | S | mG*mU*mGmGmAmAfGmUfAfAfAmAmUmCmUmGmAmGmA*mA*mG | 110 |
|  | AS | VPmU*fU*mUmCmUfCmAmGmAmUmUmUmUfAmCfUmUmCmCmAmC*mC*mU | 40 |
| 74 | S | mA*mA*fGmUfAfAfAmAmUmCmUmGmAmGmA*mA*mA | 111 |
|  | AS | VPmU*fU*mUmCmUfCmAmGmAmUmUmUmUfAmCfUmU*mC*mC*mA*mC*mC*mU | 112 |
| 75 | S | mG*mU*mGmGmAmAfGmUfAfAfAmAmUmCmUmGmAmGmAmAmAdTdT* | 113 |
|  | AS | VPmU*fU*mUmCmUfCmAmGmAmUmUmUmUfAmCfUmUmCmC*mA*mCdTdT | 114 |
| 76 | S | mG*mU*mGmGmAmAmGmUfAfAfAmAmUmCmUmGmAmGmAmA*mA* | 115 |
|  | AS | VPmU*fU*mUmCmUfCmAmGmAmUmUmUmUfAmCfUmUmCmCmA*mC*mC*mU | 116 |

Abbreviations

"m" indicates 2'-OMe; "f" indicated 2'-fluoro; "*" indicates phosphorothioate linkage; "VP" indicates 5'-vinylphosphonate; "Uhd" indicates 2'-O-hexadecyl uridine; "Chd" indicates 2'-O-hexadecyl cytidine; "Ahd" indicates 2'-O-hexadecyl adenosine; "iAb" indicates inverted abasic moiety; "n" indicates abasic moiety; "S" means the sense strand; "AS" means the antisense strand.

TABLE 3

Abasic or inverted abasic (iAb) moieties

| | Structure |
|---|---|
| 1 (abasic) | (structure shown) |
| 2 (iAb) | (structure shown) |

"5'" and "3'" indicate the 5' to 3' direction of the sequences

In some embodiments, the sense strand of the MAPT RNAi agent has a delivery moiety. In some embodiments, the sense strand of the MAPT RNAi agent has a delivery moiety conjugated to the 5' or 3' end of the sense strand. In some embodiments, the sense strand of the MAPT RNAi agent has a delivery moiety conjugated to a nucleotide of the sense strand. The delivery moiety can facilitate the entry of RNAi agent into the cells. In some embodiments, the delivery moiety is α-tocopherol or palmitic acid (see Table 4). In some embodiments, the delivery moiety is a known delivery moiety for delivering RNAi agent into a cell, e.g., a delivery moiety described in Hu et al., Signal Transduction and Targeted Therapy (2020) 5:101. Placement of a delivery moiety on the RNAi agent needs to overcome potential inefficient loading of AGO2 (Argonaute-2), or other hindrance of the RNA-induced silencing complex (RISC) complex activity.

In some embodiments, the delivery moiety is conjugated to the 5' or 3' end of the sense stand via a linker. In some embodiments, the linker is selected from Linker 1, Linker 2, Linker 3, or Linker 4 of Table 5. Other suitable linkers are known in the art. Exemplary linker-delivery moiety pairs are shown in Table 6. In some embodiments, the MAPT RNAi agent has a linker-delivery moiety pair of Table 6.

In some embodiments, the delivery moiety is conjugated to a nucleotide of the sense strand. In that case, the delivery moiety is a modified nucleotide located in the sense strand. In some embodiments, the modified nucleotide is 2'-O-hexadecyl uridine, 2'-O-hexadecyl cytidine, 2'-O-hexadecyl guanine, or 2'-O-hexadecyl adenosine (Table 4).

TABLE 4

Delivery Moieties

| Delivery Moiety | Structure |
|---|---|
| 1 | α-Tocopherol (structure shown) |

TABLE 4-continued
Delivery Moieties
| Delivery Moiety | Structure |
|---|---|
| 2 | 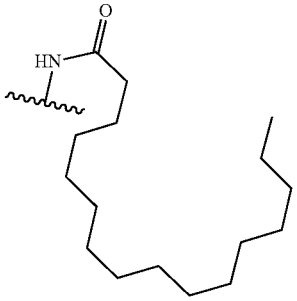 [SMILES: *NC(=O)CCCCCCCCCCCCCCC]<br>Palmitic Acid |
| 3 | 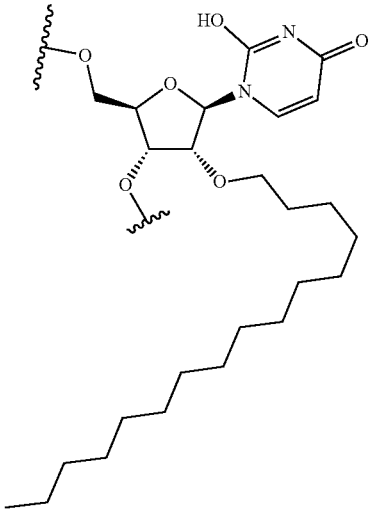 [SMILES: *OC[C@H]1O[C@@H](n2ccc(=O)nc2O)[C@H](OCCCCCCCCCCCCCCCC)[C@@H]1O*]<br>Uhd (2'-O-hexadecyl uridine) |
| 4 | 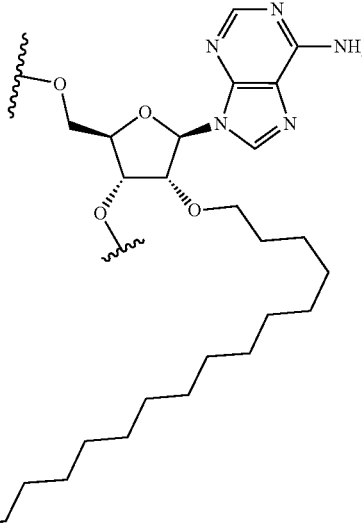<br>Ahd (2'-O-hexadecyl adenosine) |
| 5 | 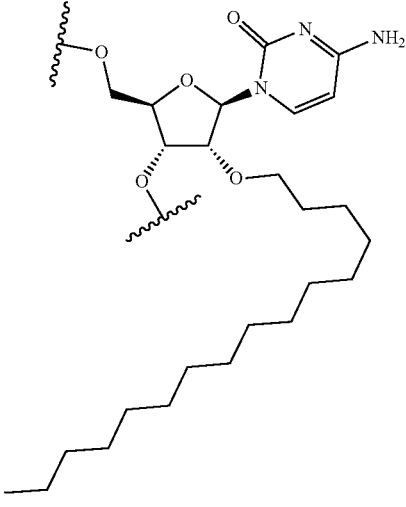 [SMILES: *OC[C@H]1O[C@@H](n2ccc(N)nc2=O)[C@H](OCCCCCCCCCCCCCCCC)[C@@H]1O*]<br>Chd (2'-O-hexadecyl cytidine) |
| 6 | 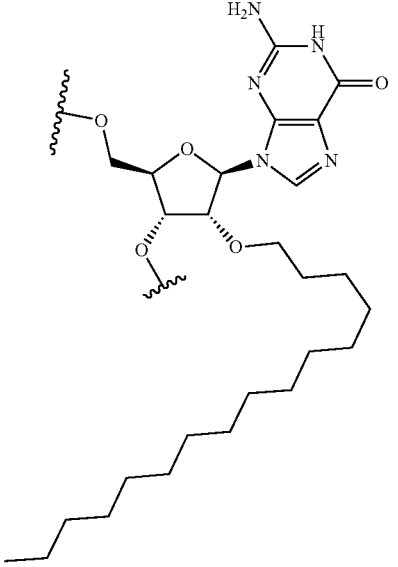 [SMILES: *OC[C@H]1O[C@@H](n2cnc3c(=O)[nH]c(N)nc32)[C@H](OCCCCCCCCCCCCCCCC)[C@@H]1O*]<br>Ghd (2'-O-hexadecyl guanine) |

| Linkers | |
|---|---|
| Linker | Structure |
1 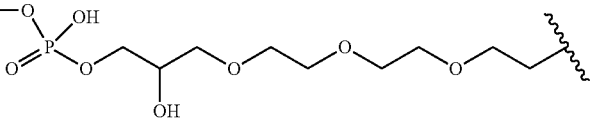
Teg (tetraethylene glycol) linker
2 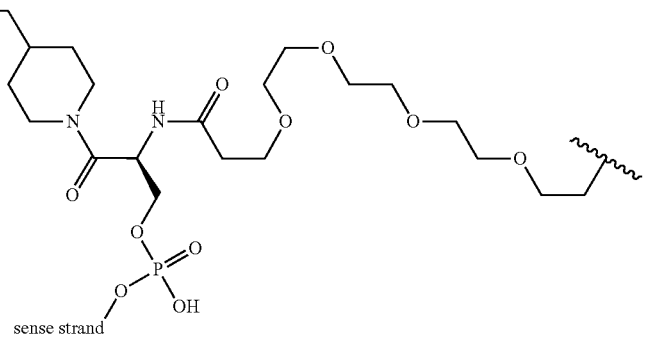
Piperidinol-PEG linker
3 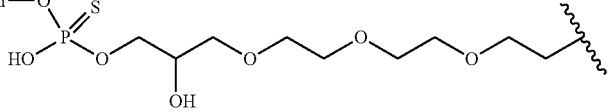
Teg (tetraethylene glycol) linker PS
4 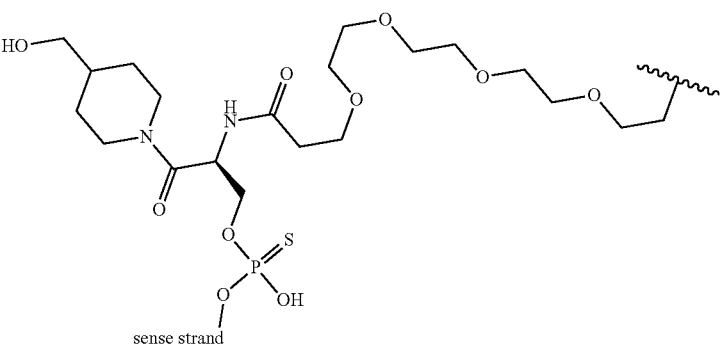
Piperidinol-PEG linker PS TABLE 6
Linker Delivery Moiety Pairs (LDP)
| LDP | Linker | Delivery Moiety |
|---|---|---|
| 1 | 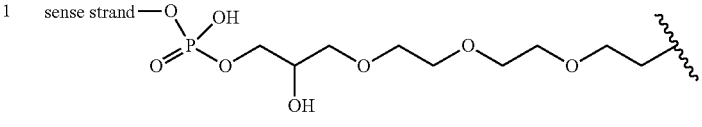<br>Teg (tetraethylene glycol) linker | 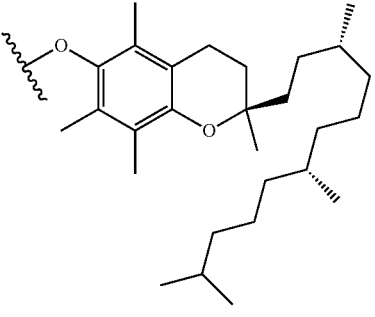 [SMILES: *Oc1c(C)c(C)c2c(c1C)CC[C@@](C)(CC[C@H](C)CCC[C@H](C)CCCC(C)C)O2]<br>α-Tocopherol |
| 2 | 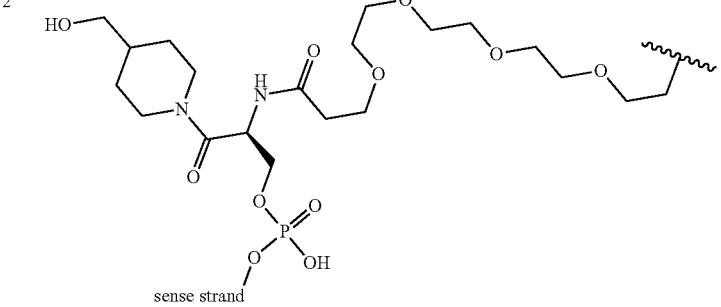<br>Piperidinol-PEG linker | 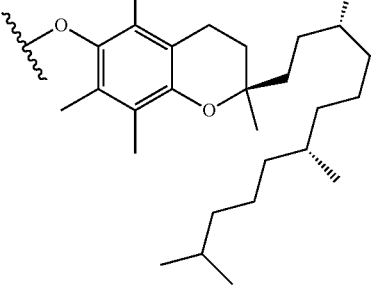<br>α-Tocopherol |
| 3 | 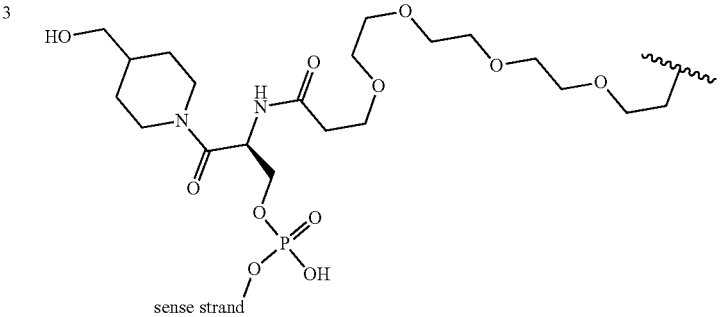<br>Piperidinol-PEG linker | 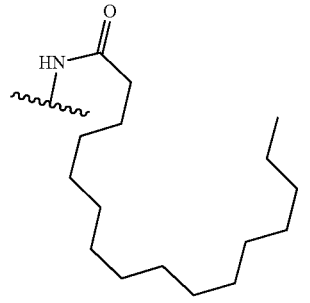 [SMILES: *NC(=O)CCCCCCCCCCCCCCC]<br>Palmitic Acid |

TABLE 6-continued
| | Linker Delivery Moiety Pairs (LDP) | |
|---|---|---|
| LDP | Linker | Delivery Moiety |
| 4 | None | 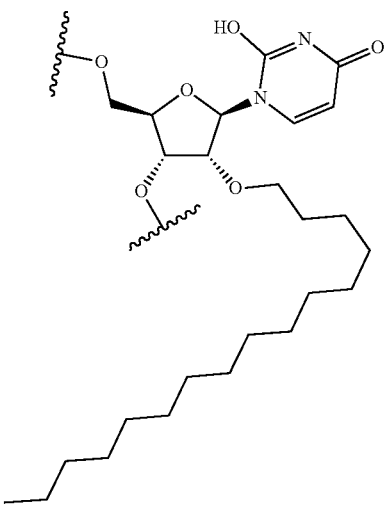 [SMILES: *OC[C@H]1O[C@@H](n2ccc(=O)nc2O)[C@H](OCCCCCCCCCCCCCCCC)[C@@H]1O*]<br>Uhd |
| 5 | None | 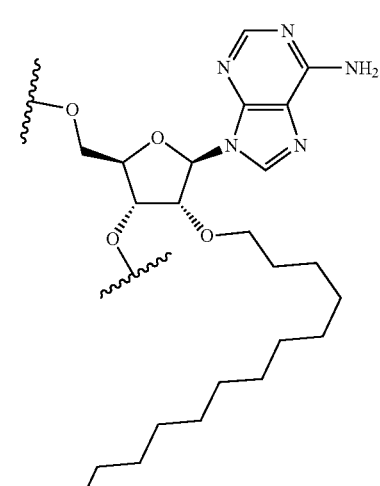<br>Ahd |

TABLE 6-continued

Linker Delivery Moiety Pairs (LDP)

| LDP | Linker | Delivery Moiety |
|---|---|---|
| 6 | None | 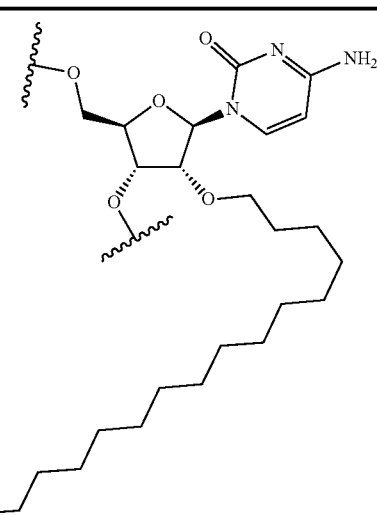<br>Chd |
| 7 | None | 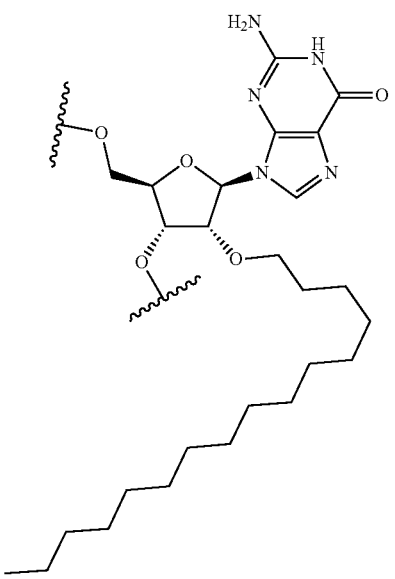 [SMILES: *OC[C@H]1O[C@@H](n2cnc3c(=O)[nH]c(N)nc32)[C@H](OCCCCCCCCCCCCCCCC)[C@@H]1O*]<br>Ghd |

In a further aspect, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprise a pair of nucleic acid sequences selected from the group consisting of:

(a) the sense strand comprises a first nucleic acid sequence of SEQ ID NO: 1, and the antisense strand comprises a second nucleic acid sequence of SEQ ID NO: 2;

(b) the sense strand comprises a first nucleic acid sequence of SEQ ID NO: 3, and the antisense strand comprises a second nucleic acid sequence of SEQ ID NO: 4;

(c) the sense strand comprises a first nucleic acid sequence of SEQ ID NO: 5, and the antisense strand comprises a second nucleic acid sequence of SEQ ID NO: 6;

(d) the sense strand comprises a first nucleic acid sequence of SEQ ID NO: 7, and the antisense strand comprises a second nucleic acid sequence of SEQ ID NO: 8;

(e) the sense strand comprises a first nucleic acid sequence of SEQ ID NO: 9, and the antisense strand comprises a second nucleic acid sequence of SEQ ID NO: 10;

(f) the sense strand comprises a first nucleic acid sequence of SEQ ID NO: 11, and the antisense strand comprises a second nucleic acid sequence of SEQ ID NO: 12;

(g) the sense strand comprises a first nucleic acid sequence of SEQ ID NO:13, and the antisense strand comprises a second nucleic acid sequence of SEQ ID NO: 14;

(h) the sense strand comprises a first nucleic acid sequence of SEQ ID NO: 15, and the antisense strand comprises a second nucleic acid sequence of SEQ ID NO: 16;

(i) the sense strand comprises a first nucleic acid sequence of SEQ ID NO: 17, and the antisense strand comprises a second nucleic acid sequence of SEQ ID NO: 18;

(j) the sense strand comprises a first nucleic acid sequence of SEQ ID NO: 19, and the antisense strand comprises a second nucleic acid sequence of SEQ ID NO: 20;

(k) the sense strand comprises a first nucleic acid sequence of SEQ ID NO:21, and the antisense strand comprises a second nucleic acid sequence of SEQ ID NO: 22;

(l) the sense strand comprises a first nucleic acid sequence of SEQ ID NO:23, and the antisense strand comprises a second nucleic acid sequence of SEQ ID NO: 24;

(m) the sense strand comprises a first nucleic acid sequence of SEQ ID NO: 55, and the antisense strand comprises a second nucleic acid sequence of SEQ ID NO: 16;

(n) the sense strand comprises a first nucleic acid sequence of SEQ ID NO: 56, and the antisense strand comprises a second nucleic acid sequence of SEQ ID NO: 16;

(o) the sense strand comprises a first nucleic acid sequence of SEQ ID NO: 57, and the antisense strand comprises a second nucleic acid sequence of SEQ ID NO: 58;

(p) the sense strand comprises a first nucleic acid sequence of SEQ ID NO: 59, and the antisense strand comprises a second nucleic acid sequence of SEQ ID NO: 58;

(q) the sense strand comprises a first nucleic acid sequence of SEQ ID NO: 60, and the antisense strand comprises a second nucleic acid sequence of SEQ ID NO: 61;

(r) the sense strand comprises a first nucleic acid sequence of SEQ ID NO: 62, and the antisense strand comprises a second nucleic acid sequence of SEQ ID NO: 61;

(s) the sense strand comprises a first nucleic acid sequence of SEQ ID NO: 117, and the antisense strand comprises a second nucleic acid sequence of SEQ ID NO: 118;

(t) the sense strand comprises a first nucleic acid sequence of SEQ ID NO: 119, and the antisense strand comprises a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:

(a) the sense strand has a first nucleic acid sequence of SEQ ID NO: 1, and the antisense strand has a second nucleic acid sequence of SEQ ID NO: 2;

(b) the sense strand has a first nucleic acid sequence of SEQ ID NO: 3, and the antisense strand has a second nucleic acid sequence of SEQ ID NO: 4;

(c) the sense strand has a first nucleic acid sequence of SEQ ID NO: 5, and the antisense strand has a second nucleic acid sequence of SEQ ID NO: 6;

(d) the sense strand has a first nucleic acid sequence of SEQ ID NO: 7, and the antisense strand has a second nucleic acid sequence of SEQ ID NO: 8;

(e) the sense strand has a first nucleic acid sequence of SEQ ID NO: 9, and the antisense strand has a second nucleic acid sequence of SEQ ID NO: 10;

(f) the sense strand has a first nucleic acid sequence of SEQ ID NO: 11, and the antisense strand has a second nucleic acid sequence of SEQ ID NO: 12;

(g) the sense strand has a first nucleic acid sequence of SEQ ID NO:13, and the antisense strand has a second nucleic acid sequence of SEQ ID NO: 14;

(h) the sense strand has a first nucleic acid sequence of SEQ ID NO:15, and the antisense strand has a second nucleic acid sequence of SEQ ID NO: 16;

(i) the sense strand has a first nucleic acid sequence of SEQ ID NO:17, and the antisense strand has a second nucleic acid sequence of SEQ ID NO: 18;

(j) the sense strand has a first nucleic acid sequence of SEQ ID NO:19, and the antisense strand has a second nucleic acid sequence of SEQ ID NO: 20;

(k) the sense strand has a first nucleic acid sequence of SEQ ID NO:21, and the antisense strand has a second nucleic acid sequence of SEQ ID NO: 22;

(l) the sense strand has a first nucleic acid sequence of SEQ ID NO:23, and the antisense strand has a second nucleic acid sequence of SEQ ID NO: 24;

(m) the sense strand has a first nucleic acid sequence of SEQ ID NO: 55, and the antisense strand has a second nucleic acid sequence of SEQ ID NO: 16;

(n) the sense strand has a first nucleic acid sequence of SEQ ID NO: 56, and the antisense strand has a second nucleic acid sequence of SEQ ID NO: 16;

(o) the sense strand has a first nucleic acid sequence of SEQ ID NO: 57, and the antisense strand has a second nucleic acid sequence of SEQ ID NO: 58;

(p) the sense strand has a first nucleic acid sequence of SEQ ID NO: 59, and the antisense strand has a second nucleic acid sequence of SEQ ID NO: 58;

(q) the sense strand has a first nucleic acid sequence of SEQ ID NO: 60, and the antisense strand has a second nucleic acid sequence of SEQ ID NO: 61;

(r) the sense strand has a first nucleic acid sequence of SEQ ID NO: 62, and the antisense strand has a second nucleic acid sequence of SEQ ID NO: 61;

(s) the sense strand has a first nucleic acid sequence of SEQ ID NO: 117, and the antisense strand has a second nucleic acid sequence of SEQ ID NO: 118; and (t) the sense strand has a first nucleic acid sequence of SEQ ID NO: 119, and the antisense strand has a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprise a pair of nucleic acid sequences selected from the group consisting of:

(a) the sense strand comprises a first nucleic acid sequence of SEQ ID NO: 25, and the antisense strand comprises a second nucleic acid sequence of SEQ ID NO: 26;

(b) the sense strand comprises a first nucleic acid sequence of SEQ ID NO: 27, and the antisense strand comprises a second nucleic acid sequence of SEQ ID NO: 28;

(c) the sense strand comprises a first nucleic acid sequence of SEQ ID NO: 29, and the antisense strand comprises a second nucleic acid sequence of SEQ ID NO: 30;

(d) the sense strand comprises a first nucleic acid sequence of SEQ ID NO: 31, and the antisense strand comprises a second nucleic acid sequence of SEQ ID NO: 32;

(e) the sense strand comprises a first nucleic acid sequence of SEQ ID NO: 33, and the antisense strand comprises a second nucleic acid sequence of SEQ ID NO: 34;

(f) the sense strand comprises a first nucleic acid sequence of SEQ ID NO: 35, and the antisense strand comprises a second nucleic acid sequence of SEQ ID NO: 36;

(g) the sense strand comprises a first nucleic acid sequence of SEQ ID NO: 37, and the antisense strand comprises a second nucleic acid sequence of SEQ ID NO: 38;

(h) the sense strand comprises a first nucleic acid sequence of SEQ ID NO: 39, and the antisense strand comprises a second nucleic acid sequence of SEQ ID NO: 40;

(i) the sense strand comprises a first nucleic acid sequence of SEQ ID NO: 41, and the antisense strand comprises a second nucleic acid sequence of SEQ ID NO: 42;

(j) the sense strand comprises a first nucleic acid sequence of SEQ ID NO: 43, and the antisense strand comprises a second nucleic acid sequence of SEQ ID NO: 44;

(k) the sense strand comprises a first nucleic acid sequence of SEQ ID NO: 45, and the antisense strand comprises a second nucleic acid sequence of SEQ ID NO: 46;

(l) the sense strand comprises a first nucleic acid sequence of SEQ ID NO: 47, and the antisense strand comprises a second nucleic acid sequence of SEQ ID NO: 48;

(m) the sense strand comprises a first nucleic acid sequence of SEQ ID NO: 105, and the antisense strand comprises a second nucleic acid sequence selected from SEQ ID NO: 65, 106-108;

(n) the sense strand comprises a first nucleic acid sequence of SEQ ID NO: 109, and the antisense strand comprises a second nucleic acid sequence of SEQ ID NO: 65;

(o) the sense strand comprises a first nucleic acid sequence of SEQ ID NO: 110, and the antisense strand comprises a second nucleic acid sequence of SEQ ID NO: 40;

(p) the sense strand comprises a first nucleic acid sequence of SEQ ID NO: 111, and the antisense strand comprises a second nucleic acid sequence of SEQ ID NO: 112;

(q) the sense strand comprises a first nucleic acid sequence of SEQ ID NO: 113, and the antisense strand comprises a second nucleic acid sequence of SEQ ID NO: 114; and (r) the sense strand comprises a first nucleic acid sequence of SEQ ID NO: 115, and the antisense strand comprises a second nucleic acid sequence of SEQ ID NO: 116.

In some embodiments, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:

(a) the sense strand has a first nucleic acid sequence of SEQ ID NO: 25, and the antisense strand has a second nucleic acid sequence of SEQ ID NO: 26;

(b) the sense strand has a first nucleic acid sequence of SEQ ID NO: 27, and the antisense strand has a second nucleic acid sequence of SEQ ID NO: 28;

(c) the sense strand has a first nucleic acid sequence of SEQ ID NO: 29, and the antisense strand has a second nucleic acid sequence of SEQ ID NO: 30;

(d) the sense strand has a first nucleic acid sequence of SEQ ID NO: 31, and the antisense strand has a second nucleic acid sequence of SEQ ID NO: 32;

(e) the sense strand has a first nucleic acid sequence of SEQ ID NO: 33, and the antisense strand has a second nucleic acid sequence of SEQ ID NO: 34;

(f) the sense strand has a first nucleic acid sequence of SEQ ID NO: 35, and the antisense strand has a second nucleic acid sequence of SEQ ID NO: 36;

(g) the sense strand has a first nucleic acid sequence of SEQ ID NO: 37, and the antisense strand has a second nucleic acid sequence of SEQ ID NO: 38;

(h) the sense strand has a first nucleic acid sequence of SEQ ID NO: 39, and the antisense strand has a second nucleic acid sequence of SEQ ID NO: 40;

(i) the sense strand has a first nucleic acid sequence of SEQ ID NO: 41, and the antisense strand has a second nucleic acid sequence of SEQ ID NO: 42;

(j) the sense strand has a first nucleic acid sequence of SEQ ID NO: 43, and the antisense strand has a second nucleic acid sequence of SEQ ID NO: 44;

(k) the sense strand has a first nucleic acid sequence of SEQ ID NO: 45, and the antisense strand has a second nucleic acid sequence of SEQ ID NO: 46;

(l) the sense strand has a first nucleic acid sequence of SEQ ID NO: 47, and the antisense strand has a second nucleic acid sequence of SEQ ID NO: 48;

(m) the sense strand has a first nucleic acid sequence of SEQ ID NO: 105, and the antisense strand has a second nucleic acid sequence selected from SEQ ID NO: 65, 106-108;

(n) the sense strand has a first nucleic acid sequence of SEQ ID NO: 109, and the antisense strand has a second nucleic acid sequence of SEQ ID NO: 65;

(o) the sense strand has a first nucleic acid sequence of SEQ ID NO: 110, and the antisense strand has a second nucleic acid sequence of SEQ ID NO: 40;

(p) the sense strand has a first nucleic acid sequence of SEQ ID NO: 111, and the antisense strand has a second nucleic acid sequence of SEQ ID NO: 112;

(q) the sense strand has a first nucleic acid sequence of SEQ ID NO: 113, and the antisense strand has a second nucleic acid sequence of SEQ ID NO: 114; and (r) the sense strand has a first nucleic acid sequence of SEQ ID NO: 115, and the antisense strand has a second nucleic acid sequence of SEQ ID NO: 116.

In some embodiments, the delivery means is conjugated to the sense strand. In some embodiments, the delivery means is conjugated to the 5' or 3' end of the sense strand. In some embodiments, the delivery means is conjugated to a nucleotide of the sense strand. In some embodiments, the delivery means is palmitic acid or α-tocopherol. In some embodiments, the linking means is selected from the group consisting of Linker 1, Linker 2, Linker 3, and Linker 4 of Table 5.

The sense strand and antisense strand of MAPT RNAi agent can be synthesized using any nucleic acid polymerization methods known in the art, for example, solid-phase synthesis by employing phosphoramidite chemistry methodology (e.g., Current Protocols in Nucleic Acid Chemistry, Beaucage, S. L. et al. (Edrs.), John Wiley & Sons, Inc., New York, NY, USA), H-phosphonate, phosphortriester chemistry, or enzymatic synthesis. Automated commercial synthesizers can be used, for example, MerMade™ 12 from LGC Biosearch Technologies, or other synthesizers from BioAutomation or Applied Biosystems. Phosphorothioate linkages can be introduced using a sulfurizing reagent such as phenylacetyl disulfide or DDTT (((dimethylaminomethylidene) amino)-3H-1,2,4-dithiazaoline-3-thione). It is well known to use similar techniques and commercially available modified amidites and controlled-pore glass (CPG) products to synthesize modified oligonucleotides or conjugated oligonucleotides.

Purification methods can be used to exclude the unwanted impurities from the final oligonucleotide product. Commonly used purification techniques for single stranded oligonucleotides include reverse-phase ion pair high performance liquid chromatography (RP-IP-HPLC), capillary gel electrophoresis (CGE), anion exchange HPLC (AX-HPLC), and size exclusion chromatography (SEC). After purification, oligonucleotides can be analyzed by mass spectrometry and quantified by spectrophotometry at a wavelength of 260 nm. The sense strand and antisense strand can then be annealed to form a duplex.

In another aspect, provided herein are pharmaceutical compositions comprising a MAPT RNAi agent described herein and a pharmaceutically acceptable carrier. Also provided herein are pharmaceutical compositions comprising a means for reducing MAPT expression in a cell and a pharmaceutically acceptable carrier. Such pharmaceutical compositions can also comprise one or more pharmaceutically acceptable excipient, diluent, or carrier. Pharmaceutical compositions can be prepared by methods well known in the art (e.g., Remington: The Science and Practice of Pharmacy, 23rd edition (2020), A. Loyd et al., Academic Press).

In a further aspect, provided herein are methods of reducing MAPT expression in a cell (e.g., a neuron), such methods can include introducing a MAPT RNAi agent described herein into the cell; and incubating the cell for a time sufficient for degradation of MAPT mRNA, thereby reducing MAPT expression in the cell. The MAPT RNAi agent can be introduced into the cell (e.g., a neuron) using a method known in the art, e.g., transfection, electroporation, microinjection, or uptake by the cell via natural transport mechanisms.

In another aspect, provided herein are methods of reducing MAPT expression in a patient in need thereof, and such method comprises administering to the patient an effective amount of a MAPT RNAi agent or a pharmaceutical composition described herein. Aggregation of MAPT can be caused by overexpression of the MAPT protein or a mutation that affects the structure of the protein, resulting in an increased tendency of the MAPT protein to self-associate. Therefore, reducing MAPT expression level can be beneficial to the patient with tauopathy.

In another aspect, provided herein are methods of treating a tauopathy in a patient in need thereof, and such method comprises administering to the patient an effective amount of the MAPT RNAi agent or a pharmaceutical composition described herein. Exemplary tauopathy includes, but are not limited to, Alzheimer's disease (AD), frontotemporal dementia (FTD), frontotemporal dementia with parkinsonism linked to chromosome 17 (FTDP-17), frontotemporal lobar degeneration (FTLD), behavioral variant frontotemporal dementia (bvFTD), nonfluent variant primary progressive aphasia (nfvPPA), Parkinson's disease, Pick's disease (PiD), primary progressive aphasia-semantic (PPA-S), primary progressive aphasia-logopenic (PPA-L), multiple system tauopathy with presenile dementia (MSTD), neurofibrillary tangle (NFT) dementia, FTD with motor neuron disease, progressive supranuclear palsy (PSP), amyotrophic lateral sclerosis/parkinsonism-dementia complex (ALS-PDC), argyrophilic grain dementia (AGD), British type amyloid angiopathy, cerebral amyloid angiopathy, chronic traumatic encephalopathy (CTE), corticobasal degeneration (CBD), Creutzfeldt-Jakob disease (CJD), dementia pugilistica, diffuse neurofibrillary tangles with calcification, Down's syndrome, epilepsy, Gerstmann-Straussler-Scheinker disease, Hallervorden-Spatz disease, Huntington's disease, inclusion body myositis, lead encephalopathy, Lytico-Bodig disease (Parkinson-dementia complex of Guam), meningioangiomatosis, multiple system atrophy, myotonic dystrophy, Niemann-Pick disease type C (NP-C), non-Guamanian motor neuron disease with neurofibrillary tangles, postencephalitic parkinsonism, prion protein cerebral amyloid angiopathy, progressive subcortical gliosis, tangle only dementia, tangle-predominant dementia, ganglioglioma, gangliocytoma, subacute sclerosingpan encephalitis, tuberous sclerosis, lipofuscinosis, primary age-related tauopathy (PART), globular glial tauopathies (GGT). In some embodiments, the tauopathy is Alzheimer's disease (AD), frontotemporal dementia (FTD), or progressive supranuclear palsy (PSP).

The MAPT RNAi agent can be administered to the patient intrathecally, intracerebroventricularly, or via intracisternal magna injection. In some embodiments, the MAPT RNAi agent is administered to the patient intrathecally via a catheter.

RNAi dosage regimens may be adjusted to provide the optimum desired response (e.g., a therapeutic response). For example, a single bolus may be administered, several divided doses may be administered over time, or the dose may be proportionally reduced or increased as indicated by the exigencies of the therapeutic situation.

Dosage values may vary with the type and severity of the condition to be alleviated. It is further understood that for any particular subject, specific dosage regimens should be adjusted over time according to the individual need and the professional judgment of the person administering or supervising the administration of the compositions.

In another aspect, provided herein are MAPT RNAi agents or pharmaceutical compositions comprising a MAPT RNAi agent for use in reducing MAPT expression. Also provided herein are MAPT RNAi agents or the pharmaceutical composition comprising a MAPT RNAi agent for use in a therapy. Also provided herein are MAPT RNAi agents or pharmaceutical compositions comprising a MAPT RNAi agent for use in the treatment of a tauopathy. Also provided herein are uses of MAPT RNAi agents in the manufacture of a medicament for the treatment of a tauopathy.

As used herein, the terms "a," "an," "the," and similar terms used in the context of the present disclosure (especially in the context of the claims) are to be construed to cover both the singular and plural unless otherwise indicated herein or clearly contradicted by the context.

As used herein, the term "alkyl" means saturated linear or branched-chain monovalent hydrocarbon radical, containing the indicated number of carbon atoms. For example, "$C_1$-$C_{20}$ alkyl" means a radical having 1-20 carbon atoms in a linear or branched arrangement.

As used herein, "antisense strand" means an oligonucleotide that is complementary to a region of a target sequence. Likewise, and as used herein, "sense strand" means an oligonucleotide that is complementary to a region of an antisense strand.

As used herein, "complementary" means a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. Complementary nucleotides can base pair in the Watson-Crick manner or in any other manner that allows for the formation of stable duplexes. Likewise, two nucleic acids may have regions of multiple nucleotides that are complementary with each other to form regions of complementarity, as described herein.

As used herein, a "delivery moiety" refers to a chemical moiety that facilitates the entry of an oligonucleotide or RNAi agent into a cell. The delivery moiety can be lipid, cholesterol, vitamin E, carbohydrate, amino sugar, polypeptide or protein.

As used herein, "duplex," in reference to nucleic acids or oligonucleotides, means a structure formed through complementary base pairing of two antiparallel sequences of nucleotides (i.e., in opposite directions), whether formed by two separate nucleic acid strands or by a single, folded strand (e.g., via a hairpin).

An "effective amount" refers to an amount necessary (for periods of time and for the means of administration) to achieve the desired therapeutic result. An effective amount of a RNAi agent may vary according to factors such as the disease state, age, sex, and weight of the individual, and the ability of the RNAi agent to elicit a desired response in the individual. An effective amount is also one in which any toxic or detrimental effects of the RNAi agent are outweighed by the therapeutically beneficial effects.

The term "have", "having" or "has", when referring to a sequence, means consists of or consists essentially of.

The term "knockdown" or "expression knockdown" refers to reduced mRNA or protein expression of a gene after treatment of a reagent, e.g., a RNAi agent.

As used herein, "modified internucleotide linkage" means an internucleotide linkage having one or more chemical modifications when compared with a reference internucleotide linkage having a phosphodiester bond. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc. In some embodiments, the modified internucleotide linkage is phosphorothioate linkage.

As used herein, "modified nucleotide" refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide, and thymidine deoxyribonucleotide. A modified nucleotide can have, for example, one or more chemical modification in its sugar, nucleobase, and/or phosphate group. Additionally, or alternatively, a modified nucleotide can have one or more chemical moieties conjugated to a corresponding reference nucleotide. In some embodiments, the modified nucleotide is a 2'-fluoro modified nucleotide, 2'-O-methyl modified nucleotide, or 2'-O-alkyl modified nucleotide, e.g., 2'-O—C16 alkyl modified nucleotide. In some embodiments, the modified nucleotide has a phosphate analog, e.g., 5'-vinylphosphonate. In some embodiments, the modified nucleotide is an abasic moiety or inverted abasic moiety, e.g., a moiety shown in Table 3.

As used herein, the term "tauopathy" refers to a disease associated with abnormal tau protein expression, secretion, phosphorylation, cleavage, and/or aggregation.

As used herein, "nucleotide" means an organic compound having a nucleoside (a nucleobase, e.g., adenine, cytosine, guanine, thymine, or uracil, and a pentose sugar, e.g., ribose or 2'-deoxyribose) linked to a phosphate group, which can serve as a monomeric unit of nucleic acid polymers such as deoxyribonucleic acid (DNA) and ribonucleic acid (RNA).

As used herein, "oligonucleotide" means a polymer of linked nucleotides, each of which can be modified or unmodified. An oligonucleotide is typically less than about 100 nucleotides in length.

As used herein, "overhang" means the unpaired nucleotide or nucleotides that protrude from the duplex structure of a double stranded oligonucleotide. An overhang may include one or more unpaired nucleotides extending from a duplex region at the 5' terminus or 3' terminus of a double stranded oligonucleotide. The overhang can be a 3' or 5' overhang on the antisense strand or sense strand of a double stranded oligonucleotide.

The term "patient", as used herein, refers to a human patient.

As used herein, "phosphate analog" means a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. A 5' phosphate analog can include a phosphatase-resistant linkage. Examples of phosphate analogs include 5' methylene phosphonate (5'-MP) and 5'-(E)-vinylphosphonate (5'-VP). In some embodiments, the phosphate analog is 5'-VP.

The term "% sequence identity" or "percentage sequence identity" with respect to a reference nucleic acid sequence is defined as the percentage of nucleotides, nucleosides, or nucleobases in a candidate sequence that are identical with the nucleotides, nucleosides, or nucleobases in the reference nucleic acid sequence, after optimally aligning the sequences and introducing gaps or overhangs, if necessary, to achieve the maximum percent sequence identity. Alignment for purposes of determining percent nucleic acid sequence identity can be achieved in various ways that are within the skill in the art, for instance, using publicly available computer software programs, for example, those described in Current Protocols in Molecular Biology (Ausubel et al., eds., 1987, Supp. 30, section 7.7.18, Table 7.7.1), and including BLAST, BLAST-2, ALIGN, Clustal W2.0, Clustal X2.0, or Megalign (DNASTAR) software. Those skilled in the art can determine appropriate parameters for measuring alignment, including any algorithms needed to achieve maximal alignment over the full length of the sequences being compared. Percentage of "sequence identity" can be determined by comparing two optimally aligned sequences over a comparison window, where the fragment of the nucleic acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical nucleotide, nucleoside, or nucleobase occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

As used herein, "RNAi," "RNAi agent," "iRNA," "iRNA agent," and "RNA interference agent" means an agent that mediates sequence-specific degradation of a target mRNA by RNA interference, e.g., via RNA-induced silencing complex (RISC) pathway. In some embodiments, the RNAi agent has a sense strand and an antisense strand, and the sense strand and the antisense strand form a duplex. In some embodiments, the sense strand has a delivery moiety, e.g., a delivery moiety conjugated to the 5' or 3' end of the sense strand or a nucleotide of the sense strand.

As used herein, "strand" refers to a single, contiguous sequence of nucleotides linked together through internucleotide linkages (e.g., phosphodiester linkages or phosphorothioate linkages). A strand can have two free ends (e.g., a 5' end and a 3' end).

As used herein, "MAPT" refers to a human MAPT mRNA transcript, encoding a microtubule associated protein Tau. The nucleotide sequences of human MAPT transcript variants and amino acid sequences of human Tau protein isoforms can be found at:

i. MAPT transcript variant 1→Tau protein isoform 1: NM_016835.5 (nucleotide sequence)→NP_058519.3 (amino acid sequence);
ii. MAPT transcript variant 2→Tau protein isoform 2: NM_005910.6 (nucleotide sequence)→NP_005901.2 (amino acid sequence);
iii. MAPT transcript variant 3→Tau protein isoform 3: NM_016834.5 (nucleotide sequence)→NP_058518.1 (amino acid sequence);
iv. MAPT transcript variant 4→Tau protein isoform 4: NM_016841.5 (nucleotide sequence)→NP_058525.1 (amino acid sequence);
v. MAPT transcript variant 5→Tau protein isoform 5: NM_001123067.4 (nucleotide sequence)→NP_001116539.1 (amino acid sequence);
vi. MAPT transcript variant 6→Tau protein isoform 6: NM_001123066.4 (nucleotide sequence)→NP_001116538.2 (amino acid sequence);
vii. MAPT transcript variant 7→Tau protein isoform 7: NM_001203251.2 (nucleotide sequence)→NP_001190180.1 (amino acid sequence);
viii. MAPT transcript variant 8→Tau protein isoform 8: NM_001203252.2 (nucleotide sequence)→NP_001190181.1 (amino acid sequence);
ix. MAPT transcript variant 9→Tau protein isoform 9: NM_001377265.1 (nucleotide sequence)→NP_001364194.1 (amino acid sequence);
x. MAPT transcript variant 10→Tau protein isoform 10: NM_001377266.1 (nucleotide sequence)→NP_001364195.1 (amino acid sequence);
xi. MAPT transcript variant 11→Tau protein isoform 11: NM_001377267.1 (nucleotide sequence)→NP_001364196.1 (amino acid sequence);
xii. MAPT transcript variant 12→Tau protein isoform 4: NM_001377268.1 (nucleotide sequence)→NP_001364197.1 (amino acid sequence).

The nucleotide sequence of the human MAPT transcript variant 6 (encoding 2N4R Tau) can be found at NM_001123066.4:

```
                                                            (SEQ ID NO: 49)
  1 GCAGTCACCG CCACCCACCA GCTCCGGCAC CAACAGCAGC GCCGCTGCCA CCGCCCACCT

61 TCTGCCGCCG CCACCACAGC CACCTTCTCC TCCTCCGCTG TCCTCTCCCG TCCTCGCCTC

121 TGTCGACTAT CAGGTGAACT TTGAACCAGG ATGGCTGAGC CCCGCCAGGA GTTCGAAGTG

181 ATGGAAGATC ACGCTGGGAC GTACGGGTTG GGGGACAGGA AAGATCAGGG GGGCTACACC

241 ATGCACCAAG ACCAAGAGGG TGACACGGAC GCTGGCCTGA AGAATCTCC CCTGCAGACC

301 CCCACTGAGG ACGGATCTGA GGAACCGGGC TCTGAAACCT CTGATGCTAA GAGCACTCCA

361 ACAGCGGAAG ATGTGACAGC ACCCTTAGTG GATGAGGGAG CTCCCGGCAA GCAGGCTGCC

421 GCGCAGCCCC ACACGGAGAT CCCAGAAGGA ACCACAGCTG AAGAAGCAGG CATTGGAGAC

481 ACCCCAGCC TGGAAGACGA AGCTGCTGGT CACGTGACCC AAGAGCCTGA AAGTGGTAAG

541 GTGGTCCAGG AAGGCTTCCT CCGAGAGCCA GGCCCCCCAG GTCTGAGCCA CCAGCTCATG
```

-continued

```
 601 TCCGGCATGC CTGGGGCTCC CCTCCTGCCT GAGGGCCCCA GAGAGGCCAC ACGCCAACCT
 661 TCGGGACAG GACCTGAGGA CACAGAGGGC GGCCGCCACG CCCCTGAGCT GCTCAAGCAC
 721 CAGCTTCTAG GAGACCTGCA CCAGGAGGGG CCGCCGCTGA AGGGGGCAGG GGGCAAAGAG
 781 AGGCCGGGGA GCAAGGAGGA GGTGGATGAA GACCGCGACG TCGATGAGTC CTCCCCCCAA
 841 GACTCCCCTC CCTCCAAGGC CTCCCCAGCC CAAGATGGGC GGCCTCCCCA GACAGCCGCC
 901 AGAGAAGCCA CCAGCATCCC AGGCTTCCCA GCGGAGGGTG CCATCCCCCT CCCTGTGGAT
 961 TTCCTCTCCA AAGTTTCCAC AGAGATCCCA GCCTCAGAGC CCGACGGGCC CAGTGTAGGG
1021 CGGGCCAAAG GGCAGGATGC CCCCCTGGAG TTCACGTTTC ACGTGGAAAT CACACCCAAC
1081 GTGCAGAAGG AGCAGGCGCA CTCGGAGGAG CATTTGGGAA GGGCTGCATT TCCAGGGGCC
1141 CCTGGAGAGG GGCCAGAGGC CCGGGGCCCC TCTTTGGGAG AGGACACAAA AGAGGCTGAC
1201 CTTCCAGAGC CCTCTGAAAA GCAGCCTGCT GCTGCTCCGC GGGGGAAGCC CGTCAGCCGG
1261 GTCCCTCAAC TCAAAGCTCG CATGGTCAGT AAAAGCAAAG ACGGGACTGG AAGCGATGAC
1321 AAAAAAGCCA AGACATCCAC ACGTTCCTCT GCTAAAACCT TGAAAAATAG GCCTTGCCTT
1381 AGCCCCAAAC ACCCCACTCC TGGTAGCTCA GACCCTCTGA TCCAACCCTC CAGCCCTGCT
1441 GTGTGCCCAG AGCCACCTTC CTCTCCTAAA TACGTCTCTT CTGTCACTTC CCGAACTGGC
1501 AGTTCTGGAG CAAAGGAGAT GAAACTCAAG GGGGCTGATG GTAAAACGAA GATCGCCACA
1561 CCGCGGGGAG CAGCCCCTCC AGGCCAGAAG GGCCAGGCCA ACGCCACCAG GATTCCAGCA
1621 AAAACCCCGC CCGCTCCAAA GACACCACCC AGCTCTGCGA CTAAGCAAGT CCAGAGAAGA
1681 CCACCCCCTG CAGGGCCCAG ATCTGAGAGA GGTGAACCTC CAAAATCAGG GGATCGCAGC
1741 GGCTACAGCA GCCCCGGCTC CCCAGGCACT CCCGGCAGCC GCTCCGGCAC CCCGTCCCTT
1801 CCAACCCCAC CCACCCGGGA GCCCAAGAAG GTGGCAGTGG TCCGTACTCC ACCCAAGTCG
1861 CCGTCTTCCG CCAAGAGCCG CCTGCAGACA GCCCCGTGC CCATGCCAGA CCTGAAGAAT
1921 GTCAAGTCCA AGATCGGCTC CACTGAGAAC CTGAAGCACC AGCCGGGAGG CGGGAAGGTG
1981 CAGATAATTA ATAAGAAGCT GGATCTTAGC AACGTCCAGT CCAAGTGTGG CTCAAAGGAT
2041 AATATCAAAC ACGTCCCGGG AGGCGGCAGT GTGCAAATAG TCTACAAACC AGTTGACCTG
2101 AGCAAGGTGA CCTCCAAGTG TGGCTCATTA GGCAACATCC ATCATAAACC AGGAGGTGGC
2161 CAGGTGGAAG TAAAATCTGA GAAGCTTGAC TTCAAGGACA GAGTCCAGTC GAAGATTGGG
2221 TCCCTGGACA ATATCACCCA CGTCCCTGGC GGAGGAAATA AAAAGATTGA AACCCACAAG
2281 CTGACCTTCC GCGAGAACGC CAAAGCCAAG ACAGACCACG GGCGGAGAT CGTGTACAAG
2341 TCGCCAGTGG TGTCTGGGA CACGTCTCCA CGGCATCTCA GCAATGTCTC CTCCACCGGC
2401 AGCATCGACA TGGTAGACTC GCCCCAGCTC GCCACGCTAG CTGACGAGGT GTCTGCCTCC
2461 CTGGCCAAGC AGGGTTTGTG ATCAGGCCCC TGGGCGGTC AATAATTGTG GAGAGGAGAG
2521 AATGAGAGAG TGTGGAAAAA AAAGAATAA TGACCCGGCC CCGCCCTCT GCCCCCAGCT
2581 GCTCCTCGCA GTTCGGTTAA TTGGTTAATC ACTTAACCTG CTTTTGTCAC TCGGCTTTGG
2641 CTCGGGACTT CAAAATCAGT GATGGGAGTA AGAGCAAATT TCATCTTTCC AAATTGATGG
2701 GTGGGCTAGT AATAAAATAT TTAAAAAAAA ACATTCAAAA ACATGGCCAC ATCCAACATT
2761 TCCTCAGGCA ATTCCTTTTG ATTCTTTTTT CTTCCCCCTC CATGTAGAAG AGGGAGAAGG
2821 AGAGGCTCTG AAAGCTGCTT CTGGGGGATT TCAAGGGACT GGGGGTGCCA ACCACCTCTG
2881 GCCCTGTTGT GGGGGTGTCA CAGAGGCAGT GGCAGCAACA AAGGATTTGA AACTTGGTGT
2941 GTTCGTGGAG CCACAGGCAG ACGATGTCAA CCTTGTGTGA GTGTGACGGG GGTTGGGGTG
3001 GGGCGGGAGG CCACGGGGGA GGCCGAGGCA GGGGCTGGGC AGAGGGGAGA GGAAGCACAA
```

```
-continued
3061 GAAGTGGGAG TGGGAGAGGA AGCCACGTGC TGGAGAGTAG ACATCCCCCT CCTTGCCGCT
3121 GGGAGAGCCA AGGCCTATGC CACCTGCAGC GTCTGAGCGG CCGCCTGTCC TTGGTGGCCG
3181 GGGGTGGGGG CCTGCTGTGG GTCAGTGTGC CACCCTCTGC AGGGCAGCCT GTGGGAGAAG
3241 GGACAGCGGG TAAAAAGAGA AGGCAAGCTG GCAGGAGGGT GGCACTTCGT GGATGACCTC
3301 CTTAGAAAAG ACTGACCTTG ATGTCTTGAG AGCGCTGGCC TCTTCCTCCC TCCCTGCAGG
3361 GTAGGGGGCC TGAGTTGAGG GGCTTCCCTC TGCTCCACAG AAACCCTGTT TTATTGAGTT
3421 CTGAAGGTTG GAACTGCTGC CATGATTTTG GCCACTTTGC AGACCTGGGA CTTTAGGGCT
3481 AACCAGTTCT CTTTGTAAGG ACTTGTGCCT CTTGGGAGAC GTCCACCCGT TTCCAAGCCT
3541 GGGCCACTGG CATCTCTGGA GTGTGTGGGG GTCTGGGAGG CAGGTCCCGA GCCCCCTGTC
3601 CTTCCCACGG CCACTGCAGT CACCCCGTCT GCGCCGCTGT GCTGTTGTCT GCCGTGAGAG
3661 CCCAATCACT GCCTATACCC CTCATCACAC GTCACAATGT CCCGAATTCC CAGCCTCACC
3721 ACCCCTTCTC AGTAATGACC CTGGTTGGTT GCAGGAGGTA CCTACTCCAT ACTGAGGGTG
3781 AAATTAAGGG AAGGCAAAGT CCAGGCACAA GAGTGGGACC CCAGCCTCTC ACTCTCAGTT
3841 CCACTCATCC AACTGGGACC CTCACCACGA ATCTCATGAT CTGATTCGGT TCCCTGTGTC
3901 CTCCTCCCGT CACAGATGTG AGCCAGGGCA CTGCTCAGCT GTGACCCTAG GTGTTTCTGC
3961 CTTGTTGACA TGGAGAGAGC CCTTTCCCCT GAGAAGGCCT GGCCCCTTCC TGTGCTGAGC
4021 CCACAGCAGC AGGCTGGGTG TCTTGGTTGT CAGTGGTGGC ACCAGGATGG AAGGGCAAGG
4081 CACCCAGGGC AGGCCCACAG TCCCGCTGTC CCCCACTTGC ACCCTAGCTT GTAGCTGCCA
4141 ACCTCCCAGA CAGCCCAGCC CGCTGCTCAG CTCCACATGC ATAGTATCAG CCCTCCACAC
4201 CCGACAAAGG GGAACACACC CCCTTGGAAA TGGTTCTTTT CCCCCAGTCC CAGCTGGAAG
4261 CCATGCTGTC TGTTCTGCTG GAGCAGCTGA ACATATACAT AGATGTTGCC CTGCCCTCCC
4321 CATCTGCACC CTGTTGAGTT GTAGTTGGAT TTGTCTGTTT ATGCTTGGAT TCACCAGAGT
4381 GACTATGATA GTGAAAAGAA AAAAAAAAA AAAAAAGGAC GCATGTATCT TGAAATGCTT
4441 GTAAAGAGGT TTCTAACCCA CCCTCACGAG GTGTCTCTCA CCCCCACACT GGGACTCGTG
4501 TGGCCTGTGT GGTGCCACCC TGCTGGGGCC TCCCAAGTTT TGAAAGGCTT TCCTCAGCAC
4561 CTGGGACCCA ACAGAGACCA GCTTCTAGCA GCTAAGGAGG CCGTTCAGCT GTGACGAAGG
4621 CCTGAAGCAC AGGATTAGGA CTGAAGCGAT GATGTCCCCT TCCCTACTTC CCCTTGGGGC
4681 TCCCTGTGTC AGGGCACAGA CTAGGTCTTG TGGCTGGTCT GGCTTGCGGC GCGAGGATGG
4741 TTCTCTCTGG TCATAGCCCG AAGTCTCATG GCAGTCCCAA AGGAGGCTTA CAACTCCTGC
4801 ATCACAAGAA AAAGGAAGCC ACTGCCAGCT GGGGGGATCT GCAGCTCCCA GAAGCTCCGT
4861 GAGCCTCAGC CACCCCTCAG ACTGGGTTCC TCTCCAAGCT CGCCCTCTGG AGGGGCAGCG
4921 CAGCCTCCCA CCAAGGGCCC TGCGACCACA GCAGGGATTG GGATGAATTG CCTGTCCTGG
4981 ATCTGCTCTA GAGGCCCAAG CTGCCTGCCT GAGGAAGGAT GACTTGACAA GTCAGGAGAC
5041 ACTGTTCCCA AAGCCTTGAC CAGAGCACCT CAGCCCGCTG ACCTTGCACA AACTCCATCT
5101 GCTGCCATGA GAAAGGGAA GCCGCCTTTG CAAAACATTG CTGCCTAAAG AAACTCAGCA
5161 GCCTCAGGCC CAATTCTGCC ACTTCTGGTT TGGGTACAGT TAAAGGCAAC CCTGAGGGAC
5221 TTGGCAGTAG AAATCCAGGG CCTCCCCTGG GGCTGGCAGC TTCGTGTGCA GCTAGAGCTT
5281 TACCTGAAAG GAAGTCTCTG GCCCAGAAC TCTCCACCAA GAGCCTCCCT GCCGTTCGCT
5341 GAGTCCCAGC AATTCTCCTA AGTTGAAGGG ATCTGAGAAG GAGAAGGAAA TGTGGGGTAG
5401 ATTTGGTGGT GGTTAGAGAT ATGCCCCCCT CATTACTGCC AACAGTTTCG GCTGCATTTC
```

```
5461 TTCACGCACC TCGGTTCCTC TTCCTGAAGT TCTTGTGCCC TGCTCTTCAG CACCATGGGC

5521 CTTCTTATAC GGAAGGCTCT GGGATCTCCC CCTTGTGGGG CAGGCTCTTG GGGCCAGCCT

5581 AAGATCATGG TTTAGGGTGA TCAGTGCTGG CAGATAAATT GAAAAGGCAC GCTGGCTTGT

5641 GATCTTAAAT GAGGACAATC CCCCCAGGGC TGGGCACTCC TCCCCTCCCC TCACTTCTCC

5701 CACCTGCAGA GCCAGTGTCC TTGGGTGGGC TAGATAGGAT ATACTGTATG CCGGCTCCTT

5761 CAAGCTGCTG ACTCACTTTA TCAATAGTTC CATTTAAATT GACTTCAGTG GTGAGACTGT

5821 ATCCTGTTTG CTATTGCTTG TTGTGCTATG GGGGAGGGG GGAGGAATGT GTAAGATAGT

5881 TAACATGGGC AAAGGGAGAT CTTGGGGTGC AGCACTTAAA CTGCCTCGTA ACCCTTTTCA

5941 TGATTTCAAC CACATTTGCT AGAGGGAGGG AGCAGCCACG GAGTTAGAGG CCCTTGGGGT

6001 TTCTCTTTTC CACTGACAGG CTTTCCCAGG CAGCTGGCTA GTTCATTCCC TCCCCAGCCA

6061 GGTGCAGGCG TAGGAATATG GACATCTGGT TGCTTTGGCC TGCTGCCCTC TTTCAGGGGT

6121 CCTAAGCCCA CAATCATGCC TCCCTAAGAC CTTGGCATCC TTCCCTCTAA GCCGTTGGCA

6181 CCTCTGTGCC ACCTCTCACA CTGGCTCCAG ACACACAGCC TGTGCTTTTG GAGCTGAGAT

6241 CACTCGCTTC ACCCTCCTCA TCTTTGTTCT CCAAGTAAAG CCACGAGGTC GGGGCGAGGG

6301 CAGAGGTGAT CACCTGCGTG TCCCATCTAC AGACCTGCAG CTTCATAAAA CTTCTGATTT

6361 CTCTTCAGCT TTGAAAAGGG TTACCCTGGG CACTGGCCTA GAGCCTCACC TCCTAATAGA

6421 CTTAGCCCCA TGAGTTTGCC ATGTTGAGCA GGACTATTTC TGGCACTTGC AAGTCCCATG

6481 ATTTCTTCGG TAATTCTGAG GGTGGGGGGA GGGACATGAA ATCATCTTAG CTTAGCTTTC

6541 TGTCTGTGAA TGTGTATATA GTGTATTGTG TGTTTAACA AATGATTTAC ACTGACTGTT

6601 GCTGTAAAAG TGAATTTGGA AATAAAGTTA TTACTCTGAT TAAA.
```

The corresponding amino acid sequence of human Tau 35 protein isoform 6 can be found at NP_001116538.2:

```
                                                          (SEQ ID NO: 50)
  1 MAEPRQEFEV MEDHAGTYGL GDRKDQGGYT MHQDQEGDTD AGLKESPLQT PTEDGSEEPG

61 SETSDAKSTP TAEDVTAPLV DEGAPGKQAA AQPHTEIPEG TTAEEAGIGD TPSLEDEAAG

121 HVTQEPESGK VVQEGFLREP GPPGLSHQLM SGMPGAPLLP EGPREATRQP SGTGPEDTEG

181 GRHAPELLKH QLLGDLHQEG PPLKGAGGKE RPGSKEEVDE DRDVDESSPQ DSPPSKASPA

241 QDGRPPQTAA REATSIPGFP AEGAIPLPVD FLSKVSTEIP ASEPDGPSVG RAKGQDAPLE

301 FTFHVEITPN VQKEQAHSEE HLGRAAFPGA PGEGPEARGP SLGEDTKEAD LPEPSEKQPA

361 AAPRGKPVSR VPQLKARMVS KSKDGTGSDD KKAKTSTRSS AKTLKNRPCL SPKHPTPGSS

421 DPLIQPSSPA VCPEPPSSPK YVSSVTSRTG SSGAKEMKLK GADGKTKIAT PRGAAPPGQK

481 GQANATRIPA KTPPAPKTPP SSATKQVQRR PPPAGPRSER GEPPKSGDRS GYSSPGSPGT

541 PGSRSRTPSL PTPPTREPKK VAVVRTPPKS PSSAKSRLQT APVPMPDLKN VKSKIGSTEN

601 LKHQPGGGKV QIINKKLDLS NVQSKCGSKD NIKHVPGGGS VQIVYKPVDL SKVTSKCGSL

661 GNIHHKPGGG QVEVKSEKLD FKDRVQSKIG SLDNITHVPG GGNKKIETHK LTFRENAKAK

721 TDHGAEIVYK SPVVSGDTSP RHLSNVSSTG SIDMVDSPQL ATLADEVSAS LAKQGL.
```

The nucleotide sequence of a human MAPT transcript variant 5 (encoding 1N4R Tau) can be found at NM_001123067.4:

```
                                                        (SEQ ID NO: 51)
   1 GCAGTCACCG CCACCCACCA GCTCCGGCAC CAACAGCAGC GCCGCTGCCA CCGCCCACCT

61 TCTGCCGCCG CCACCACAGC CACCTTCTCC TCCTCCGCTG TCCTCTCCCG TCCTCGCCTC

121 TGTCGACTAT CAGGTGAACT TTGAACCAGG ATGGCTGAGC CCCGCCAGGA GTTCGAAGTG

181 ATGGAAGATC ACGCTGGGAC GTACGGGTTG GGGGACAGGA AGATCAGGG GGGCTACACC

241 ATGCACCAAG ACCAAGAGGG TGACACGGAC GCTGGCCTGA AGAATCTCC CCTGCAGACC

301 CCCACTGAGG ACGGATCTGA GGAACCGGGC TCTGAAACCT CTGATGCTAA GAGCACTCCA

361 ACAGCGGAAG CTGAAGAAGC AGGCATTGGA GACACCCCA GCCTGGAAGA CGAAGCTGCT

421 GGTCACGTGA CCCAAGCTCG CATGGTCAGT AAAAGCAAAG ACGGGACTGA AGCGATGAC

481 AAAAAAGCCA AGGGGGCTGA TGGTAAAACG AAGATCGCCA CACCGCGGGG AGCAGCCCCT

541 CCAGGCCAGA AGGGCCAGGC CAACGCCACC AGGATTCCAG CAAAAACCCC GCCCGCTCCA

601 AAGACACCAC CCAGCTCTGG TGAACCTCCA AAATCAGGGG ATCGCAGCGG CTACAGCAGC

661 CCCGGCTCCC CAGGCACTCC CGGCAGCCGC TCCCGCACCC CGTCCCTTCC AACCCCACCC

721 ACCCGGGAGC CAAGAAGGT GGCAGTGGTC CGTACTCCAC CCAAGTCGCC GTCTTCCGCC

781 AAGAGCCGCC TGCAGACAGC CCCCGTGCCC ATGCCAGACC TGAAGAATGT CAAGTCCAAG

841 ATCGGCTCCA CTGAGAACCT GAAGCACCAG CCGGGAGGCG GAAGGTGCA GATAATTAAT

901 AAGAAGCTGG ATCTTAGCAA CGTCCAGTCC AAGTGTGGCT CAAAGGATAA TATCAAACAC

961 GTCCCGGGAG GCGGCAGTGT GCAAATAGTC TACAAACCAG TTGACCTGAG CAAGGTGACC

1021 TCCAAGTGTG GCTCATTAGG CAACATCCAT CATAAACCAG GAGGTGGCCA GGTGGAAGTA

1081 AAATCTGAGA AGCTTGACTT CAAGGACAGA GTCCAGTCGA AGATTGGGTC CCTGGACAAT

1141 ATCACCCACG TCCCTGGCGG AGGAAATAAA AAGATTGAAA CCCACAAGCT GACCTTCCGC

1201 GAGAACGCCA AAGCCAAGAC AGACCACGGG GCGGAGATCG TGTACAAGTC GCCAGTGGTG

1261 TCTGGGGACA CGTCTCCACG GCATCTCAGC AATGTCTCCT CCACCGGCAG CATCGACATG

1321 GTAGACTCGC CCCAGCTCGC CACGCTAGCT GACGAGGTGT CTGCCTCCCT GGCCAAGCAG

1381 GGTTTGTGAT CAGGCCCCTG GGCGGTCAA TAATTGTGGA GAGGAGAGAA TGAGAGAGTG

1441 TGGAAAAAAA AAGAATAATG ACCCGGCCCC CGCCCTCTGC CCCCAGCTGC TCCTCGCAGT

1501 TCGGTTAATT GGTTAATCAC TTAACCTGCT TTTGTCACTC GGCTTTGGCT CGGGACTTCA

1561 AAATCAGTGA TGGGAGTAAG AGCAAATTTC ATCTTTCCAA ATTGATGGGT GGGCTAGTAA

1621 TAAAATATTT AAAAAAAAAC ATTCAAAAAC ATGGCCACAT CCAACATTTC CTCAGGCAAT

1681 TCCTTTTGAT TCTTTTTTCT TCCCCCTCCA TGTAGAAGAG GGAGAAGGAG AGGCTCTGAA

1741 AGCTGCTTCT GGGGGATTTC AAGGGACTGG GGGTGCCAAC CACCTCTGGC CCTGTTGTGG

1801 GGGTGTCACA GAGGCAGTGG CAGCAACAAA GGATTTGAAA CTTGGTGTGT TCGTGGAGCC

1861 ACAGGCAGAC GATGTCAACC TTGTGTGAGT GTGACGGGG TTGGGGTGGG GCGGGAGGCC

1921 ACGGGGAGG CCGAGGCAGG GGCTGGGCAG AGGGAGAGG AAGCACAAGA AGTGGGAGTG

1981 GGAGAGGAAG CCACGTGCTG GAGAGTAGAC ATCCCCCTCC TTGCCGCTGG GAGAGCCAAG

2041 GCCTATGCCA CCTGCAGCGT CTGAGCGGCC GCCTGTCCTT GGTGGCCGGG GGTGGGGGCC

2101 TGCTGTGGGT CAGTGTGCCA CCCTCTGCAG GGCAGCCTGT GGGAGAAGGG ACAGCGGGTA

2161 AAAAGAGAAG GCAAGCTGGC AGGAGGGTGG CACTTCGTGG ATGACCTCCT TAGAAAAGAC

2221 TGACCTTGAT GTCTTGAGAG CGCTGGCCTC TTCCTCCCTC CCTGCAGGGT AGGGGGCCTG
```

```
2281  AGTTGAGGGG CTTCCCTCTG CTCCACAGAA ACCCTGTTTT ATTGAGTTCT GAAGGTTGGA

2341  ACTGCTGCCA TGATTTTGGC CACTTTGCAG ACCTGGGACT TTAGGGCTAA CCAGTTCTCT

2401  TTGTAAGGAC TTGTGCCTCT TGGGAGACGT CCACCCGTTT CCAAGCCTGG GCCACTGGCA

2461  TCTCTGGAGT GTGTGGGGGT CTGGGAGGCA GGTCCCGAGC CCCTGTCCT TCCCACGGCC

2521  ACTGCAGTCA CCCCGTCTGC GCCGCTGTGC TGTTGTCTGC CGTGAGAGCC CAATCACTGC

2581  CTATACCCCT CATCACACGT CACAATGTCC CGAATTCCCA GCCTCACCAC CCCTTCTCAG

2641  TAATGACCCT GGTTGGTTGC AGGAGGTACC TACTCCATAC TGAGGGTGAA ATTAAGGGAA

2701  GGCAAAGTCC AGGCACAAGA GTGGGACCCC AGCCTCTCAC TCTCAGTTCC ACTCATCCAA

2761  CTGGGACCCT CACCACGAAT CTCATGATCT GATTCGGTTC CCTGTCTCCT CCTCCCGTCA

2821  CAGATGTGAG CCAGGGCACT GCTCAGCTGT GACCCTAGGT GTTTCTGCCT TGTTGACATG

2881  GAGAGAGCCC TTTCCCCTGA GAAGGCCTGG CCCCTTCCTG TGCTGAGCCC ACAGCAGCAG

2941  GCTGGGTGTC TTGGTTGTCA GTGGTGGCAC CAGGATGGAA GGGCAAGGCA CCCAGGGCAG

3001  GCCCACAGTC CCGCTGTCCC CCACTTGCAC CCTAGCTTGT AGCTGCCAAC CTCCCAGACA

3061  GCCCAGCCCG CTGCTCAGCT CCACATGCAT AGTATCAGCC CTCCACACCC GACAAAGGGG

3121  AACACACCCC CTTGGAAATG GTTCTTTTCC CCCAGTCCCA GCTGGAAGCC ATGCTGTCTG

3181  TTCTGCTGGA GCAGCTGAAC ATATACATAG ATGTTGCCCT GCCCTCCCCA TCTGCACCCT

3241  GTTGAGTTGT AGTTGGATTT GTCTGTTTAT GCTTGGATTC ACCAGAGTGA CTATGATAGT

3301  GAAAAGAAAA AAAAAAAAAA AAAAGGACGC ATGTATCTTG AAATGCTTGT AAAGAGGTTT

3361  CTAACCCACC CTCACGAGGT GTCTCTCACC CCCACACTGG GACTCGTGTG GCCTGTGTGG

3421  TGCCACCCTG CTGGGGCCTC CCAAGTTTTG AAAGGCTTTC CTCAGCACCT GGGACCCAAC

3481  AGAGACCAGC TTCTAGCAGC TAAGGAGGCC GTTCAGCTGT GACGAAGGCC TGAAGCACAG

3541  GATTAGGACT GAAGCGATGA TGTCCCCTTC CCTACTTCCC CTTGGGGCTC CCTGTGTCAG

3601  GGCACAGACT AGGTCTTGTG GCTGGTCTGG CTTGCGGCGC GAGGATGGTT CTCTCTGGTC

3661  ATAGCCCGAA GTCTCATGGC AGTCCCAAAG GAGGCTTACA ACTCCTGCAT CACAAGAAAA

3721  AGGAAGCCAC TGCCAGCTGG GGGGATCTGC AGCTCCCAGA AGCTCCGTGA GCCTCAGCCA

3781  CCCCTCAGAC TGGGTTCCTC TCCAAGCTCG CCCTCTGGAG GGGCAGCGCA GCCTCCCACC

3841  AAGGGCCCTG CGACCACAGC AGGGATTGGG ATGAATTGCC TGTCCTGGAT CTGCTCTAGA

3901  GGCCCAAGCT GCCTGCCTGA GGAAGGATGA CTTGACAAGT CAGGAGACAC TGTTCCCAAA

3961  GCCTTGACCA GAGCACCTCA GCCCGCTGAC CTTGCACAAA CTCCATCTGC TGCCATGAGA

4021  AAAGGGAAGC CGCCTTTGCA AAACATTGCT GCCTAAAGAA ACTCAGCAGC CTCAGGCCCA

4081  ATTCTGCCAC TTCTGGTTTG GGTACAGTTA AAGGCAACCC TGAGGGACTT GGCAGTAGAA

4141  ATCCAGGGCC TCCCCTGGGG CTGGCAGCTT CGTGTGCAGC TAGAGCTTTA CCTGAAAGGA

4201  AGTCTCTGGG CCCAGAACTC TCCACCAAGA GCCTCCCTGC CGTTCGCTGA GTCCCAGCAA

4261  TTCTCCTAAG TTGAAGGGAT CTGAGAAGGA GAAGGAAATG TGGGGTAGAT TTGGTGGTGG

4321  TTAGAGATAT GCCCCCCTCA TTACTGCCAA CAGTTTCGGC TGCATTTCTT CACGCACCTC

4381  GGTTCCTCTT CCTGAAGTTC TTGTGCCCTG CTCTTCAGCA CCATGGGCCT TCTTATACGG

4441  AAGGCTCTGG GATCTCCCCC TTGTGGGGCA GGCTCTTGGG GCCAGCCTAA GATCATGGTT

4501  TAGGGTGATC AGTGCTGGCA GATAAATTGA AAAGGCACGC TGGCTTGTGA TCTTAAATGA

4561  GGACAATCCC CCCAGGGCTG GGCACTCCTC CCCTCCCCTC ACTTCTCCCA CCTGCAGAGC

4621  CAGTGTCCTT GGGTGGGCTA GATAGGATAT ACTGTATGCC GGCTCCTTCA AGCTGCTGAC
```

```
4681 TCACTTTATC AATAGTTCCA TTTAAATTGA CTTCAGTGGT GAGACTGTAT CCTGTTTGCT

4741 ATTGCTTGTT GTGCTATGGG GGGAGGGGGG AGGAATGTGT AAGATAGTTA ACATGGGCAA

4801 AGGGAGATCT TGGGGTGCAG CACTTAAACT GCCTCGTAAC CCTTTTCATG ATTTCAACCA

4861 CATTTGCTAG AGGGAGGGAG CAGCCACGGA GTTAGAGGCC CTTGGGGTTT CTCTTTTCCA

4921 CTGACAGGCT TTCCCAGGCA GCTGGCTAGT TCATTCCCTC CCCAGCCAGG TGCAGGCGTA

4981 GGAATATGGA CATCTGGTTG CTTTGGCCTG CTGCCCTCTT TCAGGGGTCC TAAGCCCACA

5041 ATCATGCCTC CCTAAGACCT TGGCATCCTT CCCTCTAAGC CGTTGGCACC TCTGTGCCAC

5101 CTCTCACACT GGCTCCAGAC ACACAGCCTG TGCTTTTGGA GCTGAGATCA CTCGCTTCAC

5161 CCTCCTCATC TTTGTTCTCC AAGTAAAGCC ACGAGGTCGG GGCGAGGGCA GAGGTGATCA

5221 CCTGCGTGTC CCATCTACAG ACCTGCAGCT TCATAAAACT TCTGATTTCT CTTCAGCTTT

5281 GAAAAGGGTT ACCCTGGGCA CTGGCCTAGA GCCTCACCTC CTAATAGACT TAGCCCCATG

5341 AGTTTGCCAT GTTGAGCAGG ACTATTTCTG GCACTTGCAA GTCCCATGAT TTCTTCGGTA

5401 ATTCTGAGGG TGGGGGGAGG GACATGAAAT CATCTTAGCT TAGCTTTCTG TCTGTGAATG

5461 TCTATATAGT GTATTGTGTG TTTTAACAAA TGATTTAGAC TGACTGTTGC TGTAAAAGTG

5521 AATTTGGAAA TAAAGTTATT ACTCTGATTA AA.
```

The corresponding amino acid sequence of human Tau protein isoform 5 can be found at NP_001116539.1:

```
                                                         (SEQ ID NO: 52)
  1 MAEPRQEFEV MEDHAGTYGL GDRKDQGGYT MHQDQEGDTD AGLKESPLQT PTEDGSEEPG

61 SETSDAKSTP TAEAEEAGIG DTPSLEDEAA GHVTQARMVS KSKDGTGSDD KKAKGADGKT

121 KIATPRGAAP PGQKGQANAT RIPAKTPPAP KTPPSSGEPP KSGDRSGYSS PGSPGTPGSR

181 SRTPSLPTPP TREPKKVAVV RTPPKSPSSA KSRLQTAPVP MPDLKNVKSK IGSTENLKHQ

241 PGGGKVQIIN KKLDLSNVQS KCGSKDNIKH VPGGGSVQIV YKPVDLSKVT SKCGSLGNIH

301 HKPGGGQVEV KSEKLDFKDR VQSKIGSLDN ITHVPGGGNK KIETHKLTFR ENAKAKTDHG

361 AEIVYKSPVV SGDTSPRHLS NVSSTGSIDM VDSPQLATLA DEVSASLAKQ GL.
```

The nucleotide sequence of the human MAPT transcript variant 4 (encoding 0N3R Tau) can be found at NM 016841.5:

```
                                                         (SEQ ID NO: 53)
  1 GCAGTCACCG CCACCCACCA GCTCCGGCAC CAACAGCAGC GCCGCTGCCA CCGCCCACCT

61 TCTGCCGCCG CCACCACAGC CACCTTCTCC TCCTCCGCTG TCCTCTCCCG TCCTCGCCTC

121 TGTCGACTAT CAGGTGAACT TTGAACCAGG ATGGCTGAGC CCGCCAGGA GTTCGAAGTG

181 ATGGAAGATC ACGCTGGGAC GTACGGGTTG GGGGACAGGA AGATCAGGG GGGCTACACC

241 ATGCACCAAG ACCAAGAGGG TGACACGGAC GCTGGCCTGA AGCTGAAGA AGCAGGCATT

301 GGAGACACCC CCAGCCTGGA AGACGAAGCT GCTGGTCACG TGACCCAAGC TCGCATGGTC

361 AGTAAAAGCA AAGACGGGAC TGGAAGCGAT GACAAAAAAG CCAAGGGGGC TGATGGTAAA

421 ACGAAGATCG CCACACCGCG GGGAGCAGCC CCTCCAGGCC AGAAGGGCCA GGCCAACGCC

481 ACCAGGATTC CAGCAAAAAC CCCGCCCGCT CCAAAGACAC CACCCAGCTC TGGTGAACCT

541 CCAAAATCAG GGGATCGCAG CGGCTACAGC AGCCCCGGCT CCCCAGGCAC TCCCGGCAGC

601 CGCTCCCGCA CCCCGTCCCT TCCAACCCCA CCCACCCGGG AGCCCAAGAA GGTGGCAGTG

661 GTCCGTACTC CACCCAAGTC GCCGTCTTCC GCCAAGAGCC GCCTGCAGAC AGCCCCCGTG
```

```
 721 CCCATGCCAG ACCTGAAGAA TGTCAAGTCC AAGATCGGCT CCACTGAGAA CCTGAAGCAC
 781 CAGCCGGGAG GCGGGAAGGT GCAAATAGTC TACAAACCAG TTGACCTGAG CAAGGTGACC
 841 TCCAAGTGTG GCTCATTAGG CAACATCCAT CATAAACCAG GAGGTGGCCA GGTGGAAGTA
 901 AAATCTGAGA AGCTTGACTT CAAGGACAGA GTCCAGTCGA AGATTGGGTC CCTGGACAAT
 961 ATCACCCACG TCCCTGGCGG AGGAAATAAA AAGATTGAAA CCCACAAGCT GACCTTCCGC
1021 GAGAACGCCA AAGCCAAGAC AGACCACGGG GCGGAGATCG TGTACAAGTC GCCAGTGGTG
1081 TCTGGGGACA CGTCTCCACG GCATCTCAGC AATGTCTCCT CCACCGGCAG CATCGACATG
1141 GTAGACTCGC CCCAGCTCGC CACGCTAGCT GACGAGGTGT CTGCCTCCCT GGCCAAGCAG
1201 GGTTTGTGAT CAGGCCCCTG GGGCGGTCAA TAATTGTGGA GAGGAGAGAA TGAGAGAGTG
1261 TGGAAAAAAA AAGAATAATG ACCCGGCCCC CGCCCTCTGC CCCCAGCTGC TCCTCGCAGT
1321 TCGGTTAATT GGTTAATCAC TTAACCTGCT TTTGTCACTC GGCTTTGGCT CGGGACTTCA
1381 AAATCAGTGA TGGGAGTAAG AGCAAATTTC ATCTTTCCAA ATTGATGGGT GGGCTAGTAA
1441 TAAAATATTT AAAAAAAAAC ATTCAAAAAC ATGGCCACAT CGAACATTTC CTCAGGCAAT
1501 TCCTTTTGAT TCTTTTTTCT TCCCCCTCCA TGTAGAAGAG GGAGAAGGAG AGGCTCTGAA
1561 AGCTGCTTCT GGGGGATTTC AAGGGACTGG GGGTGCCAAC CACCTCTGGC CCTGTTGTGG
1621 GGGTGTCACA GAGGCAGTGG CAGCAACAAA GGATTTGAAA CTTGGTGTGT TCGTGGAGCC
1681 ACAGGCAGAC GATGTCAACC TTGTGTGAGT GTGACGGGGG TTGGGGTGGG GCGGGAGGCC
1741 ACGGGGGAGG CCGAGGCAGG GGCTGGGCAG AGGGGAGAGG AAGCACAAGA AGTGGGAGTG
1801 GGAGAGGAAG CCACGTGCTG GAGAGTAGAC ATCCCCCTCC TTGCCGCTGG GAGAGCCAAG
1861 GCCTATGCCA CCTGCAGCGT CTGAGCGGCC GCCTGTCCTT GGTGGCCGGG GGTGGGGGCC
1921 TGCTGTGGGT CAGTGTGCCA CCCTCTGCAG GGCAGCCTGT GGGAGAAGGG ACAGCGGGTA
1981 AAAAGAGAAG GCAAGCTGGC AGGAGGGTGG CACTTCGTGG ATGACCTCCT TAGAAAAGAC
2041 TGACCTTGAT GTCTTGAGAG CGCTGGCCTC TTCCTCCCTC CCTGCAGGGT AGGGGGCCTG
2101 AGTTGAGGGG CTTCCCTCTG CTCCACAGAA ACCCTGTTTT ATTGAGTTCT GAAGGTTGGA
2161 ACTGCTGCCA TGATTTTGGC CACTTTGCAG ACCTGGGACT TTAGGGCTAA CCAGTTCTCT
2221 TTGTAAGGAC TTGTGCCTCT TGGGAGACGT CCACCCGTTT CCAAGCCTGG GCCACTGGCA
2281 TCTCTGGAGT GTGTGGGGGT CTGGAGGCA GGTCCCGAGC CCCCTGTCCT TCCCACGGCC
2341 ACTGCAGTCA CCCCGTCTGC GCCGCTGTGC TGTTGTCTGC CGTGAGAGCC CAATCACTGC
2401 CTATACCCCT CATCACACGT CACAATGTCC CGAATTCCCA GCCTCACCAC CCCTTCTCAG
2461 TAATGACCCT GGTTGGTTGC AGGAGGTACC TACTCCATAC TGAGGGTGAA ATTAAGGGAA
2521 GGCAAAGTCC AGGCACAAGA GTGGGACCCC AGCCTCTCAC TCTCAGTTCC ACTCATCCAA
2581 CTGGGACCCT CACCACGAAT CTCATGATCT GATTCGGTTC CCTGTCTCCT CCTCCCGTCA
2641 CAGATGTGAG CCAGGGCACT GCTCAGCTGT GACCCAGGT GTTTCTGCCT TGTTGACATG
2701 GAGAGAGCCC TTTCCCCTGA GAAGGCCTGG CCCCTTCCTG TGCTGAGCCC ACAGCAGCAG
2761 GCTGGGTGTC TTGGTTGTCA GTGGTGGCAC CAGGATGGAA GGGCAAGGCA CCCAGGGCAG
2821 GCCCACAGTC CCGCTGTCCC CCACTTGCAC CCTAGCTTGT AGCTGCCAAC CTCCCAGACA
2881 GCCCAGCCCG CTGCTCAGCT CCACATGCAT AGTATCAGCC CTCCACACCC GACAAAGGGG
2941 AACACACCCC CTTGGAAATG GTTCTTTTCC CCCAGTCCCA GCTGGAAGCC ATGCTGTCTG
3001 TTCTGCTGGA GCAGCTGAAC ATATACATAG ATGTTGCCCT GCCCTCCCCA TCTGCACCCT
3061 GTTGAGTTGT AGTTGGATTT GTCTGTTTAT GCTTGGATTC ACCAGAGTGA CTATGATAGT
```

-continued

```
3121 GAAAAGAAAA AAAAAAAAAA AAAAGGACGC ATGTATCTTG AAATGCTTGT AAAGAGGTTT
3181 CTAACCCACC CTCACGAGGT GTCTCTCACC CCCACACTGG GACTCGTGTG GCCTGTGTGG
3241 TGCCACCCTG CTGGGGCCTC CCAAGTTTTG AAAGGCTTTC CTCAGCACCT GGGACCCAAC
3301 AGAGACCAGC TTCTAGCAGC TAAGGAGGCC GTTCAGCTGT GACGAAGGCC TGAAGCACAG
3361 GATTAGGACT GAAGCGATGA TGTCCCCTTC CCTACTTCCC CTTGGGGCTC CCTGTGTCAG
3421 GGCACAGACT AGGTCTTGTG GCTGGTCTGG CTTGCGGCGC GAGGATGGTT CTCTCTGGTC
3481 ATAGCCCGAA GTCTCATGGC AGTCCCAAAG GAGGCTTACA ACTCCTGCAT CACAAGAAAA
3541 AGGAAGCCAC TGCCAGCTGG GGGGATCTGC AGCTCCCAGA AGCTCCGTGA GCCTCAGCCA
3601 CCCCTCAGAC TGGGTTCCTC TCCAAGCTCG CCCTCTGGAG GGGCAGCGCA GCCTCCCACC
3661 AAGGGCCCTG CGACCACAGC AGGGATTGGG ATGAATTGCC TGTCCTGGAT CTGCTCTAGA
3721 GGCCCAAGCT GCCTGCCTGA GGAAGGATGA CTTGACAAGT CAGGAGACAC TGTTCCCAAA
3781 GCCTTGACCA GAGCACCTCA GCCCGCTGAC CTTGCACAAA CTCCATCTGC TGCCATGAGA
3841 AAAGGGAAGC CGCCTTTGCA AACATTGCT GCCTAAAGAA ACTCAGCAGC CTCAGGCCCA
3901 ATTCTGCCAC TTCTGGTTTG GGTACAGTTA AAGGCAACCC TGAGGGACTT GGCAGTAGAA
3961 ATCCAGGGCC TCCCCTGGGG CTGGCAGCTT CGTGTGCAGC TAGAGCTTTA CCTGAAAGGA
4021 AGTCTCTGGG CCCAGAACTC TCCACCAAGA GCCTCCCTGC CGTTCGCTGA GTCCCAGCAA
4081 TTCTCCTAAG TTGAAGGGAT CTGAGAAGGA GAAGGAAATG TGGGGTAGAT TTGGTGGTGG
4141 TTAGAGATAT GCCCCCCTCA TTACTGCCAA CAGTTTCGGC TGCATTTCTT CACGCACCTC
4201 GGTTCCTCTT CCTGAAGTTC TTGTGCCCTG CTCTTCAGCA CCATGGGCCT TCTTATACGG
4261 AAGGCTCTGG GATCTCCCCC TTGTGGGGCA GGCTCTTGGG GCCAGCCTAA GATCATGGTT
4321 TAGGGTGATC AGTGCTGGCA GATAAATTGA AAAGGCACGC TGGCTTGTGA TCTTAAATGA
4381 GGACAATCCC CCCAGGGCTG GGCACTCCTC CCCTCCCCTC ACTTCTCCCA CCTGCAGAGC
4441 CAGTGTCCTT GGGTGGGCTA GATAGGATAT ACTGTATGCC GGCTCCTTCA AGCTGCTGAC
4501 TCACTTTATC AATAGTTCCA TTTAAATTGA CTTCAGTGGT GAGACTGTAT CCTGTTTGCT
4561 ATTGCTTGTT GTGCTATGGG GGGAGGGGGG AGGAATGTGT AAGATAGTTA ACATGGGCAA
4621 AGGGAGATCT TGGGGTGCAG CACTTAAACT GCCTCGTAAC CCTTTTCATG ATTTCAACCA
4681 CATTTGCTAG AGGGAGGGAG CAGCCACGGA GTTAGAGGCC CTTGGGGTTT CTCTTTTCCA
4741 CTGACAGGCT TTCCCAGGCA GCTGGCTAGT TCATTCCCTC CCCAGCCAGG TGCAGGCGTA
4801 GGAATATGGA CATCTGGTTG CTTTGGCCTG CTGCCCTCTT TCAGGGGTCC TAAGCCCACA
4861 ATCATGCCTC CCTAAGACCT TGGCATCCTT CCCTCTAAGC CGTTGGCACC TCTGTGCCAC
4921 CTCTCACACT GGCTCCAGAC ACACAGCCTG TGCTTTTGGA GCTGAGATCA CTCGCTTCAC
4981 CCTCCTCATC TTTGTTCTCC AAGTAAAGCC ACGAGGTCGG GGCGAGGGCA GAGGTGATCA
5041 CCTGCGTGTC CCATCTACAG ACCTGCAGCT TCATAAAACT TCTGATTTCT CTTCAGCTTT
5101 GAAAAGGGTT ACCCTGGGCA CTGGCCTAGA GCCTCACCTC CTAATAGACT TAGCCCCATG
5161 AGTTTGCCAT GTTGAGCAGG ACTATTTCTG GCACTTGCAA GTCCATGAT TTCTTCGGTA
5221 ATTCTGAGGG TGGGGGGAGG GACATGAAAT CATCTTAGCT TAGCTTTCTG TCTGTGAATG
5281 TCTATATAGT GTATTGTGTG TTTTAACAAA TGATTTAGAC TGACTGTTGC TGTAAAAGTG
5341 AATTTGGAAA TAAAGTTATT ACTCTGATTA AA.
```

The corresponding amino acid sequence of human Tau protein isoform 4 can be found at NP 058525.1:

```
                                                        (SEQ ID NO: 54)
  1 MAEPRQEFEV MEDHAGTYGL GDRKDQGGYT MHQDQEGDTD AGLKAEEAGI GDTPSLEDEA

61 AGHVTQARMV SKSKDGTGSD DKKAKGADGK TKIATPRGAA PPGQKGQANA TRIPAKTPPA

121 PKTPPSSGEP PKSGDRSGYS SPGSPGTPGS RSRTPSLPTP PTREPKKVAV VRTPPKSPSS

181 AKSRLQTAPV PMPDLKNVKS KIGSTENLKH QPGGGKVQIV YKPVDLSKVT SKCGSLGNIH

241 HKPGGGQVEV KSEKLDFKDR VQSKIGSLDN ITHVPGGGNK KIETHKLTFR ENAKAKTDHG

301 AEIVYKSPVV SGDTSPRHLS NVSSTGSIDM VDSPQLATLA DEVSASLAKQ GL.
```

As used herein, "subject" means a mammal, including cat, dog, mouse, rat, chimpanzee, ape, monkey, and human. Preferably the subject is a human.

As used herein, "treatment" or "treating" refers to all processes wherein there may be a slowing, controlling, delaying, or stopping of the progression of the disorders or disease disclosed herein, or ameliorating disorder or disease symptoms, but does not necessarily indicate a total elimination of all disorder or disease symptoms. Treatment includes administration of a protein or nucleic acid or vector or composition for treatment of a disease or condition in a patient, particularly in a human.

EXAMPLES

Example 1. Synthesis of Linker-Delivery Moiety Pairs

Certain abbreviations are defined as follows: "ACN" refers to acetonitrile; "AEX" refers to anion exchange; "C/D" refers to cleavage and deprotection; "CPG" refers to controlled pore glass; "DCM" refers to dichloromethane; "DEA" refers to diethylamine; "DIEA" refers to N,N-diisopropylethylamine; "DMAP" refers to 4-dimethylaminopyridine; "DMF" refers to dimethylformamide; "DMSO" refers to dimethyl sulfoxide; "DMTCl" refers to 4,4'-dimethoxytrityl chloride; "ES/MS" refers to electrospray mass spectrometry; "EtOAc" refers to ethyl acetate; "EtOH" refers to ethanol and ethyl alcohol; "HBTU" refers to 3-[bis(dimethylamino)methyliumyl]-3H-benzotriazol-1-oxide hexafluorophosphate; "HOBt" refers to 1-hydroxybenzotriazole; "IP-RP" refers to ion-pair reverse phase; "LCAA CPG" refers to long chain alkylamine controlled pore glass; "LC/MS" refers to liquid chromatography-mass spectrometry; "MeOH" refers to methanol and methyl alcohol; "MPA" refers to mobile phase A; "MPB" refers to mobile phase B; "MWCO" refers to molecular weight cut-off; "NMR" refers to nuclear magnetic resonance; "PBS" phosphate-buffered saline; "PEG" refers to polyethylene glycol; "PVDF" refers to polyvinylidene fluoride; "RP" refers to reverse phase; "RPM" refers to revolutions per minute; "siRNA" refers to small interfering ribonucleic acid; "TEA" refers to triethylamine; "THF" refers to tetrahydrofuran; "TLC" refers to thin line chromatography; "TMP" refers to 2,2,6,6-tetramethylpiperidine; "UPLC" refers to ultra-performance liquid chromatography; and "UV" refers to ultraviolet.

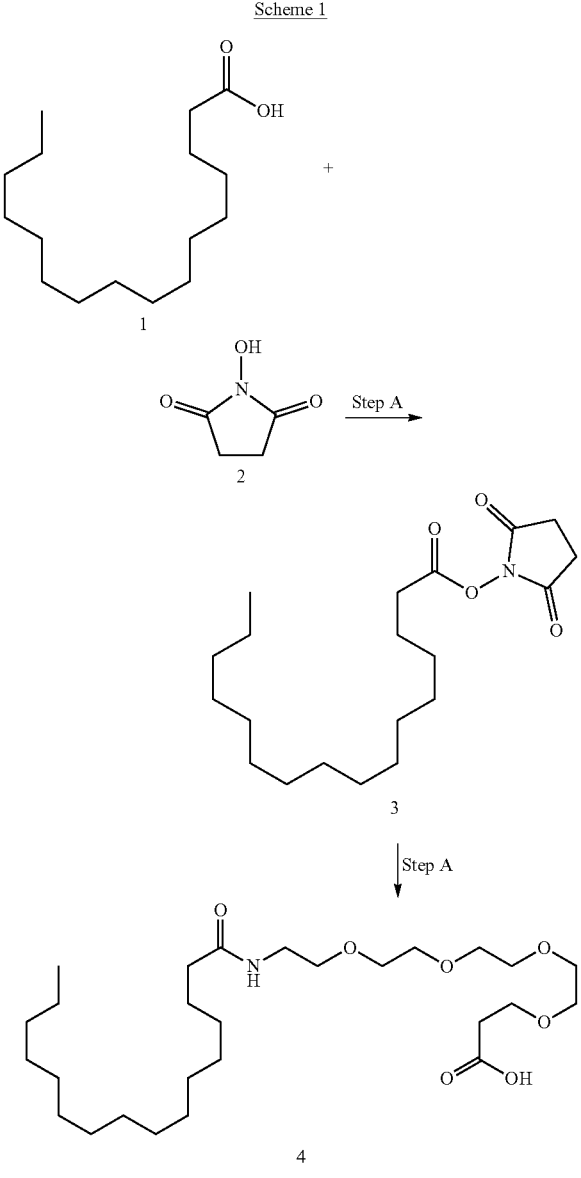

Scheme 1

Scheme 1, step A depicts the coupling of compounds (1) and (2) using an appropriate base such as DMAP in a suitable solvent such as DCM to give compound (3). Step B shows the coupling of compound (3) with 1-amino-3,6,9,12-tetraoxapentadecan-15-oic acid in the presence of a base such as potassium carbonate and in a solvent system such as water and THF to give compound (4).

Scheme 2
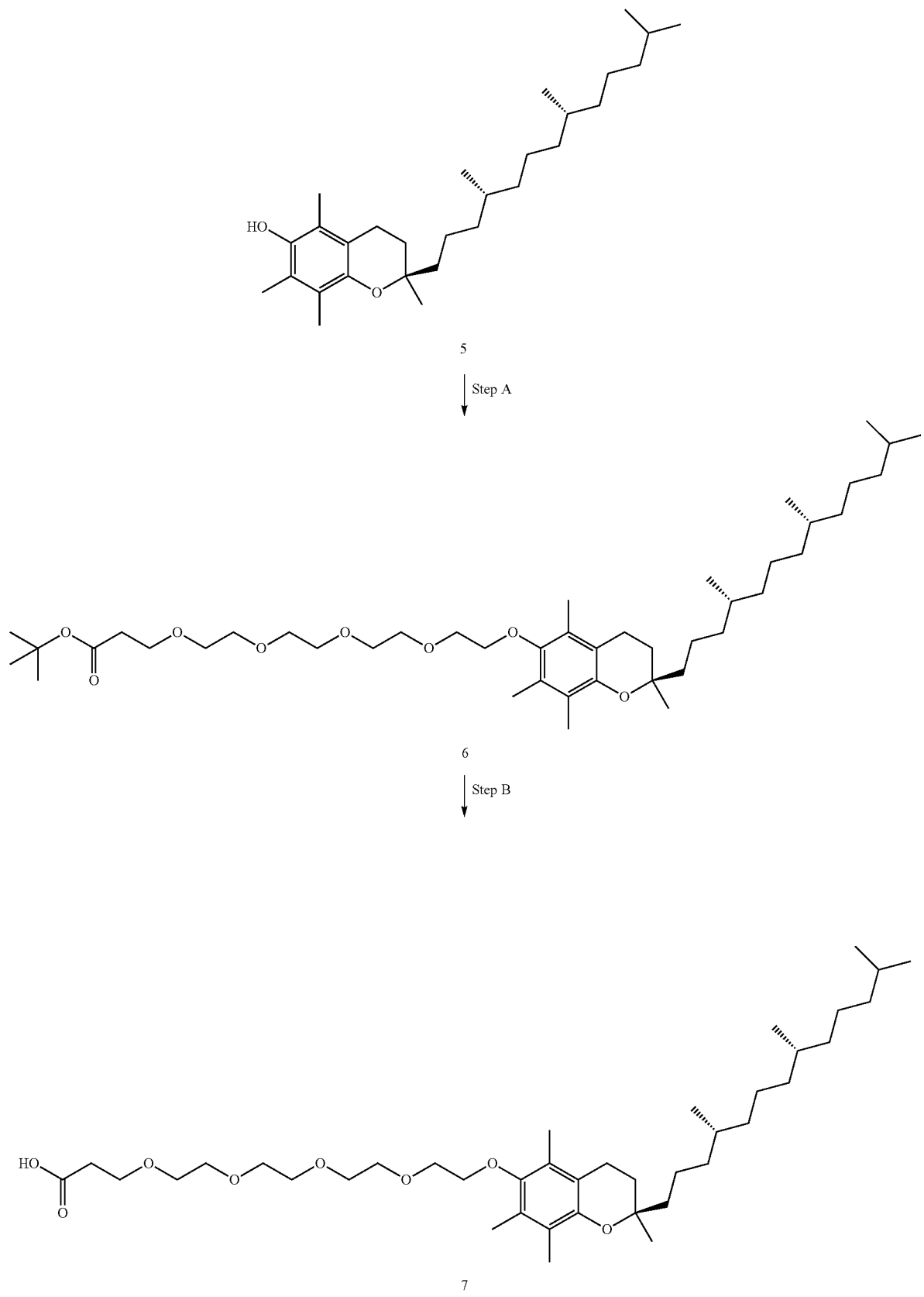

Scheme 2, step A depicts a Mitsunobu reaction between compound (5) and tert-butyl 1-hydroxy-3,6,9,12-tetraoxa-pentadecan-15-oate using triphenyl phosphene and diisopropyl azodicarboxylate in a solvent such as THF to give compound (6). Step B shows the acidic deprotection of compound (6) using an acid such as HCl in a solvent such as 1,4-dioxane to give compound (7).

Scheme 3

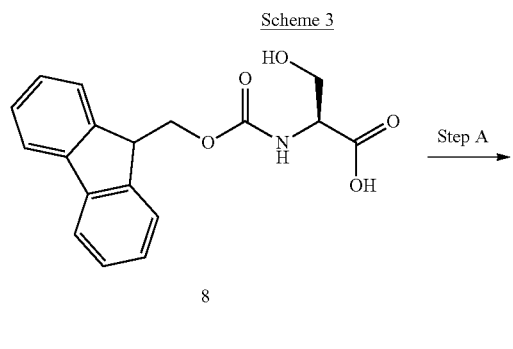

8

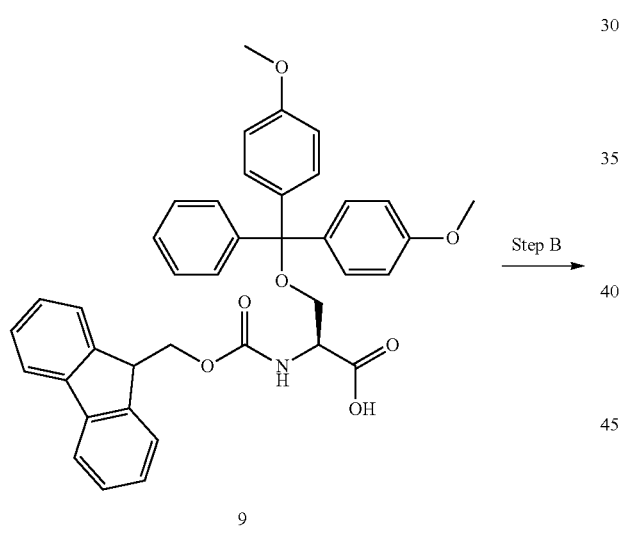

9

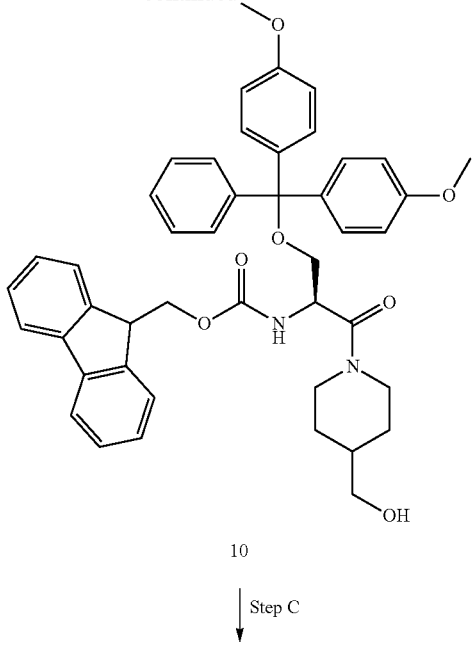

10

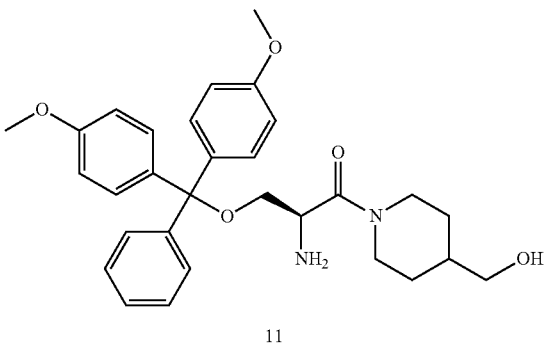 [SMILES: COc1ccc(C(OC[C@H](N)C(=O)N2CCC(CO)CC2)(c2ccccc2)c2ccc(OC)cc2)cc1]

11

Scheme 3, step A depicts the protection of compound (8) using DMTCl with a suitable base such as DIEA in a solvent such as DCM to give compound (9). Step B shows an amide coupling between compound (9) and piperidin-4-yl methanol using HBTU and HOBt with TMP in a solvent such as DCM to give compound (10). The deprotection of compound (10) with 20% piperidine in DMF to give compound (11) is shown in step C.

Scheme 4

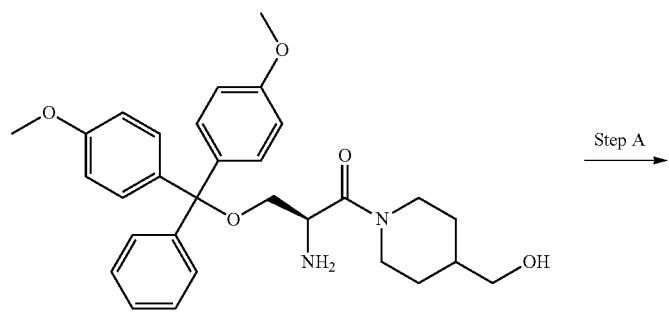

11

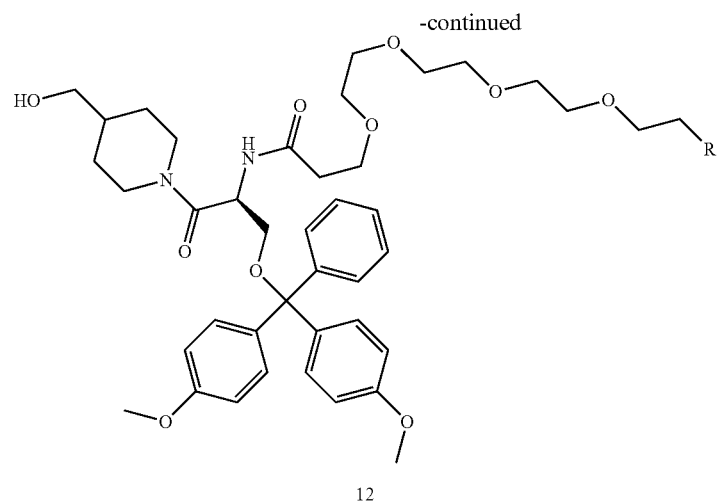
12
Step B
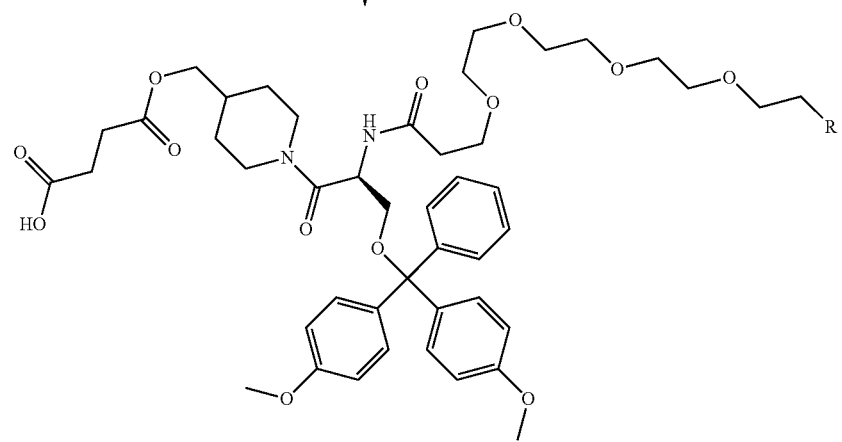
13
Step C
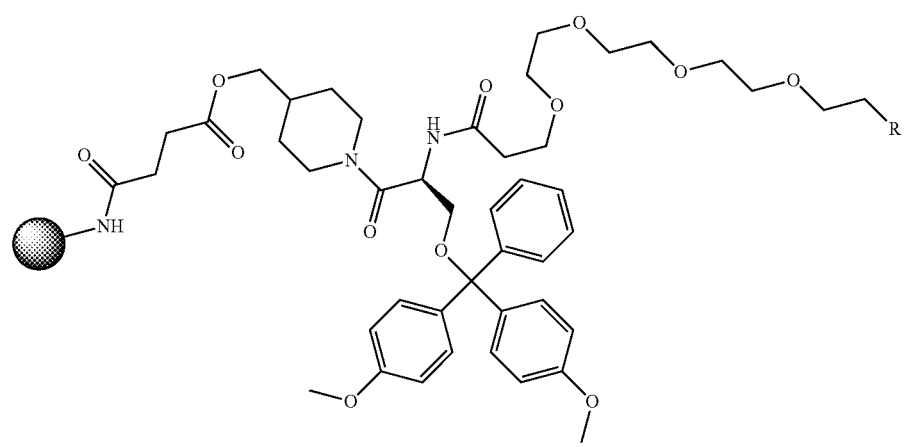
14

Scheme 4, step A depicts an amide coupling between compound (11) and either compound (4) or compound (7) using standard coupling reagents such as HBTU and HOBt with a base such as DIEA in a solvent such as DMF to give compound (12). One skilled in the art will recognize the variety of conditions which could be used to perform this amide coupling. Step B shows the coupling of compound (12) to succinic anhydride using a base such as TEA with catalytic DMAP in a solvent such as DCM to give compound (13). Step C shows the amide coupling of compound (13) to amino LCAA CPG using HBTU with a base such as DIEA in a solvent such as ACN followed by a multistep work up to give compound (14).

Preparation 1

2,5-Dioxopyrrolidin-1-yl palmitate

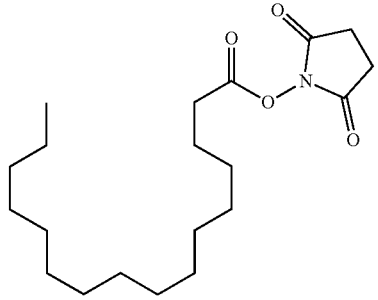 [SMILES: CCCCCCCCCCCCCCCC(=O)ON1C(=O)CCC1=O]

Added palmitic acid (2.00 g, 7.80 mmol) to a solution of 1-(3-dimethylaminopropyl)-3-ethylcarbodiimide hydrochloride (1.79 g, 9.36 mmol) and DMAP (0.19 g, 1.56 mmol) in DCM (31 mL). Stirred the mixture at ambient temperature for 5 minutes then added N-hydroxysuccinimide (0.99 g, 8.58 mmol) and stirred at ambient temperature for 18 hours. Concentrated in vacuo and purified the resulting crude material via silica gel flash chromatography eluting with a gradient of 0-80% EtOAc in hexanes to give the title compound as a white solid (2.65 g, 96%). $^1$H NMR (DMSO-$d_6$) δ 2.81 (s, 4H), 2.66 (t, 2H), 1.62 (m, 2H), 1.25 (br s, 24H), 0.87 (t, 3H).

Preparation 2

3-[2-[2-[2-[2-(Hexadecanoylamino)ethoxy]ethoxy]ethoxy]ethoxy]propanoic acid

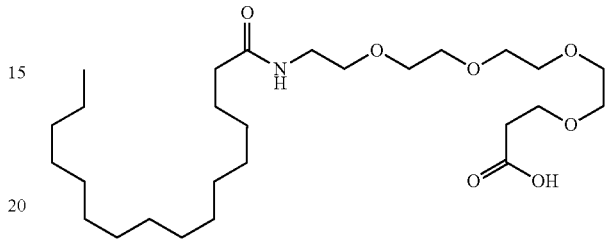

Added 1-amino-3,6,9,12-tetraoxapentadecan-15-oic acid (0.14 g, 0.53 mmol) to a solution of potassium carbonate (0.14 g, 1.00 mmol) in THF (1 mL) and water (2 mL). Added 2,5-dioxopyrrolidin-1-yl palmitate (0.18 g, 0.51 mmol) and stirred the reaction at ambient temperature for 18 hours. Quenched the reaction with water (30 mL) and adjusted the pH to ~3 with 1N aqueous HCl. A precipitate formed and was collected by vacuum filtration to give the title compound as a white solid (0.19 g, 74%). ES/MS m/z 504 (M+H).

Preparation 3 tert-Butyl 3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoate

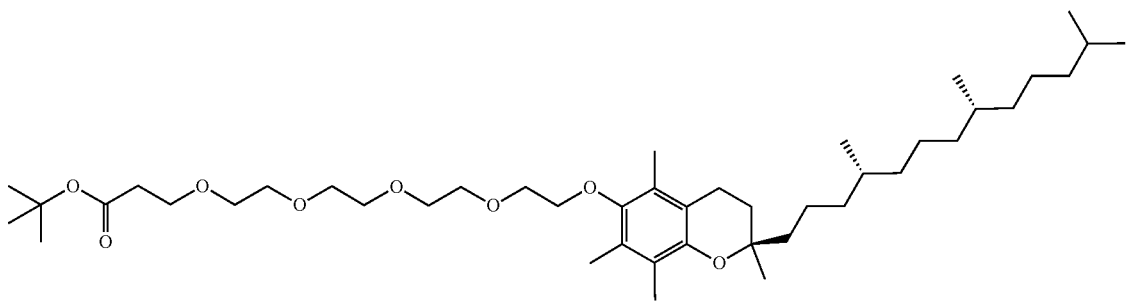 [SMILES: Cc1c(C)c2c(c(C)c1OCCOCCOCCOCCOCCC(=O)OC(C)(C)C)CC[C@@](C)(CCC[C@H](C)CCC[C@H](C)CCCC(C)C)O2]

Combined (2R)-2,5,7,8-tetramethyl-2-[(4R,8R)-4,8,12-trimethyltridecyl]chroman-6-ol (3.00 g, 6.90 mmol), tert-butyl 1-hydroxy-3,6,9,12-tetraoxapentadecan-15-oate (2.50 g, 7.60 mmol), and triphenylphosphine (2.00 g, 7.60 mmol) in THF (28.0 mL) and added diisopropyl azodicarboxylate (1.50 mL, 7.60 mmol) dropwise over 5 minutes. Heated the mixture at 60° C. for 16 hours. Cooled the mixture to ambient temperature, added silica gel, and concentrated in vacuo to give an off-white solid. Purified the mixture via silica gel flash chromatography, eluting with 0-40% EtOAc/hexanes, to give the title compound as an oil (3.33 g, 66%). $^1$H NMR (CDCl$_3$): 3.84 (s, 4H), 3.77-3.71 (m, 13H), 2.59 (t, J=6.8 Hz, 2H), 2.52 (t, J=6.6 Hz, 2H), 2.20-2.20 (m, 3H), 2.15-2.12 (m, 3H), 2.10 (s, 3H), 1.87-1.73 (m, 2H), 1.58-1.51 (m, 4H), 1.47 (s, 9H), 1.35-1.27 (m, 21H), 0.90-0.86 (m, 12H).

Preparation 4

3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoic acid

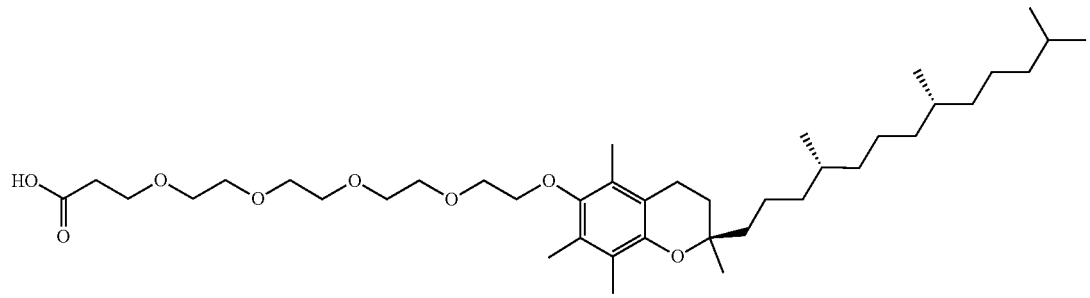 [SMILES: Cc1c(C)c2c(c(C)c1OCCOCCOCCOCCOCCC(=O)O)CC[C@@](C)(CCC[C@H](C)CCC[C@H](C)CCCC(C)C)O2]

Dissolved tert-butyl 3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoate (3.33 g, 4.53 mmol) in 4M HCl in dioxane (22.6 mL, 90.6 mmol) and stirred for 16 hours at ambient temperature. Removed the solvent under reduced pressure to give the title compound as an off-white solid (3.08 g, 100%). ES/MS m/z 678.0 (M−H).

Preparation 5

(2S)-3-[Bis(4-methoxyphenyl)-phenyl-methoxy]-2-(9H-fluoren-9ylmethoxycarbonylamino) propanoic acid

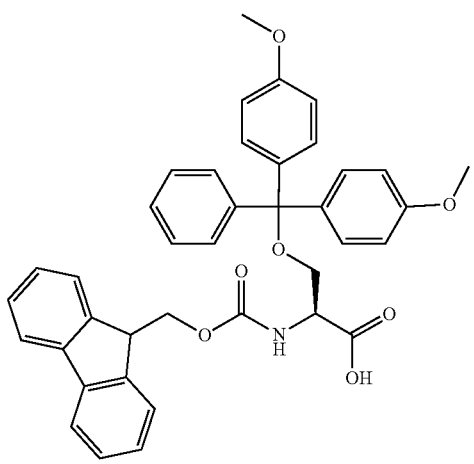 [SMILES: COc1ccc(C(OC[C@H](NC(=O)OCC2c3ccccc3-c3ccccc32)C(=O)O)(c2ccccc2)c2ccc(OC)cc2)cc1]

Added DIEA (64 mL, 0.366 mol) to a stirring solution of (2S)-2-(9H-fluoren-9-ylmethoxycarbonylamino)-3-hydroxy-propanoic acid (40 g, 0.122 mol) in dry DCM (400 mL) at 0° C. under an inert atmosphere. To this mixture, slowly added a solution of DMTCl (49.6 g, 0.146 mol) in DCM (200 mL). Allowed to warm to ambient temperature and stirred for 16 hours. After this time, diluted the reaction mixture with water and extracted with DCM. Dried organics over anhydrous sodium sulphate, filtered, and concentrated in vacuo. Washed the crude residue with 10% EtOAc/hexane and dried under vacuum to give the crude title compound as a pale brown solid (62 g, crude). TLC: 5% MeOH/CH$_2$Cl$_2$ (R$_f$: 0.5) UV, 254 nM.

Preparation 6

9H-Fluoren-9-ylmethyl N-[(1S)-1-[[bis(4-methoxyphenyl)-phenyl-methoxy]methyl]-2-[4-(hydroxymethyl)-1-piperidyl]-2-oxo-ethyl]carbamate

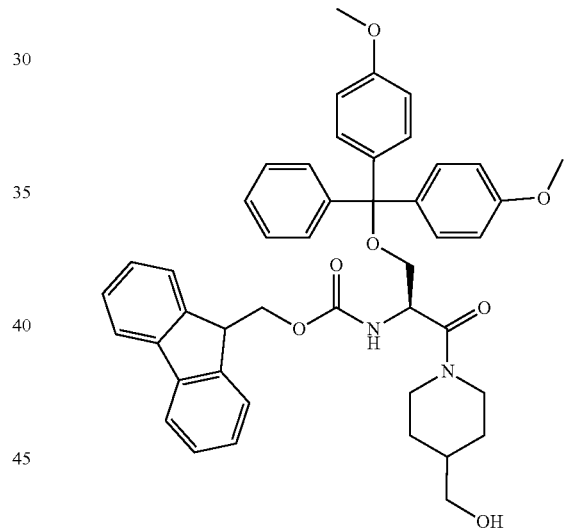

Slowly added HBTU (78.3 g, 0.206 mol), HOBt (27.9 g, 0.206 mol), and piperidin-4-yl methanol (15.4 g, 0.134 mol) followed by TMP (15 mL, 0.113 mol) to a stirring solution of (2S)-3-[bis(4-methoxyphenyl)-phenyl-methoxy]-2-(9H-fluoren-9-ylmethoxycarbonylamino) propanoic acid (62 g, 0.103 mol) in DCM (750 mL) at 0° C. under inert atmosphere. Allowed the resulting reaction mixture to reach ambient temperature and stirred for 4 hours. After this time, diluted the mixture with water and extracted with DCM. Dried the organics over anhydrous sodium sulphate, filtered, and concentrated in vacuo. Purified the resulting residue via silica gel flash chromatography eluting with 20-40% EtOAc/hexane and 1% MeOH/DCM to give the title compound (40 g, 52% over two steps). $^1$H NMR (DMSO-d$_6$) δ 7.88 (br d, J=7.5 Hz, 2H), 7.79-7.59 (m, 3H), 7.45-7.12 (m, 13H), 6.92-6.76 (m, 4H), 4.79-4.44 (m, 2H), 4.32 (br d, J=11.4 Hz, 2H), 4.20 (br s, 2H), 3.71 (s, 6H), 3.21 (br s, 4H), 2.99-2.79 (m, 1H), 2.69 (br s, 2H), 1.81-1.43 (m, 3H), 1.08-0.73 (m, 2H).

Preparation 7

(2S)-2-Amino-3-[bis(4-methoxyphenyl)-phenyl-methoxy]-1-[4-(hydroxymethyl)-1-piperidyl]propan-1-one

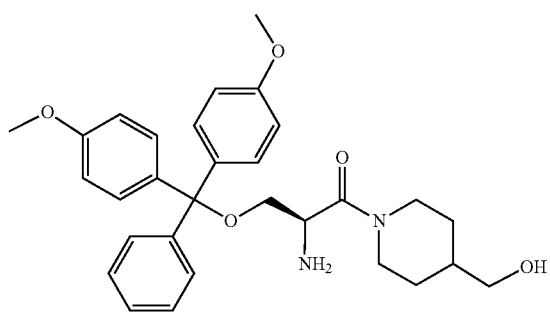 [SMILES: COc1ccc(C(OC[C@H](N)C(=O)N2CCC(CO)CC2)(c2ccccc2)c2ccc(OC)cc2)cc1]

Slowly added a solution of 20% piperidine in DMF (400 mL) to 9H-fluoren-9-ylmethyl N-[(1S)-1-[[bis(4-methoxyphenyl)-phenyl-methoxy]methyl]-2-[4-(hydroxymethyl)-1-piperidyl]-2-oxo-ethyl]carbamate (40 g, 0.055 mol) at 0° C. under inert atmosphere. Allowed the mixture to warm to ambient temperature and stirred for 1 hour. After this time, diluted the mixture with water and extracted with EtOAc. Dried organics over anhydrous sodium sulphate, filtered, and concentrated in vacuo. Purified the resulting residue via silica gel flash chromatography eluting with 1-8% MeOH/DCM to give the title compound as an off-white solid (13 g, 47%). ES/MS m/z 1009.5 (2M+H).

Preparation 8

N-[2-[2-[2-[2-[3-[[(1S)-1-[[Bis(4-methoxyphenyl)-phenyl-methoxy]methyl]-2-[4-(hydroxymethyl)-1-piperidyl]-2-oxo-ethyl]amino]-3-oxo-propoxy]ethoxy]ethoxy]ethyl]hexadecanamide

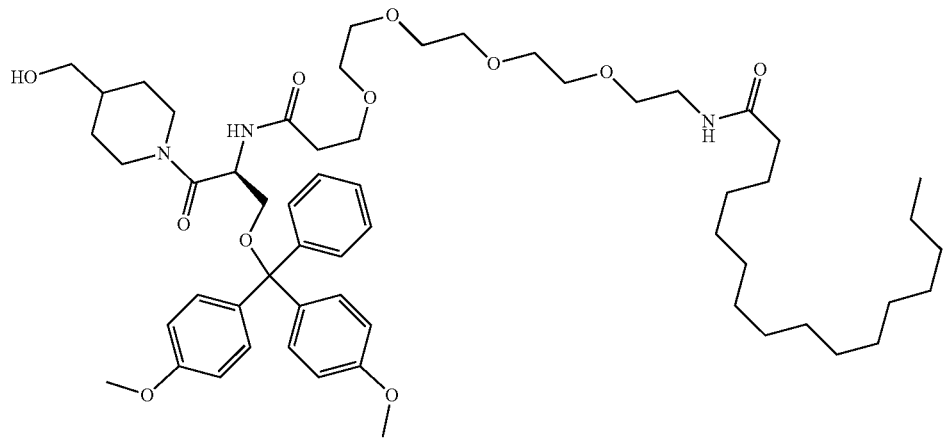 [SMILES: CCCCCCCCCCCCCCCC(=O)NCCOCCOCCOCCOCCC(=O)N[C@@H](COC(c1ccccc1)(c1ccc(OC)cc1)c1ccc(OC)cc1)C(=O)N1CCC(CO)CC1]

Combined 3-[2-[2-[2-[2-(hexadecanoylamino)ethoxy]ethoxy]ethoxy]ethoxy]propanoic acid (496 mg, 0.984 mmol), HOBt (146 mg, 1.08 mmol), HBTU (410 mg, 1.08 mmol), and DIEA (1.03 mL, 5.90 mmol) in DMF (9.84 mL) and stirred at ambient temperature for 10 minutes. Added (2S)-2-amino-3-[bis(4-methoxyphenyl)-phenyl-methoxy]-1-[4-(hydroxymethyl)-1-piperidyl]propan-1-one (546 mg, 1.08 mmol) to the mixture and stirred at ambient temperature for 16 hours. Partitioned the mixture between EtOAc and saturated aqueous sodium chloride solution. Separated the layers and washed the organics with saturated aqueous sodium chloride solution. Dried the organics over sodium sulfate, filtered, and concentrated in vacuo. Purified the resulting residue by silica gel flash chromatography eluting with 0-10% MeOH/DCM to give the title compound as an oil (327 mg, 34%). 1H NMR (DMSO-$d_6$) 8.21 (d, J=8.5 Hz, 1H), 7.80 (t, J=5.6 Hz, 1H), 7.37-7.28 (m, 4H), 7.23-7.20 (m, 5H), 6.88 (d, J=8.3 Hz, 4H), 5.06-5.02 (m, 1H), 4.51-4.49 (m, 1H), 4.45-4.40 (m, 1H), 3.97-3.93 (m, 1H), 3.74 (s, 5H), 3.63-3.56 (m, 2H), 3.49-3.48 (m, 4H), 3.47-3.45 (m, 7H), 3.40-3.35 (m, 2H), 3.30 (s, 1H), 3.23-3.13 (m, 7H), 2.41-2.33 (m, 2H), 2.04 (t, J=7.4 Hz, 2H), 1.74-1.69 (m, 3H), 1.51-1.44 (m, 2H), 1.26-1.24 (m, 24H), 1.00-0.97 (m, 1H), 0.88-0.82 (m, 5H).

Preparation 9

4-[[1-[(2S)-3-[Bis(4-methoxyphenyl)-phenyl-methoxy]-2-[3-[2-[2-[2-[2-(hexadecanoylamino)ethoxy]ethoxy]ethoxy]ethoxy]propanoylamino]propanoyl]-4-piperidyl]methoxy]-4-oxo-butanoic acid

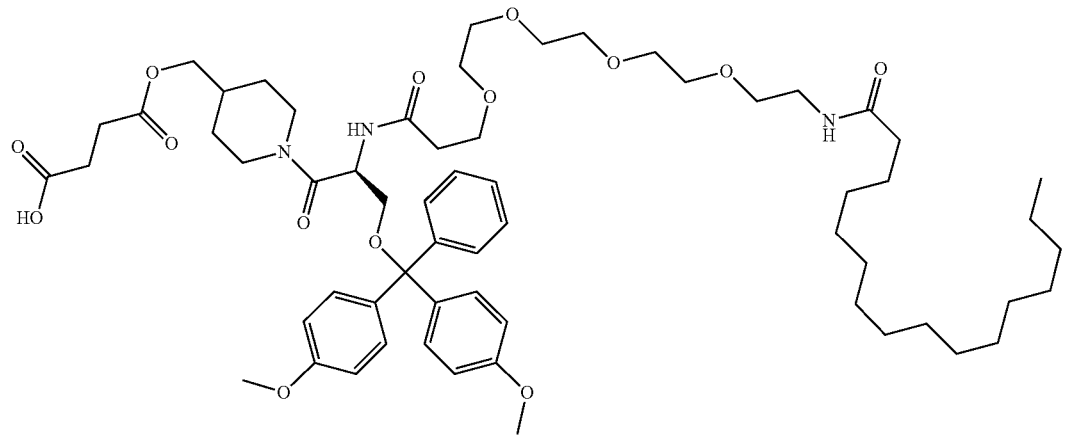 [SMILES: CCCCCCCCCCCCCCCC(=O)NCCOCCOCCOCCOCCC(=O)N[C@@H](COC(c1ccccc1)(c1ccc(OC)cc1)c1ccc(OC)cc1)C(=O)N1CCC(COC(=O)CCC(=O)O)CC1]

Combined N-[2-[2-[2-[2-[3-[[(1S)-1-[[bis(4-methoxy-phenyl)-phenyl-methoxy]methyl]-2-[4-(hydroxymethyl)-1-piperidyl]-2-oxo-ethyl]amino]-3-oxo-propoxy]ethoxy]ethoxy]ethoxy]ethyl]hexadecanamide (320 mg, 0.323 mmol), DMAP (120 mg, 0.969 mmol), TEA (225 μL, 1.62 mmol), and succinic anhydride (64.7 mg, 0.646 mmol) in DCM (6.46 mL) and stirred the mixture for 16 hours at ambient temperature. Purified the mixture directly via silica gel flash chromatography, eluting with 0% to 40% MeOH/DCM, to give the title compound as a colorless oil (279 mg, 79%). $^1$H NMR (DMSO-$d_6$) 12.65-12.64 (m, 1H), 8.24-8.19 (m, 1H), 7.80 (t, J=5.6 Hz, 1H), 7.37-7.28 (m, 4H), 7.24-7.20 (m, 5H), 6.88 (d, J=8.6 Hz, 4H), 5.05-5.01 (m, 1H), 4.44-4.40 (m, 1H), 3.97-3.95 (m, 3H), 3.74 (s, 6H), 3.61-3.56 (m, 2H), 3.49-3.45 (m, 11H), 3.38 (t, J=5.9 Hz, 3H), 3.22-3.14 (m, 6H), 2.48-2.31 (m, 7H), 2.04 (t, J=7.4 Hz, 2H), 1.90-1.87 (m, 5H), 1.24 (s, 23H), 0.98-0.96 (m, 1H), 0.87-0.82 (m, 4H).

Preparation 10

4-[[1-[(2S)-3-[Bis(4-methoxyphenyl)-phenyl-methoxy]-2-[3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoylamino]propanoyl]-4-piperidyl]methoxy]-4-oxo-butanoic acid

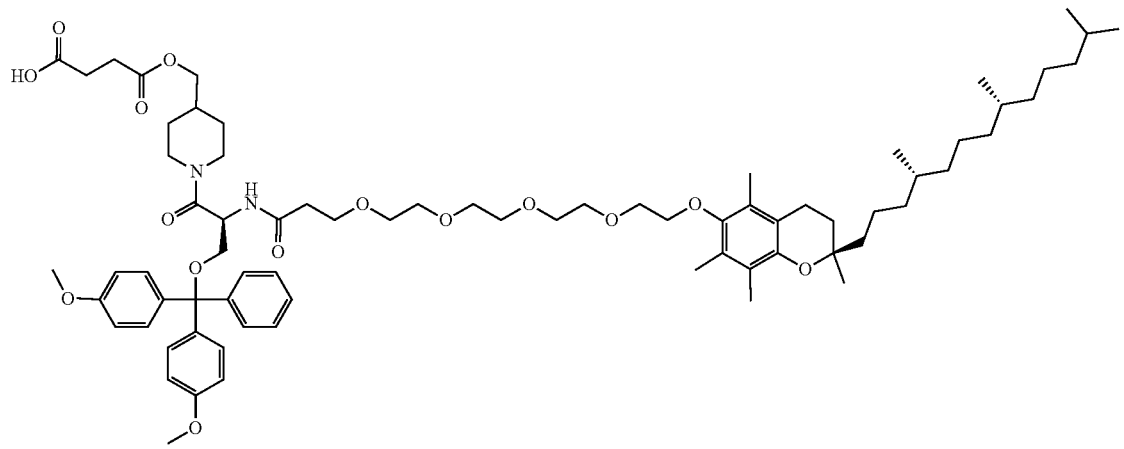 [SMILES: COc1ccc(C(OC[C@H](NC(=O)CCOCCOCCOCCOCCOc2c(C)c(C)c3c(c2C)CC[C@@](C)(CCC[C@H](C)CCC[C@H](C)CCCC(C)C)O3)C(=O)N2CCC(COC(=O)CCC(=O)O)CC2)(c2ccccc2)c2ccc(OC)cc2)cc1]

Combined 3-[2-[2-[2-[2-[(2R)-2,5,7,8-tetramethyl-2-[(4R,8R)-4,8,12-trimethyltridecyl]chroman-6-yl]oxy-ethoxy]ethoxy]ethoxy]ethoxy]propanoic acid (1.20 g, 1.80 mmol), HOBt (260 mg, 1.90 mmol), HBTU (740 mg, 1.90 mmol), and DIEA (1.80 mL, 11.0 mmol) in DMF (18.0 mL) and stirred at ambient temperature for 10 minutes. Added (2S)-2-amino-3-[bis(4-methoxyphenyl)-phenyl-methoxy]-1-[4-(hydroxymethyl)-1-piperidyl]propan-1-one (980 mg, 1.90 mmol) to the mixture and stirred at ambient temperature for 16 hours. Partitioned the mixture between EtOAc and saturated aqueous sodium chloride solution. Separated the layers and washed the organics with saturated aqueous sodium chloride solution. Dried the organic layer over sodium sulfate, filtered, and concentrated in vacuo. Purified the resulting residue by silica gel flash chromatography, eluting with 0-10% MeOH/DCM, to give N-[(1S)-1-[[bis(4-methoxyphenyl)-phenyl-methoxy]methyl]-2-[4-(hydroxymethyl)-1-piperidyl]-2-oxo-ethyl]-3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propenamide as a yellow oil.

Combined N-[(1S)-1-[[bis(4-methoxyphenyl)-phenyl-methoxy]methyl]-2-[4-(hydroxymethyl)-1-piperidyl]-2-oxo-ethyl]-3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]propenamide (1.45 g, 1.24 mmol), DMAP (456 mg, 3.73 mmol), TEA (867 µL, 6.22 mmol), and succinic anhydride (249 mg, 2.49 mmol) in DCM (24.9 mL) and stirred for 16 hours at ambient temperature. Concentrated in vacuo and purified the resulting residue via silica gel flash chromatography, eluting with 0-40% MeOH/DCM, to give the title compound as an oil (1.36 g, 60%). ES/MS m/z 1264.4 (M−H).

Preparation 11

[[4-[[1-[(2S)-3-[Bis(4-methoxyphenyl)-phenyl-methoxy]-2-[3-[2-[2-[2-[2-(hexadecanoylamino)ethoxy]ethoxy]ethoxy]ethoxy]propanoylamino]propanoyl]-4-piperidyl]methoxy]-4-oxo-butanoyl]amino] on CPG

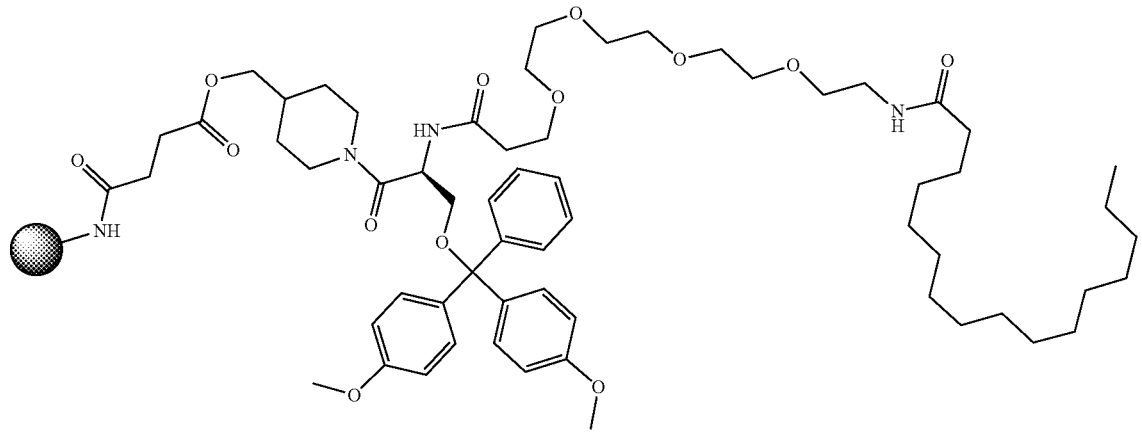 [SMILES: CCCCCCCCCCCCCCCC(=O)NCCOCCOCCOCCOCCC(=O)N[C@@H](COC(c1ccccc1)(c1ccc(OC)cc1)c1ccc(OC)cc1)C(=O)N1CCC(COC(=O)CCC(=O)NC)CC1]

Dissolved 4-[[1-[(2S)-3-[bis(4-methoxyphenyl)-phenyl-methoxy]-2-[3-[2-[2-[2-[2-(hexadecanoylamino)ethoxy]ethoxy]ethoxy]ethoxy]propanoylamino]propanoyl]-4-piperidyl]methoxy]-4-oxo-butanoic acid (270 mg, 0.248 mmol) in ACN (12.5 mL) and transferred the solution to a fritted glass dropping funnel. Added DIEA (150 µL, 0.860 mmol) and HBTU (190 mg, 0.500 mmol) to the solution and shook the mixture at ambient temperature for 10 minutes. Added native amino LCAA CPG 500 Å (1.92 g, 129 µmol/g) to the solution and shook the mixture at 500 RPM for 16 hours at ambient temperature. Drained the CPG and dried under nitrogen for 5 minutes. Washed the CPG with DCM (50 mL), 10% MeOH/DCM (50 mL), and then diethyl ether (50 mL). Dried the CPG for 30 minutes under nitrogen and then resuspended in pyridine (15 mL). Added acetic anhydride (3.30 mL, 35.0 mmol) and TEA (0.50 mL) and shook the mixture at 500 RPM for 2 hours at ambient temperature. Drained the CPG and dried for 5 minutes under nitrogen. Washed the CPG with DCM (50 mL), 10% MeOH/DCM (50 mL), and then diethyl ether (50 mL). Dried the CPG for 45 minutes under nitrogen and determined the ligand loading at 505 nm to give the title compound (1.92 g, 75.5 µmol/g).

Preparation 12

[[4-[[1-[(2S)-3-[Bis(4-methoxyphenyl)-phenyl-methoxy]-2-[3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoylamino]propanoyl]-4-piperidyl]methoxy]-4-oxo-butanoyl]amino] on CPG

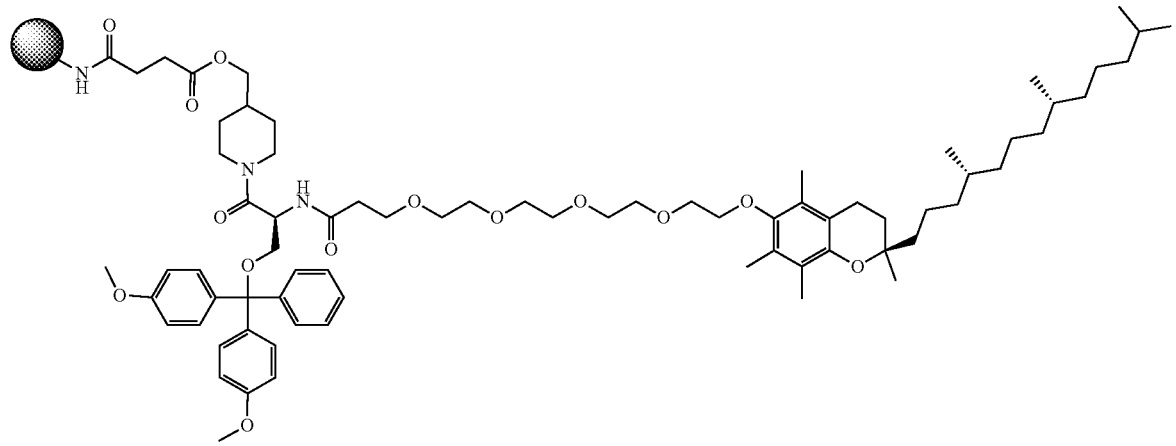 [SMILES: CNC(=O)CCC(=O)OCC1CCN(C(=O)[C@H](COC(c2ccccc2)(c2ccc(OC)cc2)c2ccc(OC)cc2)NC(=O)CCOCCOCCOCCOCCOc2c(C)c(C)c3c(c2C)CC[C@@](C)(CCC[C@H](C)CCC[C@H](C)CCCC(C)C)O3)CC1]

Prepared the title compound from 4-[[1-[(2S)-3-[bis(4-methoxyphenyl)-phenyl-methoxy]-2-[3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoylamino]propanoyl]-4-piperidyl]methoxy]-4-oxo-butanoic acid in a manner essentially analogous to Preparation 11. Determined the ligand loading at 505 nm to give the title compound (4.01 g, 66.9 μmol/g).

Preparation 13

3-[[[(2R,3R,4R,5R)-2-[[Bis(4-methoxyphenyl)-phenyl-methoxy]methyl]-4-hexadecoxy-5-(2-hydroxy-4-oxo-pyrimidin-1-yl)THF-3-yl]oxy-(diisopropylamino)phosphanyl]oxypropanenitrile

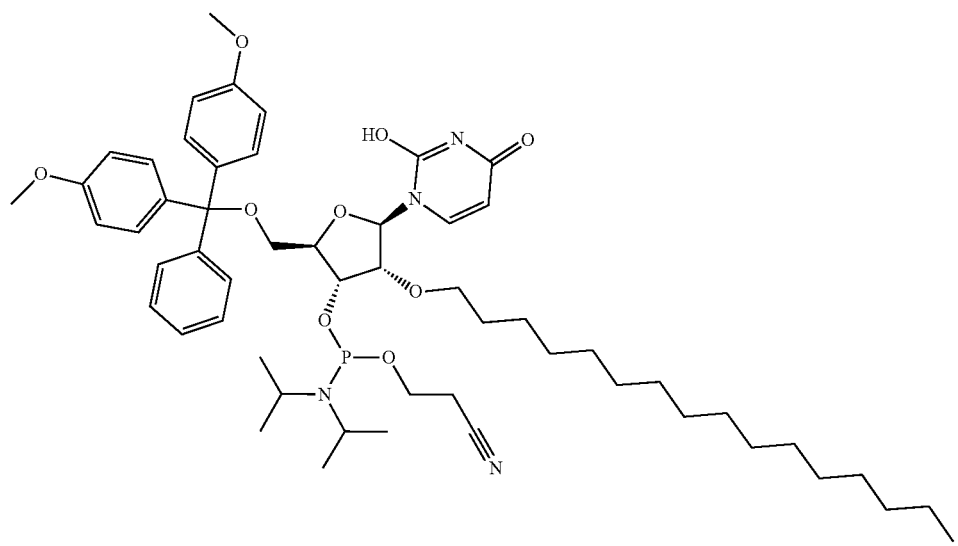 [SMILES: CCCCCCCCCCCCCCCCO[C@@H]1[C@H](OP(OCCC#N)N(C(C)C)C(C)C)[C@@H](COC(c2ccccc2)(c2ccc(OC)cc2)c2ccc(OC)cc2)O[C@H]1n1ccc(=O)nc1O]

Prepared the title compound according to the protocols described in WO2019217459. $^1$H NMR (CD$_3$CN): 7.86-7.73 (m, 1H), 7.51-7.43 (m, 2H), 7.40-7.23 (m, 7H), 6.95-6.87 (m, 4H), 5.90-5.84 (m, 1H), 5.29-5.21 (m, 1H), 4.54-4.40 (m, 1H), 4.21-4.13 (m, 1H), 4.10-3.56 (m, 13H), 3.50-3.34 (m, 2H), 2.75-2.62 (m, 1H), 2.55 (t, J=6.0 Hz, 1H), 1.66-1.51 (m, 2H), 1.40-1.14 (m, 35H), 1.08 (d, J=6.8 Hz, 3H), 0.91 (t, J=6.8 Hz, 3H). $^{31}$P NMR (CD$_3$CN): 149.6, 149.2.

Preparation 14

N-[9-[(2R,3R,4R,5R)-5-[[Bis(4-methoxyphenyl)-phenyl-methoxy]methyl]-4-[2-cyanoethoxy-(diisopropylamino)phosphanyl]oxy-3-hexadecoxy-tetrahydrofuran-2-yl]purin-6-yl]benzamide

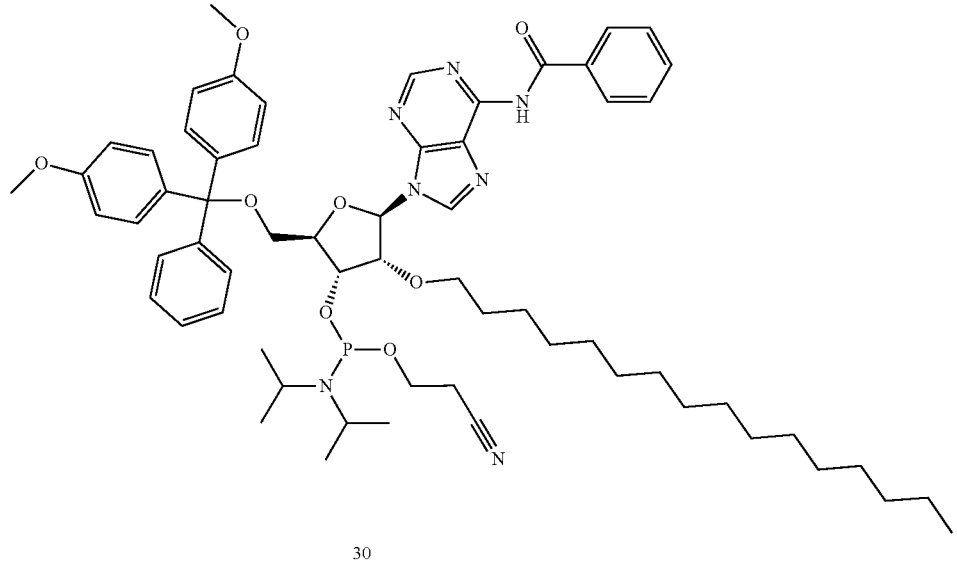

Prepared the title compound according to the protocols described in WO2019217459. $^1$H-NMR (CD$_3$CN) δ 9.37 (s, 1H), 8.57 (d, J=9.4 Hz, 1H), 8.27 (d, J=10.3 Hz, 1H), 7.99 (d, J=7.6 Hz, 2H), 7.61 (d, J=7.4 Hz, 1H), 7.52 (t, J=7.6 Hz, 2H), 7.42 (t, J=7.3 Hz, 2H), 7.34-7.16 (m, 7H), 6.85-6.77 (m, 4H), 6.11 (dd, J=5.0, 2.5 Hz, 1H), 4.80 (m, 1H), 4.69 (m, 1H), 4.32 (m, 1H), 3.97-3.78 (m, 1H), 3.74 (d, J=3.1 Hz, 7H), 3.64 (m, 4H), 3.56-3.40 (m, 2H), 3.33 (m, 1H), 2.73-2.59 (m, 1H), 2.50 (t, J=6.0 Hz, 1H), 1.52-1.45 (m, 2H), 1.33-1.12 (m, 37H), 1.09 (d, J=6.8 Hz, 3H), 0.87 (t, J=6.8 Hz, 3H). $^{31}$P NMR (CD$_3$CN) δ 151.19, 150.78.

Preparation 15

N-[1-[(2R,3R,4R,5R)-5-[[Bis(4-methoxyphenyl)-phenyl-methoxy]methyl]-4-[2-cyanoethoxy-(diisopropylamino)phosphanyl]oxy-3-hexadecoxy-tetrahydrofuran-2-yl]-2-oxo-pyrimidin-4-yl]acetamide

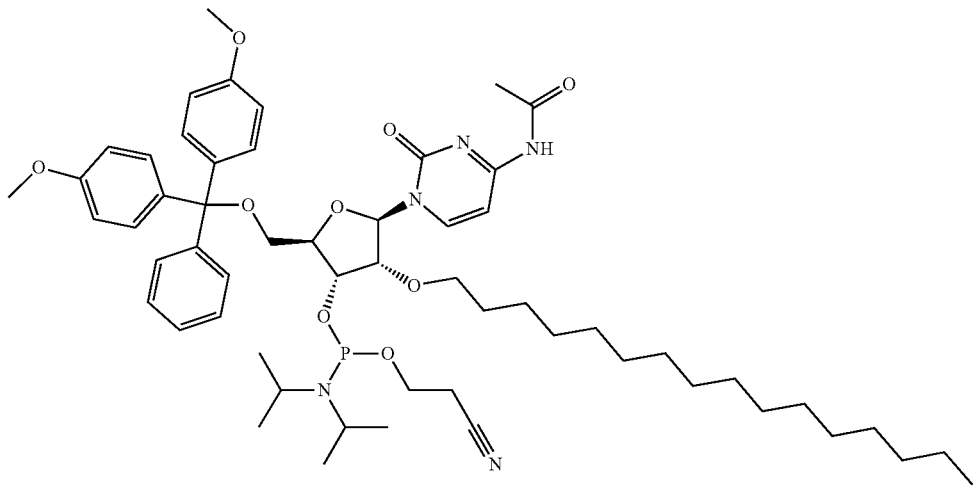 [SMILES: CCCCCCCCCCCCCCCCO[C@@H]1[C@H](OP(OCCC#N)N(C(C)C)C(C)C)[C@@H](COC(c2ccccc2)(c2ccc(OC)cc2)c2ccc(OC)cc2)O[C@H]1n1ccc(NC(C)=O)nc1=O]

Prepared the title compound according to the protocols described in WO2019217459. ¹H-NMR (CD₃CN) 9.15 (s, 1H), 8.46 (dd, J=7.5 Hz, 1H), 7.95 (d, J=7.6 Hz, 2H), 7.63 (t, J=7.5 Hz, 1H), 7.57-7.41 (m, 5H), 7.41-7.31 (m, 6H), 7.28 (m, 1H), 7.04 (d, J=15.8 Hz, 1H), 6.90 (t, J=7.9 Hz, 4H), 5.90 (d, J=7.8 Hz, 1H), 4.51 (m, 1H), 4.20 (dd, J=10.6, 8.1 Hz, 1H), 4.04 (dd, J=31.3, 4.6 Hz, 1H), 3.91-3.81 (m, 2H), 3.79 (d, J=3.1 Hz, 6H), 3.74 (m, 2H), 3.69-3.41 (m, 6H), 2.67-2.59 (m, 1H), 2.54-2.48 (m, 1H), 1.58 (m, 2H), 1.36 (m, 2H), 1.25 (d, J=4.7 Hz, 26H), 1.21-1.09 (m, 10H), 1.04 (d, J=6.8 Hz, 3H), 0.87 (t, J=6.8 Hz, 3H). ³¹P NMR (CD₃CN) δ 151.10, 150.19.

Preparation 16

N-[9-[(2R,3R,4R,5R)-5-[[Bis(4-methoxyphenyl)-phenyl-methoxy]methyl]-4-[2-cyanoethoxy-(diiso-propylamino)phosphanyl]oxy-3-hexadecoxy-tetrahy-drofuran-2-yl]-6-oxo-1H-purin-2-yl]-2-methyl-propanamide

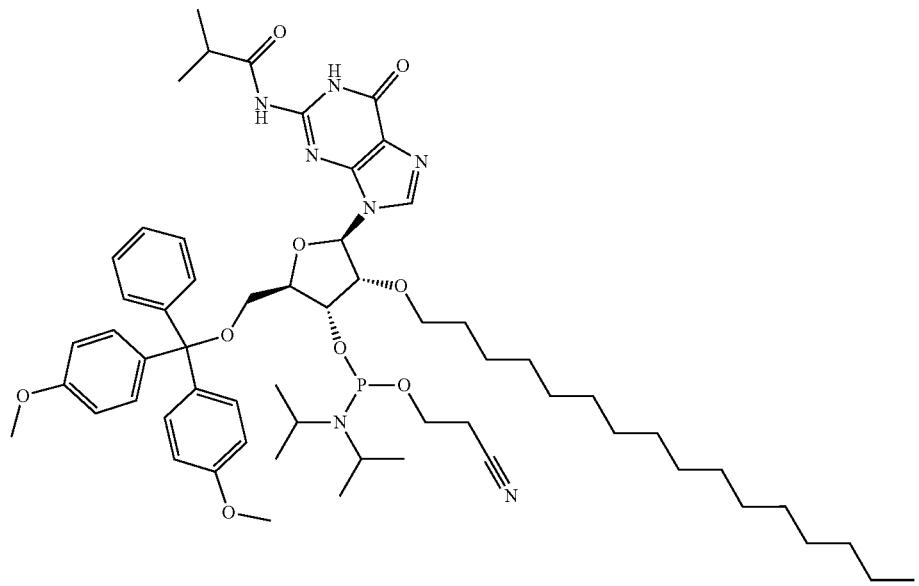 [SMILES: CCCCCCCCCCCCCCCCO[C@@H]1[C@H](OP(OCCC#N)N(C(C)C)C(C)C)[C@@H](COC(c2ccccc2)(c2ccc(OC)cc2)c2ccc(OC)cc2)O[C@H]1n1cnc2c(=O)[nH]c(NC(=O)C(C)C)nc21]

Prepared the title compound according to the protocols described in WO2019217459. ¹H-NMR (CDCl₃) δ 12.01-11.96 (m, 1H), 7.82-7.78 (m, 1H), 7.59-7.53 (m, 1H), 7.47-7.42 (m, 1H), 7.41-7.37 (m, 2H), 7.34-7.29 (m, 2H), 7.27-7.22 (m, 3H), 6.85-6.80 (m, 4H), 5.99-5.82 (m, 1H), 4.40-4.36 (m, 1H), 4.17-4.11 (m, 1H), 3.80-3.77 (m, 6H), 3.76-3.68 (m, 6H), 3.22-3.17 (m, 1H), 2.84-2.79 (m, 1H), 1.60-1.54 (m, 4H), 1.35-1.30 (m, 6H), 1.27 (s, 19H), 1.24-1.15 (m, 13H), 1.06-1.03 (m, 5H), 0.93-0.88 (m, 6H), 0.74-0.70 (m, 1H). ³¹P NMR (CDCl₃) δ 150.20, 149.92.

Example 2. Synthesis of MAPT RNAi Agents

Single strands (sense and antisense) of the RNA duplexes were synthesized on solid support via a MerMade™ 12 (LGC Biosearch Technologies). The sequences of the sense and antisense strands were shown in Table 2. The oligonucleotides were synthesized via phosphoramidite chemistry at either 5, 10, 25 or 50 μmol scales.

For the sense strands, the types of solid supports were universal CPG: (3'-Piperidinol-PEG-Palmitate) and (3'-Piperidinol-PEG-Tocopherol) were synthesized in house (see Example 1) while the Universal UnyLinker (Chemgenes, Catalog No. AT273-27) and 3'Teg-Tocopherol (LGC Biosearch Technologies, Catalog No. BG7-1190) were purchased commercially. For all the antisense strands, commercially available standard support mA was utilized. Standard reagents were used in the oligo synthesis (Table 7), where 0.1M xanthane hydride in pyridine was used as the sulfurization reagent and 20% DEA in ACN was used as an auxiliary wash post synthesis. All monomers (Table 8) were made at 0.1M in ACN and contained a molecular sieves trap bag.

The oligonucleotides were cleaved and deprotected (C/D) at 45° C. for 20 hours. The sense strands were C/D from the CPG using ammonia hydroxide (28-30%, cold), whereas 3% DEA in ammonia hydroxide (28-30%, cold) was used for the antisense strands. C/D was determined complete by IP-RP LCMS when the resulting mass data confirmed the identity of sequence. Dependent on scale, the CPG was filtered via 0.45 um PVDF syringeless filter, 0.22 um PVDF Steriflip® vacuum filtration or 0.22 um PVDF Stericup® Quick release. The CPG was back washed/rinsed with either 30% ACN/RNAse free water or 30% EtOH/RNAse free water then filtered through the same filtering device and combined with the first filtrate. This was repeated twice. The material was then divided evenly into 50 mL falcon tubes to remove organics via Genevac™. After concentration, the crude oligonucleotides were diluted back to synthesized scale with RNAse free water and filtered either by 0.45 μm PVDF syringeless filter, 0.22 μm PVDF Steriflip® vacuum filtration or 0.22 μm PVDF Stericup® Quick release.

The crude oligonucleotides were purified via AKTA™ Pure purification system using either anion-exchange (AEX) or reverse phase (RP) a source 15Q-RP column. For AEX, an ES Industry Source™ 15Q column maintaining column temperature at 65° C. with MPA: 20 mM NaH₂PO₄, 15% ACN, pH 7.4 and MPB: 20 mM NaH₂PO₄, 1M NaBr, 15% ACN, pH 7.4. For RP, a Source™ 15Q-RP column with MPA: 50 mM NaOAc with 10% ACN and MPB: 50 mM NaOAc with 80% ACN. In all cases, fractions which contained a mass purity greater than 85% without impurities >5% where combined.

The purified oligonucleotides were desalted using 15 mL 3K MWCO centrifugal spin tubes at 3500×g for ~30 min. The oligonucleotides were rinsed with RNAse free water until the eluent conductivity reached <100 usemi/cm. After desalting was complete, 2-3 mL of RNAse free water was added then aspirated 10×, the retainment was transferred to a 50 mL falcon tube, this was repeated until complete transfer of oligo by measuring concentration of compound on filter via nanodrop. The final oligonucleotide was then nano filtered 2× via 15 mL 100K MWCO centrifugal spin tubes at 3500×g for 2 min. The final desalted oligonucleotides were analyzed for concentration (nano drop at A260), characterized by IP-RP LCMS for mass purity and UPLC for UV-purity.

For the preparation of duplexes, equimolar amounts of sense and antisense strand were combined and heated at 65° C. for 10 minutes then slowly cooled to ambient temperature over 40 minutes. Integrity of the duplex was confirmed by UPLC analysis and characterized by LCMS using IP-RP. All duplexes were nano filtered then endotoxin levels measured via Charles River Endosafe® Cartridge Device to give the final compounds of conjugated RNAi (Table 9). For in vivo analysis, the appropriate amount of duplex was lyophilized then reconstituted in 1×PBS for rodent studies and a CSF for non-human primate studies.

TABLE 7

Oligonucleotide Synthesis Reagents

| Reagents |
| --- |
| Activator Solution (0.5M ETT in ACN) |
| Cap A (Acetic Anhydride, Pyridine in THF, 1:1:8) |
| Cap B (1-Methylimidazole in THF, 16:84) |
| Oxidation Solution (0.02M Iodine in THF/Pyridine/Water, 70:20:10) |
| Deblock Solution, 3% TCA in DCM (w/v) |
| Acetonitrile (Anhydrosolv, Water max. 10 ppm) |
| Xanthane Hydride (0.1M in Pyridine) |
| Diethylamine (20% in Acetonitrile) |

TABLE 8

Phosphoramidites

| Phosphoramidite | Abbreviation | Supplier | Catalog # | CAS |
| --- | --- | --- | --- | --- |
| DMT-2'-F—A(Bz)—CE Phosphoamidite | fA | Hongene | PD1-001 | 136834-22-5 |
| DMT-2'-F—C(Ac)—CE Phosphoamidite | fC | Hongene | PD3-001 | 159414-99-0 |
| DMT-2'-F—G(iBu)—CE Phosphoamidite | fG | Hongene | PD2-002 | 144089-97-4 |
| DMT-2'-F—U—CE Phosphoamidite | fU | Hongene | PD5-001 | 146954-75-8 |
| DMT-2'-O—Me—A(Bz)—CE Phosphoamidite | mA | Hongene | PR1-001 | 110782-31-5 |
| DMT-2'-O—Me—C(Ac)—CE Phosphoamidite | mC | Hongene | PR3-001 | 199593-09-4 |
| DMT-2'-O—Me—G(iBu)—CE Phosphoamidite | mG | Hongene | PR2-002 | 150780-67-9 |
| DMT-2'-O—Me—U—CE Phosphoamidite | mU | Hongene | PR5-001 | 110764-79-9 |
| 5'bis(POM) vinyl phosphate-2'-Ome—U3'CE phosphoroamidite | POM-VPmU | Hongene | PR5-032 | BVPMUP23B2A1 |
| Reverse Abasic phosphoroamidite | iAb | Chemgenes | ANP-1422 | 401813-16-9 |
| Uhd | Uhd | Lilly | | |
| Chd | Chd | Lilly | | |
| Ahd | Ahd | Lilly | | |
| Ghd | Ghd | Lilly | | |

TABLE 9

Conjugated MAPT RNAi Agents

| Conjugated MAPT RNAi Agent No. | RNAi Agent No. | Strand | LDP | MW Cal. (g/mol) | MW Obs. (g/mol) |
| --- | --- | --- | --- | --- | --- |
| 1 | 13 | S: SEQ ID NO: 25 | 1 | 7703.75 | 7704.3 |
|   |    | AS: SEQ ID NO: 26 |   | 7810.25 | 7810.7 |
| 2 | 14 | S: SEQ ID NO: 27 | 1 | 7735.81 | 7736.4 |
|   |    | AS: SEQ ID NO: 28 |   | 7655.08 | 7656.1 |
| 3 | 15 | S: SEQ ID NO: 29 | 1 | 7751.87 | 7752.7 |
|   |    | AS: SEQ ID NO: 30 |   | 7577.99 | 7579.0 |
| 4 | 16 | S: SEQ ID NO: 31 | 1 | 7831.93 | 7832.4 |
|   |    | AS: SEQ ID NO: 32 |   | 7497.93 | 7498.5 |
| 5 | 17 | S: SEQ ID NO: 33 | 1 | 7902.97 | 7903.1 |
|   |    | AS: SEQ ID NO: 34 |   | 7534.99 | 7535.3 |
| 6 | 18 | S: SEQ ID NO: 35 | 1 | 7800.86 | 7801.2 |
|   |    | AS: SEQ ID NO: 36 |   | 7582.06 | 7582.6 |
| 7 | 19 | S: SEQ ID NO: 37 | 1 | 7839.9  | 7840.1 |
|   |    | AS: SEQ ID NO: 38 |   | 7558.03 | 7558.5 |
| 8 | 20 | S: SEQ ID NO: 39 | 1 | 7840.89 | 7841.5 |
|   |    | AS: SEQ ID NO: 40 |   | 7518.99 | 7520.0 |
| 9 | 21 | S: SEQ ID NO: 41 | 1 | 7792.83 | 7793.2 |
|   |    | AS: SEQ ID NO: 42 |   | 7596.08 | 7596.9 |
| 10 | 22 | S: SEQ ID NO: 43 | 1 | 7687.75 | 7688.7 |
|   |    | AS: SEQ ID NO: 44 |   | 7755.21 | 7756.2 |
| 11 | 23 | S: SEQ ID NO: 45 | 1 | 7649.7  | 7650.3 |
|   |    | AS: SEQ ID NO: 46 |   | 7779.24 | 7779.3 |
| 12 | 24 | S: SEQ ID NO: 47 | 1 | 7816.86 | 7817.6 |
|   |    | AS: SEQ ID NO: 48 |   | 7597.07 | 7597.7 |
| / | 31 | S: SEQ ID NO: 63 | 4 | 7352.24 | 7352.5 |
|   |    | AS: SEQ ID NO: 40 |   | 7518.87 | 7519.1 |
| / | 32 | S: SEQ ID NO: 64 | 4 | 7364.27 | 7364.7 |
|   |    | AS: SEQ ID NO: 65 |   | 7506.84 | 7507.4 |
| / | 33 | S: SEQ ID NO: 66 | 5 | 7364.27 | 7364.0 |
|   |    | AS: SEQ ID NO: 65 |   | 7506.84 | 7507.4 |
| / | 34 | S: SEQ ID NO: 67 | 4 | 7213.17 | 7213.7 |
|   |    | AS: SEQ ID NO: 65 |   | 7506.84 | 7507.4 |
| / | 35 | S: SEQ ID NO: 68 | 4 | 7199.15 | 7199.6 |
|   |    | AS: SEQ ID NO: 65 |   | 7506.84 | 7507.4 |
| / | 36 | S: SEQ ID NO: 69 | 4 | 7213.17 | 7213.5 |
|   |    | AS: SEQ ID NO: 65 |   | 7506.84 | 7507.4 |

TABLE 9-continued

Conjugated MAPT RNAi Agents

| Conjugated MAPT RNAi Agent No. | RNAi Agent No. | Strand | LDP | MW Cal. (g/mol) | MW Obs. (g/mol) |
|---|---|---|---|---|---|
| / | 37 | S: SEQ ID NO: 64 | 4 | 7364.27 | 7364.8 |
|   |    | AS: SEQ ID NO: 70 |   | 7482.76 | 7482.9 |
| / | 38 | S: SEQ ID NO: 71 | 4 | 7352.24 | 7352.7 |
|   |    | AS: SEQ ID NO: 65 |   | 7506.84 | 7507.5 |
| / | 39 | S: SEQ ID NO: 64 | 4 | 7364.27 | 7364.8 |
|   |    | AS: SEQ ID NO: 72 |   | 7506.84 | 7507.5 |
| / | 40 | S: SEQ ID NO: 64 | 4 | 7364.27 | 7365.0 |
|   |    | AS: SEQ ID NO: 73 |   | 7506.84 | 7507.4 |
| / | 41 | S: SEQ ID NO: 64 | 4 | 7364.27 | 7364.9 |
|   |    | AS: SEQ ID NO: 74 |   | 7530.91 | 7531.6 |
| / | 42 | S: SEQ ID NO: 75 | 4 | 7340.20 | 7340.7 |
|   |    | AS: SEQ ID NO: 65 |   | 7506.84 | 7507.5 |
| / | 43 | S: SEQ ID NO: 76 | 7 | 7364.27 | 7365.4 |
|   |    | AS: SEQ ID NO: 65 |   | 7506.84 | 7508.0 |
| / | 44 | S: SEQ ID NO: 77 | 4 | 7364.27 | 7365.5 |
|   |    | AS: SEQ ID NO: 65 |   | 7506.84 | 7507.9 |
| / | 45 | S: SEQ ID NO: 78 | 7 | 7364.27 | 7365.5 |
|   |    | AS: SEQ ID NO: 65 |   | 7506.84 | 7508.1 |
| / | 46 | S: SEQ ID NO: 79 | 5 | 7364.27 | 7365.5 |
|   |    | AS: SEQ ID NO: 65 |   | 7506.84 | 7508.1 |
| / | 47 | S: SEQ ID NO: 80 | 4 | 7364.27 | 7365.6 |
|   |    | AS: SEQ ID NO: 65 |   | 7506.84 | 7508.0 |
| / | 48 | S: SEQ ID NO: 81 | 5 | 7376.31 | 7377.7 |
|   |    | AS: SEQ ID NO: 65 |   | 7506.84 | 7508.1 |
| / | 49 | S: SEQ ID NO: 82 | 5 | 7376.31 | 7377.7 |
|   |    | AS: SEQ ID NO: 65 |   | 7506.84 | 7508.2 |
| / | 50 | S: SEQ ID NO: 83 | 4 | 7364.27 | 7365.5 |
|   |    | AS: SEQ ID NO: 65 |   | 7506.84 | 7508.2 |
| / | 51 | S: SEQ ID NO: 84 | 5 | 7364.27 | 7365.9 |
|   |    | AS: SEQ ID NO: 65 |   | 7506.84 | 7508.2 |
| / | 52 | S: SEQ ID NO: 85 | 5 | 7364.27 | 7365.7 |
|   |    | AS: SEQ ID NO: 65 |   | 7506.84 | 7508.0 |
| / | 53 | S: SEQ ID NO: 86 | 5 | 7364.27 | 7365.6 |
|   |    | AS: SEQ ID NO: 65 |   | 7506.84 | 7508.0 |
| / | 54 | S: SEQ ID NO: 87 | 6 | 7245.13 | 7245.7 |
|   |    | AS: SEQ ID NO: 88 |   | 7749.10 | 7749.5 |
| / | 55 | S: SEQ ID NO: 89 | 6 | 7078.03 | 7079.3 |
|   |    | AS: SEQ ID NO: 88 |   | 7749.10 | 7750.7 |
| / | 56 | S: SEQ ID NO: 90 | 5 | 7037.08 | 7038.6 |
|   |    | AS: SEQ ID NO: 91 |   | 7665.95 | 7667.5 |
| / | 57 | S: SEQ ID NO: 92 | 5 | 7204.18 | 7204.2 |
|   |    | AS: SEQ ID NO: 91 |   | 7665.95 | 7665.9 |
| / | 58 | S: SEQ ID NO: 93 | 7 | 7364.27 | 7365.5 |
|   |    | AS: SEQ ID NO: 65 |   | 7506.84 | 7508.1 |
| / | 59 | S: SEQ ID NO: 94 | 5 | 7364.27 | 7365.4 |
|   |    | AS: SEQ ID NO: 65 |   | 7506.84 | 7508.1 |
| / | 60 | S: SEQ ID NO: 95 | 7 | 7364.27 | 7365.5 |
|   |    | AS: SEQ ID NO: 65 |   | 7506.84 | 7508.1 |
| / | 61 | S: SEQ ID NO: 96 | 5 | 7376.31 | 7377.6 |
|   |    | AS: SEQ ID NO: 65 |   | 7506.84 | 7508.1 |
| / | 62 | S: SEQ ID NO: 97 | 6 | 7364.27 | 7365.4 |
|   |    | AS: SEQ ID NO: 65 |   | 7506.84 | 7508.1 |
| / | 63 | S: SEQ ID NO: 98 | 7 | 7364.27 | 7365.4 |
|   |    | AS: SEQ ID NO: 65 |   | 7506.84 | 7508.1 |
| / | 64 | S: SEQ ID NO: 99 | 5 | 7364.27 | 7365.5 |
|   |    | AS: SEQ ID NO: 65 |   | 7506.84 | 7508.1 |
| / | 65 | S: SEQ ID NO: 100 | 7 | 7364.27 | 7365.4 |
|   |    | AS: SEQ ID NO: 65 |   | 7506.84 | 7508.1 |
| / | 66 | S: SEQ ID NO: 101 | 5 | 7316.22 | 7315.2 |
|   |    | AS: SEQ ID NO: 102 |   | 7583.93 | 7582.9 |
| / | 67 | S: SEQ ID NO: 103 | 4 | 7363.29 | 7362.5 |
|   |    | AS: SEQ ID NO: 104 |   | 7545.87 | 7544.8 |
| 13 | 68 | S: SEQ ID NO: 105 | 1 | 7840.74 | 7841.4 |
|    |    | AS: SEQ ID NO: 106 |  | 7530.90 | 7532.0 |
| 14 | 69 | S: SEQ ID NO: 105 | 1 | 7840.74 | 7841.5 |
|    |    | AS: SEQ ID NO: 107 |  | 7482.76 | 7483.6 |
| 15 | 70 | S: SEQ ID NO: 105 | 1 | 7840.74 | 7841.4 |
|    |    | AS: SEQ ID NO: 65 |   | 7506.83 | 7507.5 |
| 16 | 71 | S: SEQ ID NO: 105 | 1 | 7840.74 | 7841.4 |
|    |    | AS: SEQ ID NO: 108 |  | 7482.76 | 7483.6 |
| 17 | 72 | S: SEQ ID NO: 109 | 1 | 7689.64 | 7690.6 |
|    |    | AS: SEQ ID NO: 65 |   | 7506.83 | 7507.6 |
| 18 | 73 | S: SEQ ID NO: 110 | 1 | 7856.74 | 7857.3 |
|    |    | AS: SEQ ID NO: 40 |   | 7518.87 | 7520.0 |
| 19 | 74 | S: SEQ ID NO: 111 | 1 | 6442.86 | 6443.5 |
|    |    | AS: SEQ ID NO: 112 |  | 7583.13 | 7584.1 |
| 20 | 75 | S: SEQ ID NO: 113 | 1 | 8433.06 | 8434.3 |
|    |    | AS: SEQ ID NO: 114 |  | 7487.86 | 7488.9 |
| 21 | 76 | S: SEQ ID NO: 115 | 1 | 7852.78 | 7854.4 |
|    |    | AS: SEQ ID NO: 116 |  | 7534.93 | 7535.9 |

"S" means the sense strand; "AS" means the antisense strand.
* LDP 1 is linked to the 3' of the sense strand.
** LDPs 4-7 are Uhd, Ahd, Chd, Ghd respectively linked to a nucleotide in the sense strand.

Example 3. Characterization of MAPT RNAi Agents

Selected MAPT RNAi agents were tested in vitro for MAPT inhibition in cultured cells, including SH-SY5Y cells, mouse cortical neurons (MCN) and/or human induced pluripotent stem cells (hiPSC). A subset of the selected MAPT RNAi agents were tested in vivo in transgenic human Tau mouse.

Materials and Methods

SH-SY5Y Cell Culture and RNAi Treatment and Analysis: SH-SY5Y cells (ATCC CRL-2266) were derived from the SK-N-SH neuroblastoma cell line (Ross, R. A., et al., 1983. J Natl Cancer Inst 71, 741-747). The base medium was composed of a 1:1 mixture of ATCC-formulated Eagle's Minimum Essential Medium, (Cat No. 30-2003), and F12 Medium. The complete growth medium was supplemented with 10% fetal bovine serum, 1× amino acids, 1× sodium bicarbonate, and 1× penicillin-streptomycin (Gibco) and cells incubated at 37° C. in a humidified atmosphere of 5% $CO_2$. On Day One, SH-SY5Y cells were plated in 96 well fibronectin coated tissue culture plates and allowed to attach overnight. On Day Two, complete media was removed and replaced with RNAi agent in serum free media. Cells were incubated with RNAi agent for 72 hours before analysis of gene expression. Analysis of changes in gene expression in RNAi treated SH-SY5Y cells was measured using Cells-to-$C_T$ Kits following the manufacturer's protocol (ThermoFisher A35377). Predesigned gene expression assays (supplied as 20× mixtures) were selected from Applied Bio-systems (Foster City, CA, USA). The efficiencies of these assays (ThermoFisher Hs00902194_m1 MAPT and ThermoFisher Hs99999905_m1 GAPDH) were characterized with a dilution series of cDNA. RT-QPCR was performed in MicroAmp Optical 384-well reaction plates using QuantStudio 7 Flex system. The delta-delta CT method of normalizing to the housekeeping gene GAPDH was used to determine relative amounts of gene expression. GraphPad Prism v9.0 was used to determine IC50 with a four parameter logistic fit.

Mouse Primary Cortical Neuron (MCN) Culture and RNAi Treatment and Analysis: Mouse primary cortical neurons were isolated from hTau C57BL6 transgenic mouse embryos expressing human tau transgene at E18. Cells were plated in poly-D-lysine coated 96-well plates at a density of 40 k cells/well and cultured in NbActiv1 (BrainBits, LLC) containing 1% Antibiotic/Antimycotic (Corning) for 7 days at 37° C. in a tissue culture incubator in a humidified chamber with 5% $CO_2$. On Day 7, half of the medium was removed from each well and 2× concentration of RNAi in culture media with 2% FBS was added for treatment as CRC and incubated with cells for additional 7, 14 or 21 days. Half media change was done every 7 days with fresh culture media. At the end of RNAi treatment, RT-qPCR was performed to quantify MAPT mRNA levels using TaqMan Fast Advanced Cell-to-CT kit. Specifically, cells were lysed, cDNA was generated on Mastercycler X50a (Eppendorf), and qPCR was carried out on QuantStudio 7 Flex Real-Time PCR System (Applied Biosystems). Human MAPT (ThermoFisher, Hs00902194_m1) gene expression levels were normalized by 3-actin (ThermoFisher, Mm02619580_g1) using respective probes.

Human Induced Pluripotent Stem Cell-derived Neuron (hiPSC Neuron) Culture and RNAi Treatment and Analysis: Doxycycline-inducible Neurogenin2 (NGN2) human induced Pluripotent Stem Cells (hiPSC) were developed by Bioneer for Eli Lilly. The hiPSC were doxycycline-induced for three days (DIV3) to initiate neuronal differentiation and plated on 96-well PDL and laminin coated plates at 30 k/well and grown in Neuronal Differentiation Media (NDM) consisting of DMEM/F12 (Life Technologies 11330-057), Neurobasal media (Gibco 15240062), antibiotics, supplements, growth factors and doxycycline in an incubator (37° C./5% CO2). Cells were half-fed every seven days, and on DIV21, RNAi agent was serially diluted in NDM, and cells were treated with RNAi by aspirating 75 μL and adding 75 μL of 2×RNAi concentration for a final of 1×RNAi according to dilutions. Cells were half-fed every seven days after treatment by removing half of media and adding back fresh NDM. Cell lysates were harvested at DIV35 (14 days later) or DIV42 (21 days later) and RT-qPCR was performed using TaqMan Fast Advanced Cells-to-$C_T$ Kit (ThermoFisher, A35377) and to determine mRNA knock down using MAPT probe as the gene of interest (ThermoFisher, Hs00902194_m1) and ACTb probe as the housekeeping gene (ThermoFisher, Hs99999903_m1).

In Vivo Characterization of Selected RNAi Agents in Transgenic Mice

The efficacy of selected RNAi agents was also studied in hTau transgenic mice expressing human MAPT RNA and lacking murine MAPT RNA (Andorfer et al., J Neurochem 2003, 86, 582-590). Six mice received intracerebroventricular (ICV) injection of 100 μg of the RNAi agent or PBS (phosphate buffered saline) and were sacrificed on Day 14 after the injection. MAPT mRNA expression in the brain was measured and analyzed by quantitative PCR (qPCR).

Results

Table 10A summarizes the in vitro and in vivo activities of selected MAPT RNAi agents. As shown in Table 10A, the tested RNAi agents knock down MAPT expression in vitro and in vivo.

TABLE 10A

In vitro and in vivo activities of selected MAPT RNAi agents

| MAPT RNAi Agent | SHSY5Y, 3 d IC50 (nM) | SHSY5Y, 3 d % KD (knockdown) of MAPT at 1 μM | Mouse ICV, 14 d % KD Brain stem | Mouse ICV, 14 d % KD Frontal Cortex |
|---|---|---|---|---|
| Conjugated RNAi Agent NO. 1 | 204.2 | 77.3 | 37.8 | 32.6 |
| Conjugated RNAi Agent NO. 2 | 231.7 | 74.8 | 36.3 | 36.0 |
| Conjugated RNAi Agent NO. 3 | 210.1 | 84.1 | 48.0 | 36.0 |
| Conjugated RNAi Agent NO. 4 | 11051 | 69.6 | 54.4 | 33.7 |
| Conjugated RNAi Agent NO. 5 | 60503 | 59.4 | 53.7 | NE* |
| Conjugated RNAi Agent NO. 6 | 275.6 | 66.7 | 47.9 | 26.6 |
| Conjugated RNAi Agent NO. 7 | 431.3 | 65.4 | 68.0 | 34.4 |
| Conjugated RNAi Agent NO. 8 | 286.2 | 72.9 | 65.9 | 46.1 |
| Conjugated RNAi Agent NO. 9 | 124.9 | 86 | 64.9 | 44.9 |
| Conjugated RNAi Agent NO. 10 | 516.1 | 70.7 | 52.1 | 22.4 |
| Conjugated RNAi Agent NO. 11 | 424.3 | 60.1 | 41.4 | 29.1 |
| Conjugated RNAi Agent No. 12 | 309.3 | 73.4 | 54.7 | 22.5 |

*NE means no observed effect.

Additional RNAi agents with different modification patterns were also tested. Table 10B shows the in vitro and in vivo activities of additional MAPT RNAi agents with different modification patterns.

TABLE 10B

In vitro and in vivo activities of additional MAPT RNAi agents with different modification patterns

| MAPT RNAi Agent No. or Conjugate No. | SHSY5Y, 3 d IC50 (nM) | SHSY5Y, 3 d % KD (knockdown) of MAPT at 1 μM | MCN, 7 d IC50 (nM) | MCN, 7 d % KD (knockdown) of SNCA at 1 uM | Mouse ICV, 14 d % KD Brain stem | Mouse ICV, 14 d % KD Frontal Cortex |
|---|---|---|---|---|---|---|
| 31 | ND* | ND | 7.24 | 85.6 | 67 | 58 |
| 32 | ND | ND | 5.648 | 86.8 | 66 | 57 |
| 33 | ND | ND | 12.38 | 83.2 | 48 | 45 |

TABLE 10B-continued

In vitro and in vivo activities of additional MAPT RNAi agents with different modification patterns

| MAPT RNAi Agent No. or Conjugate No. | SHSY5Y, 3 d IC50 (nM) | SHSY5Y, 3 d % KD (knockdown) of MAPT at 1 μM | MCN, 7 d IC50 (nM) | MCN, 7 d % KD (knockdown) of SNCA at 1 uM | Mouse ICV, 14 d % KD Brain stem | Mouse ICV, 14 d % KD Frontal Cortex |
|---|---|---|---|---|---|---|
| 34 | ND | ND | 28.32 | 79.3 | 48 | 52 |
| 35 | ND | ND | 64.94 | 73 | 56 | 56 |
| 36 | ND | ND | 16.01 | 83 | 71 | 70 |
| 37 | ND | ND | 9.5 | 86.5 | 68 | 68 |
| 38 | ND | ND | 9.01 | 87.8 | 72 | 46 |
| 39 | ND | ND | 8.58 | 88.5 | 78 | 61 |
| 40 | ND | ND | 7.3 | 88.3 | 79 | 59 |
| 41 | ND | ND | 57.6 | 84.3 | 61 | 38 |
| 42 | ND | ND | 16.16 | 86.1 | 69 | 45 |
| 43 | ND | ND | 71.82 | 89.4 | ND | ND |
| 44 | ND | ND | 64.11 | 87.3 | ND | ND |
| 45 | ND | ND | 89.05 | 85.5 | ND | ND |
| 46 | ND | ND | 25.06 | 87.2 | ND | ND |
| 47 | ND | ND | 68.9 | 86.3 | ND | ND |
| 48 | ND | ND | 45.8 | 59.9 | ND | ND |
| 49 | ND | ND | 333.7 | 84 | ND | ND |
| 50 | ND | ND | 15.02 | 81.6 | ND | ND |
| 51 | ND | ND | 72.72 | 81.4 | ND | ND |
| 52 | ND | ND | 99.63 | 86.2 | ND | ND |
| 53 | ND | ND | 157.9 | 88.1 | ND | ND |
| 54 | ND | ND | 2.01 | 88.3 | 81 | 54 |
| 55 | ND | ND | 10.33 | 82.5 | ND | ND |
| 56 | ND | ND | 25.05 | 77.8 | ND | ND |
| 57 | ND | ND | 1.12 | 87.2 | ND | ND |
| 58 | ND | ND | 22.8 | 87.2 | ND | ND |
| 59 | ND | ND | 18.1 | 88.4 | ND | ND |
| 60 | ND | ND | 20.6 | 89.7 | ND | ND |
| 61 | ND | ND | 99.1 | 66.8 | ND | ND |
| 62 | ND | ND | 23.2 | 89.0 | ND | ND |
| 63 | ND | ND | 36.7 | 89.3 | ND | ND |
| 64 | ND | ND | 39.5 | 90.6 | ND | ND |
| 65 | ND | ND | 76.0 | 89.1 | ND | ND |
| 66 | ND | ND | 22.3 | 87.9 | ND | ND |
| 67 | ND | ND | 39.2 | 84.5 | ND | ND |
| Conjugated RNAi Agent No. 13 | 384.56 | 71.02 | ND | ND | 68 | 42 |
| Conjugated RNAi Agent No. 14 | 320.53 | 79.53 | ND | ND | 67 | 41 |
| Conjugated RNAi Agent No. 15 | 630.91 | 64.37 | ND | ND | 68 | 48 |
| Conjugated RNAi Agent No. 16 | 232.42 | 77.03 | ND | ND | 71 | 41 |
| Conjugated RNAi Agent No. 17 | >1000 | 24.79 | ND | ND | 68 | 51 |
| Conjugated RNAi Agent No. 18 | >1000 | 54.08 | ND | ND | ND | ND |
| Conjugated RNAi Agent No. 19 | 625.79 | 60.91 | ND | ND | ND | ND |
| Conjugated RNAi Agent No. 20 | 406.76 | 66.69 | ND | ND | ND | ND |

TABLE 10B-continued

In vitro and in vivo activities of additional MAPT RNAi agents with different modification patterns

| MAPT RNAi Agent No. or Conjugate No. | SHSY5Y, 3 d IC50 (nM) | SHSY5Y, 3 d % KD (knockdown) of MAPT at 1 μM | MCN, 7 d IC50 (nM) | MCN, 7 d % KD (knockdown) of SNCA at 1 uM | Mouse ICV, 14 d % KD Brain stem | Mouse ICV, 14 d % KD Frontal Cortex |
|---|---|---|---|---|---|---|
| Conjugated RNAi Agent No. 21 | 683.09 | 58.54 | ND | ND | ND | ND |

*ND means not determined.

Example 4. Knockdown of MAPT mRNA in Cynomolgus Monkey Following a Single Administration of MAPT siRNA by Intrathecal Injection In vivo testing of MAPT RNAi agent No. 31 (sense strand of SEQ ID NO: 63 and antisense strand of SEQ ID NO: 40) in Cynomolgus monkey (*Macaca fascicularis*) was conducted to assess the efficacy of MAPT siRNA. In order to elucidate the efficacy of the siRNA in silencing the target gene; n=4/group cynomolgus monkeys were ported with indwelling catheters intrathecally in the lumbar region. The monkeys were infused with either aCSF or MAPT RNAi agent No. 31 (2.4 mg/ml in aCSF) over 15 minutes and were perfused 78 days later. Tissues collected at necropsy included spinal cord (lumbar) and brain (prefrontal cortex, motor cortex, parietal cortex, hippocampus and thalamus). qPCR and ELISA was performed to determine MAPT mRNA and protein knockdown respectively in the CNS regions. Tables 11 and 12 below show MAPT mRNA and protein knockdown observed in all the regions, 78 days after a single administration of the siRNA.

TABLE 11

Mean MAPT mRNA knockdown following a single intrathecal administration of MAPT RNAi agent No. 31.

| Route of administration | Dose [mg] | Lumbar Spinal Cord | Prefrontal Cortex | Motor Cortex | Parietal Cortex | Hippo-campus | Thalamus |
|---|---|---|---|---|---|---|---|
| Intrathecal-Catheter | 6 | 80% | 73% | 62% | 72% | 61% | 34% |

TABLE 12

Mean MAPT protein knockdown following a single intrathecal administration of MAPT RNAi agent No. 31.

| Route of administration | Dose [mg] | Lumbar Spinal Cord | Prefrontal Cortex | Motor Cortex | Parietal Cortex | Hippo-campus | Thalamus |
|---|---|---|---|---|---|---|---|
| Intrathecal-Catheter | 6 | 75% | 70% | 72% | 77% | 63% | 67% |

The invention claimed is:

1. A MAPT RNAi agent having a sense strand and an antisense strand,
wherein the sense strand and the antisense strand form a duplex,
wherein the sense strand comprises SEQ ID NO:15, and the antisense strand comprises SEQ ID NO: 16,
wherein optionally one or more nucleotides of the sense strand and the antisense strand are independently modified nucleotides, and
wherein optionally one or more internucleotide linkages of the sense strand and the antisense strand are modified internucleotide linkages.

2. The MAPT RNAi agent of claim 1, wherein one or more nucleotides of the sense strand are modified nucleotides.

3. The MAPT RNAi agent of claim 1, wherein one or more nucleotides of the antisense strand are modified nucleotides.

4. The MAPT RNAi agent of claim 1, wherein the modified nucleotide is a 2'-fluoro modified nucleotide, 2'-O-methyl modified nucleotide or 2'-O—C16 alkyl modified nucleotide.

5. The MAPT RNAi agent of claim 1, wherein the sense strand has three 2'-fluoro modified nucleotides at positions 9, 10, and 11 from the 5' end of the sense strand.

6. The MAPT RNAi agent of claim 5, wherein nucleotides at positions other than positions 9, 10, and 11 of the sense strand are 2'-O-methyl modified nucleotides or 2'-O—C16 alkyl modified nucleotides.

7. The MAPT RNAi agent of claim 1, wherein the antisense strand has five 2'-fluoro modified nucleotides at positions 2, 5, 7, 14, and 16 from the 5' end of the antisense strand.

8. The MAPT RNAi agent of claim 7, wherein nucleotides at positions other than positions 2, 5, 7, 14, and 16 of the antisense strand are 2'-O-methyl modified nucleotides or 2'-O—C16 alkyl modified nucleotides.

9. The MAPT RNAi agent of claim 1, wherein the antisense strand has five 2'-fluoro modified nucleotides at positions 2, 5, 8, 14, and 16 from the 5' end of the antisense strand.

10. The MAPT RNAi agent of claim 9, wherein nucleotides at positions other than positions 2, 5, 8, 14, and 16 of the antisense strand are 2'-O-methyl modified nucleotides or 2'-O—C16 alkyl modified nucleotides.

11. The MAPT RNAi agent of claim 1, wherein the antisense strand has five 2'-fluoro modified nucleotides at positions 2, 3, 7, 14, and 16 from the 5' end of the antisense strand.

12. The MAPT RNAi agent of claim 11, wherein nucleotides at positions other than positions 2, 3, 7, 14, and 16 of the antisense strand are 2'-O-methyl modified nucleotides or 2'-O—C16 alkyl modified nucleotides.

13. The MAPT RNAi agent of claim 1, wherein the sense strand has four 2'-fluoro modified nucleotides at positions 7, 9, 10, 11 from the 5' end of the sense strand.

14. The MAPT RNAi agent of claim 13, wherein nucleotides at positions other than positions 7, 9, 10, and 11 of the sense strand are 2'-O-methyl modified nucleotides or 2'-O—C16 alkyl modified nucleotides.

15. The MAPT RNAi agent of claim 1, wherein the antisense strand has four 2'-fluoro modified nucleotides at positions 2, 6, 14, 16 from the 5' end of the antisense strand.

16. The MAPT RNAi agent of claim 15, wherein nucleotides at positions other than positions 2, 6, 14 and 16 of the antisense strand are 2'-O-methyl modified nucleotides or 2'-O—C16 alkyl modified nucleotides.

17. The MAPT RNAi agent of claim 1, wherein the sense strand and the antisense strand have one or more modified internucleotide linkages.

18. The MAPT RNAi agent of claim 17, wherein the modified internucleotide linkage is phosphorothioate linkage.

19. The MAPT RNAi agent of claim 18, wherein the sense strand has four or five phosphorothioate linkages.

20. The MAPT RNAi agent of claim 18, wherein the antisense strand has four or five phosphorothioate linkages.

21. The MAPT RNAi agent of claim 1, wherein the first nucleotide from the 5' end of the antisense strand is a modified nucleotide that has a phosphate analog.

22. The MAPT RNAi agent of claim 21, wherein the phosphate analog is 5'-vinylphosphonate.

23. The MAPT RNAi agent of claim 1, wherein the sense strand comprises an abasic moiety or inverted abasic moiety.

24. The MAPT RNAi agent of claim 1, wherein the sense strand has a delivery moiety conjugated to the 5' or 3' end of the sense strand.

25. The MAPT RNAi agent of claim 1, wherein the sense strand has a delivery moiety conjugated to a nucleotide of the sense strand.

26. The MAPT RNAi agent of claim 1, wherein the sense strand and the antisense strand comprise a pair of nucleic acid sequences selected from the group consisting of:
(a) the sense strand comprises SEQ ID NO: 63, and the antisense strand comprises SEQ ID NO: 40;
(b) the sense strand comprises SEQ ID NO: 39, and the antisense strand comprises SEQ ID NO: 40;
(c) the sense strand comprises SEQ ID NO: 64, and the antisense strand comprises SEQ ID NO: 65;
(d) the sense strand comprises SEQ ID NO: 66, and the antisense strand comprises SEQ ID NO: 65;
(e) the sense strand comprises SEQ ID NO: 64, and the antisense strand comprises SEQ ID NO: 70;
(f) the sense strand comprises SEQ ID NO: 71, and the antisense strand comprises SEQ ID NO: 65;
(g) the sense strand comprises SEQ ID NO: 64, and the antisense strand comprises SEQ ID NO: 72;
(h) the sense strand comprises SEQ ID NO: 64, and the antisense strand comprises SEQ ID NO: 73;
(i) the sense strand comprises SEQ ID NO: 64, and the antisense strand comprises SEQ ID NO: 74;
(j) the sense strand comprises SEQ ID NO: 75, and the antisense strand comprises SEQ ID NO: 65;
(k) the sense strand comprises SEQ ID NO: 76, and the antisense strand comprises SEQ ID NO: 65;
(l) the sense strand comprises SEQ ID NO: 77, and the antisense strand comprises SEQ ID NO: 65;
(m) the sense strand comprises SEQ ID NO: 78, and the antisense strand comprises SEQ ID NO: 65;
(n) the sense strand comprises SEQ ID NO: 79, and the antisense strand comprises SEQ ID NO: 65;
(o) the sense strand comprises SEQ ID NO: 80, and the antisense strand comprises SEQ ID NO: 65;
(p) the sense strand comprises SEQ ID NO: 81, and the antisense strand comprises SEQ ID NO: 65;
(q) the sense strand comprises SEQ ID NO: 82, and the antisense strand comprises SEQ ID NO: 65;
(r) the sense strand comprises SEQ ID NO: 83, and the antisense strand comprises SEQ ID NO: 65;
(s) the sense strand comprises SEQ ID NO: 84, and the antisense strand comprises SEQ ID NO: 65;
(t) the sense strand comprises SEQ ID NO: 85, and the antisense strand comprises SEQ ID NO: 65;
(u) the sense strand comprises SEQ ID NO: 86, and the antisense strand comprises SEQ ID NO: 65;
(v) the sense strand comprises SEQ ID NO: 93, and the antisense strand comprises SEQ ID NO: 65;
(w) the sense strand comprises SEQ ID NO: 94, and the antisense strand comprises SEQ ID NO: 65;
(x) the sense strand comprises SEQ ID NO: 95, and the antisense strand comprises SEQ ID NO: 65;
(y) the sense strand comprises SEQ ID NO: 96, and the antisense strand comprises SEQ ID NO: 65;
(z) the sense strand comprises SEQ ID NO: 97, and the antisense strand comprises SEQ ID NO: 65;
(aa) the sense strand comprises SEQ ID NO: 98, and the antisense strand comprises SEQ ID NO: 65;
(bb) the sense strand comprises SEQ ID NO: 99, and the antisense strand comprises SEQ ID NO: 65;
(cc) the sense strand comprises SEQ ID NO: 100, and the antisense strand comprises SEQ ID NO: 65;
(dd) the sense strand comprises SEQ ID NO: 105, and the antisense strand comprises SEQ ID NO: 65;
(ee) the sense strand comprises SEQ ID NO: 105, and the antisense strand comprises SEQ ID NO: 106;
(ff) the sense strand comprises SEQ ID NO: 105, and the antisense strand comprises SEQ ID NO: 107;
(gg) the sense strand comprises SEQ ID NO: 105, and the antisense strand comprises SEQ ID NO: 108; and
(hh) the sense strand comprises SEQ ID NO: 115, and the antisense strand comprises SEQ ID NO: 116.

27. The MAPT RNAi agent of claim 1, wherein the sense strand and the antisense strand have a pair of nucleic acid sequences selected from the group consisting of:
(a) the sense strand consists of SEQ ID NO: 63, and the antisense strand consists of SEQ ID NO: 40;
(b) the sense strand consists of SEQ ID NO: 39, and the antisense strand consists of SEQ ID NO: 40;
(c) the sense strand consists of SEQ ID NO: 64, and the antisense strand consists of SEQ ID NO: 65;
(d) the sense strand consists of SEQ ID NO: 66, and the antisense strand consists of SEQ ID NO: 65;
(e) the sense strand consists of SEQ ID NO: 64, and the antisense strand consists of SEQ ID NO: 70;
(f) the sense strand consists of SEQ ID NO: 71, and the antisense strand consists of SEQ ID NO: 65;
(g) the sense strand consists of SEQ ID NO: 64, and the antisense strand consists of SEQ ID NO: 72;
(h) the sense strand consists of SEQ ID NO: 64, and the antisense strand consists of SEQ ID NO: 73;
(i) the sense strand consists of SEQ ID NO: 64, and the antisense strand consists of SEQ ID NO: 74;
(j) the sense strand consists of SEQ ID NO: 75, and the antisense strand consists of SEQ ID NO: 65;
(k) the sense strand consists of SEQ ID NO: 76, and the antisense strand consists of SEQ ID NO: 65;
(l) the sense strand consists of SEQ ID NO: 77, and the antisense strand consists of SEQ ID NO: 65;
(m) the sense strand consists of SEQ ID NO: 78, and the antisense strand consists of SEQ ID NO: 65;
(n) the sense strand consists of SEQ ID NO: 79, and the antisense strand consists of SEQ ID NO: 65;
(o) the sense strand consists of SEQ ID NO: 80, and the antisense strand consists of SEQ ID NO: 65;
(p) the sense strand consists of SEQ ID NO: 81, and the antisense strand consists of SEQ ID NO: 65;
(q) the sense strand consists of SEQ ID NO: 82, and the antisense strand consists of SEQ ID NO: 65;
(r) the sense strand consists of SEQ ID NO: 83, and the antisense strand consists of SEQ ID NO: 65;
(s) the sense strand consists of SEQ ID NO: 84, and the antisense strand consists of SEQ ID NO: 65;
(t) the sense strand consists of SEQ ID NO: 85, and the antisense strand consists of SEQ ID NO: 65;
(u) the sense strand consists of SEQ ID NO: 86, and the antisense strand consists of SEQ ID NO: 65;
(v) the sense strand consists of SEQ ID NO: 93, and the antisense strand consists of SEQ ID NO: 65;
(w) the sense strand consists of SEQ ID NO: 94, and the antisense strand consists of SEQ ID NO: 65;
(x) the sense strand consists of SEQ ID NO: 95, and the antisense strand consists of SEQ ID NO: 65;
(y) the sense strand consists of SEQ ID NO: 96, and the antisense strand consists of SEQ ID NO: 65;
(z) the sense strand consists of SEQ ID NO: 97, and the antisense strand consists of SEQ ID NO: 65;
(aa) the sense strand consists of SEQ ID NO: 98, and the antisense strand consists of SEQ ID NO: 65;
(bb) the sense strand consists of SEQ ID NO: 99, and the antisense strand consists of SEQ ID NO: 65;

(cc) the sense strand consists of SEQ ID NO: 100, and the antisense strand consists of SEQ ID NO: 65;
(dd) the sense strand consists of SEQ ID NO: 105, and the antisense strand consists of SEQ ID NO: 65;
(ee) the sense strand consists of SEQ ID NO: 105, and the antisense strand consists of SEQ ID NO: 106;
(ff) the sense strand consists of SEQ ID NO: 105, and the antisense strand consists of SEQ ID NO: 107;
(gg) the sense strand consists of SEQ ID NO: 105, and the antisense strand consists of SEQ ID NO: 108; and
(hh) the sense strand consists of SEQ ID NO: 115, and the antisense strand consists of SEQ ID NO: 116.

28. A pharmaceutical composition comprising the MAPT RNAi agent of claim 1 and a pharmaceutically acceptable carrier.

29. A pharmaceutical composition comprising the MAPT RNAi agent of claim 26 and a pharmaceutically acceptable carrier.

30. A pharmaceutical composition comprising the MAPT RNAi agent of claim 27 and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 11,926,827 B2 | Page 1 of 1 |
| APPLICATION NO. | : 18/311354 | |
| DATED | : March 12, 2024 | |
| INVENTOR(S) | : Barbara Calamini et al. | |

It is certified that error appears in the above-identified patent and that said Letters Patent is hereby corrected as shown below:

On the Title Page

Item (56), In References Cited, FOREIGN PATENT DOCUMENTS, "WO202/188626" should read --WO2021/188626--.

In the Specification

In Columns 118, 119, and 121, Line 4 in TABLE 10B, in the Heading of the 5th Column, "SNCA" should be changed to --MAPT--.

Signed and Sealed this
Fourth Day of June, 2024

Katherine Kelly Vidal
*Director of the United States Patent and Trademark Office*

SEQUENCE LISTING

```
Sequence total quantity: 119
SEQ ID NO: 1              moltype = RNA  length = 21
FEATURE                   Location/Qualifiers
misc_feature              1..21
                          note = Description of Artificial Sequence: Synthetic
                          oligonucleotide
source                    1..21
                          mol_type = other RNA
                          organism = synthetic construct
SEQUENCE: 1
acaagctgac cttccgcgag a                                                 21

SEQ ID NO: 2              moltype = RNA  length = 23
FEATURE                   Location/Qualifiers
```

```
misc_feature          1..23
                      note = Description of Artificial Sequence: Synthetic
                        oligonucleotide
source                1..23
                      mol_type = other RNA
                      organism = synthetic construct
SEQUENCE: 2
tctcgcggaa ggtcagcttg tgg                                              23

SEQ ID NO: 3          moltype = RNA   length = 21
FEATURE               Location/Qualifiers
misc_feature          1..21
                      note = Description of Artificial Sequence: Synthetic
                        oligonucleotide
source                1..21
                      mol_type = other RNA
                      organism = synthetic construct
SEQUENCE: 3
agattgaaac ccacaagctg a                                                21

SEQ ID NO: 4          moltype = RNA   length = 23
FEATURE               Location/Qualifiers
misc_feature          1..23
                      note = Description of Artificial Sequence: Synthetic
                        oligonucleotide
source                1..23
                      mol_type = other RNA
                      organism = synthetic construct
SEQUENCE: 4
tcagcttgtg ggtttcaatc ttt                                              23

SEQ ID NO: 5          moltype = RNA   length = 21
FEATURE               Location/Qualifiers
misc_feature          1..21
                      note = Description of Artificial Sequence: Synthetic
                        oligonucleotide
source                1..21
                      mol_type = other RNA
                      organism = synthetic construct
SEQUENCE: 5
aataaaaaga ttgaaaccca a                                                21

SEQ ID NO: 6          moltype = RNA   length = 23
FEATURE               Location/Qualifiers
misc_feature          1..23
                      note = Description of Artificial Sequence: Synthetic
                        oligonucleotide
source                1..23
                      mol_type = other RNA
                      organism = synthetic construct
SEQUENCE: 6
ttgggtttca atctttttat ttc                                              23

SEQ ID NO: 7          moltype = RNA   length = 21
FEATURE               Location/Qualifiers
misc_feature          1..21
                      note = Description of Artificial Sequence: Synthetic
                        oligonucleotide
source                1..21
                      mol_type = other RNA
                      organism = synthetic construct
SEQUENCE: 7
ggaaataaaa agattgaaac a                                                21

SEQ ID NO: 8          moltype = RNA   length = 23
FEATURE               Location/Qualifiers
misc_feature          1..23
                      note = Description of Artificial Sequence: Synthetic
                        oligonucleotide
source                1..23
                      mol_type = other RNA
                      organism = synthetic construct
SEQUENCE: 8
tgtttcaatc tttttatttc ctc                                              23

SEQ ID NO: 9          moltype = RNA   length = 21
FEATURE               Location/Qualifiers
misc_feature          1..21
                      note = Description of Artificial Sequence: Synthetic
```

```
                        oligonucleotide
source                  1..21
                        mol_type = other RNA
                        organism = synthetic construct
SEQUENCE: 9
ggcggaggaa ataaaaagat a                                              21

SEQ ID NO: 10           moltype = RNA  length = 23
FEATURE                 Location/Qualifiers
misc_feature            1..23
                        note = Description of Artificial Sequence: Synthetic
                        oligonucleotide
source                  1..23
                        mol_type = other RNA
                        organism = synthetic construct
SEQUENCE: 10
tatcttttta tttcctccgc cag                                            23

SEQ ID NO: 11           moltype = RNA  length = 21
FEATURE                 Location/Qualifiers
misc_feature            1..21
                        note = Description of Artificial Sequence: Synthetic
                        oligonucleotide
source                  1..21
                        mol_type = other RNA
                        organism = synthetic construct
SEQUENCE: 11
gaagtaaaat ctgagaagct a                                              21

SEQ ID NO: 12           moltype = RNA  length = 23
FEATURE                 Location/Qualifiers
misc_feature            1..23
                        note = Description of Artificial Sequence: Synthetic
                        oligonucleotide
source                  1..23
                        mol_type = other RNA
                        organism = synthetic construct
SEQUENCE: 12
tagcttctca gattttactt cca                                            23

SEQ ID NO: 13           moltype = RNA  length = 21
FEATURE                 Location/Qualifiers
misc_feature            1..21
                        note = Description of Artificial Sequence: Synthetic
                        oligonucleotide
source                  1..21
                        mol_type = other RNA
                        organism = synthetic construct
SEQUENCE: 13
ggaagtaaaa tctgagaagc a                                              21

SEQ ID NO: 14           moltype = RNA  length = 23
FEATURE                 Location/Qualifiers
misc_feature            1..23
                        note = Description of Artificial Sequence: Synthetic
                        oligonucleotide
source                  1..23
                        mol_type = other RNA
                        organism = synthetic construct
SEQUENCE: 14
tgcttctcag attttacttc cac                                            23

SEQ ID NO: 15           moltype = RNA  length = 21
FEATURE                 Location/Qualifiers
misc_feature            1..21
                        note = Description of Artificial Sequence: Synthetic
                        oligonucleotide
source                  1..21
                        mol_type = other RNA
                        organism = synthetic construct
SEQUENCE: 15
gtggaagtaa aatctgagaa a                                              21

SEQ ID NO: 16           moltype = RNA  length = 23
FEATURE                 Location/Qualifiers
misc_feature            1..23
                        note = Description of Artificial Sequence: Synthetic
                        oligonucleotide
source                  1..23
```

```
                        mol_type = other RNA
                        organism = synthetic construct
SEQUENCE: 16
tttctcagat tttacttcca cct                                              23

SEQ ID NO: 17           moltype = RNA   length = 21
FEATURE                 Location/Qualifiers
misc_feature            1..21
                        note = Description of Artificial Sequence: Synthetic
                         oligonucleotide
source                  1..21
                        mol_type = other RNA
                        organism = synthetic construct
SEQUENCE: 17
ccaggtggaa gtaaaatctg a                                                21

SEQ ID NO: 18           moltype = RNA   length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 18
tcagatttta cttccacctg gcc                                              23

SEQ ID NO: 19           moltype = RNA   length = 21
FEATURE                 Location/Qualifiers
misc_feature            1..21
                        note = Description of Artificial Sequence: Synthetic
                         oligonucleotide
source                  1..21
                        mol_type = other RNA
                        organism = synthetic construct
SEQUENCE: 19
caagtccaag atcggctcca a                                                21

SEQ ID NO: 20           moltype = RNA   length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 20
ttggagccga tcttggactt gac                                              23

SEQ ID NO: 21           moltype = RNA   length = 21
FEATURE                 Location/Qualifiers
misc_feature            1..21
                        note = Description of Artificial Sequence: Synthetic
                         oligonucleotide
source                  1..21
                        mol_type = other RNA
                        organism = synthetic construct
SEQUENCE: 21
tctggtgaac ctccaaaatc a                                                21

SEQ ID NO: 22           moltype = RNA   length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 22
tgattttgga ggttcaccag agc                                              23

SEQ ID NO: 23           moltype = RNA   length = 21
FEATURE                 Location/Qualifiers
misc_feature            1..21
                        note = Description of Artificial Sequence: Synthetic
                         oligonucleotide
source                  1..21
                        mol_type = other RNA
                        organism = synthetic construct
```

```
SEQUENCE: 23
caggtggaag taaaatctga a                                           21

SEQ ID NO: 24           moltype = RNA  length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 24
ttcagatttt acttccacct ggc                                         23

SEQ ID NO: 25           moltype = RNA  length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methyladenosine with a 3'-phosphorothioate
                         linkage
modified_base           2
                        mod_base = OTHER
                        note = 2'-O-methylcytidine with a 3'-phosphorothioate
                         linkage
modified_base           11
                        mod_base = OTHER
                        note = 2'-fluorocytidine
modified_base           14
                        mod_base = cm
source                  1..21
                        mol_type = other RNA
                        organism = synthetic construct
modified_base           3
                        mod_base = OTHER
                        note = 2'-O-methyladenosine
modified_base           4
                        mod_base = OTHER
                        note = 2'-O-methyladenosine
modified_base           5
                        mod_base = gm
modified_base           6
                        mod_base = cm
modified_base           7
                        mod_base = OTHER
                        note = 2'-fluorouridine
modified_base           8
                        mod_base = gm
modified_base           9
                        mod_base = OTHER
                        note = 2'-fluoroadenosine
modified_base           10
                        mod_base = OTHER
                        note = 2'-fluorocytidine
modified_base           12
                        mod_base = um
modified_base           13
                        mod_base = um
modified_base           15
                        mod_base = cm
modified_base           16
                        mod_base = gm
modified_base           17
                        mod_base = cm
modified_base           18
                        mod_base = gm
modified_base           19
                        mod_base = OTHER
                        note = 2'-O-methyladenosine with a 3'-phosphorothioate
                         linkage
modified_base           20
                        mod_base = OTHER
                        note = 2'-O-methylguanosine with a 3'-phosphorothioate
                         linkage
modified_base           21
                        mod_base = OTHER
                        note = 2'-O-methyladenosine
```

```
SEQUENCE: 25
acaagctgac cttccgcgag a                                                    21

SEQ ID NO: 26           moltype = RNA   length = 23
FEATURE                 Location/Qualifiers
misc_feature            1..23
                        note = Description of Artificial Sequence: Synthetic
                        oligonucleotide
modified_base           1
                        mod_base = OTHER
                        note = 2'-O-methyluridine with a 3'-phosphorothioate
                        linkage and a 5'-vinylphosphonate substitution
modified_base           2
                        mod_base = OTHER
                        note = 2'-fluorocytidine with a 3'-phosphorothioate linkage
modified_base           3
                        mod_base = um
modified_base           4
                        mod_base = cm
modified_base           5
                        mod_base = gm
modified_base           6
                        mod_base = OTHER
                        note = 2'-fluorocytidine
modified_base           7
                        mod_base = gm
modified_base           8
                        mod_base = gm
modified_base           9
                        mod_base = OTHER
                        note = 2'-O-methyladenosine
modified_base           10
                        mod_base = OTHER
                        note = 2'-O-methyladenosine
modified_base           11
                        mod_base = gm
modified_base           12
                        mod_base = gm
modified_base           13
                        mod_base = um
modified_base           14
                        mod_base = OTHER
                        note = 2'-fluorocytidine
modified_base           15
                        mod_base = OTHER
                        note = 2'-O-methyladenosine
modified_base           16
                        mod_base = OTHER
                        note = 2'-fluoroguanosine
modified_base           17
                        mod_base = cm
modified_base           18
                        mod_base = um
modified_base           19
                        mod_base = um
modified_base           20
                        mod_base = gm
modified_base           21
                        mod_base = OTHER
                        note = 2'-O-methyluridine with a 3'-phosphorothioate linkage
modified_base           22
                        mod_base = OTHER
                        note = 2'-O-methylguanosine with a 3'-phosphorothioate
                        linkage
modified_base           23
                        mod_base = gm
source                  1..23
                        mol_type = other RNA
                        organism = synthetic construct
SEQUENCE: 26
tctcgcggaa ggtcagcttg tgg                                                  23

SEQ ID NO: 27           moltype = RNA   length = 21
FEATURE                 Location/Qualifiers
misc_feature            1..21
                        note = Description of Artificial Sequence: Synthetic
                        oligonucleotide
modified_base           1
                        mod_base = OTHER
```

```
                            note = 2'-O-methyladenosine with a 3'-phosphorothioate
                              linkage
modified_base               2
                            mod_base = OTHER
                            note = 2'-O-methylguanosine with a 3'-phosphorothioate
                              linkage
modified_base               3
                            mod_base = OTHER
                            note = 2'-O-methyladenosine
modified_base               4
                            mod_base = um
modified_base               5
                            mod_base = um
modified_base               6
                            mod_base = gm
modified_base               7
                            mod_base = OTHER
                            note = 2'-fluoroadenosine
modified_base               8
                            mod_base = OTHER
                            note = 2'-O-methyladenosine
modified_base               9
                            mod_base = OTHER
                            note = 2'-fluoroadenosine
modified_base               10
                            mod_base = OTHER
                            note = 2'-fluorocytidine
modified_base               11
                            mod_base = OTHER
                            note = 2'-fluorocytidine
modified_base               12
                            mod_base = cm
modified_base               13
                            mod_base = OTHER
                            note = 2'-O-methyladenosine
modified_base               14
                            mod_base = cm
modified_base               15
                            mod_base = OTHER
                            note = 2'-O-methyladenosine
modified_base               16
                            mod_base = OTHER
                            note = 2'-O-methyladenosine
modified_base               17
                            mod_base = gm
modified_base               18
                            mod_base = cm
modified_base               19
                            mod_base = OTHER
                            note = 2'-O-methyluridine with a 3'-phosphorothioate linkage
modified_base               20
                            mod_base = OTHER
                            note = 2'-O-methylguanosine with a 3'-phosphorothioate
                              linkage
modified_base               21
                            mod_base = OTHER
                            note = 2'-O-methyladenosine
source                      1..21
                            mol_type = other RNA
                            organism = synthetic construct
SEQUENCE: 27
agattgaaac ccacaagctg a                                          21

SEQ ID NO: 28              moltype = RNA  length = 23
FEATURE                    Location/Qualifiers
misc_feature               1..23
                            note = Description of Artificial Sequence: Synthetic
                              oligonucleotide
modified_base               1
                            mod_base = OTHER
                            note = 2'-O-methyluridine with a 3'-phosphorothioate
                              linkage and a 5'-vinylphosphonate substitution
modified_base               2
                            mod_base = OTHER
                            note = 2'-fluorocytidine with a 3'-phosphorothioate linkage
modified_base               3
                            mod_base = OTHER
                            note = 2'-O-methyladenosine
modified_base               4
```

|  |  |
|---|---|
| modified_base | mod_base = gm<br>5 |
| modified_base | mod_base = cm<br>6 |
| modified_base | mod_base = OTHER<br>note = 2'-fluorouridine<br>7 |
| modified_base | mod_base = um<br>8 |
| modified_base | mod_base = gm<br>9 |
| modified_base | mod_base = um<br>10 |
| modified_base | mod_base = gm<br>11 |
| modified_base | mod_base = gm<br>12 |
| modified_base | mod_base = gm<br>13 |
| modified_base | mod_base = um<br>14 |
| modified_base | mod_base = OTHER<br>note = 2'-fluorouridine<br>15 |
| modified_base | mod_base = um<br>16 |
| modified_base | mod_base = OTHER<br>note = 2'-fluorocytidine<br>17 |
| modified_base | mod_base = OTHER<br>note = 2'-O-methyladenosine<br>18 |
| modified_base | mod_base = OTHER<br>note = 2'-O-methyladenosine<br>19 |
| modified_base | mod_base = um<br>20 |
| modified_base | mod_base = cm<br>21 |
| modified_base | mod_base = OTHER<br>note = 2'-O-methyluridine with a 3'-phosphorothioate linkage<br>22 |
| modified_base | mod_base = OTHER<br>note = 2'-O-methyluridine with a 3'-phosphorothioate linkage<br>23 |
| modified_base | mod_base = um |
| source | 1..23<br>mol_type = other RNA<br>organism = synthetic construct |

SEQUENCE: 28
tcagcttgtg ggtttcaatc ttt                                                23

|  |  |
|---|---|
| SEQ ID NO: 29<br>FEATURE<br>misc_feature | moltype = RNA  length = 21<br>Location/Qualifiers<br>1..21<br>note = Description of Artificial Sequence: Synthetic oligonucleotide |
| modified_base | 1<br>mod_base = OTHER<br>note = 2'-O-methyladenosine with a 3'-phosphorothioate linkage |
| modified_base | 2<br>mod_base = OTHER<br>note = 2'-O-methyladenosine with a 3'-phosphorothioate linkage |
| modified_base | 3<br>mod_base = um |
| modified_base | 4<br>mod_base = OTHER<br>note = 2'-O-methyladenosine |
| modified_base | 5<br>mod_base = OTHER<br>note = 2'-O-methyladenosine |
| modified_base | 6<br>mod_base = OTHER<br>note = 2'-O-methyladenosine |
| modified_base | 7<br>mod_base = OTHER<br>note = 2'-fluoroadenosine |

| | | |
|---|---|---|
| modified_base | 8 | |
| | mod_base = OTHER | |
| | note = 2'-O-methyladenosine | |
| modified_base | 9 | |
| | mod_base = OTHER | |
| | note = 2'-fluoroguanosine | |
| modified_base | 10 | |
| | mod_base = OTHER | |
| | note = 2'-fluoroadenosine | |
| modified_base | 11 | |
| | mod_base = OTHER | |
| | note = 2'-fluorouridine | |
| modified_base | 12 | |
| | mod_base = um | |
| modified_base | 13 | |
| | mod_base = gm | |
| modified_base | 14 | |
| | mod_base = OTHER | |
| | note = 2'-O-methyladenosine | |
| modified_base | 15 | |
| | mod_base = OTHER | |
| | note = 2'-O-methyladenosine | |
| modified_base | 16 | |
| | mod_base = OTHER | |
| | note = 2'-O-methyladenosine | |
| modified_base | 17 | |
| | mod_base = cm | |
| modified_base | 18 | |
| | mod_base = cm | |
| modified_base | 19 | |
| | mod_base = OTHER | |
| | note = 2'-O-methylcytidine with a 3'-phosphorothioate linkage | |
| modified_base | 20 | |
| | mod_base = OTHER | |
| | note = 2'-O-methyladenosine with a 3'-phosphorothioate linkage | |
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 29 | | |
| aataaaaaga ttgaaaccca a | | 21 |
| | | |
| SEQ ID NO: 30 | moltype = RNA   length = 23 | |
| FEATURE | Location/Qualifiers | |
| misc_feature | 1..23 | |
| | note = Description of Artificial Sequence: Synthetic oligonucleotide | |
| modified_base | 1 | |
| | mod_base = OTHER | |
| | note = 2'-O-methyluridine with a 3'-phosphorothioate linkage and a 5'-vinylphosphonate substitution | |
| modified_base | 2 | |
| | mod_base = OTHER | |
| | note = 2'-fluorouridine with a 3'-phosphorothioate linkage | |
| modified_base | 3 | |
| | mod_base = gm | |
| modified_base | 4 | |
| | mod_base = gm | |
| modified_base | 5 | |
| | mod_base = gm | |
| modified_base | 6 | |
| | mod_base = OTHER | |
| | note = 2'-fluorouridine | |
| modified_base | 7 | |
| | mod_base = um | |
| modified_base | 8 | |
| | mod_base = um | |
| modified_base | 9 | |
| | mod_base = cm | |
| modified_base | 10 | |
| | mod_base = OTHER | |
| | note = 2'-O-methyladenosine | |
| modified_base | 11 | |
| | mod_base = OTHER | |
| | note = 2'-O-methyladenosine | |

```
modified_base            12
                         mod_base = um
modified_base            13
                         mod_base = cm
modified_base            14
                         mod_base = OTHER
                         note = 2'-fluorouridine
modified_base            15
                         mod_base = um
modified_base            16
                         mod_base = OTHER
                         note = 2'-fluorouridine
modified_base            17
                         mod_base = um
modified_base            18
                         mod_base = um
modified_base            19
                         mod_base = OTHER
                         note = 2'-O-methyladenosine
modified_base            20
                         mod_base = um
modified_base            21
                         mod_base = OTHER
                         note = 2'-O-methyluridine with a 3'-phosphorothioate linkage
modified_base            22
                         mod_base = OTHER
                         note = 2'-O-methyluridine with a 3'-phosphorothioate linkage
modified_base            23
                         mod_base = cm
source                   1..23
                         mol_type = other RNA
                         organism = synthetic construct
SEQUENCE: 30
ttgggtttca atctttttat ttc                                        23

SEQ ID NO: 31            moltype = RNA   length = 21
FEATURE                  Location/Qualifiers
misc_feature             1..21
                         note = Description of Artificial Sequence: Synthetic
                         oligonucleotide
modified_base            1
                         mod_base = OTHER
                         note = 2'-O-methylguanosine with a 3'-phosphorothioate
                         linkage
modified_base            2
                         mod_base = OTHER
                         note = 2'-O-methylguanosine with a 3'-phosphorothioate
                         linkage
modified_base            3
                         mod_base = OTHER
                         note = 2'-O-methyladenosine
modified_base            4
                         mod_base = OTHER
                         note = 2'-O-methyladenosine
modified_base            5
                         mod_base = OTHER
                         note = 2'-O-methyladenosine
modified_base            6
                         mod_base = um
modified_base            7
                         mod_base = OTHER
                         note = 2'-fluoroadenosine
modified_base            8
                         mod_base = OTHER
                         note = 2'-O-methyladenosine
modified_base            9
                         mod_base = OTHER
                         note = 2'-fluoroadenosine
modified_base            10
                         mod_base = OTHER
                         note = 2'-fluoroadenosine
modified_base            11
                         mod_base = OTHER
                         note = 2'-fluoroadenosine
modified_base            12
                         mod_base = gm
modified_base            13
                         mod_base = OTHER
                         note = 2'-O-methyladenosine
```

```
modified_base      14
                   mod_base = um
modified_base      15
                   mod_base = um
modified_base      16
                   mod_base = gm
modified_base      17
                   mod_base = OTHER
                   note = 2'-O-methyladenosine
modified_base      18
                   mod_base = OTHER
                   note = 2'-O-methyladenosine
modified_base      19
                   mod_base = OTHER
                   note = 2'-O-methyladenosine with a 3'-phosphorothioate
                     linkage
modified_base      20
                   mod_base = OTHER
                   note = 2'-O-methylcytidine with a 3'-phosphorothioate
                     linkage
modified_base      21
                   mod_base = OTHER
                   note = 2'-O-methyladenosine
source             1..21
                   mol_type = other RNA
                   organism = synthetic construct
SEQUENCE: 31
ggaaataaaa agattgaaac a                                            21

SEQ ID NO: 32      moltype = RNA  length = 23
FEATURE            Location/Qualifiers
misc_feature       1..23
                   note = Description of Artificial Sequence: Synthetic
                     oligonucleotide
modified_base      1
                   mod_base = OTHER
                   note = 2'-O-methyluridine with a 3'-phosphorothioate
                     linkage and a 5'-vinylphosphonate substitution
modified_base      2
                   mod_base = OTHER
                   note = 2'-fluoroguanosine with a 3'-phosphorothioate linkage
modified_base      3
                   mod_base = um
modified_base      4
                   mod_base = um
modified_base      5
                   mod_base = um
modified_base      6
                   mod_base = OTHER
                   note = 2'-fluorocytidine
modified_base      7
                   mod_base = OTHER
                   note = 2'-O-methyladenosine
modified_base      8
                   mod_base = OTHER
                   note = 2'-O-methyladenosine
modified_base      9
                   mod_base = um
modified_base      10
                   mod_base = cm
modified_base      11
                   mod_base = um
modified_base      12
                   mod_base = um
modified_base      13
                   mod_base = um
modified_base      14
                   mod_base = OTHER
                   note = 2'-fluorouridine
modified_base      15
                   mod_base = um
modified_base      16
                   mod_base = OTHER
                   note = 2'-fluoroadenosine
modified_base      17
                   mod_base = um
modified_base      18
                   mod_base = um
modified_base      19
```

```
                        mod_base = um
modified_base           20
                        mod_base = cm
modified_base           21
                        mod_base = OTHER
                        note = 2'-O-methylcytidine with a 3'-phosphorothioate
                           linkage
modified_base           22
                        mod_base = OTHER
                        note = 2'-O-methyluridine with a 3'-phosphorothioate linkage
modified_base           23
                        mod_base = cm
source                  1..23
                        mol_type = other RNA
                        organism = synthetic construct
SEQUENCE: 32
tgtttcaatc tttttatttc ctc                                              23

SEQ ID NO: 33           moltype = RNA  length = 21
FEATURE                 Location/Qualifiers
misc_feature            1..21
                        note = Description of Artificial Sequence: Synthetic
                           oligonucleotide
modified_base           1
                        mod_base = OTHER
                        note = 2'-O-methylguanosine with a 3'-phosphorothioate
                           linkage
modified_base           2
                        mod_base = OTHER
                        note = 2'-O-methylguanosine with a 3'-phosphorothioate
                           linkage
modified_base           3
                        mod_base = cm
modified_base           4
                        mod_base = gm
modified_base           5
                        mod_base = gm
modified_base           6
                        mod_base = OTHER
                        note = 2'-O-methyladenosine
modified_base           7
                        mod_base = OTHER
                        note = 2'-fluoroguanosine
modified_base           8
                        mod_base = gm
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = um
modified_base           13
                        mod_base = OTHER
                        note = 2'-O-methyladenosine
modified_base           14
                        mod_base = OTHER
                        note = 2'-O-methyladenosine
modified_base           15
                        mod_base = OTHER
                        note = 2'-O-methyladenosine
modified_base           16
                        mod_base = OTHER
                        note = 2'-O-methyladenosine
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                           linkage
modified_base           20
                        mod_base = OTHER
```

```
                        note = 2'-O-methyluridine with a 3'-phosphorothioate linkage
modified_base           21
                        mod_base = OTHER
                        note = 2'-O-methyladenosine
source                  1..21
                        mol_type = other RNA
                        organism = synthetic construct
SEQUENCE: 33
ggcggaggaa ataaaaagat a                                             21

SEQ ID NO: 34           moltype = RNA  length = 23
FEATURE                 Location/Qualifiers
misc_feature            1..23
                        note = Description of Artificial Sequence: Synthetic
                         oligonucleotide
modified_base           1
                        mod_base = OTHER
                        note = 2'-O-methyluridine with a 3'-phosphorothioate
                         linkage and a 5'-vinylphosphonate substitution
modified_base           2
                        mod_base = OTHER
                        note = 2'-fluoroadenosine with a 3'-phosphorothioate linkage
modified_base           3
                        mod_base = um
modified_base           4
                        mod_base = cm
modified_base           5
                        mod_base = um
modified_base           6
                        mod_base = OTHER
                        note = 2'-fluorouridine
modified_base           7
                        mod_base = um
modified_base           8
                        mod_base = um
modified_base           9
                        mod_base = um
modified_base           10
                        mod_base = OTHER
                        note = 2'-O-methyladenosine
modified_base           11
                        mod_base = um
modified_base           12
                        mod_base = um
modified_base           13
                        mod_base = um
modified_base           14
                        mod_base = OTHER
                        note = 2'-fluorocytidine
modified_base           15
                        mod_base = cm
modified_base           16
                        mod_base = OTHER
                        note = 2'-fluorouridine
modified_base           17
                        mod_base = cm
modified_base           18
                        mod_base = cm
modified_base           19
                        mod_base = gm
modified_base           20
                        mod_base = cm
modified_base           21
                        mod_base = OTHER
                        note = 2'-O-methylcytidine with a 3'-phosphorothioate
                         linkage
modified_base           22
                        mod_base = OTHER
                        note = 2'-O-methyladenosine with a 3'-phosphorothioate
                         linkage
modified_base           23
                        mod_base = gm
source                  1..23
                        mol_type = other RNA
                        organism = synthetic construct
SEQUENCE: 34
tatctttttta tttcctccgc cag                                          23

SEQ ID NO: 35           moltype = RNA  length = 21
```

| FEATURE | Location/Qualifiers |
|---|---|
| misc_feature | 1..21<br>note = Description of Artificial Sequence: Synthetic oligonucleotide |
| modified_base | 1<br>mod_base = OTHER<br>note = 2'-O-methylguanosine with a 3'-phosphorothioate linkage |
| modified_base | 2<br>mod_base = OTHER<br>note = 2'-O-methyladenosine with a 3'-phosphorothioate linkage |
| modified_base | 3<br>mod_base = OTHER<br>note = 2'-O-methyladenosine |
| modified_base | 4<br>mod_base = gm |
| modified_base | 5<br>mod_base = um |
| modified_base | 6<br>mod_base = OTHER<br>note = 2'-O-methyladenosine |
| modified_base | 7<br>mod_base = OTHER<br>note = 2'-fluoroadenosine |
| modified_base | 8<br>mod_base = OTHER<br>note = 2'-O-methyladenosine |
| modified_base | 9<br>mod_base = OTHER<br>note = 2'-fluoroadenosine |
| modified_base | 10<br>mod_base = OTHER<br>note = 2'-fluorouridine |
| modified_base | 11<br>mod_base = OTHER<br>note = 2'-fluorocytidine |
| modified_base | 12<br>mod_base = um |
| modified_base | 13<br>mod_base = gm |
| modified_base | 14<br>mod_base = OTHER<br>note = 2'-O-methyladenosine |
| modified_base | 15<br>mod_base = gm |
| modified_base | 16<br>mod_base = OTHER<br>note = 2'-O-methyladenosine |
| modified_base | 17<br>mod_base = OTHER<br>note = 2'-O-methyladenosine |
| modified_base | 18<br>mod_base = gm |
| modified_base | 19<br>mod_base = OTHER<br>note = 2'-O-methylcytidine with a 3'-phosphorothioate linkage |
| modified_base | 20<br>mod_base = OTHER<br>note = 2'-O-methyluridine with a 3'-phosphorothioate linkage |
| modified_base | 21<br>mod_base = OTHER<br>note = 2'-O-methyladenosine |
| source | 1..21<br>mol_type = other RNA<br>organism = synthetic construct |

SEQUENCE: 35
gaagtaaaat ctgagaagct a                                              21

| SEQ ID NO: 36 | moltype = RNA   length = 23 |
|---|---|
| FEATURE | Location/Qualifiers |
| misc_feature | 1..23<br>note = Description of Artificial Sequence: Synthetic oligonucleotide |
| modified_base | 1<br>mod_base = OTHER<br>note = 2'-O-methyluridine with a 3'-phosphorothioate linkage and a 5'-vinylphosphonate substitution |

```
modified_base        2
                     mod_base = OTHER
                     note = 2'-fluoroadenosine with a 3'-phosphorothioate linkage
modified_base        3
                     mod_base = gm
modified_base        4
                     mod_base = cm
modified_base        5
                     mod_base = um
modified_base        6
                     mod_base = OTHER
                     note = 2'-fluorouridine
modified_base        7
                     mod_base = cm
modified_base        8
                     mod_base = um
modified_base        9
                     mod_base = cm
modified_base        10
                     mod_base = OTHER
                     note = 2'-O-methyladenosine
modified_base        11
                     mod_base = gm
modified_base        12
                     mod_base = OTHER
                     note = 2'-O-methyladenosine
modified_base        13
                     mod_base = um
modified_base        14
                     mod_base = OTHER
                     note = 2'-fluorouridine
modified_base        15
                     mod_base = um
modified_base        16
                     mod_base = OTHER
                     note = 2'-fluorouridine
modified_base        17
                     mod_base = OTHER
                     note = 2'-O-methyladenosine
modified_base        18
                     mod_base = cm
modified_base        19
                     mod_base = um
modified_base        20
                     mod_base = um
modified_base        21
                     mod_base = OTHER
                     note = 2'-O-methylcytidine with a 3'-phosphorothioate
                        linkage
modified_base        22
                     mod_base = OTHER
                     note = 2'-O-methylcytidine with a 3'-phosphorothioate
                        linkage
modified_base        23
                     mod_base = OTHER
                     note = 2'-O-methyladenosine
source               1..23
                     mol_type = other RNA
                     organism = synthetic construct
SEQUENCE: 36
tagcttctca gatttactt cca                                              23

SEQ ID NO: 37        moltype = RNA   length = 21
FEATURE              Location/Qualifiers
misc_feature         1..21
                     note = Description of Artificial Sequence: Synthetic
                        oligonucleotide
modified_base        1
                     mod_base = OTHER
                     note = 2'-O-methylguanosine with a 3'-phosphorothioate
                        linkage
modified_base        2
                     mod_base = OTHER
                     note = 2'-O-methylguanosine with a 3'-phosphorothioate
                        linkage
modified_base        3
                     mod_base = OTHER
                     note = 2'-O-methyladenosine
modified_base        4
```

|  |  |
|---|---|
| | mod_base = OTHER |
| | note = 2'-O-methyladenosine |
| modified_base | 5 |
| | mod_base = gm |
| modified_base | 6 |
| | mod_base = um |
| modified_base | 7 |
| | mod_base = OTHER |
| | note = 2'-fluoroadenosine |
| modified_base | 8 |
| | mod_base = OTHER |
| | note = 2'-O-methyladenosine |
| modified_base | 9 |
| | mod_base = OTHER |
| | note = 2'-fluoroadenosine |
| modified_base | 10 |
| | mod_base = OTHER |
| | note = 2'-fluoroadenosine |
| modified_base | 11 |
| | mod_base = OTHER |
| | note = 2'-fluorouridine |
| modified_base | 12 |
| | mod_base = cm |
| modified_base | 13 |
| | mod_base = um |
| modified_base | 14 |
| | mod_base = gm |
| modified_base | 15 |
| | mod_base = OTHER |
| | note = 2'-O-methyladenosine |
| modified_base | 16 |
| | mod_base = gm |
| modified_base | 17 |
| | mod_base = OTHER |
| | note = 2'-O-methyladenosine |
| modified_base | 18 |
| | mod_base = OTHER |
| | note = 2'-O-methyladenosine |
| modified_base | 19 |
| | mod_base = OTHER |
| | note = 2'-O-methylguanosine with a 3'-phosphorothioate linkage |
| modified_base | 20 |
| | mod_base = OTHER |
| | note = 2'-O-methylcytidine with a 3'-phosphorothioate linkage |
| modified_base | 21 |
| | mod_base = OTHER |
| | note = 2'-O-methyladenosine |
| source | 1..21 |
| | mol_type = other RNA |
| | organism = synthetic construct |
| SEQUENCE: 37 | |
| ggaagtaaaa tctgagaagc a | 21 |
| SEQ ID NO: 38 | moltype = RNA  length = 23 |
| FEATURE | Location/Qualifiers |
| misc_feature | 1..23 |
| | note = Description of Artificial Sequence: Synthetic oligonucleotide |
| modified_base | 1 |
| | mod_base = OTHER |
| | note = 2'-O-methyluridine with a 3'-phosphorothioate linkage and a 5'-vinylphosphonate substitution |
| modified_base | 2 |
| | mod_base = OTHER |
| | note = 2'-fluoroguanosine with a 3'-phosphorothioate linkage |
| modified_base | 3 |
| | mod_base = cm |
| modified_base | 4 |
| | mod_base = um |
| modified_base | 5 |
| | mod_base = um |
| modified_base | 6 |
| | mod_base = OTHER |
| | note = 2'-fluorocytidine |
| modified_base | 7 |
| | mod_base = um |
| modified_base | 8 |

```
                         mod_base = cm
modified_base        9
                         mod_base = OTHER
                         note = 2'-O-methyladenosine
modified_base        10
                         mod_base = gm
modified_base        11
                         mod_base = OTHER
                         note = 2'-O-methyladenosine
modified_base        12
                         mod_base = um
modified_base        13
                         mod_base = um
modified_base        14
                         mod_base = OTHER
                         note = 2'-fluorouridine
modified_base        15
                         mod_base = um
modified_base        16
                         mod_base = OTHER
                         note = 2'-fluoroadenosine
modified_base        17
                         mod_base = cm
modified_base        18
                         mod_base = um
modified_base        19
                         mod_base = um
modified_base        20
                         mod_base = cm
modified_base        21
                         mod_base = OTHER
                         note = 2'-O-methylcytidine with a 3'-phosphorothioate
                            linkage
modified_base        22
                         mod_base = OTHER
                         note = 2'-O-methyladenosine with a 3'-phosphorothioate
                            linkage
modified_base        23
                         mod_base = cm
source               1..23
                         mol_type = other RNA
                         organism = synthetic construct
SEQUENCE: 38
tgcttctcag attttacttc cac                                                    23

SEQ ID NO: 39        moltype = RNA   length = 21
FEATURE              Location/Qualifiers
misc_feature         1..21
                         note = Description of Artificial Sequence: Synthetic
                            oligonucleotide
modified_base        1
                         mod_base = OTHER
                         note = 2'-O-methylguanosine with a 3'-phosphorothioate
                            linkage
modified_base        2
                         mod_base = OTHER
                         note = 2'-O-methyluridine with a 3'-phosphorothioate linkage
modified_base        3
                         mod_base = gm
modified_base        4
                         mod_base = gm
modified_base        5
                         mod_base = OTHER
                         note = 2'-O-methyladenosine
modified_base        6
                         mod_base = OTHER
                         note = 2'-O-methyladenosine
modified_base        7
                         mod_base = OTHER
                         note = 2'-fluoroguanosine
modified_base        8
                         mod_base = um
modified_base        9
                         mod_base = OTHER
                         note = 2'-fluoroadenosine
modified_base        10
                         mod_base = OTHER
                         note = 2'-fluoroadenosine
modified_base        11
```

```
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                         linkage
modified_base           20
                        mod_base = OTHER
                        note = 2'-O-methyladenosine with a 3'-phosphorothioate
                         linkage
modified_base           21
                        mod_base = OTHER
                        note = 2'-O-methyladenosine
source                  1..21
                        mol_type = other RNA
                        organism = synthetic construct
SEQUENCE: 39
gtggaagtaa aatctgagaa a                                                  21

SEQ ID NO: 40           moltype = RNA  length = 23
FEATURE                 Location/Qualifiers
misc_feature            1..23
                        note = Description of Artificial Sequence: Synthetic
                         oligonucleotide
modified_base           1
                        mod_base = OTHER
                        note = 2'-O-methyluridine with a 3'-phosphorothioate
                         linkage and a 5'-vinylphosphonate substitution
modified_base           2
                        mod_base = OTHER
                        note = 2'-fluorouridine with a 3'-phosphorothioate linkage
modified_base           3
                        mod_base = um
modified_base           4
                        mod_base = cm
modified_base           5
                        mod_base = um
modified_base           6
                        mod_base = OTHER
                        note = 2'-fluorocytidine
modified_base           7
                        mod_base = OTHER
                        note = 2'-O-methyladenosine
modified_base           8
                        mod_base = gm
modified_base           9
                        mod_base = OTHER
                        note = 2'-O-methyladenosine
modified_base           10
                        mod_base = um
modified_base           11
                        mod_base = um
modified_base           12
                        mod_base = um
modified_base           13
                        mod_base = um
modified_base           14
                        mod_base = OTHER
                        note = 2'-fluoroadenosine
modified_base           15
                        mod_base = cm
modified_base           16
                        mod_base = OTHER
```

```
                        note = 2'-fluorouridine
modified_base           17
                        mod_base = um
modified_base           18
                        mod_base = cm
modified_base           19
                        mod_base = cm
modified_base           20
                        mod_base = OTHER
                        note = 2'-O-methyladenosine
modified_base           21
                        mod_base = OTHER
                        note = 2'-O-methylcytidine with a 3'-phosphorothioate
                          linkage
modified_base           22
                        mod_base = OTHER
                        note = 2'-O-methylcytidine with a 3'-phosphorothioate
                          linkage
modified_base           23
                        mod_base = um
source                  1..23
                        mol_type = other RNA
                        organism = synthetic construct
SEQUENCE: 40
tttctcagat tttacttcca cct                                              23

SEQ ID NO: 41           moltype = RNA  length = 21
FEATURE                 Location/Qualifiers
misc_feature            1..21
                        note = Description of Artificial Sequence: Synthetic
                          oligonucleotide
modified_base           1
                        mod_base = OTHER
                        note = 2'-O-methylcytidine with a 3'-phosphorothioate
                          linkage
modified_base           2
                        mod_base = OTHER
                        note = 2'-O-methylcytidine with a 3'-phosphorothioate
                          linkage
modified_base           3
                        mod_base = OTHER
                        note = 2'-O-methyladenosine
modified_base           4
                        mod_base = gm
modified_base           5
                        mod_base = gm
modified_base           6
                        mod_base = um
modified_base           7
                        mod_base = OTHER
                        note = 2'-fluoroguanosine
modified_base           8
                        mod_base = gm
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroguanosine
modified_base           12
                        mod_base = um
modified_base           13
                        mod_base = OTHER
                        note = 2'-O-methyladenosine
modified_base           14
                        mod_base = OTHER
                        note = 2'-O-methyladenosine
modified_base           15
                        mod_base = OTHER
                        note = 2'-O-methyladenosine
modified_base           16
                        mod_base = OTHER
                        note = 2'-O-methyladenosine
modified_base           17
                        mod_base = um
modified_base           18
```

```
                        mod_base = cm
modified_base           19
                        mod_base = OTHER
                        note = 2'-O-methyluridine with a 3'-phosphorothioate linkage
modified_base           20
                        mod_base = OTHER
                        note = 2'-O-methylguanosine with a 3'-phosphorothioate
                          linkage
modified_base           21
                        mod_base = OTHER
                        note = 2'-O-methyladenosine
source                  1..21
                        mol_type = other RNA
                        organism = synthetic construct
SEQUENCE: 41
ccaggtggaa gtaaaatctg a                                           21

SEQ ID NO: 42           moltype = RNA  length = 23
FEATURE                 Location/Qualifiers
misc_feature            1..23
                        note = Description of Artificial Sequence: Synthetic
                          oligonucleotide
modified_base           1
                        mod_base = OTHER
                        note = 2'-O-methyluridine with a 3'-phosphorothioate
                          linkage and a 5'-vinylphosphonate substitution
modified_base           2
                        mod_base = OTHER
                        note = 2'-fluorocytidine with a 3'-phosphorothioate linkage
modified_base           3
                        mod_base = OTHER
                        note = 2'-O-methyladenosine
modified_base           4
                        mod_base = gm
modified_base           5
                        mod_base = OTHER
                        note = 2'-O-methyladenosine
modified_base           6
                        mod_base = OTHER
                        note = 2'-fluorouridine
modified_base           7
                        mod_base = um
modified_base           8
                        mod_base = um
modified_base           9
                        mod_base = um
modified_base           10
                        mod_base = OTHER
                        note = 2'-O-methyladenosine
modified_base           11
                        mod_base = cm
modified_base           12
                        mod_base = um
modified_base           13
                        mod_base = um
modified_base           14
                        mod_base = OTHER
                        note = 2'-fluorocytidine
modified_base           15
                        mod_base = cm
modified_base           16
                        mod_base = OTHER
                        note = 2'-fluoroadenosine
modified_base           17
                        mod_base = cm
modified_base           18
                        mod_base = cm
modified_base           19
                        mod_base = um
modified_base           20
                        mod_base = gm
modified_base           21
                        mod_base = OTHER
                        note = 2'-O-methylguanosine with a 3'-phosphorothioate
                          linkage
modified_base           22
                        mod_base = OTHER
                        note = 2'-O-methylcytidine with a 3'-phosphorothioate
                          linkage
```

```
modified_base              23
                           mod_base = cm
source                     1..23
                           mol_type = other RNA
                           organism = synthetic construct
SEQUENCE: 42
tcagattta cttccacctg gcc                                              23

SEQ ID NO: 43              moltype = RNA  length = 21
FEATURE                    Location/Qualifiers
misc_feature               1..21
                           note = Description of Artificial Sequence: Synthetic
                            oligonucleotide
modified_base              1
                           mod_base = OTHER
                           note = 2'-O-methylcytidine with a 3'-phosphorothioate
                            linkage
modified_base              2
                           mod_base = OTHER
                           note = 2'-O-methyladenosine with a 3'-phosphorothioate
                            linkage
modified_base              3
                           mod_base = OTHER
                           note = 2'-O-methyladenosine
modified_base              4
                           mod_base = gm
modified_base              5
                           mod_base = um
modified_base              6
                           mod_base = cm
modified_base              7
                           mod_base = OTHER
                           note = 2'-fluorocytidine
modified_base              8
                           mod_base = OTHER
                           note = 2'-O-methyladenosine
modified_base              9
                           mod_base = OTHER
                           note = 2'-fluoroadenosine
modified_base              10
                           mod_base = OTHER
                           note = 2'-fluoroguanosine
modified_base              11
                           mod_base = OTHER
                           note = 2'-fluoroadenosine
modified_base              12
                           mod_base = um
modified_base              13
                           mod_base = cm
modified_base              14
                           mod_base = gm
modified_base              15
                           mod_base = gm
modified_base              16
                           mod_base = cm
modified_base              17
                           mod_base = um
modified_base              18
                           mod_base = cm
modified_base              19
                           mod_base = OTHER
                           note = 2'-O-methylcytidine with a 3'-phosphorothioate
                            linkage
modified_base              20
                           mod_base = OTHER
                           note = 2'-O-methyladenosine with a 3'-phosphorothioate
                            linkage
modified_base              21
                           mod_base = OTHER
                           note = 2'-O-methyladenosine
source                     1..21
                           mol_type = other RNA
                           organism = synthetic construct
SEQUENCE: 43
caagtccaag atcggctcca a                                               21

SEQ ID NO: 44              moltype = RNA  length = 23
FEATURE                    Location/Qualifiers
misc_feature               1..23
```

```
                        note = Description of Artificial Sequence: Synthetic
                         oligonucleotide
modified_base           1
                        mod_base = OTHER
                        note = 2'-O-methyluridine with a 3'-phosphorothioate
                         linkage and a 5'-vinylphosphonate substitution
modified_base           2
                        mod_base = OTHER
                        note = 2'-fluorouridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-fluoroguanosine
modified_base           7
                        mod_base = cm
modified_base           8
                        mod_base = cm
modified_base           9
                        mod_base = gm
modified_base           10
                        mod_base = OTHER
                        note = 2'-O-methyladenosine
modified_base           11
                        mod_base = um
modified_base           12
                        mod_base = cm
modified_base           13
                        mod_base = um
modified_base           14
                        mod_base = OTHER
                        note = 2'-fluorouridine
modified_base           15
                        mod_base = gm
modified_base           16
                        mod_base = OTHER
                        note = 2'-fluoroguanosine
modified_base           17
                        mod_base = OTHER
                        note = 2'-O-methyladenosine
modified_base           18
                        mod_base = cm
modified_base           19
                        mod_base = um
modified_base           20
                        mod_base = um
modified_base           21
                        mod_base = OTHER
                        note = 2'-O-methylguanosine with a 3'-phosphorothioate
                         linkage
modified_base           22
                        mod_base = OTHER
                        note = 2'-O-methyladenosine with a 3'-phosphorothioate
                         linkage
modified_base           23
                        mod_base = cm
source                  1..23
                        mol_type = other RNA
                        organism = synthetic construct
SEQUENCE: 44
ttggagccga tcttggactt gac                                              23

SEQ ID NO: 45          moltype = RNA   length = 21
FEATURE                Location/Qualifiers
misc_feature           1..21
                        note = Description of Artificial Sequence: Synthetic
                         oligonucleotide
modified_base           1
                        mod_base = OTHER
                        note = 2'-O-methyluridine with a 3'-phosphorothioate linkage
modified_base           2
                        mod_base = OTHER
                        note = 2'-O-methylcytidine with a 3'-phosphorothioate
                         linkage
```

```
modified_base         3
                      mod_base = um
modified_base         4
                      mod_base = gm
modified_base         5
                      mod_base = gm
modified_base         6
                      mod_base = um
modified_base         7
                      mod_base = OTHER
                      note = 2'-fluoroguanosine
modified_base         8
                      mod_base = OTHER
                      note = 2'-O-methyladenosine
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = cm
modified_base         14
                      mod_base = cm
modified_base         15
                      mod_base = OTHER
                      note = 2'-O-methyladenosine
modified_base         16
                      mod_base = OTHER
                      note = 2'-O-methyladenosine
modified_base         17
                      mod_base = OTHER
                      note = 2'-O-methyladenosine
modified_base         18
                      mod_base = OTHER
                      note = 2'-O-methyladenosine
modified_base         19
                      mod_base = OTHER
                      note = 2'-O-methyluridine with a 3'-phosphorothioate linkage
modified_base         20
                      mod_base = OTHER
                      note = 2'-O-methylcytidine with a 3'-phosphorothioate
                       linkage
modified_base         21
                      mod_base = OTHER
                      note = 2'-O-methyladenosine
source                1..21
                      mol_type = other RNA
                      organism = synthetic construct
SEQUENCE: 45
tctggtgaac ctccaaaatc a                                              21

SEQ ID NO: 46         moltype = RNA  length = 23
FEATURE               Location/Qualifiers
misc_feature          1..23
                      note = Description of Artificial Sequence: Synthetic
                       oligonucleotide
modified_base         1
                      mod_base = OTHER
                      note = 2'-O-methyluridine with a 3'-phosphorothioate
                       linkage and a 5'-vinylphosphonate substitution
modified_base         2
                      mod_base = OTHER
                      note = 2'-fluoroguanosine with a 3'-phosphorothioate linkage
modified_base         3
                      mod_base = OTHER
                      note = 2'-O-methyladenosine
modified_base         4
                      mod_base = um
modified_base         5
                      mod_base = um
modified_base         6
                      mod_base = OTHER
                      note = 2'-fluorouridine
```

| | | |
|---|---|---|
| modified_base | 7 | |
| | mod_base = um | |
| modified_base | 8 | |
| | mod_base = gm | |
| modified_base | 9 | |
| | mod_base = gm | |
| modified_base | 10 | |
| | mod_base = OTHER | |
| | note = 2'-O-methyladenosine | |
| modified_base | 11 | |
| | mod_base = gm | |
| modified_base | 12 | |
| | mod_base = gm | |
| modified_base | 13 | |
| | mod_base = um | |
| modified_base | 14 | |
| | mod_base = OTHER | |
| | note = 2'-fluorouridine | |
| modified_base | 15 | |
| | mod_base = cm | |
| modified_base | 16 | |
| | mod_base = OTHER | |
| | note = 2'-fluoroadenosine | |
| modified_base | 17 | |
| | mod_base = cm | |
| modified_base | 18 | |
| | mod_base = cm | |
| modified_base | 19 | |
| | mod_base = OTHER | |
| | note = 2'-O-methyladenosine | |
| modified_base | 20 | |
| | mod_base = gm | |
| modified_base | 21 | |
| | mod_base = OTHER | |
| | note = 2'-O-methyladenosine with a 3'-phosphorothioate linkage | |
| modified_base | 22 | |
| | mod_base = OTHER | |
| | note = 2'-O-methylguanosine with a 3'-phosphorothioate linkage | |
| modified_base | 23 | |
| | mod_base = cm | |
| source | 1..23 | |
| | mol_type = other RNA | |
| | organism = synthetic construct | |
| SEQUENCE: 46 | | |
| tgattttgga ggttcaccag agc | | 23 |
| | | |
| SEQ ID NO: 47 | moltype = RNA  length = 21 | |
| FEATURE | Location/Qualifiers | |
| misc_feature | 1..21 | |
| | note = Description of Artificial Sequence: Synthetic oligonucleotide | |
| modified_base | 1 | |
| | mod_base = OTHER | |
| | note = 2'-O-methylcytidine with a 3'-phosphorothioate linkage | |
| modified_base | 2 | |
| | mod_base = OTHER | |
| | note = 2'-O-methyladenosine with a 3'-phosphorothioate linkage | |
| modified_base | 3 | |
| | mod_base = gm | |
| modified_base | 4 | |
| | mod_base = gm | |
| modified_base | 5 | |
| | mod_base = um | |
| modified_base | 6 | |
| | mod_base = gm | |
| modified_base | 7 | |
| | mod_base = OTHER | |
| | note = 2'-fluoroguanosine | |
| modified_base | 8 | |
| | mod_base = OTHER | |
| | note = 2'-O-methyladenosine | |
| modified_base | 9 | |
| | mod_base = OTHER | |
| | note = 2'-fluoroadenosine | |
| modified_base | 10 | |

```
                              mod_base = OTHER
                              note = 2'-fluoroguanosine
modified_base        11
                              mod_base = OTHER
                              note = 2'-fluorouridine
modified_base        12
                              mod_base = OTHER
                              note = 2'-O-methyladenosine
modified_base        13
                              mod_base = OTHER
                              note = 2'-O-methyladenosine
modified_base        14
                              mod_base = OTHER
                              note = 2'-O-methyladenosine
modified_base        15
                              mod_base = OTHER
                              note = 2'-O-methyladenosine
modified_base        16
                              mod_base = um
modified_base        17
                              mod_base = cm
modified_base        18
                              mod_base = um
modified_base        19
                              mod_base = OTHER
                              note = 2'-O-methylguanosine with a 3'-phosphorothioate
                                linkage
modified_base        20
                              mod_base = OTHER
                              note = 2'-O-methyladenosine with a 3'-phosphorothioate
                                linkage
modified_base        21
                              mod_base = OTHER
                              note = 2'-O-methyladenosine
source               1..21
                              mol_type = other RNA
                              organism = synthetic construct
SEQUENCE: 47
caggtggaag taaaatctga a                                                     21

SEQ ID NO: 48       moltype = RNA  length = 23
FEATURE             Location/Qualifiers
misc_feature        1..23
                              note = Description of Artificial Sequence: Synthetic
                                oligonucleotide
modified_base        1
                              mod_base = OTHER
                              note = 2'-O-methyluridine with a 3'-phosphorothioate
                                linkage and a 5'-vinylphosphonate substitution
modified_base        2
                              mod_base = OTHER
                              note = 2'-fluorouridine with a 3'-phosphorothioate linkage
modified_base        3
                              mod_base = cm
modified_base        4
                              mod_base = OTHER
                              note = 2'-O-methyladenosine
modified_base        5
                              mod_base = gm
modified_base        6
                              mod_base = OTHER
                              note = 2'-fluoroadenosine
modified_base        7
                              mod_base = um
modified_base        8
                              mod_base = um
modified_base        9
                              mod_base = um
modified_base        10
                              mod_base = um
modified_base        11
                              mod_base = OTHER
                              note = 2'-O-methyladenosine
modified_base        12
                              mod_base = cm
modified_base        13
                              mod_base = um
modified_base        14
                              mod_base = OTHER
```

|   |   |   |
|---|---|---|
| modified_base | | note = 2'-fluorouridine |
| | 15 | |
| | mod_base = cm | |
| modified_base | 16 | |
| | mod_base = OTHER | |
| | note = 2'-fluorocytidine | |
| modified_base | 17 | |
| | mod_base = OTHER | |
| | note = 2'-O-methyladenosine | |
| modified_base | 18 | |
| | mod_base = cm | |
| modified_base | 19 | |
| | mod_base = cm | |
| modified_base | 20 | |
| | mod_base = um | |
| modified_base | 21 | |
| | mod_base = OTHER | |
| | note = 2'-O-methylguanosine with a 3'-phosphorothioate linkage | |
| modified_base | 22 | |
| | mod_base = OTHER | |
| | note = 2'-O-methylguanosine with a 3'-phosphorothioate linkage | |
| modified_base | 23 | |
| | mod_base = cm | |
| source | 1..23 | |
| | mol_type = other RNA | |
| | organism = synthetic construct | |

SEQUENCE: 48
```
ttcagatttt acttccacct ggc                                              23
```

SEQ ID NO: 49        moltype = DNA  length = 6644
FEATURE              Location/Qualifiers
source              1..6644
                      mol_type = genomic DNA
                      organism = Homo sapiens SEQUENCE: 49
```
gcagtcaccg ccacccacca gctccggcac caacagcagc gccgctgcca ccgcccacct      60
tctgccgccg ccaccacagc caccttctcc tcctccgctg tcctctcccg tcctcgcctc     120
tgtcgactat caggtgaact ttgaaccagg atggctgagc cccgccagga gttcgaagtg     180
atggaagatc acgctgggac gtacggggttg ggggacagga agatcagggg gggctacacc    240
atgcaccaag accaagaggg tgacacggac gctggcctga agaatctccc cctgcagacc     300
cccactgagg acggatctga ggaacccggc tctgaaacct ctgatgctaa gagcactcca     360
acagcggaag atgtgacagc acccttagtg gatgagggag ctcccggcaa gcaggctgcc     420
gcgcagcccc acacggagat cccagaagga accacagctg aagaagcagg cattggagac     480
accccagcc tggaagacga agctgctggt cacgtgaccc aagagcctga aagtggtaag     540
gtggtccagg aaggcttcct ccgagagcca ggccccccag gtctgaagcc ccagctcatg     600
tccggcatgc ctgggggctcc cctcctgcct gagggcccca gagaggccac acgcaacctt    660
tcgggggacag gacctgagga cacagagggc ggccgccacg cccctgagct gctcaagcac    720
cagcttctag gagacctgca ccaggagggg ccgccgctga gggggcagg gggcaaagag     780
aggccgggga gcaaggagga ggtgatgaa gaccgcgagg tcgatgagtc ctccccccaa     840
gactcccctc cctccaaggc ctccccagcc caagatgggg ggcctcccca gacagccgcc    900
agagaagcca ccagcatccc aggcttccca gcggagggtg ccatccccct ccctgtggat    960
ttcctctcca aagtttccac agagatccca gcctcagagc ccgacgggcc cagtgtaggg   1020
cgggccaaag ggcaggatgc ccccctggag ttcacgtttc acgtggaaat cacacccaaa   1080
gtgcagaagg agcaggcgca ctcggaggag catttgggaa aggctgcatt tccaggggcc    1140
cctggagagg ggcagaggc ccggggcccc tctttgggag aggacacaaa agaggctgac    1200
cttccagagc cctctgaaaa gcagcctgct gctgctccgc gggggaagcc cgtcagccgg   1260
gtccctcaac tcaaagctcg catggtcagt aaaagcaaag acgatggctgg aagcgatgac   1320
aaaaaagcca agacatccac acgttcctct gctaaaacct tgaaaaatag gccttgcctt    1380
agccccaaac accccactcc tggtagctca gaccctctga tccaaccctc cagccctgct   1440
gtgtgcccag agccaccttc ctctcctaaa tacgtctctt ctgtcacttc ccgaactggc   1500
agttctggag caaaggagat gaaactcaag ggggctgatg gtaaaacgaa gatcgccaca   1560
ccgcggggag cagccctcc aggccagaag ggccaggcca acgccaccag gattccagca   1620
aaaaccccgc ccgctccaaa gacaccaccc agctctgcga ctaagcaagt ccagagaaga   1680
ccacccctg cagggcccag atctgagaga ggtgaacctc caaaatcagg ggatcgcagc   1740
ggctacagca gccccggctc cccaggcact cccggcagcc gctcccgcac ccgtccctta   1800
ccaacccac ccaccggga gccaagaag gtggcagtga tccgtactcc acccaagtcg    1860
ccgtcttccg ccaagagccg cctgcagaca gccccgcgtg ccatgccaga cctgaagaat   1920
gtcaagtcca agatcggctc cactgagaac ctgaagcacc agccgggagg cgggaaggtg   1980
cagataatta ataagaagct ggatcttagc aacgttccagt ccaagtgtgg ctcaaaggat   2040
aatatcaaac acgtcccggg aggcggcagt gtgcaaatag tctacaaacc agttgacctg   2100
agcaaggtga cctccaagtg tggctcattta ggcaacatcc atcataaacc aggaggtggc   2160
caggtggaag taaaatctga gaagcttgac ttcaaggaca gagtccagtc gaagattgga   2220
tccctggaca atatcacccca cgtccctggc ggaggaaata aaaagattga acccacaag   2280
ctgaccttcc gcgagaacgc caaagccaag acagaccacg gggcggagat cgtgtacaag   2340
tcgccagtgg tgtctggga cacgtctcca cggcatctca gcaatgtctc ctccaccggc   2400
agcatcgaca tggtagactc gccccagctc gccacgctag ctgacgaggt gtctgcctcc   2460
ctggccaagc agggtttgtg atcaggcccc tgggcggtca ataattgtg gagaggagag   2520
```

```
aatgagagag tgtggaaaaa aaaagaataa tgacccggcc cccgccctct gcccccagct   2580
gctcctcgca gttcggttaa ttggttaatc acttaacctg cttttgtcac tcggctttgg   2640
ctcgggactt caaaatcagt gatgggagta agagcaaatt tcatctttcc aaattgatgg   2700
gtgggctagt aataaaatat ttaaaaaaaa acattcaaaa acatggccac atccaacatt   2760
tcctcaggca attcctttg attcttttt cttcccctc catgtagaag agggagaagg      2820
agaggctctg aaagctgctt ctgggggatt tcaaggact gggggtgcca accacctctg    2880
gccctgttgt gggggtgtca cagaggcagt ggcagcaaca aaggatttga aacttggtgt   2940
gttcgtggag ccacaggcag acgatgtcaa ccttgtgtga gtgtgacggg ggttggggtg   3000
gggcgggagg ccacggggga ggccgaggca ggggctgggc agaggggaga ggaagcacaa   3060
gaagtgggag tgggagagga agccacgtgc tggagagtag acatcccct ccttgccgct    3120
gggagagcca aggcctatgc cacctgcagc gtctgagcgg ccgcctgtcc ttggtggccg   3180
ggggtggggg cctgctgtgg gtcagtgtgc caccctctgc agggcagcct gtgggagaag   3240
ggacagcggg taaaaagaga aggcaagctg gcaggaggt ggcacttcgt ggatgacctc    3300
cttagaaaag actgaccttg atgtcttgag agcgctggcc tcttcctccc tccctgcagg   3360
gtaggggcc tgagttgagg ggcttccctc tgctccacag aaacccctgtt ttattgagtt   3420
ctgaaggttg gaactgctgc catgatttt gccactttgc agacctggga ctttagggct    3480
aaccagttct ctttgtaagg acttgtgcct cttgggagac gtccaccgt ttccaagcct    3540
gggccactgg catctctgga gtgtgtgggg gtctggggga caggtcccga gcccctgtc    3600
cttcccacgg ccactgcagt caccccgtct gcgccgctgt gctgttgtct gccgtgagag   3660
cccaatcact gcctataccc ctcatcacac gtcacaatgt cccgaattcc cagcctcacc   3720
accccttctc agtaatgacc ctggttggtt gcaggaggta cctactccat actgagggtg   3780
aaattaaggg aaggcaaagt ccaggcacaa gagtgggacc ccagcctctc actctcagtt   3840
ccactcatcc aactgggacc ctcaccacga atctcatgat ctgattcggt tcctgtctc    3900
ctcctcccgt cacagatgtg agccagggca ctgctcagct gtgacccctag gtgtttctgc   3960
cttgttgaca tggagagagc cctttcccct gagaaggcct ggccccttcc tgtgctgagc   4020
ccacagcaga aggctgggtg tcttggttgt cagtggtggc accaggatgg aagggcaagg   4080
cacccagggc aggccacag tcccgctgtc ccccacttgc accctagctt gtagctgcca    4140
acctcccaga cagcccagcc cgctgctcag ctccacatgc atagtatcag ccctccacac   4200
ccgacaaagg ggaacacacc cccttggaaa tggttctttt cccccagtcc cagctggaag   4260
ccatgctgtc tgttctgctg gagcagctga acatatacat agatgttgcc ctgccctccc   4320
catctgcacc ctgttgagtt gtagttggat ttgtctgttt atgcttggat tcaccagagt   4380
gactatgata gtgaaaagaa aaaaaaaaaa aaaaaggac gcatgtatct tgaaatgctt    4440
gtaaagaggt ttctaaccca ccctcacgag gtgtctctca ccccacact gggactcgtg    4500
tggcctgtgt ggtgccaccc tgctggggcc tcccaagttt tgaaaggctt tcctccagcac  4560
ctgggaccca acagacca gcttctagca gctaaggagg ccgttcagct gtgacgaagg    4620
cctgaagcac aggattagga ctgaagcgat gatgtcccct tcctactc cccttgggc      4680
tccctgtgtc agggcacaga ctaggtcttg tggctggtct ggcttgcggc gcgaggatgc   4740
ttctctctgg tcatagcccg aagtctcatg gcagtcccaa aggaggctta caactcctgc   4800
atcacaagaa aaaggaagcc actgccagct gggggacct gcagctccca gaagctccgt    4860
gagcctcagc cacccctcag actgggttcc tctccaagct cgccctctgg aggggcagcg   4920
cagcctccca ccaagggccc tgcgaccaca gcagggattg ggatgaattg cctgtcctgg   4980
atctgctcta gaggcccaag ctgcctgcct gaggaaggat gacttgacaa gtcaggagac   5040
actgttccca aagccttgac cagagcacct cagcccgcct ccaccttgcaca aactccatct  5100
gctgccatga gaaagggaa gccgcctttg caaaacattg ctgcctaaag aaactcagca   5160
gcctcaggcc caattctgcc acttctggtt tgggtacagt taaaggcaac cctgagggac    5220
ttggcagtag aaatccaggg cctccctgg ggctggcagc ttcgtgtgca gctagagctt    5280
tacctgaaag gaagtctctg ggcccagaac tctccaccaa gcccctcct gccgttcgct    5340
gagtcccagc aattctccta agttgaaggg atctgagaag gagaaggaaa tgtggggtag   5400
attttggtggt ggtagagat atgccccct cattactgcc aacagtttcg gctgcattc      5460
tcacgcacc tcggttcctc ttcctgaagt tcttgtgccc tgctcttcag caccatgggc    5520
cttcttatac ggaaggctct gggatctccc cctttgtgggg caggctcttg gggccagcct   5580
aagatcatgg tttagggtga tcagtgctgg cagataaatt gaaaaggcac gctggcttgt    5640
gatcttaaat gaggacaatc cccccagggc tgggcactcc tccctccc tcactctcc      5700
cacctgcaga gccagtgtcc ttgggtgggc tagataggat atactgtatg ccggctcctt   5760
caagctgctg actcacttta tcaatagttc catttaaatt gacttcagtg gtgagactgt   5820
atcctgtttg ctattgcttg ttgtgctatg gggggagggg ggaggaatgt gtaagatagt   5880
taacatgggc aaagggagat cttggggtgc agcacttaaa ctgcctcgta acccttttca   5940
tgatttcaac cacatttgct agaggggaggg agcagccacg gagttagagg cccttggggt   6000
ttctcttttc cactgacagg cttttcccagg cagctggcta gttcattccc tccccagcca   6060
ggtgcaggcg taggaatatg gacatctggt tgctttggcc tgctgccctc tttcagggggt   6120
cctaagccca caatcatgcc tccctaagac cttggcatcc ttccctctaa gccgttggca   6180
cctctgtgcc acctctcaca ctggctccag acacacagcc tgtgcttttg gagctgagat   6240
cactcgcttc accctcctca tctttgttct ccaagtaaag ccacgaggtc ggggcgaggg   6300
cagaggtgat cacctgcgtg tcccatctac agacctgcag cttcataaaa cttctgattt   6360
ctcttcagct ttgaaagggg ttaccctggg cactggccta gagcctcacc tcctaataga   6420
cttagcccca tgagtttgcc atgttgagca ggactatttc tggcacttgc aagtcccatg   6480
atttcttcgg taattctgag ggtgggggga gggacatgaa atcatcttag cttagctttc   6540
tgtctgtgaa tgtctatata gtgtattgtg tgttttaaca aatgatttac actgactgtt   6600
gctgtaaaag tgaatttgga aataaagtta ttactctgat taaa               6644
```

| SEQ ID NO: 50 | moltype = AA   length = 776 |
|---|---|
| FEATURE | Location/Qualifiers |
| source | 1..776 |
|  | mol_type = protein |
|  | organism = Homo sapiens |

SEQUENCE: 50
MAEPRQEFEV MEDHAGTYGL GDRKDQGGYT MHQDQEGDTD AGLKESPLQT PTEDGSEEPG   60
SETSDAKSTP TAEDVTAPLV DEGAPGKQAA AQPHTEIPEG TTAEEAGIGD TPSLEDEAAG  120
HVTQEPESGK VVQEGFLREP GPPGLSHQLM SGMPGAPLLP EGPREATRQP SGTGPEDTEG  180

```
GRHAPELLKH QLLGDLHQEG PPLKGAGGKE RPGSKEEVDE DRDVDESSPQ DSPPSKASPA   240
QDGRPPQTAA REATSIPGFP AEGAIPLPVD FLSKVSTEIP ASEPDGPSVG RAKGQDAPLE   300
FTFHVEITPN VQKEQAHSEE HLGRAAFPGA PGEGPEARGP SLGEDTKEAD LPEPSEKQPA   360
AAPRGKPVSR VPQLKARMVS KSKDGTGSDD KKAKTSTRSS AKTLKNRPCL SPKHPTPGSS   420
DPLIQPSSPA VCPEPPSSPK YVSSVTSRTG SSGAKEMKLK GADGKTKIAT PRGAAPPGQK   480
GQANATRIPA KTPPAPKTPP SSATKQVQRR PPPAGPRSER GEPPKSGDRS GYSSPGSPGT   540
PGSRSRTPSL PTPPTREPKK VAVVRTPPKS PSSAKSRLQT APVPMPDLKN VKSKIGSTEN   600
LKHQPGGGKV QIINKKLDLS NVQSKCGSKD NIKHVPGGGS VQIVYKPVDL SKVTSKCGSL   660
GNIHHKPGGG QVEVKSEKLD FKDRVQSKIG SLDNITHVPG GGNKKIETHK LTFRENAKAK   720
TDHGAEIVYK SPVVSGDTSP RHLSNVSSTG SIDMVDSPQL ATLADEVSAS LAKQGL      776

SEQ ID NO: 51           moltype = DNA   length = 5552
FEATURE                 Location/Qualifiers
source                  1..5552
                        mol_type = genomic DNA
                        organism = Homo sapiens
SEQUENCE: 51
gcagtcaccg ccacccacca gctccggcac caacagcagc gccgctgcca ccgcccacct    60
tctgccgccg ccaccacagc caccttctcc tcctccgctg tcctctcccg tcctcgcctc   120
tgtcgactat caggtgaact tgaaccagg atggctgagc cccgccagga gttcgaagtg   180
atggaagatc acgctgggac gtacggggttg ggggacagga aagatcaggg gggctacacc   240
atgcaccaag accaagaggg tgacacggac gctggcctga aagaatctcc cctgcagacc   300
cccactgagg acggatctga ggaaccgggc tctgaaacct ctgatgctaa gagcactcca   360
acagcggaag ctgaagaagc aggcattgga gacaccccca gctggaaga cgaagctgct   420
ggtcacgtga cccaagctcg catggtcagt aaaagcaaag acgggactgg aagcgatgac   480
aaaaaagcca agggggctga tggtaaaacg aagatcgtca caccgcgggg agcagcccct   540
ccaggccaga agggccaggc caacgccacc aggattccag caaaaacccc gcccgctcca   600
aagacaccac ccagctctgg tgaacctcca aaatcagggg atcgcagcgg ctacagcagc   660
cccggctccc caggcactcc cggcagccgc tcccgcaccc cgtcccttcc aaccccaccc   720
accggaggca ccaagaaggt ggcagtggtc cgtactccac ccaagtcgcc gtcttccgcc   780
aagagccgcc tgcagacagc ccccgtgccc atgccagacc tgaagaatgt caagtccaag   840
atcggctcca ctgagaacct gaagcaccag ccggggaggcg ggaaggtgca gataattaat   900
aagaagctga tcttagcaa cgtccagtcc aagtgtggct caaggataa tatcaaacac   960
gtcccgggag gcggcagtgt gcaaatagtc tacaaaccag ttgacctgag caaggtgacc  1020
tccaagtgtg gctcattagg caacatccat cataaaccag gaggcggcca ggtgaagta  1080
aaatctgaga agcttgactt caaggacaga gtccagtcga agattgggtc cctggacaat  1140
atcacccacg tccctggcgg aggaaataaa aagattgaaa cccacaagct gaccttccgc  1200
gagaacgcca agccaagac agaccacggg gcggagatcg tgtacaagtc gccagtggtg  1260
tctgggacca cgtctccacg gcatctcagc aatgtctcac gcaccggcag catcgacatg  1320
gtagactcgc cccagctcgc cacgctagct gacgaggtgt ctgcctccct ggccaagcag  1380
ggtttgtgat caggccctg gggcggtcaa taattgtgga gaggagagaa tgagagagtg  1440
tggaaaaaaa aagaataatg acccggcccc cgccctctgc ccccagctgc tcctcgcagt  1500
tcggttaatt ggttaatcac ttaacctgct tttgtcactc ggctttggct cgggacttca  1560
aaatcagtga tgggagtaag agcaaatttc atctttccaa attgatgggt gggctagtaa  1620
taaaatattt aaaaaaaaac attcaaaaac atggccacat ccaacatttc ctcaggcaat  1680
tcctttttgat tctttttct tccccctcca tgtagaagag ggaaggag aggctctgaa   1740
agctgcttct gggggatttc aagggactgg gggtgccaac cacctcctgg cctgttgtgg  1800
gggtgtcaca gaggcagtgg cagcaacaaa ggatttgaaa cttggtgtgt tcgtggagcc  1860
acaggcagac gatgtcaacc ttgtgtgagt gtgacggggg ttgggtggg gcggaggcc   1920
acggggggagg ccgaggcagg ggctgggcag aggggagagg aagcacaaga agtgggagtg  1980
ggagaggaag ccacgtgctg gagagtagac atccccctcc ttgccgctgg gagagccaag  2040
gcctatgcca cctgcagcgt ctgagcggcc gcctgtcctt ggtggccggg ggtgggggcc  2100
tgctgtgggt cagtgtgcca ccctctgcag ggcagcctgt gggagaaggg acagcgggta  2160
aaaagagaag gcaagctggc aggagggtgg cacttcgtgg atgacctcct tagaaaagac  2220
tgaccttgat gtcttgagag cgctggcctc ttcctccctc cctgcagggt aggggcctg  2280
agttgagggg cttccctctg ctccacagaa accctgtttt attgagttct gaaggttgga  2340
actgctgcca tgattttggc cactttgcag acctgggact ttagggctaa ccagttctct  2400
ttgtaaggac ttgtgcctct tgggagacgt ccacccgttt ccaagcctgg gccactggca  2460
tctctggagt gtgtggggt ctgggaggca ggtcccgagc cccctgtcct tcccacgcca  2520
actgcagtca cccccgtctgc gccgctgtgc tgtttgctgc cgtgagagcc caatcactgc  2580
ctataccct catcacacgt cacaatgtcc cgaattccca gcctcaccac cccttctcag  2640
taatgaccct ggttggttgc aggaggtacc tactccatac tgagggtgaa attaagggaa  2700
ggcaaagtcc aggcacaaga gtgggacccc agcctctcac tctcagttcc actcatccaa  2760
ctgggacctt caccacgaat ctcatgatct gattcggttc cctgtctcct cctcccgtca  2820
cagatgtgag ccaggcact gctcagctgt gaccctaggt gtttctgcct tgttgacatg  2880
gagagagccc tttcccctga aaggcctggg cccttcctg tgctgagccc acagcagcag  2940
gctgggtgtc ttggttgtca gtggtggcac caggatggaa gggcaaggca cccagggcag  3000
gcccacagtc ccgctgtccc ccacttgcac cctagcttgt agctgccaac ctcccagaca  3060
gcccagcccg ctgctcagct ccacatgcat agtatcagcc ctccacaccc gacaaagggg  3120
aacacacccc cttggaaatg gttctttttcc cccagtccca gctggaagcc atgctgtctg  3180
ttctgctgga gcagctgaac atatacatag atgttgccct gccctcccca tctgcaccct  3240
gttgagttgt agtggatttt gtctgtttat gcttggattc accagagtga ctatgatagt  3300
gaaaagaaaa aaaaaaaaaaa aaaggacgc atgtatcttg aaatgcttgt aaagaggttt  3360
ctaacccacc ctcactgaggt gtctctcacc cccacatgcc tctagccgtg ctgtgttgga  3420
tgccaccctg ctggggcctc ccaagttttg aaaggctttc ctcagcacct gggacccaac  3480
agagaccagc ttctagcagc taaggaggcc gttcagctgt gacgaaggcc tgaagcacag  3540
gattaggact gaacgcgatga tgtccccttc cctcttccc cttgggggctc cctgtgtcag  3600
ggcacagact aggtcttgtg gctggtctgg cttgcggcgc gaggatggtt ctctctggtc  3660
atagcccgaa gtctcatggc agtcccaaag gaggcttaca actcctgcat cacaagaaaa  3720
```

```
aggaagccac tgccagctgg ggggatctgc agctcccaga agctccgtga gcctcagcca  3780
cccctcagac tgggttcctc tccaagctcg ccctctggag gggcagcgca gcctcccacc  3840
aagggccctg cgaccacagc agggattggg atgaattgcc tgtcctggat ctgctctaga  3900
ggcccaagct gcctgcctga ggaaggatga cttgacaagt caggagacac tgttcccaaa  3960
gccttgacca gagcacctca gcccgctgac cttgcacaaa ctccatctgc tgccatgaga  4020
aaagggaagc cgcctttgca aaacattgct gcctaaagaa actcagcagc ctcaggccca  4080
attctgccac ttctggtttg ggtacagtta aaggcaaccc tgagggactt ggcagtagaa  4140
atccagggcc tcccctgggg ctggcagctt cgtgtgcagc tagagcttta cctgaaagga  4200
agtctctggg cccagaactc tccaccaaga gcctccctgc cgttcgctga gtcccagcaa  4260
ttctcctaag ttgaagggat ctgagaagga aaggaaatg tggggtagat ttggtggtgg  4320
ttagagatat gccccctca ttactgccaa cagtttcggc tgcatttctt cacgcacctc  4380
ggttcctctt cctgaagttc ttgtgccctg ctcttcagca ccatgggcct tcttatacgg  4440
aaggctctgg atctcccc ttgtggggca ggctcttggg gccagcctaa gatcatggtt  4500
tagggtgatc agtgctggca gataaattga aaaggcacgc tggcttgtga tcttaaatga  4560
ggacaatccc cccagggctg ggcactcctc ccctcccctc acttctccca cctgcagagc  4620
cagtgtcctt gggtgggcta gataggatat actgtatgcc ggctccttca agctgctgac  4680
tcactttatc aatagttcca tttaaattga cttcagtggt gagactgtat cctgtttgct  4740
attgcttgtt gtgctatggg gggaggggg aggaatgtat aagatagtta acatgggcaa  4800
agggagatct tggggtgcag cacttaaact gcctcgtaac ccttttcatg atttcaacca  4860
catttgctag agggagggag cagccacgga gttagaggcc cttgggttt ctcttttcca  4920
ctgacaggct ttcccaggca gctggctagt tcattccctc cccagccagg tgcaggcgta  4980
ggaatatgga catctggttg cttttggcctg ctgccctctt tcaggggtcc taagcccaca  5040
atcatgcctc cctaagacct tggcatcctt ccctctaagc cgttggcacc tctgtgccac  5100
ctctcacact ggctccagac acacagcctg tgctttggga gctgagatca ctcgcttcac  5160
cctcctcatc tttgttctcc aagtaaagcc acgaggtcgg ggcgagggca gaggtgatca  5220
cctgcgtgtc ccatctcag acctgcagct tcataaaact tctgatttct cttcagcttt  5280
gaaaagggtt accctgggca ctggcctaga gcctcacctc ctaatagact tagccccatg  5340
agtttgccat gttgagcagg actatttctg gcacttgcaa gtccatgat ttcttcggta  5400
attctgaggg tgggggagg gacatgaaat catcttagct tagctttctg tctgtgaatg  5460
tctatatagt gtattgtgtg ttttaacaaa tgatttacac tgactgttgc tgtaaaagtg  5520
aatttggaaa taaagttatt actctgatta aa                                5552

SEQ ID NO: 52         moltype = AA   length = 412
FEATURE               Location/Qualifiers
source                1..412
                      mol_type = protein
                      organism = Homo sapiens
SEQUENCE: 52
MAEPRQEFEV MEDHAGTYGL GDRKDQGGYT MHQDQEGDTD AGLKESPLQT PTEDGSEEPG     60
SETSDAKSTP TAEAEEAGIG DTPSLEDEAA GHVTQARMVS KSKDGTGSDD KKAKGADGKT    120
KIATPRGAAP PGQKGQANAT RIPAKTPPAP KTPPSSGEPP KSGDRSGYSS PGSPGTPGSR    180
SRTPSLPTPP TREPKKVAVV RTPPKSPSSA KSRLQTAPVP MPDLKNVKSK IGSTENLKHQ    240
PGGGKVQIIN KKLDLSNVQS KCGSKDNIKH VPGGGSVQIV YKPVDLSKVT SKCGSLGNIH    300
HKPGGGQVEV KSEKLDFKDR VQSKIGSLDN ITHVPGGGNK KIETHKLTFR ENAKAKTDHG    360
AEIVYKSPVV SGDTSPRHLS NVSSTGSIDM VDSPQLATLA DEVSASLAKQ GL            412

SEQ ID NO: 53         moltype = DNA   length = 5372
FEATURE               Location/Qualifiers
source                1..5372
                      mol_type = genomic DNA
                      organism = Homo sapiens
SEQUENCE: 53
gcagtcaccg ccacccacca gctccggcac aacagcagc gccgctgcca ccgcccacct      60
tctgccgccg ccaccacagc caccttctcc tcctccgctg tcctctcccg tcctcgcctc    120
tgtcgactat caggtgaact ttgaaccagg atggctgagc ccgccagga gttcgaagtg    180
atggaagatc acgctgggac gtacgggttg ggggacagga agatcaggg gggctacacc    240
atgcaccaag accaagaggg tgacacggac gctggcctga agctgaaga gcaggcatt    300
ggagacaccc ccagcctgga agacgaagct gctggtcacg tgacccaagc tcgcatggtc    360
agtaaaagca aagacgggac tggaagcgat gacaaaaaag ccaaggggc tgatggtaaa    420
acgaagatcg ccacaccgcg gggagcagcc cctccaggcc agaagggca ggccaacgcc    480
accaggattc agcaaaaaac cccgcccgct ccaaagacac acccagctc tggtgaacct    540
ccaaaatcag gggatcgcag cggctacagc agccccggct cccaggcac tcccggcagc    600
cgctcccgca ccccgtccct tccaacccca cccaccgg agcccaagaa ggtggcagtg    660
gtccgtactc caccaagtc gccgtcttcc gccaagagc gcctgcagac gccccgtg    720
cccatgccag acctgaagaa tgtcaagtcc aagatcggc ccactgagaa cctgaagcac    780
cagccgggag cgggaaggt gcaaatagtc tacaaaccag ttgacctgag caaggtgacc    840
tccaagtgtg gctcattagg caacatccat cataaaccag aggtggcca ggtggaagta    900
aaatctgaga agcttgactt caaggacaga gtcagtcga agatttgggtc cctgacaat    960
atcacccacg tccctcgcgg aggaaataaa aagattgaaa cccacaagct gaccttccg   1020
gagaacgcca agccaagac agaccacggg gcggagatcg tgtacaagtc gccagtggtg   1080
tctggggaca cgtctccacg gcatctcagc aatgtctcct ccaccggcag catcgacatg   1140
gtagactcgc cccagctcgc cacgctagct gacgaggtgt ctgcctccct ggccaagcag   1200
ggttttgtgat caggcccctg gggcggtcaa taattggga ggagagaa tgagagagtg   1260
tggaaaaaaa aagaataatg acccggcccc ccctctgc tccctcgcag cctctcagt    1320
tcggttaatt ggttaatcac ttaacctgct tttgtcactc ggctttggct cgggacttca   1380
aaatcagtga tgggagtaag agcaaatttc atctttccaa attgatgggt gggctagtaa   1440
taaaatattt aaaaaaaaac attcaaaaac atggccacat ccaacatttc ctcaggcaat   1500
tccttttgat tcttttttct tccccctcca tgtagaagag ggagaggag aggctctgaa    1560
agctgcttct gggggatttc aagggactgg gggtgccaac cacctctggc cctgttgtgg   1620
```

-continued

```
gggtgtcaca gaggcagtgg cagcaacaaa ggatttgaaa cttgtgtgt tcgtggagcc   1680
acaggcagac gatgtcaacc ttgtgtgagt gtgacggggg ttggggtggg gcggaaggcc   1740
acggggagg ccgaggcagg ggctgggcag aggggagagg aagcacaaga agtgggagtg    1800
ggagaggaag ccacgtgctg gagagtagac atcccctcc ttgccgctgg gagagccaag    1860
gcctatgcca cctgcagcgt ctgagcggcc gcctgtcctt ggtggccggg ggtggggcc    1920
tgctgtgggt cagtgtgcca ccctctcag ggcagcctgt gggagaaggg acagcgggta    1980
aaaagagaag gcaagctggc aggagggtgg cacttcgtgg atgacctcct tagaaaagac   2040
tgaccttgat gtcttgagag cgctggcctc ttcctccctc cctgcagggt aggggcctg    2100
agttgagggg cttccctctg ctccacagaa accctgtttt attgagttct gaaggttgga   2160
actgctgcca tgattttggc cactttgcag acctgggact ttagggctaa ccagttctct   2220
ttgtaaggac ttgtgcctct tgggagacgt ccaccgtttt ccaagcctgg gccactggca   2280
tctctggagt gtgtggggt ctgggaggca ggtcccgagc cccctgtcct tcccacggcc    2340
actgcagtca ccccgtctgc gccgctgtgc tgttgtctgc cgtgagagcc caatcactgc   2400
ctataccct catcacacgt cacaatgtcc cgaattccca gcctcaccac cccttctcag    2460
taatgacct ggttggttgc aggaggtacc tactccatac tgagggtgaa attaagggaa    2520
ggcaaagtcc aggcacaaga gtgggacccc agcctctcac tctcagttcc actcatccaa   2580
ctgggaccct caccacgaat ctcatgatct gattcggttc cctgtctcct cctcccgtca   2640
cagatgtgag ccagggcact gctcagctgt gaccctaggt gtttctgcct tgttgacatg   2700
gagagagccc tttcccctga gaaggcctgg cccttcctg tgctgagccc acagcagcag    2760
gctgggtgtc ttggttgtca gtggtggcac caggatggaa gggcaaggca cccagggcag   2820
gcccacagtc ccgctgtccc ccacttgcac cctagcttgt agctgccaac ctcccagaca   2880
gcccagcccg ctgctcagct ccacatgcat agtatccagc ctccacaccc gacaaagggg   2940
aacacacccc cttggaaatg gttcttttcc cccagtccca gctggaagcc atgctgtctg   3000
ttctgctgga gcagctgaac atatacatag atgttgccct gccctcccca tctgcaccct   3060
gttgagttgt agttggattt gtctgtttat gcttggattc accagagtga ctatgatagt   3120
gaaaagaaaa aaaaaaaaaa aaaaggacgc atgtatcttg aaatgcttgt aaagagggttt   3180
ctaacccacc ctcacgaggt gtctctcacc cccacactgg gactcgtgtg gcctgtgtgg   3240
tgccaccctg ctgggccctc caagttttg aaaggctttc ctcagcacct gggacccaac    3300
agagaccagc ttctagcagc taaggaggcc gttcagctgt gacgaaggcc tgaagcacag   3360
gattaggact gaagcgatga tgtccccttc cctacttccc cttgggggcc cctgtgtcag   3420
ggcacagact aggtcttgtg gctggtctgg cttgcggcgc gaggatggtt ctctctggtc   3480
atagccgaa gtctcatggc agtcccaaag gaggcttaca actcctgcat cacaagaaaa    3540
aggaagccac tgccagctgg ggggatctgc agctcccaga agctccgtga gcctcagcca   3600
cccctcagac tgggttcctc tccaagctcg ccctctggag gggcagcgca gcctcccacc   3660
aagggccctg cgaccacagc agggattggg atgaattgcc tgtcctggat ctgctctaga   3720
ggcccaagct gcctgcctga ggaaggatga cttgacaagt caggagacac tgttcccaaa   3780
gccttgacca gagcacctca gcccgctgac cttgcacaaa ctccatctgc tgccatgaga   3840
aaagggaagc cgccttgca aaacattgct gcctaaagaa actcagcagc ctcaggccca    3900
attctgccac ttctggtttg ggtacagtta aaggcaaccc tgagggactt ggcagtagaa   3960
atccagggcc tcccctgggg ctggcagctt cgtgtgcagc tagagcttta cctgaaagga   4020
agtctctggg cccagaactc tccaccaaga gcctccctgc cgttcgctga gtcccagcaa   4080
ttctcctaag ttgaagggat ctgagaagga gaaggaaatg tggggtagat ttggtggtgg   4140
ttagagatat gccccctca ttactgccaa cagtttcggc tgcattctt cacgcacctc     4200
ggttcctctt cctgaagttc ttgtgccctg ctcttcagca ccatgggcct tcttatacgg   4260
aaggctctgg gatctccccc ttgtgggca ggctctgg gccagcctaa gatcatggtt      4320
tagggtgatc agtgctggca gataaattga aaaggcacgc tggcttgtga tcttaaatga   4380
ggacaatccc cccagggctg ggcactcctc ccctccctc acttctccca cctgcagagc    4440
cagtgtcctt gggtgggcta gataggatat actcctatgcc ggctccttca agctgctgac   4500
tcactttatc aatagttcca tttaaattga cttcagtggt gagactgtat cctgtttgct   4560
attgcttgtt gtgctatggg gggagggggg aggaatgtgt aagatagtta acatgggcaa   4620
agggagatct tggggtgcag cacttaaact gcctcgtaac ccttttcatg atttcaacca   4680
catttgctag agggaggag cagccacgga gttagaggcc cttgggggttt ctcttttcca    4740
ctgacaggct ttcccaggca gctggctagt tcattccctc cccagccagg tgcaggcgta   4800
ggaatatgga catctggttg cttggcctg ctgcccctctt tcaggggtcc taagcccaca    4860
atcatgcctc cctaagacct tggcatcctt ccctctaagc cgttggcacc tctgtgccac   4920
ctctcacact ggctcagac acacagcctg tgcttttgga gctgagatca ctcgcttcac    4980
cctcctcatc tttgttctcc aagtaaagcc acgaggtcgg ggcgagggca gaggtgatca    5040
cctgcgtgtc ccatctacag acctgcagct tcataaaact tctgatttct cttcagcttt   5100
gaaaagggtt accctgggca ctggcctaga gcctcacctc ctaatagact tagcccccag   5160
agtttgccat gttgagcagg actatttctg gcacttgcaa gtcccatgat ttcttccgta   5220
attctgaggg tggggggagg gacatgaaat catcttagct tagctttctg tctgtgaatg   5280
tctatatagt gtattgtgtg ttttaacaaa tgatttacac tgactgttgc tgtaaaagtg   5340
aatttggaaa taaagttatt actctgatta aa                                 5372

SEQ ID NO: 54           moltype = AA  length = 352
FEATURE                 Location/Qualifiers
source                  1..352
                        mol_type = protein
                        organism = Homo sapiens
SEQUENCE: 54
MAEPRQEFEV MEDHAGTYGL GDRKDQGGYT MHQDQEGDTD AGLKAEEEAGI GDTPSLEDEA    60
AGHVTQARMV SKSKDGTGSD DKKAKGADGK TKIATPRGAA PPGQKGQANA TRIPAKTPPA   120
PKTPPSSGEP PKSGDRSGYS SPGSPGTPGS RSRTPSLPTP PTREPKKVAV VRTPPKSPSS   180
AKSRLQTAPV PMPDLKNVKS KIGSTENLKH QPGGGKVQII YKPVDLSKVT SKCGSLGNIH   240
HKPGGGQVEV KSEKLDFKDR VQSKIGSLDN ITHVPGGGNK KIETHKLTFR ENAKAKTDHG   300
AEIVYKSPVV SGDTSPRHLS NVSSTGSIDM VDSPQLATLA DEVSASLAKQ GL           352

SEQ ID NO: 55           moltype = RNA  length = 21
FEATURE                 Location/Qualifiers
```

```
misc_feature            1..21
                        note = Description of Artificial Sequence: Synthetic
                         oligonucleotide
modified_base           10
                        mod_base = OTHER
                        note = abasic nucleotide
source                  1..21
                        mol_type = other RNA
                        organism = synthetic construct
SEQUENCE: 55
gtggaagtan aatctgagaa a                                                     21

SEQ ID NO: 56           moltype = RNA  length = 21
FEATURE                 Location/Qualifiers
misc_feature            1..21
                        note = Description of Artificial Sequence: Synthetic
                         oligonucleotide
modified_base           9
                        mod_base = OTHER
                        note = abasic nucleotide
source                  1..21
                        mol_type = other RNA
                        organism = synthetic construct
SEQUENCE: 56
gtggaagtna aatctgagaa a                                                     21

SEQ ID NO: 57           moltype = RNA  length = 21
FEATURE                 Location/Qualifiers
misc_feature            1..21
                        note = Description of Artificial Sequence: Synthetic
                         oligonucleotide
source                  1..21
                        mol_type = other RNA
                        organism = synthetic construct
SEQUENCE: 57
ccaagtgtgg ctcattaggc a                                                     21

SEQ ID NO: 58           moltype = RNA  length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 58
tgcctaatga gccacacttg gag                                                   23

SEQ ID NO: 59           moltype = RNA  length = 21
FEATURE                 Location/Qualifiers
misc_feature            1..21
                        note = Description of Artificial Sequence: Synthetic
                         oligonucleotide
modified_base           9
                        mod_base = OTHER
                        note = abasic nucleotide
source                  1..21
                        mol_type = other RNA
                        organism = synthetic construct
SEQUENCE: 59
ccaagtgtng ctcattaggc a                                                     21

SEQ ID NO: 60           moltype = RNA  length = 21
FEATURE                 Location/Qualifiers
misc_feature            1..21
                        note = Description of Artificial Sequence: Synthetic
                         oligonucleotide
modified_base           9
                        mod_base = OTHER
                        note = abasic nucleotide
source                  1..21
                        mol_type = other RNA
                        organism = synthetic construct
SEQUENCE: 60
tgcaaatant ctacaaacca a                                                     21

SEQ ID NO: 61           moltype = RNA  length = 23
FEATURE                 Location/Qualifiers
misc_feature            1..23
```

```
                        note = Description of Artificial Sequence: Synthetic
                          oligonucleotide
source                  1..23
                        mol_type = other RNA
                        organism = synthetic construct
SEQUENCE: 61
ttggtttgta gactatttgc acc                                                 23

SEQ ID NO: 62           moltype = RNA  length = 21
FEATURE                 Location/Qualifiers
misc_feature            1..21
                        note = Description of Artificial Sequence: Synthetic
                          oligonucleotide
source                  1..21
                        mol_type = other RNA
                        organism = synthetic construct
SEQUENCE: 62
tgcaaatagt ctacaaacca a                                                   21

SEQ ID NO: 63           moltype = RNA  length = 21
FEATURE                 Location/Qualifiers
misc_feature            1..21
                        note = Description of Artificial Sequence: Synthetic
                          oligonucleotide
modified_base           1
                        mod_base = OTHER
                        note = 2'-O-methylguanosine with a 3'-phosphorothioate
                          linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = OTHER
                        note = 2'-fluoroguanosine
modified_base           8
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = OTHER
                        note = 2'-O-C16 alkyl uridine
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                          linkage
modified_base           20
                        mod_base = OTHER
                        note = 2'-O-methyladenosine with a 3'-phosphorothioate
```

|  |  |
|---|---|
|  | linkage |
| modified_base | 21 |
|  | mod_base = OTHER |
|  | note = 2'-O-methyladenosine |
| source | 1..21 |
|  | mol_type = other RNA |
|  | organism = synthetic construct |

SEQUENCE: 63
gtggaagtaa aatctgagaa a                                        21

|  |  |
|---|---|
| SEQ ID NO: 64 | moltype = RNA length = 21 |
| FEATURE | Location/Qualifiers |
| misc_feature | 1..21 |
|  | note = Description of Artificial Sequence: Synthetic oligonucleotide |
| modified_base | 1 |
|  | mod_base = OTHER |
|  | note = 2'-O-methylguanosine with a 3'-phosphorothioate linkage |
| modified_base | 2 |
|  | mod_base = OTHER |
|  | note = 2'-O-methyluridine with a 3'-phosphorothioate linkage |
| modified_base | 3 |
|  | mod_base = gm |
| modified_base | 4 |
|  | mod_base = gm |
| modified_base | 5 |
|  | mod_base = OTHER |
|  | note = 2'-O-methyladenosine |
| modified_base | 6 |
|  | mod_base = OTHER |
|  | note = 2'-O-methyladenosine |
| modified_base | 7 |
|  | mod_base = gm |
| modified_base | 8 |
|  | mod_base = um |
| modified_base | 9 |
|  | mod_base = OTHER |
|  | note = 2'-fluoroadenosine |
| modified_base | 10 |
|  | mod_base = OTHER |
|  | note = 2'-fluoroadenosine |
| modified_base | 11 |
|  | mod_base = OTHER |
|  | note = 2'-fluoroadenosine |
| modified_base | 12 |
|  | mod_base = OTHER |
|  | note = 2'-O-methyladenosine |
| modified_base | 13 |
|  | mod_base = OTHER |
|  | note = 2'-O-C16 alkyl uridine |
| modified_base | 14 |
|  | mod_base = cm |
| modified_base | 15 |
|  | mod_base = um |
| modified_base | 16 |
|  | mod_base = gm |
| modified_base | 17 |
|  | mod_base = OTHER |
|  | note = 2'-O-methyladenosine |
| modified_base | 18 |
|  | mod_base = gm |
| modified_base | 19 |
|  | mod_base = OTHER |
|  | note = 2'-O-methyladenosine with a 3'-phosphorothioate linkage |
| modified_base | 20 |
|  | mod_base = OTHER |
|  | note = 2'-O-methyladenosine with a 3'-phosphorothioate linkage |
| modified_base | 21 |
|  | mod_base = OTHER |
|  | note = 2'-O-methyladenosine |
| source | 1..21 |
|  | mol_type = other RNA |
|  | organism = synthetic construct |

SEQUENCE: 64
gtggaagtaa aatctgagaa a                                        21

| | |
|---|---|
| SEQ ID NO: 65 | moltype = RNA  length = 23 |
| FEATURE | Location/Qualifiers |
| misc_feature | 1..23<br>note = Description of Artificial Sequence: Synthetic<br>oligonucleotide |
| modified_base | 1<br>mod_base = OTHER<br>note = 2'-O-methyluridine with a 3'-phosphorothioate<br>linkage and a 5'-vinylphosphonate substitution |
| modified_base | 2<br>mod_base = OTHER<br>note = 2'-fluorouridine with a 3'-phosphorothioate linkage |
| modified_base | 3<br>mod_base = um |
| modified_base | 4<br>mod_base = cm |
| modified_base | 5<br>mod_base = OTHER<br>note = 2'-fluorouridine |
| modified_base | 6<br>mod_base = cm |
| modified_base | 7<br>mod_base = OTHER<br>note = 2'-O-methyladenosine |
| modified_base | 8<br>mod_base = OTHER<br>note = 2'-fluoroguanosine |
| modified_base | 9<br>mod_base = OTHER<br>note = 2'-O-methyladenosine |
| modified_base | 10<br>mod_base = um |
| modified_base | 11<br>mod_base = um |
| modified_base | 12<br>mod_base = um |
| modified_base | 13<br>mod_base = um |
| modified_base | 14<br>mod_base = OTHER<br>note = 2'-fluoroadenosine |
| modified_base | 15<br>mod_base = cm |
| modified_base | 16<br>mod_base = OTHER<br>note = 2'-fluorouridine |
| modified_base | 17<br>mod_base = um |
| modified_base | 18<br>mod_base = cm |
| modified_base | 19<br>mod_base = cm |
| modified_base | 20<br>mod_base = OTHER<br>note = 2'-O-methyladenosine |
| modified_base | 21<br>mod_base = OTHER<br>note = 2'-O-methylcytidine with a 3'-phosphorothioate<br>linkage |
| modified_base | 22<br>mod_base = OTHER<br>note = 2'-O-methylcytidine with a 3'-phosphorothioate<br>linkage |
| modified_base | 23<br>mod_base = um |
| source | 1..23<br>mol_type = other RNA<br>organism = synthetic construct |
| SEQUENCE: 65 | |
| tttctcagat tttacttcca cct | 23 |
| | |
| SEQ ID NO: 66 | moltype = RNA  length = 21 |
| FEATURE | Location/Qualifiers |
| misc_feature | 1..21<br>note = Description of Artificial Sequence: Synthetic<br>oligonucleotide |
| modified_base | 1<br>mod_base = OTHER<br>note = 2'-O-methylguanosine with a 3'-phosphorothioate |

```
modified_base        2
                     mod_base = OTHER
                     note = 2'-O-methyluridine with a 3'-phosphorothioate linkage
modified_base        3
                     mod_base = gm
modified_base        4
                     mod_base = gm
modified_base        5
                     mod_base = OTHER
                     note = 2'-O-methyladenosine
modified_base        6
                     mod_base = OTHER
                     note = 2'-O-methyladenosine
modified_base        7
                     mod_base = gm
modified_base        8
                     mod_base = um
modified_base        9
                     mod_base = OTHER
                     note = 2'-fluoroadenosine
modified_base        10
                     mod_base = OTHER
                     note = 2'-fluoroadenosine
modified_base        11
                     mod_base = OTHER
                     note = 2'-fluoroadenosine
modified_base        12
                     mod_base = OTHER
                     note = 2'-O-C16 alkyl adenosine
modified_base        13
                     mod_base = um
modified_base        14
                     mod_base = cm
modified_base        15
                     mod_base = um
modified_base        16
                     mod_base = gm
modified_base        17
                     mod_base = OTHER
                     note = 2'-O-methyladenosine
modified_base        18
                     mod_base = gm
modified_base        19
                     mod_base = OTHER
                     note = 2'-O-methyladenosine with a 3'-phosphorothioate
                      linkage
modified_base        20
                     mod_base = OTHER
                     note = 2'-O-methyladenosine with a 3'-phosphorothioate
                      linkage
modified_base        21
                     mod_base = OTHER
                     note = 2'-O-methyladenosine
source               1..21
                     mol_type = other RNA
                     organism = synthetic construct
SEQUENCE: 66
gtggaagtaa aatctgagaa a                                              21

SEQ ID NO: 67        moltype = RNA  length = 21
FEATURE              Location/Qualifiers
misc_feature         1..21
                     note = Description of Artificial Sequence: Synthetic
                      oligonucleotide
modified_base        1
                     mod_base = OTHER
                     note = 2'-O-methylguanosine with a 3'-phosphorothioate
                      linkage
modified_base        2
                     mod_base = OTHER
                     note = 2'-O-methyluridine with a 3'-phosphorothioate linkage
modified_base        3
                     mod_base = gm
modified_base        4
                     mod_base = gm
modified_base        5
                     mod_base = OTHER
                     note = 2'-O-methyladenosine
```

|  |  |
|---|---|
| modified_base | 6 |
|  | mod_base = OTHER |
|  | note = 2'-O-methyladenosine |
| modified_base | 7 |
|  | mod_base = gm |
| modified_base | 8 |
|  | mod_base = um |
| modified_base | 9 |
|  | mod_base = OTHER |
|  | note = 2'-fluoroadenosine |
| modified_base | 10 |
|  | mod_base = OTHER |
|  | note = abasic nucleotide |
| modified_base | 11 |
|  | mod_base = OTHER |
|  | note = 2'-fluoroadenosine |
| modified_base | 12 |
|  | mod_base = OTHER |
|  | note = 2'-O-methyladenosine |
| modified_base | 13 |
|  | mod_base = OTHER |
|  | note = 2'-O-C16 alkyl uridine |
| modified_base | 14 |
|  | mod_base = cm |
| modified_base | 15 |
|  | mod_base = um |
| modified_base | 16 |
|  | mod_base = gm |
| modified_base | 17 |
|  | mod_base = OTHER |
|  | note = 2'-O-methyladenosine |
| modified_base | 18 |
|  | mod_base = gm |
| modified_base | 19 |
|  | mod_base = OTHER |
|  | note = 2'-O-methyladenosine with a 3'-phosphorothioate linkage |
| modified_base | 20 |
|  | mod_base = OTHER |
|  | note = 2'-O-methyladenosine with a 3'-phosphorothioate linkage |
| modified_base | 21 |
|  | mod_base = OTHER |
|  | note = 2'-O-methyladenosine |
| source | 1..21 |
|  | mol_type = other RNA |
|  | organism = synthetic construct |
| SEQUENCE: 67 |  |
| gtggaagtan aatctgagaa a | 21 |
|  |  |
| SEQ ID NO: 68 | moltype = RNA  length = 21 |
| FEATURE | Location/Qualifiers |
| misc_feature | 1..21 |
|  | note = Description of Artificial Sequence: Synthetic oligonucleotide |
| modified_base | 1 |
|  | mod_base = OTHER |
|  | note = 2'-O-methylguanosine with a 3'-phosphorothioate linkage |
| modified_base | 2 |
|  | mod_base = OTHER |
|  | note = 2'-O-methyluridine with a 3'-phosphorothioate linkage |
| modified_base | 3 |
|  | mod_base = gm |
| modified_base | 4 |
|  | mod_base = gm |
| modified_base | 5 |
|  | mod_base = OTHER |
|  | note = 2'-O-methyladenosine |
| modified_base | 6 |
|  | mod_base = OTHER |
|  | note = 2'-O-methyladenosine |
| modified_base | 8 |
|  | mod_base = um |
| modified_base | 9 |
|  | mod_base = OTHER |
|  | note = 2'-fluoroadenosine |
| modified_base | 10 |
|  | mod_base = OTHER |

```
modified_base        11
                     mod_base = OTHER
                     note = 2'-fluoroadenosine
modified_base        12
                     mod_base = OTHER
                     note = 2'-O-methyladenosine
modified_base        13
                     mod_base = OTHER
                     note = 2'-O-C16 alkyl uridine
modified_base        14
                     mod_base = cm
modified_base        15
                     mod_base = um
modified_base        16
                     mod_base = gm
modified_base        17
                     mod_base = OTHER
                     note = 2'-O-methyladenosine
modified_base        18
                     mod_base = gm
modified_base        19
                     mod_base = OTHER
                     note = 2'-O-methyladenosine with a 3'-phosphorothioate
                       linkage
modified_base        20
                     mod_base = OTHER
                     note = 2'-O-methyladenosine with a 3'-phosphorothioate
                       linkage
modified_base        21
                     mod_base = OTHER
                     note = 2'-O-methyladenosine
source               1..21
                     mol_type = other RNA
                     organism = synthetic construct
SEQUENCE: 68
gtggaagtan aatctgagaa a                                             21

SEQ ID NO: 69       moltype = RNA   length = 21
FEATURE             Location/Qualifiers
misc_feature        1..21
                    note = Description of Artificial Sequence: Synthetic
                      oligonucleotide
modified_base       1
                    mod_base = OTHER
                    note = 2'-O-methylguanosine with a 3'-phosphorothioate
                      linkage
modified_base       2
                    mod_base = OTHER
                    note = 2'-O-methyluridine with a 3'-phosphorothioate linkage
modified_base       3
                    mod_base = gm
modified_base       4
                    mod_base = gm
modified_base       5
                    mod_base = OTHER
                    note = 2'-O-methyladenosine
modified_base       6
                    mod_base = OTHER
                    note = 2'-O-methyladenosine
modified_base       7
                    mod_base = gm
modified_base       8
                    mod_base = um
modified_base       9
                    mod_base = OTHER
                    note = abasic nucleotide
modified_base       10
                    mod_base = OTHER
                    note = 2'-fluoroadenosine
modified_base       11
                    mod_base = OTHER
                    note = 2'-fluoroadenosine
modified_base       12
                    mod_base = OTHER
                    note = 2'-O-methyladenosine
modified_base       13
                    mod_base = OTHER
                    note = 2'-O-C16 alkyl uridine
```

| | |
|---|---|
| modified_base | 14<br>mod_base = cm |
| modified_base | 15<br>mod_base = um |
| modified_base | 16<br>mod_base = gm |
| modified_base | 17<br>mod_base = OTHER<br>note = 2'-O-methyladenosine |
| modified_base | 18<br>mod_base = gm |
| modified_base | 19<br>mod_base = OTHER<br>note = 2'-O-methyladenosine with a 3'-phosphorothioate linkage |
| modified_base | 20<br>mod_base = OTHER<br>note = 2'-O-methyladenosine with a 3'-phosphorothioate linkage |
| modified_base | 21<br>mod_base = OTHER<br>note = 2'-O-methyladenosine |
| source | 1..21<br>mol_type = other RNA<br>organism = synthetic construct |

SEQUENCE: 69
gtggaagtna aatctgagaa a                                                  21

| | |
|---|---|
| SEQ ID NO: 70 | moltype = RNA  length = 23 |
| FEATURE | Location/Qualifiers |
| misc_feature | 1..23<br>note = Description of Artificial Sequence: Synthetic oligonucleotide |
| modified_base | 1<br>mod_base = OTHER<br>note = 2'-O-methyluridine with a 3'-phosphorothioate linkage and a 5'-vinylphosphonate substitution |
| modified_base | 2<br>mod_base = OTHER<br>note = 2'-fluorouridine with a 3'-phosphorothioate linkage |
| modified_base | 3<br>mod_base = um |
| modified_base | 4<br>mod_base = cm |
| modified_base | 5<br>mod_base = um |
| modified_base | 6<br>mod_base = OTHER<br>note = 2'-fluorocytidine |
| modified_base | 7<br>mod_base = OTHER<br>note = 2'-O-methyladenosine |
| modified_base | 8<br>mod_base = gm |
| modified_base | 9<br>mod_base = OTHER<br>note = 2'-O-methyladenosine |
| modified_base | 10<br>mod_base = OTHER<br>note = 2'-fluorouridine |
| modified_base | 11<br>mod_base = um |
| modified_base | 12<br>mod_base = um |
| modified_base | 13<br>mod_base = um |
| modified_base | 14<br>mod_base = OTHER<br>note = 2'-fluoroadenosine |
| modified_base | 15<br>mod_base = cm |
| modified_base | 16<br>mod_base = OTHER<br>note = 2'-fluorouridine |
| modified_base | 17<br>mod_base = um |
| modified_base | 18<br>mod_base = OTHER<br>note = 2'-fluorocytidine |

```
modified_base        19
                     mod_base = cm
modified_base        20
                     mod_base = OTHER
                     note = 2'-fluoroadenosine
modified_base        21
                     mod_base = OTHER
                     note = 2'-O-methylcytidine with a 3'-phosphorothioate
                      linkage
modified_base        22
                     mod_base = OTHER
                     note = 2'-O-methylcytidine with a 3'-phosphorothioate
                      linkage
modified_base        23
                     mod_base = um
source               1..23
                     mol_type = other RNA
                     organism = synthetic construct
SEQUENCE: 70
tttctcagat tttacttcca cct                                              23

SEQ ID NO: 71        moltype = RNA  length = 21
FEATURE              Location/Qualifiers
misc_feature         1..21
                     note = Description of Artificial Sequence: Synthetic
                      oligonucleotide
modified_base        1
                     mod_base = OTHER
                     note = 2'-O-methylguanosine with a 3'-phosphorothioate
                      linkage
modified_base        2
                     mod_base = OTHER
                     note = 2'-O-methyluridine with a 3'-phosphorothioate linkage
modified_base        3
                     mod_base = gm
modified_base        4
                     mod_base = gm
modified_base        5
                     mod_base = OTHER
                     note = 2'-O-methyladenosine
modified_base        6
                     mod_base = OTHER
                     note = 2'-O-methyladenosine
modified_base        7
                     mod_base = gm
modified_base        8
                     mod_base = um
modified_base        9
                     mod_base = OTHER
                     note = 2'-fluoroadenosine
modified_base        10
                     mod_base = OTHER
                     note = 2'-fluoroadenosine
modified_base        11
                     mod_base = OTHER
                     note = 2'-fluoroadenosine
modified_base        12
                     mod_base = OTHER
                     note = 2'-O-methyladenosine
modified_base        13
                     mod_base = OTHER
                     note = 2'-O-C16 alkyl uridine
modified_base        14
                     mod_base = cm
modified_base        15
                     mod_base = OTHER
                     note = 2'-fluorouridine
modified_base        16
                     mod_base = gm
modified_base        17
                     mod_base = OTHER
                     note = 2'-O-methyladenosine
modified_base        18
                     mod_base = gm
modified_base        19
                     mod_base = OTHER
                     note = 2'-O-methyladenosine with a 3'-phosphorothioate
                      linkage
modified_base        20
```

```
                        mod_base = OTHER
                        note = 2'-O-methyladenosine with a 3'-phosphorothioate
                         linkage
modified_base          21
                        mod_base = OTHER
                        note = 2'-O-methyladenosine
source                 1..21
                        mol_type = other RNA
                        organism = synthetic construct
SEQUENCE: 71
gtggaagtaa aatctgagaa a                                               21

SEQ ID NO: 72          moltype = RNA  length = 23
FEATURE                Location/Qualifiers
misc_feature           1..23
                        note = Description of Artificial Sequence: Synthetic
                         oligonucleotide
modified_base          1
                        mod_base = OTHER
                        note = 2'-O-methyluridine with a 3'-phosphorothioate
                         linkage and a 5'-vinylphosphonate substitution
modified_base          2
                        mod_base = OTHER
                        note = 2'-fluorouridine with a 3'-phosphorothioate linkage
modified_base          3
                        mod_base = um
modified_base          4
                        mod_base = cm
modified_base          5
                        mod_base = OTHER
                        note = 2'-fluorouridine
modified_base          6
                        mod_base = cm
modified_base          7
                        mod_base = OTHER
                        note = 2'-fluoroadenosine
modified_base          8
                        mod_base = gm
modified_base          9
                        mod_base = OTHER
                        note = 2'-O-methyladenosine
modified_base          10
                        mod_base = um
modified_base          11
                        mod_base = um
modified_base          12
                        mod_base = um
modified_base          13
                        mod_base = um
modified_base          14
                        mod_base = OTHER
                        note = 2'-fluoroadenosine
modified_base          15
                        mod_base = cm
modified_base          16
                        mod_base = OTHER
                        note = 2'-fluorouridine
modified_base          17
                        mod_base = um
modified_base          18
                        mod_base = cm
modified_base          19
                        mod_base = cm
modified_base          20
                        mod_base = OTHER
                        note = 2'-O-methyladenosine
modified_base          21
                        mod_base = OTHER
                        note = 2'-O-methylcytidine with a 3'-phosphorothioate
                         linkage
modified_base          22
                        mod_base = OTHER
                        note = 2'-O-methylcytidine with a 3'-phosphorothioate
                         linkage
modified_base          23
                        mod_base = um
source                 1..23
                        mol_type = other RNA
                        organism = synthetic construct
```

```
SEQUENCE: 72
tttctcagat tttacttcca cct                                                23

SEQ ID NO: 73            moltype = RNA  length = 23
FEATURE                  Location/Qualifiers
misc_feature             1..23
                         note = Description of Artificial Sequence: Synthetic
                          oligonucleotide
modified_base            1
                         mod_base = OTHER
                         note = 2'-O-methyluridine with a 3'-phosphorothioate
                          linkage and a 5'-vinylphosphonate substitution
modified_base            2
                         mod_base = OTHER
                         note = 2'-fluorouridine with a 3'-phosphorothioate linkage
modified_base            3
                         mod_base = OTHER
                         note = 2'-fluorouridine
modified_base            4
                         mod_base = cm
modified_base            5
                         mod_base = um
modified_base            6
                         mod_base = cm
modified_base            7
                         mod_base = OTHER
                         note = 2'-fluoroadenosine
modified_base            8
                         mod_base = gm
modified_base            9
                         mod_base = OTHER
                         note = 2'-O-methyladenosine
modified_base            10
                         mod_base = um
modified_base            11
                         mod_base = um
modified_base            12
                         mod_base = um
modified_base            13
                         mod_base = um
modified_base            14
                         mod_base = OTHER
                         note = 2'-fluoroadenosine
modified_base            15
                         mod_base = cm
modified_base            16
                         mod_base = OTHER
                         note = 2'-fluorouridine
modified_base            17
                         mod_base = um
modified_base            18
                         mod_base = cm
modified_base            19
                         mod_base = cm
modified_base            20
                         mod_base = OTHER
                         note = 2'-O-methyladenosine
modified_base            21
                         mod_base = OTHER
                         note = 2'-O-methylcytidine with a 3'-phosphorothioate
                          linkage
modified_base            22
                         mod_base = OTHER
                         note = 2'-O-methylcytidine with a 3'-phosphorothioate
                          linkage
modified_base            23
                         mod_base = um
source                   1..23
                         mol_type = other RNA
                         organism = synthetic construct
SEQUENCE: 73
tttctcagat tttacttcca cct                                                23

SEQ ID NO: 74            moltype = RNA  length = 23
FEATURE                  Location/Qualifiers
misc_feature             1..23
                         note = Description of Artificial Sequence: Synthetic
                          oligonucleotide
modified_base            1
```

|  |  |
|---|---|
|  | mod_base = OTHER |
|  | note = 2'-O-methyluridine with a 3'-phosphorothioate |
|  |   linkage and a 5'-vinylphosphonate substitution |
| modified_base | 2 |
|  | mod_base = OTHER |
|  | note = 2'-fluorouridine with a 3'-phosphorothioate linkage |
| modified_base | 3 |
|  | mod_base = um |
| modified_base | 4 |
|  | mod_base = cm |
| modified_base | 5 |
|  | mod_base = OTHER |
|  | note = 2'-fluorouridine |
| modified_base | 6 |
|  | mod_base = cm |
| modified_base | 7 |
|  | mod_base = OTHER |
|  | note = 2'-O-methyladenosine |
| modified_base | 8 |
|  | mod_base = gm |
| modified_base | 9 |
|  | mod_base = OTHER |
|  | note = 2'-O-methyladenosine |
| modified_base | 10 |
|  | mod_base = um |
| modified_base | 11 |
|  | mod_base = um |
| modified_base | 12 |
|  | mod_base = um |
| modified_base | 13 |
|  | mod_base = um |
| modified_base | 14 |
|  | mod_base = OTHER |
|  | note = 2'-fluoroadenosine |
| modified_base | 15 |
|  | mod_base = cm |
| modified_base | 16 |
|  | mod_base = um |
| modified_base | 17 |
|  | mod_base = um |
| modified_base | 18 |
|  | mod_base = cm |
| modified_base | 19 |
|  | mod_base = cm |
| modified_base | 20 |
|  | mod_base = OTHER |
|  | note = 2'-O-methyladenosine |
| modified_base | 21 |
|  | mod_base = OTHER |
|  | note = 2'-O-methylcytidine with a 3'-phosphorothioate |
|  |   linkage |
| modified_base | 22 |
|  | mod_base = OTHER |
|  | note = 2'-O-methylcytidine with a 3'-phosphorothioate |
|  |   linkage |
| modified_base | 23 |
|  | mod_base = um |
| source | 1..23 |
|  | mol_type = other RNA |
|  | organism = synthetic construct |
| SEQUENCE: 74 |  |
| tttctcagat tttacttcca cct |                                        23 |
|  |  |
| SEQ ID NO: 75 | moltype = RNA   length = 21 |
| FEATURE | Location/Qualifiers |
| misc_feature | 1..21 |
|  | note = Description of Artificial Sequence: Synthetic |
|  |   oligonucleotide |
| modified_base | 1 |
|  | mod_base = OTHER |
|  | note = 2'-O-methylguanosine with a 3'-phosphorothioate |
|  |   linkage |
| modified_base | 2 |
|  | mod_base = OTHER |
|  | note = 2'-O-methyluridine with a 3'-phosphorothioate linkage |
| modified_base | 3 |
|  | mod_base = gm |
| modified_base | 4 |
|  | mod_base = gm |

```
modified_base      5
                   mod_base = OTHER
                   note = 2'-O-methyladenosine
modified_base      6
                   mod_base = OTHER
                   note = 2'-O-methyladenosine
modified_base      7
                   mod_base = gm
modified_base      8
                   mod_base = um
modified_base      9
                   mod_base = OTHER
                   note = 2'-fluoroadenosine
modified_base      10
                   mod_base = OTHER
                   note = 2'-fluoroadenosine
modified_base      11
                   mod_base = OTHER
                   note = 2'-fluoroadenosine
modified_base      12
                   mod_base = OTHER
                   note = 2'-O-C16 alkyl adenosine
modified_base      13
                   mod_base = OTHER
                   note = 2'-fluorouridine
modified_base      14
                   mod_base = cm
modified_base      15
                   mod_base = OTHER
                   note = 2'-fluorouridine
modified_base      16
                   mod_base = gm
modified_base      17
                   mod_base = OTHER
                   note = 2'-O-methyladenosine
modified_base      18
                   mod_base = gm
modified_base      19
                   mod_base = OTHER
                   note = 2'-O-methyladenosine with a 3'-phosphorothioate
                    linkage
modified_base      20
                   mod_base = OTHER
                   note = 2'-O-methyladenosine with a 3'-phosphorothioate
                    linkage
modified_base      21
                   mod_base = OTHER
                   note = 2'-O-methyladenosine
source             1..21
                   mol_type = other RNA
                   organism = synthetic construct
SEQUENCE: 75
gtggaagtaa aatctgagaa a                                              21

SEQ ID NO: 76         moltype = RNA  length = 21
FEATURE               Location/Qualifiers
misc_feature          1..21
                      note = Description of Artificial Sequence: Synthetic
                       oligonucleotide
modified_base         1
                      mod_base = OTHER
                      note = 2'-O-C16 alkyl guanosine with a 3'-phosphorothioate
                       linkage
modified_base         2
                      mod_base = OTHER
                      note = 2'-O-methyluridine with a 3'-phosphorothioate linkage
modified_base         3
                      mod_base = gm
modified_base         4
                      mod_base = gm
modified_base         5
                      mod_base = OTHER
                      note = 2'-O-methyladenosine
modified_base         6
                      mod_base = OTHER
                      note = 2'-O-methyladenosine
modified_base         7
                      mod_base = gm
modified_base         8
```

```
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                         linkage
modified_base           20
                        mod_base = OTHER
                        note = 2'-O-methyladenosine with a 3'-phosphorothioate
                         linkage
modified_base           21
                        mod_base = OTHER
                        note = 2'-O-methyladenosine
source                  1..21
                        mol_type = other RNA
                        organism = synthetic construct
SEQUENCE: 76
gtggaagtaa aatctgagaa a                                                   21

SEQ ID NO: 77           moltype = RNA   length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methylguanosine with a 3'-phosphorothioate
                         linkage
modified_base           2
                        mod_base = OTHER
                        note = 2'-O-C16 alkyl uridine with a 3'-phosphorothioate
                         linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = gm
modified_base           8
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
```

```
modified_base     12
                  mod_base = OTHER
                  note = 2'-O-methyladenosine
modified_base     13
                  mod_base = um
modified_base     14
                  mod_base = cm
modified_base     15
                  mod_base = um
modified_base     16
                  mod_base = gm
modified_base     17
                  mod_base = OTHER
                  note = 2'-O-methyladenosine
modified_base     18
                  mod_base = gm
modified_base     19
                  mod_base = OTHER
                  note = 2'-O-methyladenosine with a 3'-phosphorothioate
                    linkage
modified_base     20
                  mod_base = OTHER
                  note = 2'-O-methyladenosine with a 3'-phosphorothioate
                    linkage
modified_base     21
                  mod_base = OTHER
                  note = 2'-O-methyladenosine
source            1..21
                  mol_type = other RNA
                  organism = synthetic construct
SEQUENCE: 77
gtggaagtaa aatctgagaa a                                              21

SEQ ID NO: 78         moltype = RNA  length = 21
FEATURE               Location/Qualifiers
misc_feature          1..21
                      note = Description of Artificial Sequence: Synthetic
                        oligonucleotide
modified_base     1
                  mod_base = OTHER
                  note = 2'-O-methylguanosine with a 3'-phosphorothioate
                    linkage
modified_base     2
                  mod_base = OTHER
                  note = 2'-O-methyluridine with a 3'-phosphorothioate linkage
modified_base     3
                  mod_base = OTHER
                  note = 2'-O-C16 alkyl guanosine
modified_base     4
                  mod_base = gm
modified_base     5
                  mod_base = OTHER
                  note = 2'-O-methyladenosine
modified_base     6
                  mod_base = OTHER
                  note = 2'-O-methyladenosine
modified_base     7
                  mod_base = gm
modified_base     8
                  mod_base = um
modified_base     9
                  mod_base = OTHER
                  note = 2'-fluoroadenosine
modified_base     10
                  mod_base = OTHER
                  note = 2'-fluoroadenosine
modified_base     11
                  mod_base = OTHER
                  note = 2'-fluoroadenosine
modified_base     12
                  mod_base = OTHER
                  note = 2'-O-methyladenosine
modified_base     13
                  mod_base = um
modified_base     14
                  mod_base = cm
modified_base     15
                  mod_base = um
modified_base     16
```

```
                            mod_base = gm
modified_base               17
                            mod_base = OTHER
                            note = 2'-O-methyladenosine
modified_base               18
                            mod_base = gm
modified_base               19
                            mod_base = OTHER
                            note = 2'-O-methyladenosine with a 3'-phosphorothioate
                              linkage
modified_base               20
                            mod_base = OTHER
                            note = 2'-O-methyladenosine with a 3'-phosphorothioate
                              linkage
modified_base               21
                            mod_base = OTHER
                            note = 2'-O-methyladenosine
source                      1..21
                            mol_type = other RNA
                            organism = synthetic construct
SEQUENCE: 78
gtggaagtaa aatctgagaa a                                              21

SEQ ID NO: 79               moltype = RNA  length = 21
FEATURE                     Location/Qualifiers
misc_feature                1..21
                            note = Description of Artificial Sequence: Synthetic
                              oligonucleotide
modified_base               1
                            mod_base = OTHER
                            note = 2'-O-methylguanosine with a 3'-phosphorothioate
                              linkage
modified_base               2
                            mod_base = OTHER
                            note = 2'-O-methyluridine with a 3'-phosphorothioate linkage
modified_base               3
                            mod_base = gm
modified_base               4
                            mod_base = gm
modified_base               5
                            mod_base = OTHER
                            note = 2'-O-methyladenosine
modified_base               6
                            mod_base = OTHER
                            note = 2'-O-C16 alkyl adenosine
modified_base               7
                            mod_base = gm
modified_base               8
                            mod_base = um
modified_base               9
                            mod_base = OTHER
                            note = 2'-fluoroadenosine
modified_base               10
                            mod_base = OTHER
                            note = 2'-fluoroadenosine
modified_base               11
                            mod_base = OTHER
                            note = 2'-fluoroadenosine
modified_base               12
                            mod_base = OTHER
                            note = 2'-O-methyladenosine
modified_base               13
                            mod_base = um
modified_base               14
                            mod_base = cm
modified_base               15
                            mod_base = um
modified_base               16
                            mod_base = gm
modified_base               17
                            mod_base = OTHER
                            note = 2'-O-methyladenosine
modified_base               18
                            mod_base = gm
modified_base               19
                            mod_base = OTHER
                            note = 2'-O-methyladenosine with a 3'-phosphorothioate
                              linkage
modified_base               20
```

```
                        mod_base = OTHER
                        note = 2'-O-methyladenosine with a 3'-phosphorothioate
                         linkage
modified_base           21
                        mod_base = OTHER
                        note = 2'-O-methyladenosine
source                  1..21
                        mol_type = other RNA
                        organism = synthetic construct
SEQUENCE: 79
gtggaagtaa aatctgagaa a                                                   21

SEQ ID NO: 80           moltype = RNA   length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methylguanosine with a 3'-phosphorothioate
                         linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = gm
modified_base           8
                        mod_base = OTHER
                        note = 2'-O-C16 alkyl uridine
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                         linkage
modified_base           20
                        mod_base = OTHER
                        note = 2'-O-methyladenosine with a 3'-phosphorothioate
                         linkage
modified_base           21
                        mod_base = OTHER
                        note = 2'-O-methyladenosine
source                  1..21
                        mol_type = other RNA
                        organism = synthetic construct
SEQUENCE: 80
```

```
gtggaagtaa aatctgagaa a                                              21

SEQ ID NO: 81           moltype = RNA  length = 21
FEATURE                 Location/Qualifiers
misc_feature            1..21
                        note = Description of Artificial Sequence: Synthetic
                        oligonucleotide
modified_base           1
                        mod_base = OTHER
                        note = 2'-O-methylguanosine with a 3'-phosphorothioate
                        linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = gm
modified_base           8
                        mod_base = um
modified_base           9
                        mod_base = OTHER
                        note = 2'-O-C16 alkyl adenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                        linkage
modified_base           20
                        mod_base = OTHER
                        note = 2'-O-methyladenosine with a 3'-phosphorothioate
                        linkage
modified_base           21
                        mod_base = OTHER
                        note = 2'-O-methyladenosine
source                  1..21
                        mol_type = other RNA
                        organism = synthetic construct
SEQUENCE: 81
gtggaagtaa aatctgagaa a                                              21

SEQ ID NO: 82           moltype = RNA  length = 21
FEATURE                 Location/Qualifiers
misc_feature            1..21
                        note = Description of Artificial Sequence: Synthetic
                        oligonucleotide
modified_base           1
                        mod_base = OTHER
                        note = 2'-O-methylguanosine with a 3'-phosphorothioate
                        linkage
```

| | |
|---|---|
| modified_base | 2<br>mod_base = OTHER<br>note = 2'-O-methyluridine with a 3'-phosphorothioate linkage |
| modified_base | 3<br>mod_base = gm |
| modified_base | 4<br>mod_base = gm |
| modified_base | 5<br>mod_base = OTHER<br>note = 2'-O-methyladenosine |
| modified_base | 6<br>mod_base = OTHER<br>note = 2'-O-methyladenosine |
| modified_base | 7<br>mod_base = gm |
| modified_base | 8<br>mod_base = um |
| modified_base | 9<br>mod_base = OTHER<br>note = 2'-fluoroadenosine |
| modified_base | 10<br>mod_base = OTHER<br>note = 2'-O-C16 alkyl adenosine |
| modified_base | 11<br>mod_base = OTHER<br>note = 2'-fluoroadenosine |
| modified_base | 12<br>mod_base = OTHER<br>note = 2'-O-methyladenosine |
| modified_base | 13<br>mod_base = um |
| modified_base | 14<br>mod_base = cm |
| modified_base | 15<br>mod_base = um |
| modified_base | 16<br>mod_base = gm |
| modified_base | 17<br>mod_base = OTHER<br>note = 2'-O-methyladenosine |
| modified_base | 18<br>mod_base = gm |
| modified_base | 19<br>mod_base = OTHER<br>note = 2'-O-methyladenosine with a 3'-phosphorothioate linkage |
| modified_base | 20<br>mod_base = OTHER<br>note = 2'-O-methyladenosine with a 3'-phosphorothioate linkage |
| modified_base | 21<br>mod_base = OTHER<br>note = 2'-O-methyladenosine |
| source | 1..21<br>mol_type = other RNA<br>organism = synthetic construct |

SEQUENCE: 82 gtggaagtaa aatctgagaa a                                          21

| | |
|---|---|
| SEQ ID NO: 83<br>FEATURE | moltype = RNA  length = 21<br>Location/Qualifiers |
| misc_feature | 1..21<br>note = Description of Artificial Sequence: Synthetic oligonucleotide |
| modified_base | 1<br>mod_base = OTHER<br>note = 2'-O-methylguanosine with a 3'-phosphorothioate linkage |
| modified_base | 2<br>mod_base = OTHER<br>note = 2'-O-methyluridine with a 3'-phosphorothioate linkage |
| modified_base | 3<br>mod_base = gm |
| modified_base | 4<br>mod_base = gm |
| modified_base | 5<br>mod_base = OTHER<br>note = 2'-O-methyladenosine |
| modified_base | 6 |

|               |                                                                      |
|---------------|----------------------------------------------------------------------|
|               | mod_base = OTHER                                                     |
|               | note = 2'-O-methyladenosine                                          |
| modified_base | 7                                                                    |
|               | mod_base = gm                                                        |
| modified_base | 8                                                                    |
|               | mod_base = um                                                        |
| modified_base | 9                                                                    |
|               | mod_base = OTHER                                                     |
|               | note = 2'-fluoroadenosine                                            |
| modified_base | 10                                                                   |
|               | mod_base = OTHER                                                     |
|               | note = 2'-fluoroadenosine                                            |
| modified_base | 11                                                                   |
|               | mod_base = OTHER                                                     |
|               | note = 2'-fluoroadenosine                                            |
| modified_base | 12                                                                   |
|               | mod_base = OTHER                                                     |
|               | note = 2'-O-methyladenosine                                          |
| modified_base | 13                                                                   |
|               | mod_base = um                                                        |
| modified_base | 14                                                                   |
|               | mod_base = cm                                                        |
| modified_base | 15                                                                   |
|               | mod_base = OTHER                                                     |
|               | note = 2'-O-C16 alkyl uridine                                        |
| modified_base | 16                                                                   |
|               | mod_base = gm                                                        |
| modified_base | 17                                                                   |
|               | mod_base = OTHER                                                     |
|               | note = 2'-O-methyladenosine                                          |
| modified_base | 18                                                                   |
|               | mod_base = gm                                                        |
| modified_base | 19                                                                   |
|               | mod_base = OTHER                                                     |
|               | note = 2'-O-methyladenosine with a 3'-phosphorothioate               |
|               |        linkage                                                       |
| modified_base | 20                                                                   |
|               | mod_base = OTHER                                                     |
|               | note = 2'-O-methyladenosine with a 3'-phosphorothioate               |
|               |        linkage                                                       |
| modified_base | 21                                                                   |
|               | mod_base = OTHER                                                     |
|               | note = 2'-O-methyladenosine                                          |
| source        | 1..21                                                                |
|               | mol_type = other RNA                                                 |
|               | organism = synthetic construct                                       |
| SEQUENCE: 83  |                                                                      |
| gtggaagtaa aatctgagaa a                                                         21     |
|               |                                                                      |
| SEQ ID NO: 84 | moltype = RNA  length = 21                                           |
| FEATURE       | Location/Qualifiers                                                  |
| misc_feature  | 1..21                                                                |
|               | note = Description of Artificial Sequence: Synthetic                 |
|               |  oligonucleotide                                                     |
| modified_base | 1                                                                    |
|               | mod_base = OTHER                                                     |
|               | note = 2'-O-methylguanosine with a 3'-phosphorothioate               |
|               |        linkage                                                       |
| modified_base | 2                                                                    |
|               | mod_base = OTHER                                                     |
|               | note = 2'-O-methyluridine with a 3'-phosphorothioate linkage         |
| modified_base | 3                                                                    |
|               | mod_base = gm                                                        |
| modified_base | 4                                                                    |
|               | mod_base = gm                                                        |
| modified_base | 5                                                                    |
|               | mod_base = OTHER                                                     |
|               | note = 2'-O-methyladenosine                                          |
| modified_base | 6                                                                    |
|               | mod_base = OTHER                                                     |
|               | note = 2'-O-methyladenosine                                          |
| modified_base | 7                                                                    |
|               | mod_base = gm                                                        |
| modified_base | 8                                                                    |
|               | mod_base = um                                                        |
| modified_base | 9                                                                    |
|               | mod_base = OTHER                                                     |
|               | note = 2'-fluoroadenosine                                            |
| modified_base | 10                                                                   |

```
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-C16 alkyl adenosine with a 3'-phosphorothioate
                          linkage
modified_base           20
                        mod_base = OTHER
                        note = 2'-O-methyladenosine with a 3'-phosphorothioate
                          linkage
modified_base           21
                        mod_base = OTHER
                        note = 2'-O-methyladenosine
source                  1..21
                        mol_type = other RNA
                        organism = synthetic construct
SEQUENCE: 84
gtggaagtaa aatctgagaa a                                                    21

SEQ ID NO: 85           moltype = RNA   length = 21
FEATURE                 Location/Qualifiers
misc_feature            1..21
                        note = Description of Artificial Sequence: Synthetic
                          oligonucleotide
modified_base           1
                        mod_base = OTHER
                        note = 2'-O-methylguanosine with a 3'-phosphorothioate
                          linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = gm
modified_base           8
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
```

```
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                         linkage
modified_base           20
                        mod_base = OTHER
                        note = 2'-O-C16 alkyl adenosine with a 3'-phosphorothioate
                         linkage
modified_base           21
                        mod_base = OTHER
                        note = 2'-O-methyladenosine
source                  1..21
                        mol_type = other RNA
                        organism = synthetic construct
SEQUENCE: 85
gtggaagtaa aatctgagaa a                                             21

SEQ ID NO: 86           moltype = RNA  length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methylguanosine with a 3'-phosphorothioate
                         linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = gm
modified_base           8
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
```

|                   |                                                                                                |
|-------------------|------------------------------------------------------------------------------------------------|
|                   | mod_base = OTHER                                                                               |
|                   | note = 2'-O-methyladenosine with a 3'-phosphorothioate linkage                                 |
| modified_base     | 20                                                                                             |
|                   | mod_base = OTHER                                                                               |
|                   | note = 2'-O-methyladenosine with a 3'-phosphorothioate linkage                                 |
| modified_base     | 21                                                                                             |
|                   | mod_base = OTHER                                                                               |
|                   | note = 2'-O-C16 alkyl adenosine                                                                |
| source            | 1..21                                                                                          |
|                   | mol_type = other RNA                                                                           |
|                   | organism = synthetic construct                                                                 |
| SEQUENCE: 86      |                                                                                                |
| gtggaagtaa aatctgagaa a                                                                                         21         |

| SEQ ID NO: 87     | moltype = RNA  length = 21                                                                     |
| FEATURE           | Location/Qualifiers                                                                            |
| misc_feature      | 1..21                                                                                          |
|                   | note = Description of Artificial Sequence: Synthetic oligonucleotide                           |
| modified_base     | 1                                                                                              |
|                   | mod_base = OTHER                                                                               |
|                   | note = 2'-O-methylcytidine with a 3'-phosphorothioate linkage                                  |
| modified_base     | 2                                                                                              |
|                   | mod_base = OTHER                                                                               |
|                   | note = 2'-O-methylcytidine with a 3'-phosphorothioate linkage                                  |
| modified_base     | 3                                                                                              |
|                   | mod_base = OTHER                                                                               |
|                   | note = 2'-O-methyladenosine                                                                    |
| modified_base     | 4                                                                                              |
|                   | mod_base = OTHER                                                                               |
|                   | note = 2'-O-methyladenosine                                                                    |
| modified_base     | 5                                                                                              |
|                   | mod_base = gm                                                                                  |
| modified_base     | 6                                                                                              |
|                   | mod_base = um                                                                                  |
| modified_base     | 7                                                                                              |
|                   | mod_base = gm                                                                                  |
| modified_base     | 8                                                                                              |
|                   | mod_base = um                                                                                  |
| modified_base     | 9                                                                                              |
|                   | mod_base = OTHER                                                                               |
|                   | note = 2'-fluoroguanosine                                                                      |
| modified_base     | 10                                                                                             |
|                   | mod_base = OTHER                                                                               |
|                   | note = 2'-fluoroguanosine                                                                      |
| modified_base     | 11                                                                                             |
|                   | mod_base = OTHER                                                                               |
|                   | note = 2'-fluorocytidine                                                                       |
| modified_base     | 12                                                                                             |
|                   | mod_base = um                                                                                  |
| modified_base     | 13                                                                                             |
|                   | mod_base = OTHER                                                                               |
|                   | note = 2'-O-C16 alkyl cytidine                                                                 |
| modified_base     | 14                                                                                             |
|                   | mod_base = OTHER                                                                               |
|                   | note = 2'-O-methyladenosine                                                                    |
| modified_base     | 15                                                                                             |
|                   | mod_base = um                                                                                  |
| modified_base     | 16                                                                                             |
|                   | mod_base = um                                                                                  |
| modified_base     | 17                                                                                             |
|                   | mod_base = OTHER                                                                               |
|                   | note = 2'-O-methyladenosine                                                                    |
| modified_base     | 18                                                                                             |
|                   | mod_base = gm                                                                                  |
| modified_base     | 19                                                                                             |
|                   | mod_base = OTHER                                                                               |
|                   | note = 2'-O-methylguanosine with a 3'-phosphorothioate linkage                                 |
| modified_base     | 20                                                                                             |
|                   | mod_base = OTHER                                                                               |
|                   | note = 2'-O-methylcytidine with a 3'-phosphorothioate linkage                                  |
| modified_base     | 21                                                                                             |
|                   | mod_base = OTHER                                                                               |

```
                         note = 2'-O-methyladenosine
source                   1..21
                         mol_type = other RNA
                         organism = synthetic construct
SEQUENCE: 87
ccaagtgtgg ctcattaggc a                                                  21

SEQ ID NO: 88            moltype = RNA  length = 23
FEATURE                  Location/Qualifiers
misc_feature             1..23
                         note = Description of Artificial Sequence: Synthetic
                           oligonucleotide
modified_base            1
                         mod_base = OTHER
                         note = 2'-O-methyluridine with a 3'-phosphorothioate
                           linkage and a 5'-vinylphosphonate substitution
modified_base            2
                         mod_base = OTHER
                         note = 2'-fluoroguanosine with a 3'-phosphorothioate linkage
modified_base            3
                         mod_base = cm
modified_base            4
                         mod_base = cm
modified_base            5
                         mod_base = OTHER
                         note = 2'-fluorouridine
modified_base            6
                         mod_base = OTHER
                         note = 2'-O-methyladenosine
modified_base            7
                         mod_base = OTHER
                         note = 2'-O-methyladenosine
modified_base            8
                         mod_base = OTHER
                         note = 2'-fluorouridine
modified_base            9
                         mod_base = gm
modified_base            10
                         mod_base = OTHER
                         note = 2'-O-methyladenosine
modified_base            11
                         mod_base = gm
modified_base            12
                         mod_base = cm
modified_base            13
                         mod_base = cm
modified_base            14
                         mod_base = OTHER
                         note = 2'-fluoroadenosine
modified_base            15
                         mod_base = cm
modified_base            16
                         mod_base = OTHER
                         note = 2'-fluoroadenosine
modified_base            17
                         mod_base = cm
modified_base            18
                         mod_base = um
modified_base            19
                         mod_base = um
modified_base            20
                         mod_base = gm
modified_base            21
                         mod_base = OTHER
                         note = 2'-O-methylguanosine with a 3'-phosphorothioate
                           linkage
modified_base            22
                         mod_base = OTHER
                         note = 2'-O-methyladenosine with a 3'-phosphorothioate
                           linkage
modified_base            23
                         mod_base = gm
source                   1..23
                         mol_type = other RNA
                         organism = synthetic construct
SEQUENCE: 88
tgcctaatga gccacacttg gag                                                23

SEQ ID NO: 89            moltype = RNA  length = 21
```

```
FEATURE                 Location/Qualifiers
misc_feature            1..21
                        note = Description of Artificial Sequence: Synthetic
                        oligonucleotide
modified_base           1
                        mod_base = OTHER
                        note = 2'-O-methylcytidine with a 3'-phosphorothioate
                        linkage
modified_base           2
                        mod_base = OTHER
                        note = 2'-O-methylcytidine with a 3'-phosphorothioate
                        linkage
modified_base           3
                        mod_base = OTHER
                        note = 2'-O-methyladenosine
modified_base           4
                        mod_base = OTHER
                        note = 2'-O-methyladenosine
modified_base           5
                        mod_base = gm
modified_base           6
                        mod_base = um
modified_base           7
                        mod_base = gm
modified_base           8
                        mod_base = um
modified_base           9
                        mod_base = OTHER
                        note = abasic nucleotide
modified_base           10
                        mod_base = OTHER
                        note = 2'-fluoroguanosine
modified_base           11
                        mod_base = OTHER
                        note = 2'-fluorocytidine
modified_base           12
                        mod_base = um
modified_base           13
                        mod_base = OTHER
                        note = 2'-O-C16 alkyl cytidine
modified_base           14
                        mod_base = OTHER
                        note = 2'-O-methyladenosine
modified_base           15
                        mod_base = um
modified_base           16
                        mod_base = um
modified_base           17
                        mod_base = OTHER
                        note = 2'-O-methyladenosine
modified_base           18
                        mod_base = gm
modified_base           19
                        mod_base = OTHER
                        note = 2'-O-methylguanosine with a 3'-phosphorothioate
                        linkage
modified_base           20
                        mod_base = OTHER
                        note = 2'-O-methylcytidine with a 3'-phosphorothioate
                        linkage
modified_base           21
                        mod_base = OTHER
                        note = 2'-O-methyladenosine
source                  1..21
                        mol_type = other RNA
                        organism = synthetic construct
SEQUENCE: 89
ccaagtgtng ctcattaggc a                                              21

SEQ ID NO: 90           moltype = RNA   length = 21
FEATURE                 Location/Qualifiers
misc_feature            1..21
                        note = Description of Artificial Sequence: Synthetic
                        oligonucleotide
modified_base           1
                        mod_base = OTHER
                        note = 2'-O-methyluridine with a 3'-phosphorothioate linkage
modified_base           2
                        mod_base = OTHER
```

```
                        note = 2'-O-methylguanosine with a 3'-phosphorothioate
                        linkage
modified_base           3
                        mod_base = cm
modified_base           4
                        mod_base = OTHER
                        note = 2'-O-methyladenosine
modified_base           5
                        mod_base = OTHER
                        note = 2'-O-methyladenosine
modified_base           6
                        mod_base = OTHER
                        note = 2'-O-methyladenosine
modified_base           7
                        mod_base = um
modified_base           8
                        mod_base = OTHER
                        note = 2'-O-methyladenosine
modified_base           9
                        mod_base = OTHER
                        note = abasic nucleotide
modified_base           10
                        mod_base = OTHER
                        note = 2'-fluorouridine
modified_base           11
                        mod_base = OTHER
                        note = 2'-fluorocytidine
modified_base           12
                        mod_base = um
modified_base           13
                        mod_base = OTHER
                        note = 2'-O-C16 alkyl adenosine
modified_base           14
                        mod_base = cm
modified_base           15
                        mod_base = OTHER
                        note = 2'-O-methyladenosine
modified_base           16
                        mod_base = OTHER
                        note = 2'-O-methyladenosine
modified_base           17
                        mod_base = OTHER
                        note = 2'-O-methyladenosine
modified_base           18
                        mod_base = cm
modified_base           19
                        mod_base = OTHER
                        note = 2'-O-methylcytidine with a 3'-phosphorothioate
                        linkage
modified_base           20
                        mod_base = OTHER
                        note = 2'-O-methyladenosine with a 3'-phosphorothioate
                        linkage
modified_base           21
                        mod_base = OTHER
                        note = 2'-O-methyladenosine
source                  1..21
                        mol_type = other RNA
                        organism = synthetic construct
SEQUENCE: 90
tgcaaatant ctacaaacca a                                                   21

SEQ ID NO: 91           moltype = RNA   length = 23
FEATURE                 Location/Qualifiers
misc_feature            1..23
                        note = Description of Artificial Sequence: Synthetic
                        oligonucleotide
modified_base           1
                        mod_base = OTHER
                        note = 2'-O-methyluridine with a 3'-phosphorothioate
                        linkage and a 5'-vinylphosphonate substitution
modified_base           2
                        mod_base = OTHER
                        note = 2'-fluorouridine
modified_base           3
                        mod_base = gm
modified_base           4
                        mod_base = gm
modified_base           5
```

| | | |
|---|---|---|
| | | mod_base = OTHER |
| | | note = 2'-fluorouridine |
| modified_base | 6 | |
| | | mod_base = um |
| modified_base | 7 | |
| | | mod_base = um |
| modified_base | 8 | |
| | | mod_base = OTHER |
| | | note = 2'-fluoroguanosine |
| modified_base | 9 | |
| | | mod_base = um |
| modified_base | 10 | |
| | | mod_base = OTHER |
| | | note = 2'-O-methyladenosine |
| modified_base | 11 | |
| | | mod_base = gm |
| modified_base | 12 | |
| | | mod_base = OTHER |
| | | note = 2'-O-methyladenosine |
| modified_base | 13 | |
| | | mod_base = cm |
| modified_base | 14 | |
| | | mod_base = OTHER |
| | | note = 2'-fluorouridine |
| modified_base | 15 | |
| | | mod_base = OTHER |
| | | note = 2'-O-methyladenosine |
| modified_base | 16 | |
| | | mod_base = OTHER |
| | | note = 2'-fluorouridine |
| modified_base | 17 | |
| | | mod_base = um |
| modified_base | 18 | |
| | | mod_base = um |
| modified_base | 19 | |
| | | mod_base = gm |
| modified_base | 20 | |
| | | mod_base = cm |
| modified_base | 21 | |
| | | mod_base = OTHER |
| | | note = 2'-O-methyladenosine with a 3'-phosphorothioate linkage |
| modified_base | 22 | |
| | | mod_base = OTHER |
| | | note = 2'-O-methylcytidine with a 3'-phosphorothioate linkage |
| modified_base | 23 | |
| | | mod_base = cm |
| source | 1..23 | |
| | | mol_type = other RNA |
| | | organism = synthetic construct |

SEQUENCE: 91
ttggtttgta gactatttgc acc        23

| | | |
|---|---|---|
| SEQ ID NO: 92 | moltype = RNA  length = 21 | |
| FEATURE | Location/Qualifiers | |
| misc_feature | 1..21 | |
| | | note = Description of Artificial Sequence: Synthetic oligonucleotide |
| modified_base | 1 | |
| | | mod_base = OTHER |
| | | note = 2'-O-methyluridine with a 3'-phosphorothioate linkage |
| modified_base | 2 | |
| | | mod_base = OTHER |
| | | note = 2'-O-methylguanosine with a 3'-phosphorothioate linkage |
| modified_base | 3 | |
| | | mod_base = cm |
| modified_base | 4 | |
| | | mod_base = OTHER |
| | | note = 2'-O-methyladenosine |
| modified_base | 5 | |
| | | mod_base = OTHER |
| | | note = 2'-O-methyladenosine |
| modified_base | 6 | |
| | | mod_base = OTHER |
| | | note = 2'-O-methyladenosine |
| modified_base | 7 | |
| | | mod_base = um |

```
modified_base      8
                   mod_base = OTHER
                   note = 2'-O-methyladenosine
modified_base      9
                   mod_base = OTHER
                   note = 2'-fluoroguanosine
modified_base      10
                   mod_base = OTHER
                   note = 2'-fluorouridine
modified_base      11
                   mod_base = OTHER
                   note = 2'-fluorocytidine
modified_base      12
                   mod_base = um
modified_base      13
                   mod_base = OTHER
                   note = 2'-O-C16 alkyl adenosine
modified_base      14
                   mod_base = cm
modified_base      15
                   mod_base = OTHER
                   note = 2'-O-methyladenosine
modified_base      16
                   mod_base = OTHER
                   note = 2'-O-methyladenosine
modified_base      17
                   mod_base = OTHER
                   note = 2'-O-methyladenosine
modified_base      18
                   mod_base = cm
modified_base      19
                   mod_base = OTHER
                   note = 2'-O-methylcytidine with a 3'-phosphorothioate
                    linkage
modified_base      20
                   mod_base = OTHER
                   note = 2'-O-methyladenosine with a 3'-phosphorothioate
                    linkage
modified_base      21
                   mod_base = OTHER
                   note = 2'-O-methyladenosine
source             1..21
                   mol_type = other RNA
                   organism = synthetic construct
SEQUENCE: 92
tgcaaatagt ctacaaacca a                                               21

SEQ ID NO: 93     moltype = RNA   length = 21
FEATURE           Location/Qualifiers
misc_feature      1..21
                   note = Description of Artificial Sequence: Synthetic
                    oligonucleotide
modified_base      1
                   mod_base = OTHER
                   note = 2'-O-methylguanosine with a 3'-phosphorothioate
                    linkage
modified_base      2
                   mod_base = OTHER
                   note = 2'-O-methyluridine with a 3'-phosphorothioate linkage
modified_base      3
                   mod_base = gm
modified_base      4
                   mod_base = OTHER
                   note = 2'-O-C16 alkyl guanosine
modified_base      5
                   mod_base = OTHER
                   note = 2'-O-methyladenosine
modified_base      6
                   mod_base = OTHER
                   note = 2'-O-methyladenosine
modified_base      7
                   mod_base = gm
modified_base      8
                   mod_base = um
modified_base      9
                   mod_base = OTHER
                   note = 2'-fluoroadenosine
modified_base      10
                   mod_base = OTHER
```

```
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine with a 3'-phosphorothioate
                          linkage
modified_base           20
                        mod_base = OTHER
                        note = 2'-O-methyladenosine with a 3'-phosphorothioate
                          linkage
modified_base           21
                        mod_base = OTHER
                        note = 2'-O-methyladenosine
source                  1..21
                        mol_type = other RNA
                        organism = synthetic construct
SEQUENCE: 93
gtggaagtaa aatctgagaa a                                        21

SEQ ID NO: 94           moltype = RNA   length = 21
FEATURE                 Location/Qualifiers
misc_feature            1..21
                        note = Description of Artificial Sequence: Synthetic
                          oligonucleotide
modified_base           1
                        mod_base = OTHER
                        note = 2'-O-methylguanosine with a 3'-phosphorothioate
                          linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-C16 alkyl adenosine
modified_base           6
                        mod_base = OTHER
                        note = 2'-O-methyladenosine
modified_base           7
                        mod_base = gm
modified_base           8
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
```

```
modified_base        15
                     mod_base = um
modified_base        16
                     mod_base = gm
modified_base        17
                     mod_base = OTHER
                     note = 2'-O-methyladenosine
modified_base        18
                     mod_base = gm
modified_base        19
                     mod_base = OTHER
                     note = 2'-O-methyladenosine with a 3'-phosphorothioate
                      linkage
modified_base        20
                     mod_base = OTHER
                     note = 2'-O-methyladenosine with a 3'-phosphorothioate
                      linkage
modified_base        21
                     mod_base = OTHER
                     note = 2'-O-methyladenosine
source               1..21
                     mol_type = other RNA
                     organism = synthetic construct
SEQUENCE: 94
gtggaagtaa aatctgagaa a                                              21

SEQ ID NO: 95        moltype = RNA  length = 21
FEATURE              Location/Qualifiers
misc_feature         1..21
                     note = Description of Artificial Sequence: Synthetic
                      oligonucleotide
modified_base        1
                     mod_base = OTHER
                     note = 2'-O-methylguanosine with a 3'-phosphorothioate
                      linkage
modified_base        2
                     mod_base = OTHER
                     note = 2'-O-methyluridine with a 3'-phosphorothioate linkage
modified_base        3
                     mod_base = gm
modified_base        4
                     mod_base = gm
modified_base        5
                     mod_base = OTHER
                     note = 2'-O-methyladenosine
modified_base        6
                     mod_base = OTHER
                     note = 2'-O-methyladenosine
modified_base        7
                     mod_base = OTHER
                     note = 2'-O-C16 alkyl guanosine
modified_base        8
                     mod_base = um
modified_base        9
                     mod_base = OTHER
                     note = 2'-fluoroadenosine
modified_base        10
                     mod_base = OTHER
                     note = 2'-fluoroadenosine
modified_base        11
                     mod_base = OTHER
                     note = 2'-fluoroadenosine
modified_base        12
                     mod_base = OTHER
                     note = 2'-O-methyladenosine
modified_base        13
                     mod_base = um
modified_base        14
                     mod_base = cm
modified_base        15
                     mod_base = um
modified_base        16
                     mod_base = gm
modified_base        17
                     mod_base = OTHER
                     note = 2'-O-methyladenosine
modified_base        18
                     mod_base = gm
modified_base        19
```

|               |                                                                              |
|---------------|------------------------------------------------------------------------------|
|               | mod_base = OTHER                                                             |
|               | note = 2'-O-methyladenosine with a 3'-phosphorothioate                       |
|               |     linkage                                                                  |
| modified_base | 20                                                                           |
|               | mod_base = OTHER                                                             |
|               | note = 2'-O-methyladenosine with a 3'-phosphorothioate                       |
|               |     linkage                                                                  |
| modified_base | 21                                                                           |
|               | mod_base = OTHER                                                             |
|               | note = 2'-O-methyladenosine                                                  |
| source        | 1..21                                                                        |
|               | mol_type = other RNA                                                         |
|               | organism = synthetic construct                                               |

SEQUENCE: 95
gtggaagtaa aatctgagaa a                                          21

|               |                                                                              |
|---------------|------------------------------------------------------------------------------|
| SEQ ID NO: 96 | moltype = RNA   length = 21                                                  |
| FEATURE       | Location/Qualifiers                                                          |
| misc_feature  | 1..21                                                                        |
|               | note = Description of Artificial Sequence: Synthetic                         |
|               |     oligonucleotide                                                          |
| modified_base | 1                                                                            |
|               | mod_base = OTHER                                                             |
|               | note = 2'-O-methylguanosine with a 3'-phosphorothioate                       |
|               |     linkage                                                                  |
| modified_base | 2                                                                            |
|               | mod_base = OTHER                                                             |
|               | note = 2'-O-methyluridine with a 3'-phosphorothioate linkage                 |
| modified_base | 3                                                                            |
|               | mod_base = gm                                                                |
| modified_base | 4                                                                            |
|               | mod_base = gm                                                                |
| modified_base | 5                                                                            |
|               | mod_base = OTHER                                                             |
|               | note = 2'-O-methyladenosine                                                  |
| modified_base | 6                                                                            |
|               | mod_base = OTHER                                                             |
|               | note = 2'-O-methyladenosine                                                  |
| modified_base | 7                                                                            |
|               | mod_base = gm                                                                |
| modified_base | 8                                                                            |
|               | mod_base = um                                                                |
| modified_base | 9                                                                            |
|               | mod_base = OTHER                                                             |
|               | note = 2'-fluoroadenosine                                                    |
| modified_base | 10                                                                           |
|               | mod_base = OTHER                                                             |
|               | note = 2'-fluoroadenosine                                                    |
| modified_base | 11                                                                           |
|               | mod_base = OTHER                                                             |
|               | note = 2'-O-C16 alkyl adenosine                                              |
| modified_base | 12                                                                           |
|               | mod_base = OTHER                                                             |
|               | note = 2'-O-methyladenosine                                                  |
| modified_base | 13                                                                           |
|               | mod_base = um                                                                |
| modified_base | 14                                                                           |
|               | mod_base = cm                                                                |
| modified_base | 15                                                                           |
|               | mod_base = um                                                                |
| modified_base | 16                                                                           |
|               | mod_base = gm                                                                |
| modified_base | 17                                                                           |
|               | mod_base = OTHER                                                             |
|               | note = 2'-O-methyladenosine                                                  |
| modified_base | 18                                                                           |
|               | mod_base = gm                                                                |
| modified_base | 19                                                                           |
|               | mod_base = OTHER                                                             |
|               | note = 2'-O-methyladenosine with a 3'-phosphorothioate                       |
|               |     linkage                                                                  |
| modified_base | 20                                                                           |
|               | mod_base = OTHER                                                             |
|               | note = 2'-O-methyladenosine with a 3'-phosphorothioate                       |
|               |     linkage                                                                  |
| modified_base | 21                                                                           |
|               | mod_base = OTHER                                                             |
|               | note = 2'-O-methyladenosine                                                  |
| source        | 1..21                                                                        |

|  |  |
|---|---|
|  | mol_type = other RNA |
|  | organism = synthetic construct |
| SEQUENCE: 96 | |
| gtggaagtaa aatctgagaa a | 21 |
| | |
| SEQ ID NO: 97 | moltype = RNA  length = 21 |
| FEATURE | Location/Qualifiers |
| misc_feature | 1..21 |
|  | note = Description of Artificial Sequence: Synthetic oligonucleotide |
| modified_base | 1 |
|  | mod_base = OTHER |
|  | note = 2'-O-methylguanosine with a 3'-phosphorothioate linkage |
| modified_base | 2 |
|  | mod_base = OTHER |
|  | note = 2'-O-methyluridine with a 3'-phosphorothioate linkage |
| modified_base | 3 |
|  | mod_base = gm |
| modified_base | 4 |
|  | mod_base = gm |
| modified_base | 5 |
|  | mod_base = OTHER |
|  | note = 2'-O-methyladenosine |
| modified_base | 6 |
|  | mod_base = OTHER |
|  | note = 2'-O-methyladenosine |
| modified_base | 7 |
|  | mod_base = gm |
| modified_base | 8 |
|  | mod_base = um |
| modified_base | 9 |
|  | mod_base = OTHER |
|  | note = 2'-fluoroadenosine |
| modified_base | 10 |
|  | mod_base = OTHER |
|  | note = 2'-fluoroadenosine |
| modified_base | 11 |
|  | mod_base = OTHER |
|  | note = 2'-fluoroadenosine |
| modified_base | 12 |
|  | mod_base = OTHER |
|  | note = 2'-O-methyladenosine |
| modified_base | 13 |
|  | mod_base = um |
| modified_base | 14 |
|  | mod_base = OTHER |
|  | note = 2'-O-C16 alkyl cytidine |
| modified_base | 15 |
|  | mod_base = um |
| modified_base | 16 |
|  | mod_base = gm |
| modified_base | 17 |
|  | mod_base = OTHER |
|  | note = 2'-O-methyladenosine |
| modified_base | 18 |
|  | mod_base = gm |
| modified_base | 19 |
|  | mod_base = OTHER |
|  | note = 2'-O-methyladenosine with a 3'-phosphorothioate linkage |
| modified_base | 20 |
|  | mod_base = OTHER |
|  | note = 2'-O-methyladenosine with a 3'-phosphorothioate linkage |
| modified_base | 21 |
|  | mod_base = OTHER |
|  | note = 2'-O-methyladenosine |
| source | 1..21 |
|  | mol_type = other RNA |
|  | organism = synthetic construct |
| SEQUENCE: 97 | |
| gtggaagtaa aatctgagaa a | 21 |
| | |
| SEQ ID NO: 98 | moltype = RNA  length = 21 |
| FEATURE | Location/Qualifiers |
| misc_feature | 1..21 |
|  | note = Description of Artificial Sequence: Synthetic oligonucleotide |

| | |
|---|---|
| modified_base | 1<br>mod_base = OTHER<br>note = 2'-O-methylguanosine with a 3'-phosphorothioate linkage |
| modified_base | 2<br>mod_base = OTHER<br>note = 2'-O-methyluridine with a 3'-phosphorothioate linkage |
| modified_base | 3<br>mod_base = gm |
| modified_base | 4<br>mod_base = gm |
| modified_base | 5<br>mod_base = OTHER<br>note = 2'-O-methyladenosine |
| modified_base | 6<br>mod_base = OTHER<br>note = 2'-O-methyladenosine |
| modified_base | 7<br>mod_base = gm |
| modified_base | 8<br>mod_base = um |
| modified_base | 9<br>mod_base = OTHER<br>note = 2'-fluoroadenosine |
| modified_base | 10<br>mod_base = OTHER<br>note = 2'-fluoroadenosine |
| modified_base | 11<br>mod_base = OTHER<br>note = 2'-fluoroadenosine |
| modified_base | 12<br>mod_base = OTHER<br>note = 2'-O-methyladenosine |
| modified_base | 13<br>mod_base = um |
| modified_base | 14<br>mod_base = cm |
| modified_base | 15<br>mod_base = um |
| modified_base | 16<br>mod_base = OTHER<br>note = 2'-O-C16 alkyl guanosine |
| modified_base | 17<br>mod_base = OTHER<br>note = 2'-O-methyladenosine |
| modified_base | 18<br>mod_base = gm |
| modified_base | 19<br>mod_base = OTHER<br>note = 2'-O-methyladenosine with a 3'-phosphorothioate linkage |
| modified_base | 20<br>mod_base = OTHER<br>note = 2'-O-methyladenosine with a 3'-phosphorothioate linkage |
| modified_base | 21<br>mod_base = OTHER<br>note = 2'-O-methyladenosine |
| source | 1..21<br>mol_type = other RNA<br>organism = synthetic construct |

SEQUENCE: 98
gtggaagtaa aatctgagaa a                                          21

| | |
|---|---|
| SEQ ID NO: 99<br>FEATURE<br>misc_feature | moltype = RNA  length = 21<br>Location/Qualifiers<br>1..21<br>note = Description of Artificial Sequence: Synthetic oligonucleotide |
| modified_base | 1<br>mod_base = OTHER<br>note = 2'-O-methylguanosine with a 3'-phosphorothioate linkage |
| modified_base | 2<br>mod_base = OTHER<br>note = 2'-O-methyluridine with a 3'-phosphorothioate linkage |
| modified_base | 3<br>mod_base = gm |
| modified_base | 4 |

```
                       mod_base = gm
modified_base          5
                       mod_base = OTHER
                       note = 2'-O-methyladenosine
modified_base          6
                       mod_base = OTHER
                       note = 2'-O-methyladenosine
modified_base          7
                       mod_base = gm
modified_base          8
                       mod_base = um
modified_base          9
                       mod_base = OTHER
                       note = 2'-fluoroadenosine
modified_base          10
                       mod_base = OTHER
                       note = 2'-fluoroadenosine
modified_base          11
                       mod_base = OTHER
                       note = 2'-fluoroadenosine
modified_base          12
                       mod_base = OTHER
                       note = 2'-O-methyladenosine
modified_base          13
                       mod_base = um
modified_base          14
                       mod_base = cm
modified_base          15
                       mod_base = um
modified_base          16
                       mod_base = gm
modified_base          17
                       mod_base = OTHER
                       note = 2'-O-C16 alkyl adenosine
modified_base          18
                       mod_base = gm
modified_base          19
                       mod_base = OTHER
                       note = 2'-O-methyladenosine with a 3'-phosphorothioate
                         linkage
modified_base          20
                       mod_base = OTHER
                       note = 2'-O-methyladenosine with a 3'-phosphorothioate
                         linkage
modified_base          21
                       mod_base = OTHER
                       note = 2'-O-methyladenosine
source                 1..21
                       mol_type = other RNA
                       organism = synthetic construct
SEQUENCE: 99
gtggaagtaa aatctgagaa a                                                   21

SEQ ID NO: 100         moltype = RNA  length = 21
FEATURE                Location/Qualifiers
misc_feature           1..21
                       note = Description of Artificial Sequence: Synthetic
                         oligonucleotide
modified_base          1
                       mod_base = OTHER
                       note = 2'-O-methylguanosine with a 3'-phosphorothioate
                         linkage
modified_base          2
                       mod_base = OTHER
                       note = 2'-O-methyluridine with a 3'-phosphorothioate linkage
modified_base          3
                       mod_base = gm
modified_base          4
                       mod_base = gm
modified_base          5
                       mod_base = OTHER
                       note = 2'-O-methyladenosine
modified_base          6
                       mod_base = OTHER
                       note = 2'-O-methyladenosine
modified_base          7
                       mod_base = gm
modified_base          8
                       mod_base = um
```

```
modified_base      9
                   mod_base = OTHER
                   note = 2'-fluoroadenosine
modified_base      10
                   mod_base = OTHER
                   note = 2'-fluoroadenosine
modified_base      11
                   mod_base = OTHER
                   note = 2'-fluoroadenosine
modified_base      12
                   mod_base = OTHER
                   note = 2'-O-methyladenosine
modified_base      13
                   mod_base = um
modified_base      14
                   mod_base = cm
modified_base      15
                   mod_base = um
modified_base      16
                   mod_base = gm
modified_base      17
                   mod_base = OTHER
                   note = 2'-O-methyladenosine
modified_base      18
                   mod_base = OTHER
                   note = 2'-O-C16 alkyl guanosine
modified_base      19
                   mod_base = OTHER
                   note = 2'-O-methyladenosine with a 3'-phosphorothioate
                    linkage
modified_base      20
                   mod_base = OTHER
                   note = 2'-O-methyladenosine with a 3'-phosphorothioate
                    linkage
modified_base      21
                   mod_base = OTHER
                   note = 2'-O-methyladenosine
source             1..21
                   mol_type = other RNA
                   organism = synthetic construct
SEQUENCE: 100
gtggaagtaa aatctgagaa a                                              21

SEQ ID NO: 101     moltype = RNA  length = 21
FEATURE            Location/Qualifiers
misc_feature       1..21
                   note = Description of Artificial Sequence: Synthetic
                    oligonucleotide
modified_base      1
                   mod_base = OTHER
                   note = 2'-O-methylcytidine with a 3'-phosphorothioate
                    linkage
modified_base      2
                   mod_base = OTHER
                   note = 2'-O-methylcytidine with a 3'-phosphorothioate
                    linkage
modified_base      3
                   mod_base = OTHER
                   note = 2'-O-methyladenosine
modified_base      4
                   mod_base = gm
modified_base      5
                   mod_base = gm
modified_base      6
                   mod_base = um
modified_base      7
                   mod_base = gm
modified_base      8
                   mod_base = gm
modified_base      9
                   mod_base = OTHER
                   note = 2'-fluoroadenosine
modified_base      10
                   mod_base = OTHER
                   note = 2'-fluoroadenosine
modified_base      11
                   mod_base = OTHER
                   note = 2'-fluoroguanosine
modified_base      12
```

| | |
|---|---|
| | mod_base = um |
| modified_base | 13 |
| | mod_base = OTHER |
| | note = 2'-O-C16 alkyl adenosine |
| modified_base | 14 |
| | mod_base = OTHER |
| | note = 2'-O-methyladenosine |
| modified_base | 15 |
| | mod_base = OTHER |
| | note = 2'-O-methyladenosine |
| modified_base | 16 |
| | mod_base = OTHER |
| | note = 2'-O-methyladenosine |
| modified_base | 17 |
| | mod_base = um |
| modified_base | 18 |
| | mod_base = cm |
| modified_base | 19 |
| | mod_base = OTHER |
| | note = 2'-O-methyluridine with a 3'-phosphorothioate linkage |
| modified_base | 20 |
| | mod_base = OTHER |
| | note = 2'-O-methylguanosine with a 3'-phosphorothioate linkage |
| modified_base | 21 |
| | mod_base = OTHER |
| | note = 2'-O-methyladenosine |
| source | 1..21 |
| | mol_type = other RNA |
| | organism = synthetic construct |
| SEQUENCE: 101 | |
| ccaggtggaa gtaaaatctg a | 21 |
| SEQ ID NO: 102 | moltype = RNA   length = 23 |
| FEATURE | Location/Qualifiers |
| misc_feature | 1..23 |
| | note = Description of Artificial Sequence: Synthetic oligonucleotide |
| modified_base | 1 |
| | mod_base = OTHER |
| | note = 2'-O-methyluridine with a 3'-phosphorothioate linkage and a 5'-vinylphosphonate substitution |
| modified_base | 2 |
| | mod_base = OTHER |
| | note = 2'-fluorocytidine with a 3'-phosphorothioate linkage |
| modified_base | 3 |
| | mod_base = OTHER |
| | note = 2'-O-methyladenosine |
| modified_base | 4 |
| | mod_base = gm |
| modified_base | 5 |
| | mod_base = OTHER |
| | note = 2'-fluoroadenosine |
| modified_base | 6 |
| | mod_base = um |
| modified_base | 7 |
| | mod_base = um |
| modified_base | 8 |
| | mod_base = OTHER |
| | note = 2'-fluorouridine |
| modified_base | 9 |
| | mod_base = um |
| modified_base | 10 |
| | mod_base = OTHER |
| | note = 2'-O-methyladenosine |
| modified_base | 11 |
| | mod_base = cm |
| modified_base | 12 |
| | mod_base = um |
| modified_base | 13 |
| | mod_base = um |
| modified_base | 14 |
| | mod_base = OTHER |
| | note = 2'-fluorocytidine |
| modified_base | 15 |
| | mod_base = cm |
| modified_base | 16 |
| | mod_base = OTHER |
| | note = 2'-fluoroadenosine |

```
modified_base            17
                         mod_base = cm
modified_base            18
                         mod_base = cm
modified_base            19
                         mod_base = um
modified_base            20
                         mod_base = gm
modified_base            21
                         mod_base = OTHER
                         note = 2'-O-methylguanosine with a 3'-phosphorothioate
                           linkage
modified_base            22
                         mod_base = OTHER
                         note = 2'-O-methylcytidine with a 3'-phosphorothioate
                           linkage
modified_base            23
                         mod_base = cm
source                   1..23
                         mol_type = other RNA
                         organism = synthetic construct
SEQUENCE: 102
tcagattttta cttccacctg gcc                                             23

SEQ ID NO: 103           moltype = RNA  length = 21
FEATURE                  Location/Qualifiers
misc_feature             1..21
                         note = Description of Artificial Sequence: Synthetic
                           oligonucleotide
modified_base            1
                         mod_base = OTHER
                         note = 2'-O-methylguanosine with a 3'-phosphorothioate
                           linkage
modified_base            2
                         mod_base = OTHER
                         note = 2'-O-methylguanosine with a 3'-phosphorothioate
                           linkage
modified_base            3
                         mod_base = OTHER
                         note = 2'-O-methyladenosine
modified_base            4
                         mod_base = OTHER
                         note = 2'-O-methyladenosine
modified_base            5
                         mod_base = gm
modified_base            6
                         mod_base = um
modified_base            7
                         mod_base = OTHER
                         note = 2'-O-methyladenosine
modified_base            8
                         mod_base = OTHER
                         note = 2'-O-methyladenosine
modified_base            9
                         mod_base = OTHER
                         note = 2'-fluoroadenosine
modified_base            10
                         mod_base = OTHER
                         note = 2'-fluoroadenosine
modified_base            11
                         mod_base = OTHER
                         note = 2'-fluorouridine
modified_base            12
                         mod_base = cm
modified_base            13
                         mod_base = OTHER
                         note = 2'-O-C16 alkyl uridine
modified_base            14
                         mod_base = gm
modified_base            15
                         mod_base = OTHER
                         note = 2'-O-methyladenosine
modified_base            16
                         mod_base = gm
modified_base            17
                         mod_base = OTHER
                         note = 2'-O-methyladenosine
modified_base            18
                         mod_base = OTHER
```

```
                            note = 2'-O-methyladenosine
modified_base               19
                            mod_base = OTHER
                            note = 2'-O-methylguanosine with a 3'-phosphorothioate
                              linkage
modified_base               20
                            mod_base = OTHER
                            note = 2'-O-methylcytidine with a 3'-phosphorothioate
                              linkage
modified_base               21
                            mod_base = OTHER
                            note = 2'-O-methyladenosine
source                      1..21
                            mol_type = other RNA
                            organism = synthetic construct
SEQUENCE: 103
ggaagtaaaa tctgagaagc a                                                    21

SEQ ID NO: 104              moltype = RNA   length = 23
FEATURE                     Location/Qualifiers
misc_feature                1..23
                            note = Description of Artificial Sequence: Synthetic
                              oligonucleotide
modified_base               1
                            mod_base = OTHER
                            note = 2'-O-methyluridine with a 3'-phosphorothioate
                              linkage and a 5'-vinylphosphonate substitution
modified_base               2
                            mod_base = OTHER
                            note = 2'-fluoroguanosine with a 3'-phosphorothioate linkage
modified_base               3
                            mod_base = cm
modified_base               4
                            mod_base = um
modified_base               5
                            mod_base = OTHER
                            note = 2'-fluorouridine
modified_base               6
                            mod_base = cm
modified_base               7
                            mod_base = um
modified_base               8
                            mod_base = OTHER
                            note = 2'-fluorocytidine
modified_base               9
                            mod_base = OTHER
                            note = 2'-O-methyladenosine
modified_base               10
                            mod_base = gm
modified_base               11
                            mod_base = OTHER
                            note = 2'-O-methyladenosine
modified_base               12
                            mod_base = um
modified_base               13
                            mod_base = um
modified_base               14
                            mod_base = OTHER
                            note = 2'-fluorouridine
modified_base               15
                            mod_base = um
modified_base               16
                            mod_base = OTHER
                            note = 2'-fluoroadenosine
modified_base               17
                            mod_base = cm
modified_base               18
                            mod_base = um
modified_base               19
                            mod_base = um
modified_base               20
                            mod_base = cm
modified_base               21
                            mod_base = OTHER
                            note = 2'-O-methylcytidine with a 3'-phosphorothioate
                              linkage
modified_base               22
                            mod_base = OTHER
                            note = 2'-O-methyladenosine with a 3'-phosphorothioate
```

|  |  |  |
|---|---|---|
|  | linkage |  |
| modified_base | 23 |  |
|  | mod_base = cm |  |
| source | 1..23 |  |
|  | mol_type = other RNA |  |
|  | organism = synthetic construct |  |
| SEQUENCE: 104 |  |  |
| tgcttctcag attttacttc cac |  | 23 |
|  |  |  |
| SEQ ID NO: 105 | moltype = RNA length = 21 |  |
| FEATURE | Location/Qualifiers |  |
| misc_feature | 1..21 |  |
|  | note = Description of Artificial Sequence: Synthetic oligonucleotide |  |
| modified_base | 1 |  |
|  | mod_base = OTHER |  |
|  | note = 2'-O-methylguanosine with a 3'-phosphorothioate linkage |  |
| modified_base | 2 |  |
|  | mod_base = OTHER |  |
|  | note = 2'-O-methyluridine with a 3'-phosphorothioate linkage |  |
| modified_base | 3 |  |
|  | mod_base = gm |  |
| modified_base | 4 |  |
|  | mod_base = gm |  |
| modified_base | 5 |  |
|  | mod_base = OTHER |  |
|  | note = 2'-O-methyladenosine |  |
| modified_base | 6 |  |
|  | mod_base = OTHER |  |
|  | note = 2'-O-methyladenosine |  |
| modified_base | 7 |  |
|  | mod_base = OTHER |  |
|  | note = 2'-fluoroguanosine |  |
| modified_base | 8 |  |
|  | mod_base = um |  |
| modified_base | 9 |  |
|  | mod_base = OTHER |  |
|  | note = 2'-fluoroadenosine |  |
| modified_base | 10 |  |
|  | mod_base = OTHER |  |
|  | note = 2'-fluoroadenosine |  |
| modified_base | 11 |  |
|  | mod_base = OTHER |  |
|  | note = 2'-fluoroadenosine |  |
| modified_base | 12 |  |
|  | mod_base = OTHER |  |
|  | note = 2'-O-methyladenosine |  |
| modified_base | 13 |  |
|  | mod_base = um |  |
| modified_base | 14 |  |
|  | mod_base = cm |  |
| modified_base | 15 |  |
|  | mod_base = um |  |
| modified_base | 16 |  |
|  | mod_base = gm |  |
| modified_base | 17 |  |
|  | mod_base = OTHER |  |
|  | note = 2'-O-methyladenosine |  |
| modified_base | 18 |  |
|  | mod_base = gm |  |
| modified_base | 19 |  |
|  | mod_base = OTHER |  |
|  | note = 2'-O-methyladenosine |  |
| modified_base | 20 |  |
|  | mod_base = OTHER |  |
|  | note = 2'-O-methyladenosine with a 3'-phosphorothioate linkage |  |
| modified_base | 21 |  |
|  | mod_base = OTHER |  |
|  | note = 2'-O-methyladenosine with a 3'-phosphorothioate linkage |  |
| source | 1..21 |  |
|  | mol_type = other RNA |  |
|  | organism = synthetic construct |  |
| SEQUENCE: 105 |  |  |
| gtggaagtaa aatctgagaa a |  | 21 |
|  |  |  |
| SEQ ID NO: 106 | moltype = RNA length = 23 |  |

| FEATURE | Location/Qualifiers |
|---|---|
| misc_feature | 1..23<br>note = Description of Artificial Sequence: Synthetic oligonucleotide |
| modified_base | 1<br>mod_base = OTHER<br>note = 2'-O-methyluridine with a 3'-phosphorothioate linkage and a 5'-vinylphosphonate substitution |
| modified_base | 2<br>mod_base = OTHER<br>note = 2'-fluorouridine with a 3'-phosphorothioate linkage |
| modified_base | 3<br>mod_base = um |
| modified_base | 4<br>mod_base = cm |
| modified_base | 5<br>mod_base = um |
| modified_base | 6<br>mod_base = cm |
| modified_base | 7<br>mod_base = OTHER<br>note = 2'-O-methyladenosine |
| modified_base | 8<br>mod_base = gm |
| modified_base | 9<br>mod_base = OTHER<br>note = 2'-O-methyladenosine |
| modified_base | 10<br>mod_base = um |
| modified_base | 11<br>mod_base = um |
| modified_base | 12<br>mod_base = um |
| modified_base | 13<br>mod_base = um |
| modified_base | 14<br>mod_base = OTHER<br>note = 2'-fluoroadenosine |
| modified_base | 15<br>mod_base = cm |
| modified_base | 16<br>mod_base = OTHER<br>note = 2'-fluorouridine |
| modified_base | 17<br>mod_base = um |
| modified_base | 18<br>mod_base = cm |
| modified_base | 19<br>mod_base = cm |
| modified_base | 20<br>mod_base = OTHER<br>note = 2'-O-methyladenosine |
| modified_base | 21<br>mod_base = OTHER<br>note = 2'-O-methylcytidine with a 3'-phosphorothioate linkage |
| modified_base | 22<br>mod_base = OTHER<br>note = 2'-O-methylcytidine with a 3'-phosphorothioate linkage |
| modified_base | 23<br>mod_base = um |
| source | 1..23<br>mol_type = other RNA<br>organism = synthetic construct |

SEQUENCE: 106
tttctcagat tttacttcca cct                     23

| SEQ ID NO: 107 | moltype = RNA  length = 23 |
|---|---|
| FEATURE | Location/Qualifiers |
| misc_feature | 1..23<br>note = Description of Artificial Sequence: Synthetic oligonucleotide |
| modified_base | 1<br>mod_base = OTHER<br>note = 2'-O-methyluridine with a 3'-phosphorothioate linkage and a 5'-vinylphosphonate substitution |
| modified_base | 2<br>mod_base = OTHER |

|                | note = 2'-fluorouridine with a 3'-phosphorothioate linkage |
|---|---|
| modified_base  | 3 |
|                | mod_base = um |
| modified_base  | 4 |
|                | mod_base = OTHER |
|                | note = 2'-fluorocytidine |
| modified_base  | 5 |
|                | mod_base = um |
| modified_base  | 6 |
|                | mod_base = OTHER |
|                | note = 2'-fluorocytidine |
| modified_base  | 7 |
|                | mod_base = OTHER |
|                | note = 2'-fluoroadenosine |
| modified_base  | 8 |
|                | mod_base = gm |
| modified_base  | 9 |
|                | mod_base = OTHER |
|                | note = 2'-fluoroadenosine |
| modified_base  | 10 |
|                | mod_base = um |
| modified_base  | 11 |
|                | mod_base = um |
| modified_base  | 12 |
|                | mod_base = um |
| modified_base  | 13 |
|                | mod_base = um |
| modified_base  | 14 |
|                | mod_base = OTHER |
|                | note = 2'-fluoroadenosine |
| modified_base  | 15 |
|                | mod_base = cm |
| modified_base  | 16 |
|                | mod_base = OTHER |
|                | note = 2'-fluorouridine |
| modified_base  | 17 |
|                | mod_base = um |
| modified_base  | 18 |
|                | mod_base = cm |
| modified_base  | 19 |
|                | mod_base = cm |
| modified_base  | 20 |
|                | mod_base = OTHER |
|                | note = 2'-O-methyladenosine |
| modified_base  | 21 |
|                | mod_base = OTHER |
|                | note = 2'-O-methylcytidine with a 3'-phosphorothioate linkage |
| modified_base  | 22 |
|                | mod_base = OTHER |
|                | note = 2'-O-methylcytidine with a 3'-phosphorothioate linkage |
| modified_base  | 23 |
|                | mod_base = um |
| source         | 1..23 |
|                | mol_type = other RNA |
|                | organism = synthetic construct |
| SEQUENCE: 107  | |
| tttctcagat tttacttcca cct | 23 |

| SEQ ID NO: 108 | moltype = RNA   length = 23 |
|---|---|
| FEATURE        | Location/Qualifiers |
| misc_feature   | 1..23 |
|                | note = Description of Artificial Sequence: Synthetic oligonucleotide |
| modified_base  | 1 |
|                | mod_base = OTHER |
|                | note = 2'-O-methyluridine with a 3'-phosphorothioate linkage and a 5'-vinylphosphonate substitution |
| modified_base  | 2 |
|                | mod_base = OTHER |
|                | note = 2'-fluorouridine with a 3'-phosphorothioate linkage |
| modified_base  | 3 |
|                | mod_base = um |
| modified_base  | 4 |
|                | mod_base = cm |
| modified_base  | 5 |
|                | mod_base = OTHER |
|                | note = 2'-fluorouridine |

```
                              -continued modified_base          6
                       mod_base = OTHER
                       note = 2'-fluorocytidine
modified_base          7
                       mod_base = OTHER
                       note = 2'-fluoroadenosine
modified_base          8
                       mod_base = OTHER
                       note = 2'-fluoroguanosine
modified_base          9
                       mod_base = OTHER
                       note = 2'-O-methyladenosine
modified_base          10
                       mod_base = um
modified_base          11
                       mod_base = um
modified_base          12
                       mod_base = um
modified_base          13
                       mod_base = um
modified_base          14
                       mod_base = OTHER
                       note = 2'-fluoroadenosine
modified_base          15
                       mod_base = cm
modified_base          16
                       mod_base = OTHER
                       note = 2'-fluorouridine
modified_base          17
                       mod_base = um
modified_base          18
                       mod_base = cm
modified_base          19
                       mod_base = cm
modified_base          20
                       mod_base = OTHER
                       note = 2'-O-methyladenosine
modified_base          21
                       mod_base = OTHER
                       note = 2'-O-methylcytidine with a 3'-phosphorothioate
                         linkage
modified_base          22
                       mod_base = OTHER
                       note = 2'-O-methylcytidine with a 3'-phosphorothioate
                         linkage
modified_base          23
                       mod_base = um
source                 1..23
                       mol_type = other RNA
                       organism = synthetic construct
SEQUENCE: 108
tttctcagat tttacttcca cct                                               23

SEQ ID NO: 109         moltype = RNA  length = 21
FEATURE                Location/Qualifiers
misc_feature           1..21
                       note = Description of Artificial Sequence: Synthetic
                         oligonucleotide
modified_base          1
                       mod_base = OTHER
                       note = 2'-O-methylguanosine with a 3'-phosphorothioate
                         linkage
modified_base          2
                       mod_base = OTHER
                       note = 2'-O-methyluridine with a 3'-phosphorothioate linkage
modified_base          3
                       mod_base = gm
modified_base          4
                       mod_base = gm
modified_base          5
                       mod_base = OTHER
                       note = 2'-O-methyladenosine
modified_base          6
                       mod_base = OTHER
                       note = 2'-O-methyladenosine
modified_base          7
                       mod_base = OTHER
                       note = 2'-fluoroguanosine
modified_base          8
```

```
                        mod_base = um
modified_base           9
                        mod_base = OTHER
                        note = 2'-fluoroadenosine
modified_base           10
                        mod_base = OTHER
                        note = abasic nucleotide
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine
modified_base           20
                        mod_base = OTHER
                        note = 2'-O-methyladenosine with a 3'-phosphorothioate
                         linkage
modified_base           21
                        mod_base = OTHER
                        note = 2'-O-methyladenosine with a 3'-phosphorothioate
                         linkage
source                  1..21
                        mol_type = other RNA
                        organism = synthetic construct
SEQUENCE: 109
gtggaagtan aatctgagaa a                                              21

SEQ ID NO: 110          moltype = RNA  length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methylguanosine with a 3'-phosphorothioate
                         linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = OTHER
                        note = 2'-fluoroguanosine
modified_base           8
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
```

```
modified_base        12
                     mod_base = OTHER
                     note = 2'-O-methyladenosine
modified_base        13
                     mod_base = um
modified_base        14
                     mod_base = cm
modified_base        15
                     mod_base = um
modified_base        16
                     mod_base = gm
modified_base        17
                     mod_base = OTHER
                     note = 2'-O-methyladenosine
modified_base        18
                     mod_base = gm
modified_base        19
                     mod_base = OTHER
                     note = 2'-O-methyladenosine with a 3'-phosphorothioate
                       linkage
modified_base        20
                     mod_base = OTHER
                     note = 2'-O-methyladenosine with a 3'-phosphorothioate
                       linkage
modified_base        21
                     mod_base = gm
source               1..21
                     mol_type = other RNA
                     organism = synthetic construct
SEQUENCE: 110
gtggaagtaa aatctgagaa g                                              21

SEQ ID NO: 111       moltype = RNA  length = 17
FEATURE              Location/Qualifiers
misc_feature         1..17
                     note = Description of Artificial Sequence: Synthetic
                       oligonucleotide
modified_base        1
                     mod_base = OTHER
                     note = 2'-O-methyladenosine with a 3'-phosphorothioate
                       linkage
modified_base        2
                     mod_base = OTHER
                     note = 2'-O-methyladenosine with a 3'-phosphorothioate
                       linkage
modified_base        3
                     mod_base = OTHER
                     note = 2'-fluoroguanosine
modified_base        4
                     mod_base = um
modified_base        5
                     mod_base = OTHER
                     note = 2'-fluoroadenosine
modified_base        6
                     mod_base = OTHER
                     note = 2'-fluoroadenosine
modified_base        7
                     mod_base = OTHER
                     note = 2'-fluoroadenosine
modified_base        8
                     mod_base = OTHER
                     note = 2'-O-methyladenosine
modified_base        9
                     mod_base = um
modified_base        10
                     mod_base = cm
modified_base        11
                     mod_base = um
modified_base        12
                     mod_base = gm
modified_base        13
                     mod_base = OTHER
                     note = 2'-O-methyladenosine
modified_base        14
                     mod_base = gm
modified_base        15
                     mod_base = OTHER
                     note = 2'-O-methyladenosine with a 3'-phosphorothioate
                       linkage
```

```
modified_base       16
                    mod_base = OTHER
                    note = 2'-O-methyladenosine with a 3'-phosphorothioate
                        linkage
modified_base       17
                    mod_base = OTHER
                    note = 2'-O-methyladenosine
source              1..17
                    mol_type = other RNA
                    organism = synthetic construct
SEQUENCE: 111
aagtaaaatc tgagaaa                                                    17

SEQ ID NO: 112      moltype = RNA   length = 23
FEATURE             Location/Qualifiers
misc_feature        1..23
                    note = Description of Artificial Sequence: Synthetic
                        oligonucleotide
modified_base       1
                    mod_base = OTHER
                    note = 2'-O-methyluridine with a 3'-phosphorothioate
                        linkage and a 5'-vinylphosphonate substitution
modified_base       2
                    mod_base = OTHER
                    note = 2'-fluorouridine with a 3'-phosphorothioate linkage
modified_base       3
                    mod_base = um
modified_base       4
                    mod_base = cm
modified_base       5
                    mod_base = um
modified_base       6
                    mod_base = OTHER
                    note = 2'-fluorocytidine
modified_base       7
                    mod_base = OTHER
                    note = 2'-O-methyladenosine
modified_base       8
                    mod_base = gm
modified_base       9
                    mod_base = OTHER
                    note = 2'-O-methyladenosine
modified_base       10
                    mod_base = um
modified_base       11
                    mod_base = um
modified_base       12
                    mod_base = um
modified_base       13
                    mod_base = um
modified_base       14
                    mod_base = OTHER
                    note = 2'-fluoroadenosine
modified_base       15
                    mod_base = cm
modified_base       16
                    mod_base = OTHER
                    note = 2'-fluorouridine
modified_base       17
                    mod_base = OTHER
                    note = 2'-O-methyluridine with a 3'-phosphorothioate linkage
modified_base       18
                    mod_base = OTHER
                    note = 2'-O-methylcytidine with a 3'-phosphorothioate
                        linkage
modified_base       19
                    mod_base = OTHER
                    note = 2'-O-methylcytidine with a 3'-phosphorothioate
                        linkage
modified_base       20
                    mod_base = OTHER
                    note = 2'-O-methyladenosine with a 3'-phosphorothioate
                        linkage
modified_base       21
                    mod_base = OTHER
                    note = 2'-O-methylcytidine with a 3'-phosphorothioate
                        linkage
modified_base       22
                    mod_base = OTHER
```

```
                        note = 2'-O-methylcytidine with a 3'-phosphorothioate
                         linkage
modified_base           23
                        mod_base = um
source                  1..23
                        mol_type = other RNA
                        organism = synthetic construct
SEQUENCE: 112
tttctcagat tttacttcca cct                                              23

SEQ ID NO: 113          moltype = RNA  length = 23
FEATURE                 Location/Qualifiers
misc_feature            1..23
                        note = Description of Artificial Sequence: Synthetic
                         oligonucleotide
modified_base           1
                        mod_base = OTHER
                        note = 2'-O-methylguanosine with a 3'-phosphorothioate
                         linkage
modified_base           2
                        mod_base = OTHER
                        note = 2'-O-methyluridine with a 3'-phosphorothioate linkage
modified_base           3
                        mod_base = gm
modified_base           4
                        mod_base = gm
modified_base           5
                        mod_base = OTHER
                        note = 2'-O-methyladenosine
modified_base           6
                        mod_base = OTHER
                        note = 2'-O-methyladenosine
modified_base           7
                        mod_base = OTHER
                        note = 2'-fluoroguanosine
modified_base           8
                        mod_base = um
modified_base           9
                        mod_base = OTHER
                        note = 2'-fluoroadenosine
modified_base           10
                        mod_base = OTHER
                        note = 2'-fluoroadenosine
modified_base           11
                        mod_base = OTHER
                        note = 2'-fluoroadenosine
modified_base           12
                        mod_base = OTHER
                        note = 2'-O-methyladenosine
modified_base           13
                        mod_base = um
modified_base           14
                        mod_base = cm
modified_base           15
                        mod_base = um
modified_base           16
                        mod_base = gm
modified_base           17
                        mod_base = OTHER
                        note = 2'-O-methyladenosine
modified_base           18
                        mod_base = gm
modified_base           19
                        mod_base = OTHER
                        note = 2'-O-methyladenosine
modified_base           20
                        mod_base = OTHER
                        note = 2'-O-methyladenosine
modified_base           21
                        mod_base = OTHER
                        note = 2'-O-methyladenosine
modified_base           22
                        mod_base = OTHER
                        note = thymine
modified_base           23
                        mod_base = OTHER
                        note = thymine with a 3'-phosphorothioate linkage
source                  1..23
                        mol_type = other RNA
```

| | | |
|---|---|---|
| | organism = synthetic construct | |
| SEQUENCE: 113 | | |
| gtggaagtaa aatctgagaa att | | 23 |
| | | |
| SEQ ID NO: 114 | moltype = RNA  length = 23 | |
| FEATURE | Location/Qualifiers | |
| misc_feature | 1..23 | |
| | note = Description of Artificial Sequence: Synthetic oligonucleotide | |
| modified_base | 1 | |
| | mod_base = OTHER | |
| | note = 2'-O-methyluridine with a 3'-phosphorothioate linkage and a 5'-vinylphosphonate substitution | |
| modified_base | 2 | |
| | mod_base = OTHER | |
| | note = 2'-fluorouridine with a 3'-phosphorothioate linkage | |
| modified_base | 3 | |
| | mod_base = um | |
| modified_base | 4 | |
| | mod_base = cm | |
| modified_base | 5 | |
| | mod_base = um | |
| modified_base | 6 | |
| | mod_base = OTHER | |
| | note = 2'-fluorocytidine | |
| modified_base | 7 | |
| | mod_base = OTHER | |
| | note = 2'-O-methyladenosine | |
| modified_base | 8 | |
| | mod_base = gm | |
| modified_base | 9 | |
| | mod_base = OTHER | |
| | note = 2'-O-methyladenosine | |
| modified_base | 10 | |
| | mod_base = um | |
| modified_base | 11 | |
| | mod_base = um | |
| modified_base | 12 | |
| | mod_base = um | |
| modified_base | 13 | |
| | mod_base = um | |
| modified_base | 14 | |
| | mod_base = OTHER | |
| | note = 2'-fluoroadenosine | |
| modified_base | 15 | |
| | mod_base = cm | |
| modified_base | 16 | |
| | mod_base = OTHER | |
| | note = 2'-fluorouridine | |
| modified_base | 17 | |
| | mod_base = um | |
| modified_base | 18 | |
| | mod_base = cm | |
| modified_base | 19 | |
| | mod_base = OTHER | |
| | note = 2'-O-methylcytidine with a 3'-phosphorothioate linkage | |
| modified_base | 20 | |
| | mod_base = OTHER | |
| | note = 2'-O-methyladenosine with a 3'-phosphorothioate linkage | |
| modified_base | 21 | |
| | mod_base = cm | |
| modified_base | 22 | |
| | mod_base = OTHER | |
| | note = thymine | |
| modified_base | 23 | |
| | mod_base = OTHER | |
| | note = thymine | |
| source | 1..23 | |
| | mol_type = other RNA | |
| | organism = synthetic construct | |
| SEQUENCE: 114 | | |
| tttctcagat tttacttcca ctt | | 23 |
| | | |
| SEQ ID NO: 115 | moltype = RNA  length = 21 | |
| FEATURE | Location/Qualifiers | |
| misc_feature | 1..21 | |
| | note = Description of Artificial Sequence: Synthetic | |

|  |  |
|---|---|
| modified_base | 1<br>mod_base = OTHER<br>note = 2'-O-methylguanosine with a 3'-phosphorothioate linkage |
| modified_base | 2<br>mod_base = OTHER<br>note = 2'-O-methyluridine with a 3'-phosphorothioate linkage |
| modified_base | 3<br>mod_base = gm |
| modified_base | 4<br>mod_base = gm |
| modified_base | 5<br>mod_base = OTHER<br>note = 2'-O-methyladenosine |
| modified_base | 6<br>mod_base = OTHER<br>note = 2'-O-methyladenosine |
| modified_base | 7<br>mod_base = gm |
| modified_base | 8<br>mod_base = um |
| modified_base | 9<br>mod_base = OTHER<br>note = 2'-fluoroadenosine |
| modified_base | 10<br>mod_base = OTHER<br>note = 2'-fluoroadenosine |
| modified_base | 11<br>mod_base = OTHER<br>note = 2'-fluoroadenosine |
| modified_base | 12<br>mod_base = OTHER<br>note = 2'-O-methyladenosine |
| modified_base | 13<br>mod_base = um |
| modified_base | 14<br>mod_base = cm |
| modified_base | 15<br>mod_base = um |
| modified_base | 16<br>mod_base = gm |
| modified_base | 17<br>mod_base = OTHER<br>note = 2'-O-methyladenosine |
| modified_base | 18<br>mod_base = gm |
| modified_base | 19<br>mod_base = OTHER<br>note = 2'-O-methyladenosine |
| modified_base | 20<br>mod_base = OTHER<br>note = 2'-O-methyladenosine with a 3'-phosphorothioate linkage |
| modified_base | 21<br>mod_base = OTHER<br>note = 2'-O-methyladenosine with a 3'-phosphorothioate linkage |
| source | 1..21<br>mol_type = other RNA<br>organism = synthetic construct |
| SEQUENCE: 115 | |
| gtggaagtaa aatctgagaa a | 21 |
| SEQ ID NO: 116 | moltype = RNA  length = 23 |
| FEATURE | Location/Qualifiers |
| misc_feature | 1..23<br>note = Description of Artificial Sequence: Synthetic oligonucleotide |
| modified_base | 1<br>mod_base = OTHER<br>note = 2'-O-methyluridine with a 3'-phosphorothioate linkage and a 5'-vinylphosphonate substitution |
| modified_base | 2<br>mod_base = OTHER<br>note = 2'-fluorouridine with a 3'-phosphorothioate linkage |
| modified_base | 3<br>mod_base = um |
| modified_base | 4 |

```
modified_base              mod_base = cm
                           5
                           mod_base = um
modified_base              6
                           mod_base = OTHER
                           note = 2'-fluorocytidine
modified_base              7
                           mod_base = OTHER
                           note = 2'-O-methyladenosine
modified_base              8
                           mod_base = gm
modified_base              9
                           mod_base = OTHER
                           note = 2'-O-methyladenosine
modified_base              10
                           mod_base = um
modified_base              11
                           mod_base = um
modified_base              12
                           mod_base = um
modified_base              13
                           mod_base = um
modified_base              14
                           mod_base = OTHER
                           note = 2'-fluoroadenosine
modified_base              15
                           mod_base = cm
modified_base              16
                           mod_base = OTHER
                           note = 2'-fluorouridine
modified_base              17
                           mod_base = um
modified_base              18
                           mod_base = cm
modified_base              19
                           mod_base = cm
modified_base              20
                           mod_base = OTHER
                           note = 2'-O-methyladenosine with a 3'-phosphorothioate
                              linkage
modified_base              21
                           mod_base = OTHER
                           note = 2'-O-methylcytidine with a 3'-phosphorothioate
                              linkage
modified_base              22
                           mod_base = OTHER
                           note = 2'-O-methylcytidine with a 3'-phosphorothioate
                              linkage
modified_base              23
                           mod_base = um
source                     1..23
                           mol_type = other RNA
                           organism = synthetic construct
SEQUENCE: 116
tttctcagat tttacttcca cct                                              23

SEQ ID NO: 117             moltype = RNA  length = 23
FEATURE                    Location/Qualifiers
misc_feature               1..23
                           note = Description of Artificial Sequence: Synthetic
                              oligonucleotide
modified_base              22
                           mod_base = OTHER
                           note = thymine
modified_base              23
                           mod_base = OTHER
                           note = thymine
source                     1..23
                           mol_type = other RNA
                           organism = synthetic construct
SEQUENCE: 117
gtggaagtaa aatctgagaa att                                              23

SEQ ID NO: 118             moltype = RNA  length = 23
FEATURE                    Location/Qualifiers
misc_feature               1..23
                           note = Description of Artificial Sequence: Synthetic
                              oligonucleotide
modified_base              22
```

```
                    mod_base = OTHER
                    note = thymine
modified_base       23
                    mod_base = OTHER
                    note = thymine
source              1..23
                    mol_type = other RNA
                    organism = synthetic construct
SEQUENCE: 118
tttctcagat tttacttcca ctt                                              23

SEQ ID NO: 119      moltype = RNA  length = 21
FEATURE             Location/Qualifiers
misc_feature        1..21
                    note = Description of Artificial Sequence: Synthetic
                     oligonucleotide
source              1..21
                    mol_type = other RNA
                    organism = synthetic construct
SEQUENCE: 119
gtggaagtaa aatctgagaa g                                                21
```